US010112955B2

(12) United States Patent
Sprengeler et al.

(10) Patent No.: US 10,112,955 B2
(45) Date of Patent: Oct. 30, 2018

(54) ISOINDOLINE, AZAISOINDOLINE, DIHYDROINDENONE AND DIHYDROAZAINDENONE INHIBITORS OF MNK1 AND MNK2

(71) Applicant: eFFECTOR THERAPEUTICS, INC., San Diego, CA (US)

(72) Inventors: Paul A. Sprengeler, Escondido, CA (US); Siegfried H. Reich, La Jolla, CA (US); Justin T. Ernst, San Diego, CA (US); Stephen E. Webber, San Diego, CA (US); Mike Shaghafi, San Diego, CA (US); Douglas Murphy, Escondido, CA (US); Chinh Tran, San Diego, CA (US)

(73) Assignee: eFFECTOR Therapeutics, Inc., San Diego, CA (US)

( * ) Notice: Subject to any disclaimer, the term of this patent is extended or adjusted under 35 U.S.C. 154(b) by 0 days.

(21) Appl. No.: 15/337,184

(22) Filed: Oct. 28, 2016

(65) Prior Publication Data
US 2017/0121346 A1 May 4, 2017

Related U.S. Application Data

(60) Provisional application No. 62/247,953, filed on Oct. 29, 2015.

(51) Int. Cl.
| C07D 498/04 | (2006.01) |
| C07D 403/12 | (2006.01) |
| C07D 401/12 | (2006.01) |
| C07D 403/14 | (2006.01) |
| C07D 239/42 | (2006.01) |
| C07D 239/49 | (2006.01) |
| C07D 409/12 | (2006.01) |
| C07D 417/12 | (2006.01) |
| C07D 487/04 | (2006.01) |
| C07D 239/48 | (2006.01) |
| C07D 409/14 | (2006.01) |
| C07D 471/04 | (2006.01) |
| C07D 471/10 | (2006.01) |
| C07D 473/34 | (2006.01) |
| C07D 491/107 | (2006.01) |

(52) U.S. Cl.
CPC ......... *C07D 498/04* (2013.01); *C07D 239/42* (2013.01); *C07D 239/48* (2013.01); *C07D 239/49* (2013.01); *C07D 401/12* (2013.01); *C07D 403/12* (2013.01); *C07D 403/14* (2013.01); *C07D 409/12* (2013.01); *C07D 409/14* (2013.01); *C07D 417/12* (2013.01); *C07D 471/04* (2013.01); *C07D 471/10* (2013.01); *C07D 473/34* (2013.01); *C07D 487/04* (2013.01); *C07D 491/107* (2013.01)

(58) Field of Classification Search
CPC .................................................... C07D 498/04
See application file for complete search history.

(56) References Cited

U.S. PATENT DOCUMENTS

| 5,491,144 | A | 2/1996 | Trinks et al. |
| 8,637,525 | B2 | 1/2014 | Boy et al. |
| 9,382,248 | B2 | 7/2016 | Reich et al. |
| 9,669,031 | B2 | 6/2017 | Reich et al. |
| 2007/0219218 | A1 | 9/2007 | Yu et al. |
| 2010/0105708 | A1 | 4/2010 | Jakel et al. |
| 2015/0038506 | A1 | 2/2015 | Nacro et al. |

FOREIGN PATENT DOCUMENTS

| JP | 2009-173629 A1 | 8/2009 |
| WO | 2005082856 A2 | 9/2005 |

(Continued)

OTHER PUBLICATIONS

Pinedo et al. (2000).*
McMahon et al. (2000).*
Dec. 14, 2016 Written Opinion and International Search Report Issued in International Patent Application No. PCT/US2016/059381.
Aurora Fine Chemicals, Jan. 5, 2014 Chemical Catalog excerpt 1511646-58-4.
Aurora Fine Chemicals, Dec. 29, 2013 Chemical Catalog excerpt 1505663-52-4.

(Continued)

*Primary Examiner* — Paul V Ward
(74) *Attorney, Agent, or Firm* — Mintz, Levin, Cohn, Ferris, Glovsky and Popeo, P.C.

(57) ABSTRACT

The present invention provides synthesis, pharmaceutically acceptable formulations and uses of compounds in accordance with Formula I, or a stereoisomer, tautomer or pharmaceutically acceptable salt thereof.

(I)

For Formula I compounds $A^1$, $A^2$, $A^3$, $A^4$, $A^5$, $W^1$, Y, $R^1$, $R^2$, $R^3$, $R^4$, $R^5$, $R^{6a}$, $R^{6b}$, $R^7$, $R^8$, $R^{8a}$, $R^{8b}$, $R^9$, $R^{9a}$, $R^{9b}$, and $R^{10}$ and subscript "n" are as defined in the specification. The inventive Formula I compounds are inhibitors of Mnk and find utility in any number of therapeutic applications, including but not limited to treatment of inflammation and various cancers.

19 Claims, No Drawings
Specification includes a Sequence Listing.

(56) References Cited

FOREIGN PATENT DOCUMENTS

| | | | |
|---|---|---|---|
| WO | 2006020879 | A1 | 2/2006 |
| WO | 2007021309 | A1 | 2/2007 |
| WO | 2008115369 | A2 | 9/2008 |
| WO | 2008117061 | A2 | 10/2008 |
| WO | 2009112445 | A1 | 9/2009 |
| WO | 2011106168 | A1 | 1/2011 |
| WO | 2011014535 | A1 | 2/2011 |
| WO | 2011017296 | A1 | 2/2011 |
| WO | 2012041987 | A1 | 4/2012 |
| WO | 2012075140 | A1 | 6/2012 |
| WO | 2013000994 | A1 | 1/2013 |
| WO | 2013043192 | A1 | 3/2013 |
| WO | 2013100632 | A1 | 4/2013 |
| WO | 2013147711 | A1 | 10/2013 |
| WO | 2013148748 | A1 | 10/2013 |
| WO | 2013151975 | A1 | 10/2013 |
| WO | 2014044691 | A1 | 3/2014 |
| WO | 2014088519 | A1 | 6/2014 |
| WO | 2014099941 | A1 | 6/2014 |
| WO | 2014128093 | A1 | 8/2014 |
| WO | 2015074986 | A1 | 5/2015 |

OTHER PUBLICATIONS

Aurora Fine Chemicals, Dec. 17, 2013 Chemical Catalog excerpt 1496979-81-7.
Aurora Fine Chemicals, Dec. 1, 2013 Chemical Catalog excerpt 1484631-21-1.
Aurora Fine Chemicals, Nov. 26, 2013 Chemical Catalog excerpt 1481116-61-3.
U.S. Appl. No. 15/611,966, filed Jun. 2, 2017 in the name of eFFECTOR Therapeutics, Inc.
U.S. Appl. No. 15/337,237, filed Oct. 28, 2016 in the name of eFFECTOR Therapeutics, Inc.
U.S. Appl. No. 15/355,271, filed Nov. 18, 2016 in the name of eFFECTOR Therapeutics, Inc.
U.S. Appl. No. 15/130,538, filed Apr. 15, 2016 in the name of eFFECTOR Therapeutics, Inc.
Oyarzabal, Julen et al., "Discovery of Mitogen-Activated Protein Kinase-Interacting Kinase 1 Inhibitors by a Comprehensive Fragment-Oriented Virtual Screening Approach" Journal of Medicinal Chemistry, 2010, vol. 53, No. 18, 6618-6628.
Yu et al., "Discovery of 4-(dihydropyridinon-3-yl)amino-5-methylthieno[2,3-d] pyrimidine derivatives as potent Mnk inhibitors: synthesis, structureeactivity relationship analysis and biological evaluation" European Journal of Medicinal Chemistry, May 5, 2015, vol. 95, 116-126.
Teo et al., "An integrated approach for discovery of highly potent and selective Mnk inhibitors: Screening, synthesis and SAR analysis" European Journal of Medicinal Chemistry, Sep. 2015, vol. 103, 539-550.
Joshi, et al., "Mnk kinase pathway: Cellular functions and biological outcomes", World Journal of Biological Chemistry, 5(3): 321-333, ISSN 1949-8454, Aug. 26, 2014.
U.S. Appl. No. 15/895,523, filed Feb. 13, 2018 in the name of eFFECTOR Therapeutics, Inc.

* cited by examiner

ISOINDOLINE, AZAISOINDOLINE, DIHYDROINDENONE AND DIHYDROAZAINDENONE INHIBITORS OF MNK1 AND MNK2

CROSS-REFERENCE TO RELATED APPLICATIONS

This application claims the benefit of U.S. Provisional Patent Application No. 62/247,953, filed Oct. 29, 2015, which is incorporated herein by reference in its entirety.

INCORPORATION BY REFERENCE OF SEQUENCE LISTING

This application contains references to an amino acid sequence that has been filed herewith on Nov. 15, 2016 as a sequence listing text file. The aforementioned sequence listing is hereby incorporated by reference in its entirety pursuant to 37 C.F.R. § 1.52(e)(5).

FIELD

The present invention generally relates to compounds having activity as inhibitors of MAP kinase-interacting kinase (Mnk), for example Mnk1 and Mnk2, as well as to related compositions and methods for utilizing the inventive compounds as therapeutic agents for treatment of Mnk dependent diseases, including the treatment of cancer.

BACKGROUND

Eukaryotic initiation factor 4E (eIF4E) is a general translation factor but it has the potential to enhance preferentially the translation of messenger RNAs (mRNAs) that lead to production of malignancy-associated proteins. This selectivity may relate to an increased requirement for eIF4E and its binding partners for the translation of mRNAs containing extensive secondary structure in their 5'-untranslated regions (5'-UTRs). These mRNAs include those encoding certain proteins that control cell cycle progression and tumorigenesis. Under normal cellular conditions the translation of these malignancy-associated mRNAs is suppressed as the availability of active eIF4E is limited; however, their levels can increase when eIF4E is over-expressed or hyperactivated. Elevated levels of eIF4E have been found in many types of tumors and cancer cell lines including cancers of the colon, breast, bladder, lung, prostate, gastrointestinal tract, head and neck, Hodgkin's lymphomas and neuroblastomas.

Initiation of cap-dependent translation is thought to depend on the assembly of eIF4F, an initiation factor complex including eIF4E, the scaffold protein eIF4G, and the RNA helicase eIF4A. Because eIF4E is the only one of these proteins that binds directly to the mRNA cap structure, it is the key factor for the assembly of eIF4F at the 5' cap. The scaffold protein, eIF4G, also recruits the 40S ribosomal subunit to the mRNA via its interaction with eIF3 and binds eIF4B, a protein that aids the RNA-helicase function of eIF4A, thus facilitating the translation of mRNAs that contain structured 5'-UTRs. The availability of eIF4E as part of the eIF4F complex is a limiting factor in controlling the rate of translation and therefore eIF4E is an important regulator of mRNA translation.

Regulation of eIF4E activity forms a node of convergence of the PI3K/Akt/mTOR and Ras/Raf/MAPK signaling pathways. The PI3K (phosphoinositide 3-kinase)/PTEN (phosphatase and tensin homologue deleted on chromosome ten)/Akt/mTOR (mammalian target of rapamycin) pathway is often involved in tumorgenesis and in sensitivity and resistance to cancer therapy. Deregulated signaling through the PI3K/PTEN/Akt/mTOR pathway is often the result of genetic alterations in critical components of this pathway and/or mutations at upstream growth factor receptors or signaling components. PI3K initiates a cascade of events when activated by, for example, extracellular growth factors, mitogens, cytokines and/or receptors, PDK1 activates Akt, which in turn phosphorylates and inactivates the tumor suppressor complex comprising TSC1 and 2 (tuberous sclerosis complex 1/2), resulting in the activation of mTORC1 (target of rapamycin complex 1) by Rheb-GTP. Activation of PDK1 and Akt by PI3Ks is negatively regulated by PTEN.

PTEN is a critical tumor suppressor gene and is often mutated or silenced in human cancers. Its loss results in activation of Akt and increases downstream mTORC1 signaling. The involvement of mTOR complex 1 (mTORC1) in neoplastic transformation appears to depend on its regulatory role toward the eIF4F complex; overexpression of eIF4E can confer resistance to rapamycin. mTORC1 regulates the eIF4F complex assembly that is critical for the translation of mRNAs associated with cell growth, prevention of apoptosis and transformation. mTORC1 achieves this by phosphorylation and inactivation of 4E-BPs and the subsequent dissociation of 4E-BPs from eIF4E. This then enables eIF4E to interact with the scaffold protein eIF4G, permitting assembly of the eIF4F complex for the translation of structured mRNAs. mTORC1 also promotes activation of the translational activator, S6K, which phosphorylates the ribosomal protein S6 and other substrates, including eIF4B. mTORC1 signaling is inhibited by rapamycin and its analogues (rapalogs), although these compounds act allosterically, rather than directly inhibiting mTOR kinase activity.

Given the importance of the PI3K/Akt/mTOR pathway in regulating mRNA translation of genes that encode for pro-oncogenic proteins and activated mTORC1 signaling in a high proportion of cancers, these kinases have been actively pursued as oncology drug targets. A number of pharmacological inhibitors have been identified, some of which have reached advanced clinical stages. However, it has recently become clear that the mTOR pathway participates in a complicated feedback loop that can impair activation of Akt. It has been shown that prolonged treatment of cancer cells or patients with mTOR inhibitors causes elevated PI3K activity that leads to phosphorylation of Akt and eIF4E, and promotes cancer cell survival. eIF4E, acting downstream of Akt and mTOR, recapitulates Akt's action in tumorigenesis and drug resistance, and Akt signaling via eIF4E is an important mechanism of oncogenesis and drug resistance in vivo.

In addition to the PI3K/Akt/mTOR pathway, eIF4E is also the target of the Ras/Raf/MAP signaling cascade which is activated by growth factors and for the stress-activated p38 MAP kinase pathway. Erk1/2 and p38 then phosphorylate MAP kinase-interacting kinase 1 (Mnk1) and MAP kinase-interacting kinase 2 (Mnk2). The Erk pathway is also activated in many cancers, reflecting, for example, activating mutations in Ras (found in around 20% of tumors) or loss of function of the Ras GTPase-activator protein NF1. Mnk1 and Mnk2 are threonine/serine protein kinases and specifically phosphorylate serine 209 (Ser209) of eIF4E within the eIF4F complex, by virtue of the interaction between eIF4E and the Mnks, which serves to recruit Mnks to act on eIF4E. Mice with mutated eIF4E, in which Ser209 is replaced by alanine, shows no eIF4E phosphorylation and significantly attenuated tumor growth. Significantly, while Mnk activity is necessary for eIF4E-mediated oncogenic transformation, it is dispensable for normal development. Pharmacologically inhibiting Mnks thus presents an attractive therapeutic strategy for cancer.

Despite increased understanding of Mnk structure and function, little progress has been made with regard to the discovery of pharmacological Mnk inhibitors and relatively few Mnk inhibitors have been reported: CGP052088 (Tschopp et al., *Mol Cell Biol Res Commun.* 3(4):205-211, 2000); CGP57380 (Rowlett et al., *Am J Physiol Gastrointest Liver Physiol.* 294(2):G452-459, 2008); and Cercosporamide (Konicek et al., *Cancer Res.* 71(5):1849-1857, 2011). These compounds, however, have mainly been used for the purpose of Mnk target validation. More recently, investigators have proposed further compounds for treating diseases influenced by the inhibition of kinase activity of Mnk1 and/or Mnk2, including, for example, the compounds disclosed in WO 2014/044691 and the various patent documents cited therein and the 4-(dihydropyridinon-3-yl) amino-5-methylthieno[2,3,-d]pyrimidines disclosed by Yu et al., *European Journal of Med. Chem.*, 95: 116-126, 2015).

Accordingly, while advances have been made in this field there remains a significant need in the art for compounds that specifically inhibit Mnk kinase activity, particularly with regard to Mnk's role in regulation of cancer pathways, as well as for associated composition and methods. The present invention fulfills this need and provides further related advantages.

SUMMARY

The present invention is directed to compounds that inhibit or modulate the activity of Mnk, as well as stereoisomers, tautomers and pharmaceutically acceptable salts of such compounds. The present invention also is directed to pharmaceutically acceptable compositions containing such compounds and associated methods for treating conditions that would benefit from Mnk inhibition, such as cancer.

In one embodiment the invention is directed to compounds according to Formula I as well as to a stereoisomer, tautomer or pharmaceutically acceptable salt of such compounds, wherein

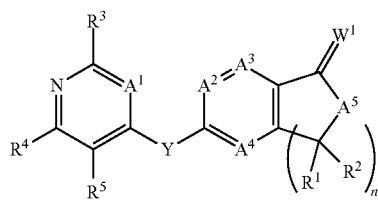

I $A^1$ and $A^2$ independently are —N— or —$CR^{6a}$;
$A^3$ is —N— or —$CR^7$;
$A^4$ is —N— or —$CR^{6b}$;
$A^5$ is —$NR^8$ or —$CR^{8a}R^{8b}$;
$W^1$ is O, S, NH, NO($R^9$) or $CR^{9a}R^{9b}$;
Y is —O—, —S—, —C(O)—, —$NR^{10}$, —S=O, —$S(O)_2$—, —$CH_2$— or —CH(OH);
n is 1, 2 or 3;
$R^1$ and $R^2$ independently are —H, —$NHR^{10}$, $NHR^{10}$-alkylene, ($C_1$-$C_8$)alkyl, ($C_2$-$C_8$)alkenyl, ($C_2$-$C_8$)alkynyl, cycloalkyl, heterocyclyl, heteroaryl, aryl, arylalkylene, cycloalkylalkylene, heterocyclylalkylene, or heteroarylalkylene, such that at least one of $R^1$ or $R^2$ is not —H; or $R^1$ and $R^2$ together with the carbon atom to which they are attached form a cycloalkyl or heterocyclyl ring;

$R^3$, $R^4$, $R^5$ and $R^{6b}$ independently are —H, —OH, —CN, —$SR^{10}$, halogen, —$S(O)_2(C_1$-$C_8)$ alkyl, —C(O)$NHR^{10}$, —C(O)$NR^{10}R^{10}$, —$NHR^{10}$, —$NR^{10}R^{10}$, $NHR^{10}$-alkylene, $NR^{10}R^{10}$-alkylene, ($C_1$-$C_8$)alkyl, ($C_2$-$C_8$)alkenyl, ($C_2$-$C_8$) alkynyl, ($C_1$-$C_8$)haloalkyl, —O($C_1$-$C_8$)alkyl, —O($C_1$-$C_8$) haloalkyl, —O($C_1$-$C_8$)alkylene$NHR^{10}$, —O($C_1$-$C_8$) alkylene$NR^{10}R^{10}$, cycloalkyl, heterocyclyl, heteroaryl, aryl, arylalkylene, cycloalkylalkylene, heterocyclylalkylene, heteroarylalkylene, alkylaminyl, alkylcarbonylaminyl, cycloalkylcarbonylaminyl, cycloalkylaminyl, or heterocyclylaminyl; or $R^4$ and $R^5$ together with the respective carbon atoms to which they are attached form a fused aryl, cycloalkyl, heterocyclyl or heteroaryl ring;

$R^{6a}$ is —H, —OH, halogen, —CN, acetyl, —($C_1$-$C_8$) alkyl, —S($C_1$-$C_8$)alkyl, —($C_2$-$C_8$)alkenyl, —($C_2$-$C_8$)alkynyl, —O($C_1$-$C_8$)alkyl, —($C_1$-$C_8$)haloalkyl, —$NHR^{10}$, —$NR^{10}R^{10}$, $NHR^{10}$-alkylene, $NR^{10}R^{10}$-alkylene or —O($C_1$-$C_8$)haloalkyl;

$R^7$ is —H, —OH, —SH, —CN, —$S(O)_2R^{10}$, halogen, —$S(C_1$-$C_8)$alkyl, —$NHR^{10}$, —$NR^{10}R^{10}$, ($C_1$-$C_8$)alkyl, ($C_2$-$C_8$)alkenyl, ($C_2$-$C_8$)alkynyl, ($C_1$-$C_8$)haloalkyl, —O($C_1$-$C_8$) haloalkyl, —O($C_1$-$C_8$)alkyl, —O($C_1$-$C_8$)alkylene$NHR^{10}$, —O($C_1$-$C_8$)alkylene$NR^{10}R^{10}$, —($C_1$-$C_8$)alkylene$NHR^{10}$, —($C_1$-$C_8$)alkylene$NR^{10}R^{10}$, —S($C_1$-$C_8$)alkyl, cycloalkyl, heterocyclyl, heteroaryl or aryl;

$R^8$ is —H, —OH, acetyl, —($C_1$-$C_8$)alkyl, —C(O)alkyl, —C(O)cycloalkyl, —C(O)O—($C_1$-$C_8$)alkyl, cycloalkyl, aryl, heteroaryl or heterocyclyl;

$R^{8a}$ and $R^{8b}$ independently are —H, —OH, acetyl, —($C_1$-$C_8$)alkyl, —O($C_1$-$C_8$)alkyl, —C(O)alkyl, —C(O)cycloalkyl, —C(O)O—($C_1$-$C_8$)alkyl, cycloalkyl, aryl, heteroaryl or heterocyclyl;

$R^9$, $R^{9a}$ and $R^{9b}$ are independently —H, ($C_1$-$C_8$)alkyl, ($C_2$-$C_8$)alkenyl, ($C_2$-$C_8$)alkynyl, cycloalkyl, heterocyclyl, heteroaryl, aryl, arylalkylene, cycloalkylalkylene, heterocyclylalkylene, or heteroarylalkylene; or $R^{9a}$ and $R^{9b}$ together with the carbon atom to which they are attached form a cycloalkyl or heterocyclyl ring;

$R^{10}$ is —H, —OH, —C(O)O($C_1$-$C_8$)alkyl, —C(O)($C_1$-$C_8$)alkyl, —C(O)—$NH_2$, —C(O)—NH($C_1$-$C_8$)alkyl, $NH_2$—C(O)-alkylene, —S($C_1$-$C_8$)alkyl, acetyl, —($C_1$-$C_8$) alkyl, ($C_2$-$C_8$)alkenyl, ($C_2$-$C_8$)alkynyl, —O($C_1$-$C_8$)alkyl, —($C_1$-$C_8$) haloalkyl, alkylcarbonylaminyl, alkylaminyl, —C(O)alkyl, —C(O)cycloalkyl, —C(O)O—($C_1$-$C_8$)alkyl, aryl, heteroaryl, heterocyclyl or cycloalkyl;

wherein any alkyl, cycloalkyl, heterocyclyl, heteroaryl, aryl, arylalkylene, cycloalkylalkylene, heterocyclylalkylene, heteroarylalkylene, alkylaminyl, alkylcarbonylaminyl, cycloalkylcarbonylaminyl, cycloalkylaminyl, or heterocyclylaminyl is optionally substituted with 1, 2 or 3 groups selected from —OH, —CN, —SH, —$S(O)NH_2$, —$S(O) NH_2$, halogen, —$NH_2$, —NH($C_1$-$C_4$)alkyl, —N[($C_1$-$C_4$) alkyl]$_2$, —C(O)$NH_2$, —COOH, —COOMe, acetyl, —($C_1$-$C_8$)alkyl, —O($C_1$-$C_8$)alkyl ($C_2$-$C_8$)alkenyl, ($C_2$-$C_8$)alkynyl, haloalkyl, thioalkyl, cyanomethylene, alkylaminyl, $NH_2$— C(O)-alkylene, $NH_2$—C(O)-alkylene, —NH(Me)-C(O)- alkylene, —$CH_2$—C(O)-lower alkyl, —C(O)-lower alkyl, alkylcarbonylaminyl, cycloalkyl, cycloalkylalkylene, cycloalkylalkenylene, cycloalkylcarbonylaminyl, cycloalkylaminyl, —$CH_2$—C(O)-cycloalkyl, —C(O)-cycloalkyl, —$CH_2$—C(O)-aryl, —$CH_2$-aryl, —C(O)-aryl, —$CH_2$—C(O)-heterocycloalkyl, —C(O)-heterocycloalkyl, heterocyclylaminyl or heterocyclyl.

The present invention also provides a pharmaceutical composition comprising (i) a therapeutically effective amount of at least one compound according to Formula I or a stereoisomer, a tautomer or a pharmaceutically acceptable salt thereof; (ii) in combination with a pharmaceutically acceptable carrier, diluent or excipient.

Also provided by the present invention is a method for attenuating or inhibiting the activity of MnK in at least one cell overexpressing Mnk, comprising contacting the at least one cell with a compound according to claim 1 or a stereoisomer, tautomer or pharmaceutically acceptable salt thereof.

According to the inventive method at least one cell is a colon cancer cell, a gastric cancer cell, a thyroid cancer cell, a lung cancer cell, a leukemia cell, a B-cell lymphoma, a T-cell lymphoma, a hairy cell lymphoma, Hodgkin's lymphoma cell, non-Hodgkin's lymphoma cell, Burkitt's lymphoma cell, a pancreatic cancer cell, a melanoma cell, a multiple melanoma cell, a brain cancer cell, a CNS cancer cell, a renal cancer cell, a prostate cancer cell, an ovarian cancer cell, or a breast cancer cell.

According to yet another embodiment the invention provides a method for treating a Mnk dependent condition in a mammal in need thereof, comprising administering to the mammal (i) a therapeutically effective amount of at least one compound according to claim 1 or a stereoisomer, tautomer or pharmaceutically acceptable salt thereof, or (ii) a pharmaceutical composition in accordance with the invention.

Compounds and pharmaceutically acceptable formulations in accordance with the invention are useful for treating an Mnk dependent condition such as colon cancer, gastric cancer, thyroid cancer, lung cancer, leukemia, B-cell lymphoma, T-cell lymphoma, hairy cell lymphoma, Hodgkin's lymphoma, non-Hodgkin's lymphoma, Burkitt's lymphoma, pancreatic cancer, melanoma, multiple melanoma, brain cancer, CNS cancer, renal cancer, prostate cancer, ovarian cancer or breast cancer.

The above embodiments and other aspects of the invention are readily apparent in the detailed description that follows. To this end, various references are set forth herein which describe in more detail certain background information, procedures, compounds and/or compositions, and are each hereby incorporated by reference in their entirety.

DETAILED DESCRIPTION

In the following description certain specific details are set forth in order to provide a thorough understanding of various embodiments of the invention. However, one skilled in the art will understand that the invention may be practiced without these details. Unless the context requires otherwise, throughout the present specification and claims, the word "comprise" and variations thereof, such as, "comprises" and "comprising" are to be construed in an open, inclusive sense (i.e., as "including, but not limited to").

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment.

Furthermore, the particular features, structures, or characteristics may be combined in any suitable manner in one or more embodiments.

Definitions

As used herein, and unless noted to the contrary, the following terms and phrases have the meaning noted below.

"Amino" refers to the —$NH_2$ substituent.

"Aminocarbonyl" refers to the —$C(O)NH_2$ substituent.

"Carboxyl" refers to the —$CO_2H$ substituent.

"Carbonyl" refers to a —C(O)— or —C(=O)— group. Both notations are used interchangeably within the specification.

"Cyano" refers to the —C≡N substituent.

"Cyanoalkylene" refers to the -(alkylene)C≡N substituent.

"Acetyl" refers to the —$C(O)CH_3$ substituent.

"Hydroxy" or "hydroxyl" refers to the —OH substituent.

"Hydroxyalkylene" refers to the -(alkylene)OH substituent.

"Oxo" refers to a =O substituent.

"Thio" or "thiol" refer to a —SH substituent.

"Alkyl" refers to a saturated, straight or branched hydrocarbon chain radical consisting solely of carbon and hydrogen atoms, having from one to twelve carbon atoms ($C_1$-$C_{12}$ alkyl), from one to eight carbon atoms ($C_1$-$C_8$ alkyl) or from one to six carbon atoms ($C_1$-$C_6$ alkyl), and which is attached to the rest of the molecule by a single bond. Exemplary alkyl groups include methyl, ethyl, n-propyl, 1-methylethyl (isopropyl), n-butyl, n-pentyl, 1,1-dimethylethyl (t-butyl), 3-methylhexyl, 2-methylhexyl, and the like.

"Lower alkyl" has the same meaning as alkyl defined above but having from one to four carbon atoms ($C_1$-$C_4$ alkyl).

"Alkenyl" refers to an unsaturated alkyl group having at least one double bond and from two to twelve carbon atoms ($C_2$-$C_{12}$ alkenyl), from two to eight carbon atoms ($C_2$-$C_8$ alkenyl) or from two to six carbon atoms ($C_2$-$C_6$ alkenyl), and which is attached to the rest of the molecule by a single bond, e.g., ethenyl, propenyl, butenyl, pentenyl, hexenyl, and the like.

"Alkynyl" refers to an unsaturated alkyl group having at least one triple bond and from two to twelve carbon atoms ($C_2$-$C_{12}$ alkynyl), from two to ten carbon atoms ($C_2$-$C_{10}$ alkynyl) from two to eight carbon atoms ($C_2$-$C_8$ alkynyl) or from two to six carbon atoms ($C_2$-$C_6$ alkynyl), and which is attached to the rest of the molecule by a single bond, e.g., ethynyl, propynyl, butynyl, pentynyl, hexynyl, and the like.

"Alkylene" or "alkylene chain" refers to a straight or branched divalent hydrocarbon (alkyl) chain linking the rest of the molecule to a radical group, consisting solely of carbon and hydrogen, respectively. Alkylenes can have from one to twelve carbon atoms, e.g., methylene, ethylene, propylene, n-butylene, and the like. The alkylene chain is attached to the rest of the molecule through a single or double bond. The points of attachment of the alkylene chain to the rest of the molecule can be through one carbon or any two carbons within the chain. "Optionally substituted alkylene" refers to alkylene or substituted alkylene.

"Alkenylene" refers to divalent alkene. Examples of alkenylene include without limitation, ethenylene (—CH=CH—) and all stereoisomeric and conformational isomeric forms thereof. "Substituted alkenylene" refers to divalent substituted alkene. "Optionally substituted alkenylene" refers to alkenylene or substituted alkenylene.

"Alkynylene" refers to divalent alkyne. Examples of alkynylene include without limitation, ethynylene, propynylene. "Substituted alkynylene" refers to divalent substituted alkyne.

"Alkoxy" refers to a radical of the formula —OR$_a$ where R$_a$ is an alkyl having the indicated number of carbon atoms as defined above. Examples of alkoxy groups include without limitation —O-methyl (methoxy), —O-ethyl (ethoxy), —O-propyl (propoxy), —O-isopropyl (iso propoxy) and the like.

"Alkylaminyl" refers to a radical of the formula —NHR$_a$ or —NR$_a$R$_a$ where each R$_a$ is, independently, an alkyl radical having the indicated number of carbon atoms as defined above.

"Cycloalkylaminyl" refers to a radical of the formula —NHR$_a$ where R$_a$ is a cycloalkyl radical as defined herein.

"Alkylcarbonylaminyl" refers to a radical of the formula —NHC(O)R$_a$, where R$_a$ is an alkyl radical having the indicated number of carbon atoms as defined herein.

"Cycloalkylcarbonylaminyl" refers to a radical of the formula —NHC(O)R$_a$, where R$_a$ is a cycloalkyl radical as defined herein.

"Alkylaminocarbonyl" refers to a radical of the formula —C(O)NHR$_a$ or —C(O)NR$_a$R$_a$, where each R$_a$ is independently, an alkyl radical having the indicated number of carbon atoms as defined herein.

"Cyclolkylaminocarbonyl" refers to a radical of the formula —C(O)NHR$_a$, where R$_a$ is a cycloalkyl radical as defined herein.

"Aryl" refers to a hydrocarbon ring system radical comprising hydrogen, 6 to 18 carbon atoms and at least one aromatic ring. Exemplary aryls are hydrocarbon ring system radical comprising hydrogen and 6 to 9 carbon atoms and at least one aromatic ring; hydrocarbon ring system radical comprising hydrogen and 9 to 12 carbon atoms and at least one aromatic ring; hydrocarbon ring system radical comprising hydrogen and 12 to 15 carbon atoms and at least one aromatic ring; or hydrocarbon ring system radical comprising hydrogen and 15 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. "Optionally substituted aryl" refers to an aryl group or a substituted aryl group.

"Arylene" denotes divalent aryl, and "substituted arylene" refers to divalent substituted aryl.

"Aralkyl" or "araalkylene" may be used interchangeably and refer to a radical of the formula —R$_b$—R$_c$ where R$_b$ is an alkylene chain as defined herein and R$_c$ is one or more aryl radicals as defined herein, for example, benzyl, diphenylmethyl and the like.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, three to nine carbon atoms, three to eight carbon atoms, three to seven carbon atoms, three to six carbon atoms, three to five carbon atoms, a ring with four carbon atoms, or a ring with three carbon atoms. The cycloalkyl ring may be saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like.

"Cycloalkylalkylene" or "cycloalkylalkyl" may be used interchangeably and refer to a radical of the formula —R$_b$R$_e$ where R$_b$ is an alkylene chain as defined herein and R$_e$ is a cycloalkyl radical as defined herein. In certain embodiments, R$_b$ is further substituted with a cycloalkyl group, such that the cycloalkylalkylene comprises two cycloalkyl moieties. Cyclopropylalkylene and cyclobutylalkylene are exemplary cycloalkylalkylene groups, comprising at least one cyclopropyl or at least one cyclobutyl group, respectively.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo (bromine), chloro (chlorine), fluoro (fluorine), or iodo (iodine).

"Haloalkyl" refers to an alkyl radical having the indicated number of carbon atoms, as defined herein, wherein one or more hydrogen atoms of the alkyl group are substituted with a halogen (halo radicals), as defined above. The halogen atoms can be the same or different. Exemplary haloalkyls are trifluoromethyl, difluoromethyl, trichloromethyl, 2,2,2-trifluoroethyl, 1,2-difluoroethyl, 3-bromo-2-fluoropropyl, 1,2-dibromoethyl, and the like.

"Heterocyclyl", "heterocycle", or "heterocyclic ring" refers to a stable 3- to 18-membered saturated or unsaturated radical which consists of two to twelve carbon atoms and from one to six heteroatoms, for example, one to five heteroatoms, one to four heteroatoms, one to three heteroatoms, or one to two heteroatoms selected from the group consisting of nitrogen, oxygen and sulfur. Exemplary heterocycles include without limitation stable 3-15 membered saturated or unsaturated radicals, stable 3-12 membered saturated or unsaturated radicals, stable 3-9 membered saturated or unsaturated radicals, stable 8-membered saturated or unsaturated radicals, stable 7-membered saturated or unsaturated radicals, stable 6-membered saturated or unsaturated radicals, or stable 5-membered saturated or unsaturated radicals.

Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of non-aromatic heterocyclyl radicals include, but are not limited to, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, thietanyl, trithianyl, tetrahydropyranyl, thiomorpholinyl, thiamorpholinyl, 1-oxo-thiomorpholinyl, and 1,1-dioxo-thiomorpholinyl. Heterocyclyls include heteroaryls as defined herein, and examples of aromatic heterocyclyls are listed in the definition of heteroaryls below.

"Heterocyclylalkyl" or "heterocyclylalkylene" refers to a radical of the formula —R$_b$R$_f$ where R$_b$ is an alkylene chain as defined herein and R$_f$ is a heterocyclyl radical as defined above, and if the heterocyclyl is a nitrogen-containing heterocyclyl, the heterocyclyl may be attached to the alkyl radical at the nitrogen atom.

"Heteroaryl" or "heteroarylene" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a stable 5-12 membered ring, a stable 5-10 membered ring, a stable 5-9 membered ring, a stable 5-8 membered ring, a stable 5-7 membered ring, or a stable 6 membered ring that comprises at least 1 heteroatom, at least 2 heteroatoms, at least 3 heteroatoms, at least 4 heteroatoms, at least 5 heteroatoms or at least 6 heteroatoms. Heteroaryls may be a monocyclic, bicyclic, tricyclic or tetracyclic ring system, which may include fused or bridged ring systems; and the nitrogen, 2 carbon or sulfur atoms in the heteroaryl radical may be optionally oxidized; the nitrogen atom may be optionally quaternized. The heteroatom may be a member of an aromatic or non-aromatic ring, provided at least one ring in the heteroaryl is aromatic. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e. thienyl).

"Heteroarylalkyl" or "heteroarylalkylene" refers to a radical of the formula —$R_bR_g$ where $R_b$ is an alkylene chain as defined above and $R_g$ is a heteroaryl radical as defined above.

"Thioalkyl" refers to a radical of the formula —$SR_a$ where $R_a$ is an alkyl radical as defined above containing one to twelve carbon atoms, at least 1-10 carbon atoms, at least 1-8 carbon atoms, at least 1-6 carbon atoms, or at least 1-4 carbon atoms.

"Heterocyclylaminyl" refers to a radical of the formula —$NHR_f$ where $R_f$ is a heterocyclyl radical as defined above.

"Thione" refers to a =S group attached to a carbon atom of a saturated or unsaturated ($C_3$-$C_8$)cyclic or a ($C_1$-$C_8$) acyclic moiety.

"Sulfoxide" refers to a —S(O)— group in which the sulfur atom is covalently attached to two carbon atoms.

"Sulfone" refers to a —$S(O)_2$— group in which a hexavalent sulfur is attached to each of the two oxygen atoms through double bonds and is further attached to two carbon atoms through single covalent bonds.

The term "oxime" refers to a —$C(R_a)$=N—$OR_a$ radical where $R_a$ is hydrogen, lower alkyl, an alkylene or arylene group as defined above.

The compound of the invention can exist in various isomeric forms, as well as in one or more tautomeric forms, including both single tautomers and mixtures of tautomers. The term "isomer" is intended to encompass all isomeric forms of a compound of this invention, including tautomeric forms of the compound.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

In this description, a "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosaliculate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease. In the context of the present invention the terms "treat", "treating" and "treatment" also refer to:
(i) preventing the disease or condition from occurring in a mammal, in particular, when such mammal is predisposed to the condition but has not yet been diagnosed as having it;
(ii) inhibiting the disease or condition, i.e., arresting its development;
(iii) relieving the disease or condition, i.e., causing regression of the disease or condition; or
(iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The terms "modulate", "modulation" and the like refer to the ability of a compound to increase or decrease the function, or activity of, for example, MAP kinase interacting kinase (Mnk). "Modulation", in its various forms, is intended to encompass inhibition, antagonism, partial antagonism, activation, agonism and/or partial agonism of the activity associated with Mnk. Mnk inhibitors are compounds that bind to, partially or totally block stimulation, decrease, prevent, delay activation, inactivate, desensitize, or down regulate signal transduction. The ability of a compound to modulate Mnk activity can be demonstrated in an enzymatic assay or a cell-based assay.

A "patient" or subject" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug, a compound which upon administration to a patient, must undergo chemical conversion by metabolic processes before becoming an active pharmacological agent. Exemplary prodrugs of compounds in accordance with Formula I are esters, acetamides, and amides.

Compounds of the Invention

The present invention generally is directed to compounds encompassed by the genus of Formula I, a stereoisomer, a tautomer or a pharmaceutically acceptable salt thereof.

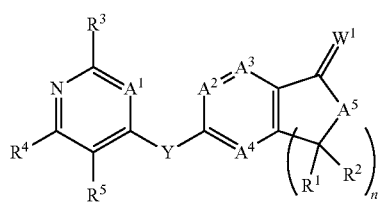

I

For Formula I compounds $A^1$, $A^2$, $A^3$, $A^4$, $A^5$, $W^1$, Y, $R^1$, $R^2$, $R^3$, $R^4$, $R^5$, $R^{6a}$, $R^{6b}$, $R^7$, $R^8$, $R^{8a}$, $R^{8b}$, $R^9$, $R^{9a}$, $R^{9b}$, and $R^{10}$ and subscript "n" are as defined in the specification. Also described below are specific embodiments of Formula I compounds.

In one embodiment $A^1$ and $A^2$ are —$CR^{6a}$.

In another embodiment $A^1$ is —N and $A^2$ is —CH or —C(Me). In yet another embodiment $A^1$ is —CH and $A^2$ is —N.

In one embodiment $A^3$ is —$CR^7$.

In one embodiment $A^4$ is —$CR^{6b}$.

In one embodiment $A^5$ is —$NR^8$. In another embodiment $A^5$ is —NH or —N(alkyl).

In one embodiment $A^5$ is —$CR^{8a}R^{8b}$. In another embodiment $A^5$ is —$CH_2$.

In one embodiment Y is —NH or —N(Me). In another embodiment Y is —NH.

In one embodiment $W^1$ is O.

In one embodiment subscript "n" is 1 or 2. In another embodiment subscript "n" is 1.

In one embodiment at least one of $R^1$ and $R^2$ independently are ($C_1$-$C_8$)alkyl, —$NHR^{10}$ or —$NHR^{10}$-alkylene.

In one embodiment at least one of $R^1$ or $R^2$ is ($C_1$-$C_8$)alkyl. In another embodiment at least one of $R^1$ or $R^2$ is methyl, ethyl, propyl, isopropyl, butyl, sec-butyl, t-butyl, isobutyl, pentyl or hexyl.

In one embodiment at least one of $R^1$ or $R^2$ is a halogen substituted ($C_1$-$C_8$)alkyl, ($C_2$-$C_8$)alkenyl, ($C_2$-$C_8$)alkynyl, cycloalkyl, heterocyclyl, heteroaryl, aryl, arylalkylene, cycloalkylalkylene, heterocyclylalkylene or heteroarylalkylene.

In one embodiment at least one of $R^1$ or $R^2$ is $NH_2$ or —$NH_2$-alkylene. In another embodiment at least one of $R^1$ or $R^2$ is an aminomethylene.

In one embodiment at least one of $R^1$ or $R^2$ is an optionally substituted heteroaryl. In another one embodiment the heteroaryl is a thiophene.

In one embodiment $R^1$ and $R^2$ together with the respective carbon atom to which they are attached form a fused cycloalkyl ring. In another embodiment the cycloalkyl is cyclobutyl, cyclopentyl, cyclohexyl, 2,2-dimethylcyclobutyl, 4-aminocyclohexyl, 4-methylcyclohexyl, 4-ethylcyclohexyl, 2,2-difluoroethyl-4-cyclohexyl, 4,4-difluorocyclohexy, 4-cyanocyclohexyl, 4-trifluoromethylcyclohexyl, 4-hydroxycyclohexyl, 3-hydroxycyclopently, 3-aminocyclopentyl or 3-methylcyclopentyl ring systems. In yet another embodiment the cycloalkyl is cyclobutyl, cyclopentyl or cyclohexyl.

In one embodiment $R^1$ and $R^2$ together with the respective carbon atom to which they are attached form a fused heterocyclyl. In another embodiment the heterocyclyl is piperidine, 1-(2,2-difluorethylpiperidine), N-methylpiperidine, tetrahydropyran or pyrrolidine.

In one embodiment $R^3$ is —H, alkyl, halogen or —$NHR^{10}$. In another embodiment $R^3$ is methyl, ethyl, —$NH_2$, Cl or F. In yet another embodiment $R^3$ is —H.

In one embodiment $R^4$ is —H, halogen, —$NHR^{10}$, —SMe or alkyl. In another embodiment $R^4$ is methyl, ethyl or propyl. In another embodiment $R^4$ is —$NH_2$, —NHC(O) cyclopropyl, —NHC(O)$CH_3$, —NHC(O)—C(Me)$_3$, —NH (Me) or —NH(1-methylpyrazole). In yet another embodiment $R^4$ is —H or —$NH_2$.

In one embodiment $R^5$ is —H, —OH, halogen or —($C_1$-$C_8$)alkyl. In another embodiment $R^5$ is methyl, ethyl, propyl or butyl.

In one embodiment $R^5$ is —O($C_1$-$C_8$)alkyleneNHR$^{10}$ or —C(O)NH$_2$. In another embodiment $R^5$ is —O(CH$_2$)$_2$NH$_2$ or —O(CH$_2$)$_3$NH$_2$.

In one embodiment $R^5$ is —O($C_1$-$C_8$)alkyl. In another embodiment $R^5$ is —O(Me) or —O(Et).

In one embodiment $R^5$ is —O($C_1$-$C_8$)haloalkyl. In another embodiment $R^5$ is —O(CHF$_2$) or —O(CF$_3$).

In one embodiment $R^3$, $R^4$ and $R^5$ are —H. In another embodiment $R^3$ is —H and $R^4$ and $R^5$ independently are —CN, chlorine, fluorine, methyl, ethyl, difluoromethyl, trifluoromethyl, methoxy, —NHR$^{10}$ or —O($C_1$-$C_8$)alkyl-NHR$^{10}$.

In one embodiment $R^4$ and $R^5$ together with the carbon atom to which they are attached form a heteroaryl or heterocyclyl. In another embodiment $R^4$ and $R^5$ together with the carbon atom to which they are attached form a thiazole, thiophene, pyrazole, N-methylpyrazole, pyrrole, pyrrole-2-one or imidazole. In yet another embodiment $R^4$ and $R^5$ together with the carbon atom to which they are attached form morpholine, pyrrolidine or pyrrolidin-2-one.

In one embodiment $R^{6a}$ is —H, —OH, halogen, —CN, acetyl or —($C_1$-$C_8$)alkyl. In another embodiment $R^{6a}$ is methyl, ethyl, propyl or butyl. In yet another embodiment $R^{6a}$ is —H.

In one embodiment $R^{6b}$ is —H, —OH, —CN, —Cl, —F or —($C_1$-$C_8$)alkyl. In another embodiment $R^{6b}$ is methyl, ethyl or propyl. In yet another embodiment $R^{6b}$ is —H.

In one embodiment $R^{6b}$ is NH$_2$—($C_1$-$C_8$)alkylene. In another embodiment $R^{6b}$ is —NH$_2$-methylene or —NH$_2$-ethylene.

In one embodiment $R^{6b}$ is —O($C_1$-$C_8$)alkyl or —($C_1$-$C_8$)haloalkyl. In another embodiment $R^{6b}$ is —OMe and —OEt. In yet another embodiment $R^{6b}$ is —CHF$_2$, —CH$_2$Cl or —CF$_3$.

In one embodiment $R^{6b}$ is —C(O)($C_1$-$C_8$)alkyl. In another embodiment $R^{6b}$ is —C(O)methyl or —C(O)ethyl.

In one embodiment $R^7$ is —H, —OH, —SH, —CN, -halogen or —NHR$^{10}$.

In one embodiment $R^7$ is methyl or ethyl.

In one embodiment $R^7$ is a —($C_1$-$C_8$)haloalkyl. In one embodiment $R^7$ is —CHF$_2$ or —CF$_3$.

In one embodiment $R^7$ is —O($C_1$-$C_8$)alkyl. In another embodiment $R^7$ is —OMe or —OEt.

In one embodiment $R^8$, $R^{8a}$ and $R^{8b}$ are hydrogen.

In one embodiment $R^9$, $R^{9a}$ and $R^{9b}$ are independently —H or —($C_1$-$C_8$)alkyl.

In one embodiment $R^{10}$ is —H, —OH, methyl, ethyl, propyl, butyl, t-butyl, acetyl, —COOMe, —NH$_2$, —NH(Me) or —N(Me)$_2$. In another embodiment $R^{10}$ is —H or methyl.

In one embodiment $A^1$ is —N, $A^2$, $A^3$, $A^4$ are —CH, $A^5$ is —NH, $W^1$ is O, and subscript "n" is 1.

In one embodiment $A^1$ is —N, $A^2$ and $A^4$ are —CH, $A^3$ is —C(OH), —C(CN), —C(F), —C(Cl), —C(OMe), —C(Me), —C(Et), —C(CHF$_2$) or —C(CF$_3$), $A^5$ is —NH, $W^1$ is O, and subscript "n" is 1.

In one embodiment $A^1$ is —N, $A^2$ and $A^3$ are —CH, $A^4$ is —CR$^{6b}$, As is —NH, $W^1$ is O, and subscript "n" is 1.

In one embodiment $A^2$ is —N, $A^1$, $A^3$, $A^4$ are —CH, $A^5$ is —NH, $W^1$ is O, and subscript "n" is 1.

In one embodiment $A^1$ is —N—, $A^2$, $A^3$ and $A^4$ independently are —CH, $W^1$ is O, and subscript "n" is 2.

In one embodiment $R^1$ and $R^2$ are —H, —NH$_2$ or ($C_1$-$C_8$)alkyl, $R^3$, $R^4$ and $R^5$ are —H, —OH, or methyl, and subscript "n" is 2.

The inventive compounds according to Formula I may be isotopically-labelled by having one or more atoms replaced by an atom having a different atomic mass or mass number. Examples of isotopes that can be incorporated into compounds of according to Formula I include isotopes of hydrogen, carbon, nitrogen, oxygen, phosphorous, fluorine, chlorine, or iodine. Illustrative of such isotopes are $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{36}$C, $^{123}$I, and $^{125}$I, respectively. These radiolabelled compounds can be used to measure the biodistribution, tissue concentration and the kinetics of transport and excretion from biological tissues including a subject to which such a labelled compound is administered. Labeled compounds are also used to determine therapeutic effectiveness, the site or mode of action, and the binding affinity of a candidate therapeutic to a pharmacologically important target. Certain radioactive-labelled compounds according to Formula I, therefore, are useful in drug and/or tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, affords certain therapeutic advantages resulting from the greater metabolic stability, for example, increased in vivo half-life of compounds containing deuterium. Substitution of hydrogen with deuterium may reduce dose required for therapeutic effect, and hence may be preferred in a discovery or clinical setting.

Substitution with positron emitting isotopes, such as $^{11}$C, $^{18}$F, $^{15}$O and $^{13}$N, provides labeled analogs of the inventive compounds that are useful in Positron Emission Tomography (PET) studies, e.g., for examining substrate receptor occupancy. Isotopically-labeled compounds according to Formula I can generally be prepared by conventional techniques known to those skilled in the art or by processes analogous to those described in the Preparations and Examples section as set out below using an appropriate isotopic-labeling reagent.

Embodiments of the invention disclosed herein are also meant to encompass the in vivo metabolic products of compounds according to Formula I. Such products may result from, for example, the oxidation, reduction, hydrolysis, amidation, esterification, and like processes primarily due to enzymatic activity upon administration of a compound of the invention. Accordingly, the invention includes compounds that are produced as by-products of enzymatic or non-enzymatic activity on an inventive compound following the administration of such a compound to a mammal for a period of time sufficient to yield a metabolic product. Metabolic products, particularly pharmaceutically active metabolites are typically identified by administering a radio-labelled compound of the invention in a detectable dose to a subject, such as rat, mouse, guinea pig, monkey, or human, for a sufficient period of time during which metabolism occurs, and isolating the metabolic products from urine, blood or other biological samples that are obtained from the subject receiving the radiolabelled compound.

The invention also provides pharmaceutically acceptable salt forms of Formula I compounds. Encompassed within the scope of the invention are both acid and base addition salts that are formed by contacting a pharmaceutically suitable acid or a pharmaceutically suitable base with a compound of the invention.

A "pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

A "pharmaceutically acceptable base addition salt" refers to those salts which retain the biological effectiveness and properties of the free acids, which are not biologically or otherwise undesirable. These salts are prepared by addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposable mirror images of one another.

Compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers. Likewise, all tautomeric forms are also intended to be included.

The term "tautomer" refers to a proton shift from one atom of a molecule to another atom of the same molecule. For example, when $W^1$ is oxo and $A^5$ is —NH, the present invention provides tautomers of a Formula I compound as illustrated below:

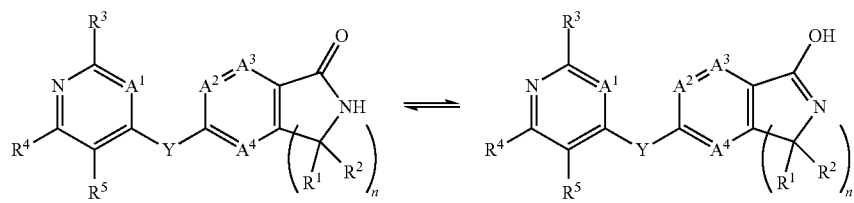

The inventive compounds are synthesized using conventional synthetic methods, and more specifically using the general methods noted below. Specific synthetic protocols for compounds in accordance with the present invention are described in the Examples.

Pharmaceutical Formulations

In one embodiment, a compounds according Formulae I, are formulated as pharmaceutically acceptable compositions that contain a Formulae I compound in an amount effective to treat a particular disease or condition of interest upon administration of the pharmaceutical composition to a mammal. Pharmaceutical compositions in accordance with the present invention can comprise a Formula I compound in combination with a pharmaceutically acceptable carrier, diluent or excipient.

In this regard, a "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Further, a "mammal" includes humans and both domestic animals such as laboratory animals and household pets (e.g., cats, dogs, swine, cattle, sheep, goats, horses, rabbits), and non-domestic animals such as wildlife and the like.

The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, for example, inhalatory administration. When intended for oral administration, the pharmaceutical composition is preferably in either solid or liquid form, where semi-solid, semi-liquid, suspension and gel forms are included within the forms considered herein as either solid or liquid.

As a solid composition for oral administration the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients.

The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by any methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

In certain embodiments a pharmaceutical composition comprising a compound of Formula I is administered to a mammal in an amount sufficient to inhibit Mnk activity upon administration, and preferably with acceptable toxicity to the same. Mnk activity of Formula I compounds can be determined by one skilled in the art, for example, as described in the Examples below. Appropriate concentrations and dosages can be readily determined by one skilled in the art.

Therapeutic Use

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

"Effective amount" or "therapeutically effective amount" refers to that amount of a compound of the invention which, when administered to a mammal, preferably a human, is sufficient to effect treatment, as defined below, of a Mnk related condition or disease in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

Compounds of the invention, or pharmaceutically acceptable salt thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

In certain embodiments the disclosed compounds are useful for inhibiting the activity of Mnk and/or can be useful in analyzing Mnk signaling activity in model systems and/or for preventing, treating, or ameliorating a symptom associated with a disease, disorder, or pathological condition involving Mnk, preferably one afflicting humans. A compound which inhibits the activity of Mnk will be useful in preventing, treating, ameliorating, or reducing the symptoms or progression of diseases of uncontrolled cell growth, proliferation and/or survival, inappropriate cellular immune responses, or inappropriate cellular inflammatory responses or diseases which are accompanied with uncontrolled cell growth, proliferation and/or survival, inappropriate cellular immune responses, or inappropriate cellular inflammatory responses, particularly in which the uncontrolled cell growth, proliferation and/or survival, inappropriate cellular immune responses, or inappropriate cellular inflammatory responses is mediated by Mnk, such as, for example, haematological tumors, solid tumors, and/or metastases thereof, including leukaemias and myelodysplastic syndrome, Waldenstrom macroglobulinemia, and malignant lymphomas, for example, B-cell lymphoma, T-cell lymphoma, hairy cell lymphoma, Hodgkin's lymphoma, non-Hodgin's lymphoma, and Burkitt's lymphoma, head and neck tumors including brain tumors and brain metastases, tumors of the thorax including non-small cell and small cell lung tumors, gastrointestinal tumors, endocrine tumors, mammary and other gynecological tumors, urological tumors including renal, bladder and prostate tumors, skin tumors, and sarcomas, and/or metastases thereof.

Furthermore, the inventive compounds and their pharmaceutical compositions are candidate therapeutics for the prophylaxis and/or therapy of cytokine related diseases, such as inflammatory diseases, allergies, or other conditions associated with proinflammatory cytokines. Exemplary inflammatory diseases include without limitation, chronic or acute inflammation, inflammation of the joints such as chronic inflammatory arthritis, rheumatoid arthritis, psoriatic arthritis, osteoarthritis, juvenile rheumatoid arthritis, Reiter's syndrome, rheumatoid traumatic arthritis, rubella arthritis, acute synovitis and gouty arthritis; inflammatory skin diseases such as sunburn, psoriasis, erythrodermic psoriasis, pustular psoriasis, eczema, dermatitis, acute or chronic graft formation, atopic dermatitis, contact dermatitis, urticaria and scleroderma; inflammation of the gastrointestinal tract such as inflammatory bowel disease, Crohn's disease and related conditions, ulcerative colitis, colitis, and diverticulitis; nephritis, urethritis, salpingitis, oophoritis, endomyometritis, spondylitis, systemic lupus erythematosus and related disorders, multiple sclerosis, asthma, meningitis, myelitis, encephalomyelitis, encephalitis, phlebitis, thrombophlebitis, respiratory diseases such as asthma, bronchitis, chronic obstructive pulmonary disease (COPD), inflammatory lung disease and adult respiratory distress syndrome, and allergic rhinitis; endocarditis, osteomyelitis, rheumatic fever, rheumatic pericarditis, rheumatic endocarditis, rheumatic myocarditis, rheumatic mitral valve disease, rheumatic aortic valve disease, prostatitis, prostatocystitis, spondoarthropathies ankylosing spondylitis, synovitis, tenosynovotis, myositis, pharyngitis, polymyalgia rheumatica, shoulder tendonitis or bursitis, gout, pseudo gout, vasculitides, inflammatory diseases of the thyroid selected from granulomatous thyroiditis, lymphocytic thyroiditis, invasive fibrous thyroiditis, acute thyroiditis; Hashimoto's thyroiditis, Kawasaki's disease, Raynaud's phenomenon, Sjogren's syndrome, neuroinflammatory disease, sepsis, conjunctivitis, keratitis, iridocyclitis, optic neuritis, otitis, lymphoadenitis, nasopaharingitis, sinusitis, pharyngitis, tonsillitis, laryngitis, epiglottitis, bronchitis, pneumonitis, stomatitis, gingivitis. oesophagitis, gastritis, peritonitis, hepatitis, cholelithiasis, cholecystitis, glomerulonephritis, goodpasture's disease, crescentic glomerulonephritis, pancreatitis, endomyometritis, myometritis, metritis, cervicitis, endocervicitis, exocervicitis, parametritis, tuberculosis, vaginitis, vulvitis, silicosis, sarcoidosis, pneumoconiosis, pyresis, inflammatory polyarthropathies, psoriatric arthropathies, intestinal fibrosis, bronchiectasis and enteropathic arthropathies.

Although inflammation is the unifying pathogenic process of these diseases, current therapies only treat the symptoms of the disease and not the underlying cause of inflammation. The compositions of the present invention are useful for the treatment and/or prophylaxis of inflammatory diseases and related complications and disorders.

Accordingly, certain embodiments are directed to a method for treating a Mnk dependent condition in a mammal in need thereof, the method comprising administering an effective amount of a pharmaceutical composition as described above (i.e., a pharmaceutical composition comprising any one or more compounds of Formula I) to a mammal.

As described above deregulation of protein synthesis is a common event in human cancers. A key regulator of translational control is eIF4E whose activity is a key determinant of tumorigenicity. Because activation of eIF4E involves phosphorylation of a key serine (Ser209) specifically by MAP kinase interacting kinases (Mnk), inhibitors of Mnk are suitable candidate therapeutics for treating cell proliferative disorders such as cancer. A wide variety of cancers, including solid tumors, lymphomas and leukemias, are amenable to the compositions and methods disclosed herein. Types of cancer that may be treated include, but are not limited to: adenocarcinoma of the breast, prostate and colon; all forms of bronchogenic carcinoma of the lung; myeloid; melanoma; hepatoma; neuroblastoma; papilloma; apudoma; choristoma; branchioma; malignant carcinoid syndrome; carcinoid heart disease; and carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell). Additional types of cancers that may be treated include: histiocytic disorders; acute and chronic leukemia, both myeloid and lymphoid/lymphoblastic, including hairy cell leukemia; histiocytosis malignant; Hodgkin's disease; immunoproliferative small; Hodgkin's lymphoma; B-cell and T-cell non-Hodgkin's lymphoma, including diffuse large B-cell and Burkitt's lymphoma; plasmacytoma; reticuloendotheliosis; melanoma; multiple myeloma; chondroblastoma; chondroma; chondrosarcoma; fibroma; fibrosarcoma; myelofibrosis; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor.

Other cancers that can be treated using the inventive compounds include without limitation adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin.

In one embodiment the inventive compounds are candidate therapeutic agents for the treatment of cancers such as angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

In a particular embodiment the present disclosure provides methods for treating colon cancer, colorectal cancer, gastric cancer, thyroid cancer, lung cancer, leukemia, pancreatic cancer, melanoma, multiple melanoma, brain cancer, primary and secondary CNS cancer, including malignant glioma and glioblastoma, renal cancer, prostate cancer, including castration-resistant prostate cancer, ovarian cancer, or breast cancer, including triple negative, HER2 positive, and hormone receptor positive breast cancers. According to such a method, a therapeutically effective amount of at least one compound according to Formula I or a stereoisomer, tautomer or pharmaceutically acceptable salt thereof can be administered to a subject who has been diagnosed with a cell proliferative disease, such as a cancer. Alternatively, a pharmaceutical composition comprising at least one compound according to Formula I or a stereoisomer, tautomer or pharmaceutically acceptable salt thereof can be administered to a subject who has been diagnosed with cancer.

In certain embodiments the compounds in accordance with the invention are administered to a subject with cancer in conjunction with other conventional cancer therapies such as radiation treatment or surgery. Radiation therapy is well-known in the art and includes X-ray therapies, such as gamma-irradiation, and radiopharmaceutical therapies.

In certain embodiments the inventive Mnk inhibitor compounds are used with at least one anti-cancer agent. Anti-cancer agents include chemotherapeutic drugs. A chemotherapeutic agent includes, but is not limited to, an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and a DNA repair inhibitor.

Illustrative chemotherapeutic agents include, without limitation, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, Cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, temozolamide, teniposide, triethylenethiophosphoramide and etoposide (VP 16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); chimeric antigen receptors; cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, Pseudomonas exotoxin, Bordetella pertussis adenylate cyclase toxin, or diphtheria toxin, and caspase activators; and chromatin disruptors.

In certain embodiments an Mnk inhibitor in accordance with the present invention is used simultaneously, in the same formulation or in separate formulations, or sequentially with an additional agent(s) as part of a combination therapy regimen.

Mnk inhibitors according to Formula I including their corresponding salts and pharmaceutical compositions of Formula I compounds are also effective as therapeutic agents for treating or preventing cytokine mediated disorders, such as inflammation in a patient, preferably in a human. In one embodiment, a compound or composition in accordance with the invention is particularly useful for treating or preventing a disease selected from chronic or acute inflammation, chronic inflammatory arthritis, rheumatoid arthritis, psoriasis, COPD, inflammatory bowel disease, septic shock, Crohn's disease, ulcerative colitis, multiple sclerosis and asthma.

The inventive compounds their corresponding salts and pharmaceutically acceptable compositions are candidate therapeutics for treating brain related disorders which include without limitation autism, Fragile X-syndrome, Parkinson's disease and Alzheimer's disease. Treatment is effected by administering to a subject in need of treatment a Formula I compound, its pharmaceutically acceptable salt form, or a pharmaceutically acceptable composition of a Formula I compound or its salt.

In a further aspect of the invention the inventive compounds or pharmaceutically acceptable formulations of the inventive compounds are provided as inhibitors of Mnk activity. Such inhibition is achieved by contacting a cell expressing Mnk with a compound or a pharmaceutically acceptable formulation, to lower or inhibit Mnk activity, to provide therapeutic efficacy for a Mnk dependent condition in a mammal in need thereof.

Therapeutically effective dosages of a compound according to Formula I or a composition of a Formula I compound will generally range from about 1 to 2000 mg/day, from about 10 to about 1000 mg/day, from about 10 to about 500 mg/day, from about 10 to about 250 mg/day, from about 10 to about 100 mg/day, or from about 10 to about 50 mg/day. The therapeutically effective dosages may be administered in one or multiple doses. It will be appreciated, however, that specific doses of the compounds of the invention for any particular patient will depend on a variety of factors such as age, sex, body weight, general health condition, diet, individual response of the patient to be treated, time of administration, severity of the disease to be treated, the activity of particular compound applied, dosage form, mode of application and concomitant medication. The therapeutically effective amount for a given situation will readily be determined by routine experimentation and is within the skills and judgment of the ordinary clinician or physician. In any case the compound or composition will be administered at dosages and in a manner which allows a therapeutically effective amount to be delivered based upon patient's unique condition.

GENERAL SYNTHETIC METHODS

Method 1:

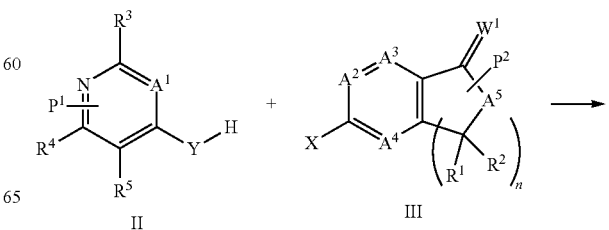

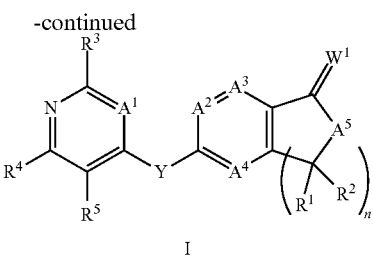

I

The formation of I (Y is —NR$^{10}$) is accomplished by reacting compound II (P$^1$ is an optional protecting group) and compound III (X is a leaving group, such as halogen, —OTf, —OTs or —OMs, and P$^2$ is an optional protecting group) under the Buchwald-Hartwig conditions (such as palladium catalyst, ligand, base, solvent and heat), followed by de-protection and/or further functional group manipulation if necessary.

Alternatively, formation of I (Y is —NR$^{10}$, —O—) is accomplished by reacting compound II (P$^1$ is an optional protecting group) and compound III (X is a leaving group, such as halogen, —OTf, —OTs or —OMs, and P$^2$ is an optional protecting group) under the copper-mediated Ullmann type conditions (such as copper(I) iodide, base, solvent and heat), followed by de-protection and/or further functional group manipulation if necessary.

Alternatively, formation of I (Y is —NR$^{10}$, —O—, —S—) is accomplished by reacting compound II (P$^1$ is an optional protecting group) and compound III (X is a leaving group, such as halogen, —OTf, —OTs or —OMs, and P$^2$ is an optional protecting group) under the nucleophilic aromatic substitution conditions (such as base or acid, solvent, and heat), followed by de-protection and/or further functional group manipulation if necessary.

The formation of I (Y is —S=O, —S(O)$_2$—) is accomplished by oxidizing I (Y is —S—) using an oxidizing reagent such as m-chloroperoxybenzoic acid.

Method 2:

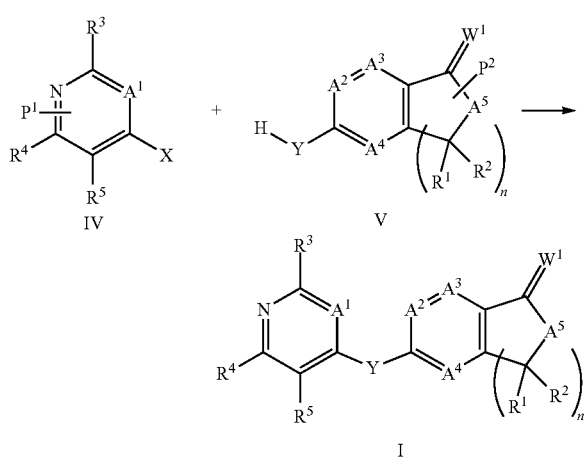

The formation of I (Y is —NR$^{10}$) is accomplished by contacting compound IV (X is a leaving group, such as halogen, —OTf, —OTs or —OMs, and P$^1$ is an optional protecting group) with compound V (P$^2$ is an optional protecting group) under the Buchwald-Hartwig conditions (such as palladium catalyst, ligand, base, solvent and heat), followed by de-protection and/or further functional group manipulation if necessary.

Alternatively, formation of I (Y is —NR$^{10}$, —O—) is accomplished by contacting compound IV (X is a leaving group, such as halogen, —OTf, —OTs or —OMs, and P$^1$ is an optional protecting group) with compound V (P$^2$ is an optional protecting group) under the copper-mediated Ullmann type conditions (such as copper(I) iodide, base, solvent and heat), followed by de-protection and/or further functional group manipulation if necessary.

Alternatively, formation of I (Y is —NR$^{10}$, —O—, —S—) is accomplished by contacting compound IV (X is a leaving group, such as halogen, —OTf, —OTs or —OMs, and P$^1$ is an optional protecting group) with compound V (P$^2$ is an optional protecting group) under the nucleophilic aromatic substitution conditions (such as base or acid, solvent and heat), followed by de-protection and/or further functional group manipulation if necessary.

Method 3:

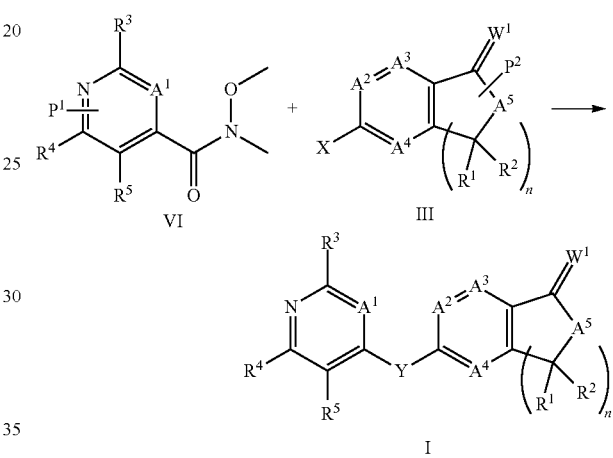

The formation of I (Y is —C(O)—) is accomplished by contacting compound VI (P$^1$ is an optional protecting group) with compound III (X is a leaving group, such as halogen, —OTf, —OTs or —OMs, and P$^2$ is an optional protecting group) in the presence of a base such as n-butyllithium, followed by de-protection and/or further functional group manipulation if necessary.

The formation of I (Y is —CH(OH)) is accomplished by reducing I (Y is —C(O)—) in the presence of a reducing reagent such as sodium borohydride, followed by de-protection and/or further functional group manipulation if necessary.

The formation of I (Y is —CH$_2$—) is accomplished by exposing I (Y is —C(O)—) to the conditions of Clemmensen reduction (such as zinc mercury amalgam, acid, heat) or Wolff-Kishner reduction (such as hydrazine, base, heat), followed by de-protection and/or further functional group manipulation if necessary.

Method 4:

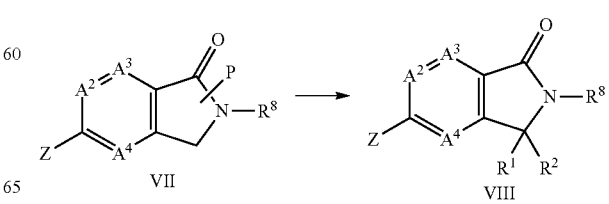

The formation of intermediate VIII (when Z is —NR[10]H, OH, SH or halogen) is accomplished by exposing compound VII (when NH, OH or SH protons are properly protected) to an alkyl halide under basic conditions (such as sodium hydride in tetrahydrofuran), followed by de-protection and/or further functional group manipulation if necessary.

Method 5:

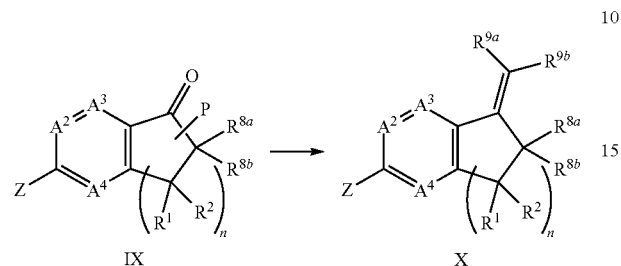

The formation of X (when Z is —NR[10]H, OH, SH or halogen) is accomplished by exposing IX (when NH, OH or SH protons are properly protected) to the Wittig olefination conditions (such as $Ph_3P=CR^{9a}R^{9b}$, solvent and heat), followed by de-protection and/or further functional group manipulation if necessary.

Synthesis of Formula I Compounds

The following examples are provided for purpose of illustration only.

Example 1

Synthesis of 5-((9H-purin-6-yl)amino)isoindolin-1-one (Cpd. No. 1F)

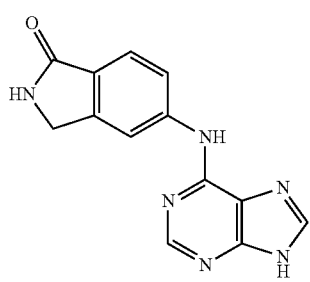

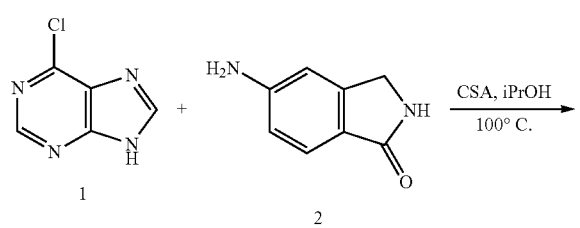

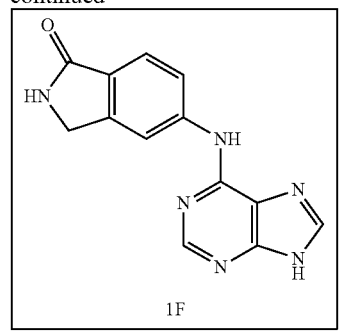

Synthesis of 5-((9H-purin-6-yl)amino)isoindolin-1-one (Cpd. No. 1F)

A mixture of 6-chloro-9H-purine (1, 0.15 g, 0.97 mmol), 5-aminoisoindoline-1-one (2, 0.14 g, 0.97 mmol) and (1S)-(+)-camphor-10-sulfonic acid (0.27 g, 1.16 mmol) in isopropanol (10 mL) was heated in a sealed tube at 100° C. for 4 h. After completion of the reaction, the mixture was concentrated. The obtained solid was filtered and re-crystallized from ethanol and isopropanol to afford 5-((9H-purin-6-yl)amino)isoindolin-1-one (Cpd. No. 1F) as off-white solid. Yield: 0.15 g, 58%; MS (ESI) m/z 267 [M+1]$^+$; $^1$H NMR (400 MHz, DMSO-$d_6$) δ 11.01 (s, 1H), 8.66 (s, 2H), 8.44 (s, 1H), 8.31 (d, J=1.9 Hz, 1H), 7.99 (dd, J=8.3, 1.8 Hz, 1H), 7.67 (d, J=8.3 Hz, 1H), 4.40 (s, 2H).

Example 2

Synthesis of 5-((9H-purin-6-yl)amino)-2-methyl-isoindolin-1-one (Cpd. No. 2F)

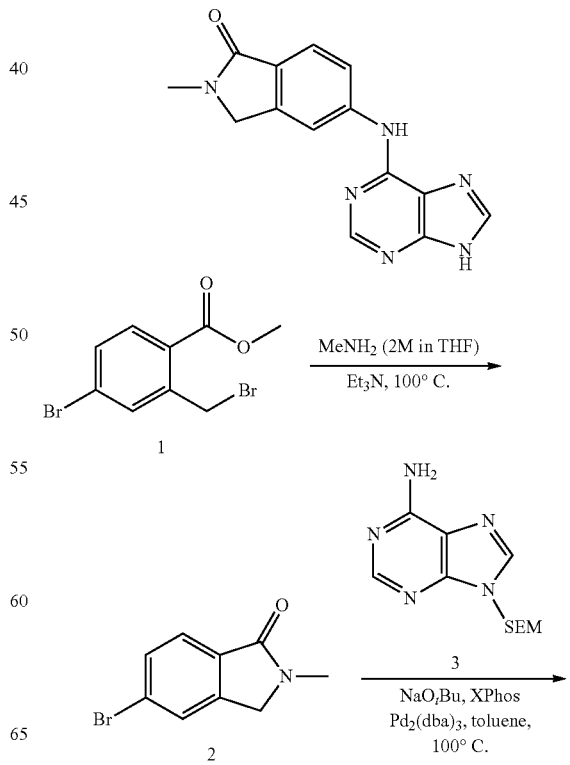

-continued

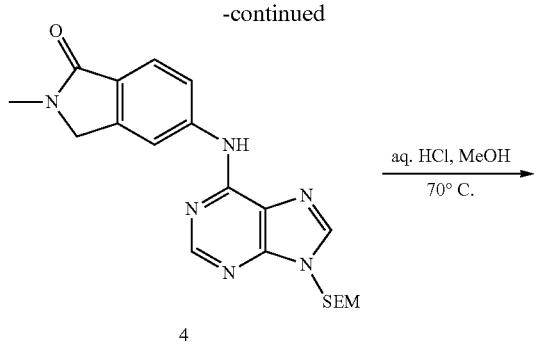

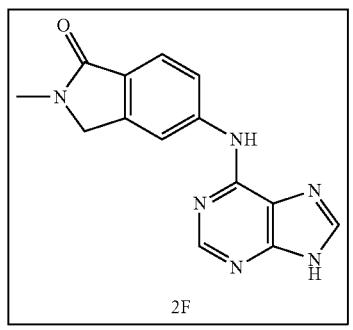

Synthesis of 5-bromo-2-methylisoindolin-1-one (2)

A mixture of methyl 4-bromo-2-(bromomethyl)benzoate (1, 1 g, 3.26 mmol), 2 M methylamine in tetrahydrofuran (1.95 mL, 3.9 mmol) and triethylamine (0.9 mL, 6.52 mmol) was heated at 100° C. for 12 h in a sealed tube. After completion of the reaction, the mixture was concentrated under reduced pressure. The obtained residue was diluted with ethyl acetate and washed with water. The organic was dried over anhydrous sodium sulfate, filtered and concentrated under reduced pressure. The residue was triturated with hexane to afford 5-bromo-2-methylisoindolin-1-one (2). Yield: 0.5 g, 68%; MS (ESI) m/z 226, 228 [M+1]+.

Synthesis of 2-methyl-5-((9-((2-(trimethylsilyl)ethoxy)methyl)-9H-purin-6-yl)amino)isoindolin-1-one (4)

Procedure A: A mixture of 9-((2-(trimethylsilyl)ethoxy)methyl)-9H-purin-6-amine (3, 0.10 g, 0.37 mmol), 5-bromo-2-methylisoindolin-1-one (2, 0.10 g, 0.45 mmol), sodium tert-butoxide (54 mg, 0.56 mmol) and XPhos (5 mg, 0.01 mmol) in toluene (10 mL) was degassed with argon for 30 min. Tris(dibenzylideneacetone)dipalladium(0) (20 mg, 0.022 mmol) was added under argon atmosphere and the reaction mixture was heated at 100° C. for 12 h. After completion of the reaction, the reaction mixture was filtered through celite pad and the filtrate was concentrated. The crude residue was purified by silica gel column chromatography using 0-10% ethyl acetate in hexanes as eluent to afford 2-methyl-5-((9-((2-(trimethylsilyl)ethoxy)methyl)-9H-purin-6-yl)amino)isoindolin-1-one (4). Yield: 0.11 g, 71%; MS (ESI) m/z 411 [M+1]+.

Synthesis of 5-((9H-purin-6-yl)amino)-2-methylisoindolin-1-one (Cpd. No. 2F)

To a solution of 2-methyl-5-((9-((2-(trimethylsilyl)ethoxy)methyl)-9H-purin-6-yl)amino)isoindolin-1-one (4, 0.11 g, 0.26 mmol) in ethanol (2 mL), 3 M hydrochloric acid (3 mL) was added and the reaction mixture was heated at 70° C. for 3 h. After completion of the reaction, the reaction mixture was concentrated under reduced pressure and neutralized with saturated aqueous sodium bicarbonate solution. The residue was filtered and triturated with methanol/acetonitrile/water (2:2:1) to afford 5-((9H-purin-6-yl)amino)-2-methylisoindolin-1-one (Cpd. No. 2F) as white solid. Yield: 0.04 g, 54%; MS (ESI) m/z 281 [M+1]+; $^1$H NMR (400 MHz, DMSO-$d_6$) δ 13.19 (s, 1H), 10.10 (s, 1H), 8.46 (s, 1H), 8.35 (d, J=10.6 Hz, 2H), 8.00 (d, J=8.4 Hz, 1H), 7.60 (d, J=8.3 Hz, 1H), 4.46 (s, 2H), 3.05 (s, 3H).

Example 3

Synthesis of 5-(pyrimidin-4-ylamino)isoindolin-1-one (Cpd. No. 3F)

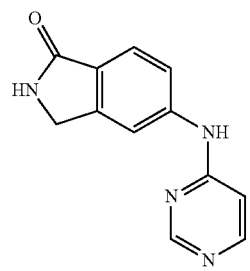

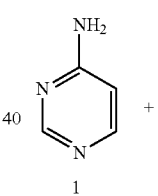

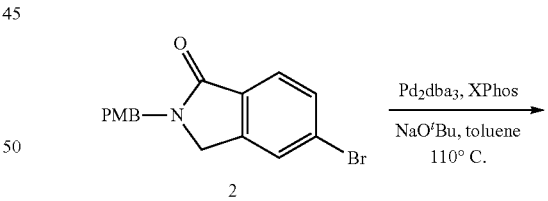

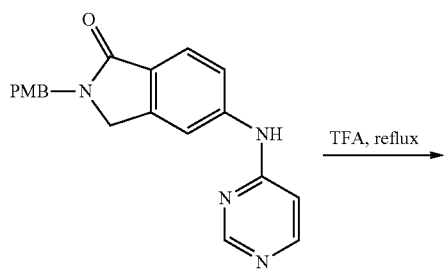

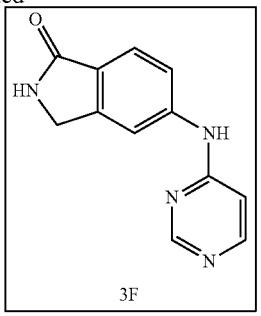

3F

Synthesis of 2-(4-methoxybenzyl)-5-(pyrimidin-4-ylamino)isoindolin-1-one (3)

The synthesis of intermediate 3 was carried out as described above using the general protocol of Procedure A. Yield: 0.05 g, 32%; MS (ESI) m/z 347 [M+1]$^+$.

Synthesis of 5-(pyrimidin-4-ylamino)isoindolin-1-one (Cpd. No. 3F)

Procedure B: A mixture of 2-(4-methoxybenzyl)-5-(pyrimidin-4-ylamino)isoindolin-1-one (3, 0.048 g, 0.14 mmol) in trifluoroacetic acid (0.5 mL) was heated at reflux for 24 h. After completion of the reaction (monitored by TLC), the reaction mixture was cooled to 0° C. and basified with aqueous saturated sodium bicarbonate solution. The residue was filtered, washed with water followed by hexane and dried to afford 5-(pyrimidin-4-ylamino)isoindolin-1-one (Cpd. No. 3F) as off-white solid. Yield: 0.03 g, 96%; MS (ESI) m/z 227 [M+1]$^+$; $^1$H NMR (400 MHz, DMSO-d$_6$) δ 9.94 (s, 1H), 8.70 (s, 1H), 8.38-8.30 (m, 2H), 8.12 (s, 1H), 7.68-7.57 (m, 2H), 6.95 (s, 1H), 4.36 (s, 2H).

Example 4

Synthesis of 5-((6-chloropyrimidin-4-yl)amino)isoindolin-1-one (Cpd. No. 4F)

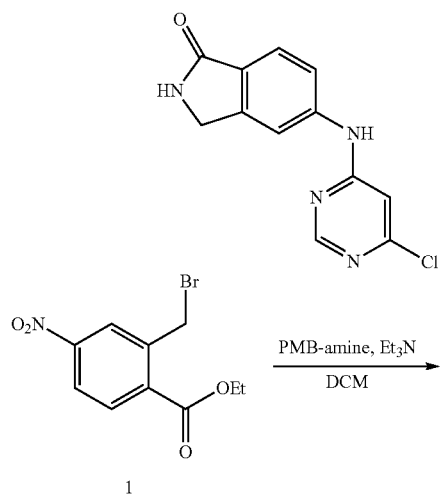

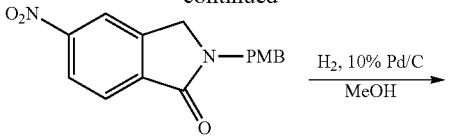

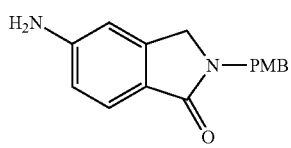 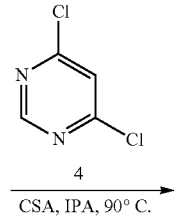

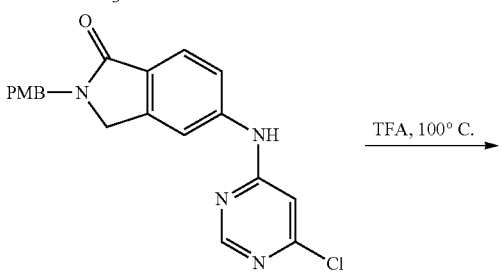

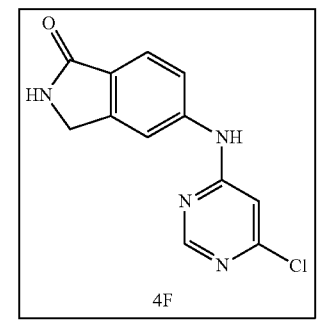

4F

Synthesis of 2-(4-methoxybenzyl)-5-nitroisoindolin-1-one (2)

To a stirred solution of ethyl 2-(bromomethyl)-4-nitrobenzoate (1, 1.5 g, 4.85 mmol) in dichloromethane (30 mL), triethylamine (0.74 g, 7.27 mmol) and p-methoxybenzylamine (0.59 g, 4.36 mmol) was added dropwise and the reaction mixture was stirred at room temperature for 15 h. After completion of the reaction (monitored by TLC), the reaction mixture was poured into water and extracted with dichloromethane. The organic layer was dried over anhydrous sodium sulfate, filtered and concentrated under reduced pressure to afford 2-(4-methoxybenzyl)-5-nitroisoindolin-1-one (2). Yield: 1.1 g, 76%.

Synthesis of 5-amino-2-(4-methoxybenzyl)isoindolin-1-one (3)

To a solution of 2-(4-methoxybenzyl)-5-nitroisoindolin-1-one (2, 1.1 g, 3.69 mmol) in methanol (25 mL), 10% palladium on carbon (1.1 g) was added and the reaction mixture was hydrogenated under balloon pressure at room temperature for 10 h. After completion of the reaction (monitored by TLC), the reaction mixture was filtered through celite pad and washed with ethyl acetate. The filtrate was concentrated under reduced pressure to afford 5-amino-2-(4-methoxybenzyl)isoindolin-1-one (3). Yield: 0.8 g, 81%; MS (ESI) m/z 269 [M+1]+.

Synthesis of 5-((6-chloropyrimidin-4-yl)amino)-2-(4-methoxybenzyl)isoindolin-1-one (5)

To a stirred solution of 5-amino-2-(4-methoxybenzyl)isoindolin-1-one (3, 0.3 g, 1.11 mmol) and 4,6-dichloropyrimidine (4, 0.33 g, 2.23 mmol) in isopropyl alcohol (15 mL), (1S)-(+)-10-camphorsulfonic acid (0.28 g, 1.22 mmol) was added and the reaction mixture was heated at 90° C. for 4 h. After completion of the reaction (monitored by TLC), the reaction mixture was cooled and concentrated under reduced pressure. The residue was triturated with ethanol and acetonitrile (1:4) to afford 5-((6-chloropyrimidin-4-yl)amino)-2-(4-methoxybenzyl)isoindolin-1-one (5). Yield: 0.19 g, 45%; MS (ESI) m/z 381 [M+1]+.

Synthesis of 5-((6-chloropyrimidin-4-yl)amino)isoindolin-1-one (Cpd. No. 4F)

The synthesis of compound 4F was carried out as described above using the general protocol of Procedure B. Off-white solid; Yield: 0.03 g, 31%; MS (ESI) m/z 261 [M+1]+; $^1$H NMR (400 MHz, DMSO-$d_6$) δ 8.54 (s, 1H), 8.38 (s, 1H), 8.02 (s, 1H), 7.62 (t, J=6.4 Hz, 2H), 6.90 (s, 1H), 4.36 (s, 2H), 3.68 (s, 1H).

Example 5

Synthesis of 5-(pyrimidin-4-ylamino)-2,3-dihydro-1H-inden-1-one (Cpd. No. 5)

Synthesis of 5-(pyrimidin-4-ylamino)-2,3-dihydro-1H-inden-1-one (Cpd. No. 5)

A mixture of 5-amino-2,3-dihydro-1H-inden-1-one (1, 0.1 g, 0.68 mmol), 4-chloropyrimidine (2, 0.20 g, 1.36 mmol) and potassium carbonate (0.23 g, 1.7 mmol) in dimethylformamide (3 mL) was heated at 110° C. for 15 h. The reaction mixture was cooled to room temperature and poured into water. The aqueous layer was extracted with ethyl acetate. The organic layer was dried over anhydrous sodium sulfate, filtered and concentrated under reduced pressure. The residue was purified by silica gel column chromatography using 3% methanol in dichloromethane to afford 5-(pyrimidin-4-ylamino)-2,3-dihydro-1H-inden-1-one (Cpd. No. 5) as light yellow solid. Yield: 0.08 g, 52%; MS (ESI) m/z 226 [M+1]+; $^1$H NMR (400 MHz, DMSO-$d_6$) δ 10.09 (s, 1H), 8.76 (s, 1H), 8.39 (d, J=5.9 Hz, 1H), 8.12 (s, 1H), 7.66-7.53 (m, 2H), 6.93 (dd, J=6.0, 1.3 Hz, 1H), 3.12-3.04 (m, 2H), 2.63-2.51 (m, 2H).

Example 6

Synthesis of 5-((6-((1-methyl-1H-pyrazol-4-yl)amino)pyrimidin-4-yl)amino)isoindolin-1-one (Cpd. No. 6F)

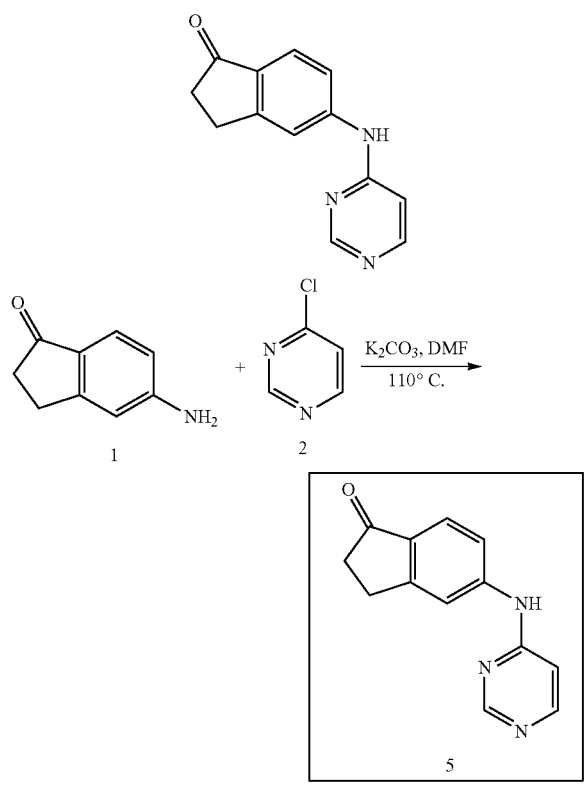

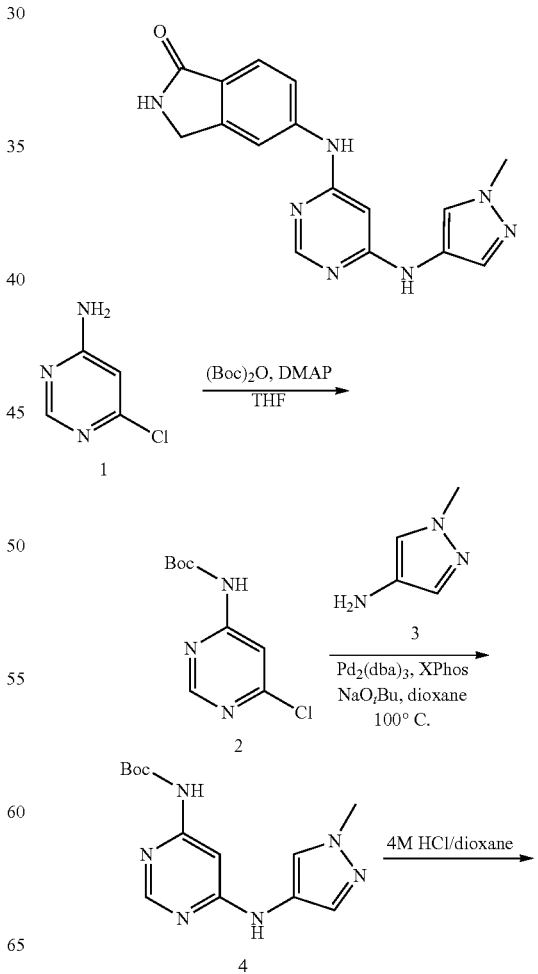

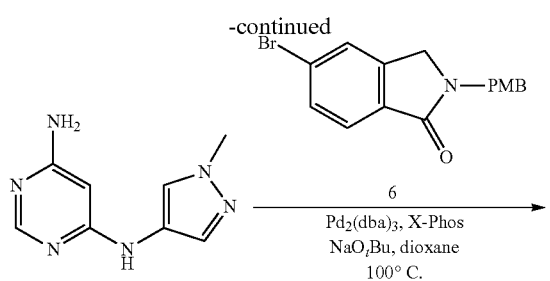

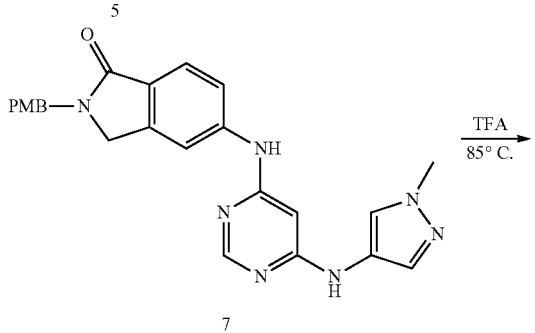

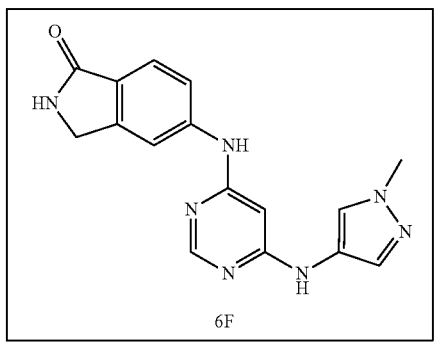 [SMILES: Cn1cc(Nc2cc(Nc3ccc4c(c3)CNC4=O)ncn2)cn1]

6F

Synthesis of tert-butyl (6-chloropyrimidin-4-yl)carbamate (2)

To a stirred solution of 6-chloropyrimidin-4-amine (1, 0.54 g, 4.18 mmol) in tetrahydrofuran (12 mL), di-tert-butyl dicarbonate (1.92 g, 8.8 mmol) and 4-(dimethylamino) pyridine (0.026 g, 0.21 mmol) were added. The reaction mixture was stirred at room temperature for 16 h. After completion of the reaction (monitored by TLC), the reaction mixture was diluted with water and extracted with ethyl acetate. The organic layer was washed with brine, dried over anhydrous sodium sulfate, filtered and concentrated under reduced pressure. The residue was triturated with pentane to afford tert-butyl (6-chloropyrimidin-4-yl)carbamate (2). Yield: 0.64 g, 66%; MS (ESI) m/z 230 [M+1]$^+$.

Synthesis of tert-butyl (6-((1-methyl-1H-pyrazol-4-yl)amino)pyrimidin-4-yl)carbamate (4)

The synthesis of intermediate 4 was carried out as described above using the general protocol of Procedure A. Yield: 0.39 g, 58%; MS (ESI) m/z 291 [M+1]$^+$.

Synthesis of $N^4$-(1-methyl-1H-pyrazol-4-yl)pyrimidine-4,6-diamine (5)

Procedure C: A mixture of tert-butyl (6-((1-methyl-1H-pyrazol-4-yl)amino)pyrimidin-4-yl)carbamate (4, 0.38 g, 1.31 mmol) in 4 M hydrogenchloride in dioxane (4 mL) was stirred at room temperature for 3 h. After completion of the reaction (monitored by TLC), the reaction mixture was concentrated under reduced pressure. The crude was diluted with dichloromethane and washed with aqueous saturated sodium bicarbonate solution. The organic was dried over sodium sulfate, filtered and concentrated to afford crude $N^4$-(1-methyl-1H-pyrazol-4-yl)pyrimidine-4,6-diamine (5) which was used for the next step without further purification. Yield: 0.3 g, crude; MS (ESI) m/z 191 [M+1]$^+$.

Synthesis of 2-(4-methoxybenzyl)-5-((6-((1-methyl-1H-pyrazol-4-yl)amino)pyrimidin-4-yl)amino)isoindolin-1-one (7)

The synthesis of intermediate 7 was carried out as described above using the general protocol of Procedure A. White solid. Yield: 0.12 g, 30%; MS (ESI) m/z 442 [M+1]$^+$.

Synthesis of 5-((6-((1-methyl-1H-pyrazol-4-yl)amino)pyrimidin-4-yl)amino)isoindolin-1-one (Cpd. No. 6F)

The synthesis of compound 6F was carried out as described above using the general protocol of Procedure B. Off-white solid. Yield: 0.025 g, 31%; MS (ESI) m/z 322 [M+1]$^+$; $^1$H NMR (400 MHz, DMSO-d$_6$) δ 9.41 (s, 1H), 8.91 (s, 1H), 8.27 (d, J=11.0 Hz, 2H), 8.01 (s, 1H), 7.85 (s, 1H), 7.53 (s, 2H), 7.41 (s, 1H), 6.03 (s, 1H), 4.32 (s, 2H), 3.81 (s, 3H).

Example 7

Synthesis of 5-(methyl(pyrimidin-4-yl)amino)isoindolin-1-one (Cpd. No. 7)

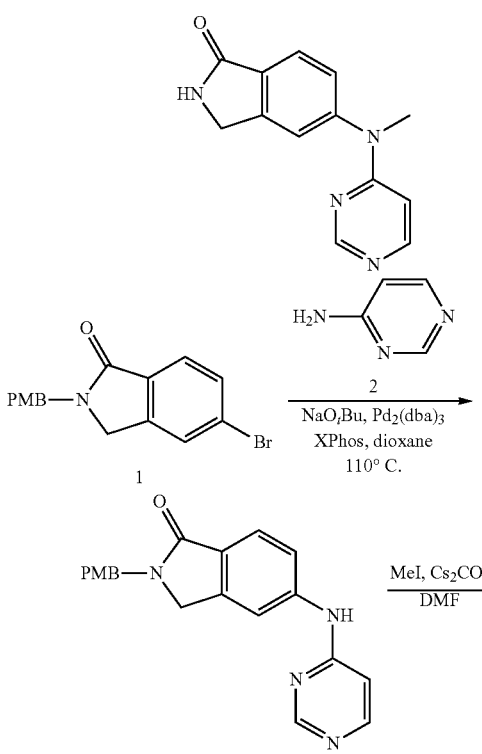

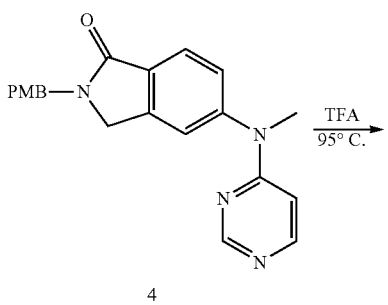

4

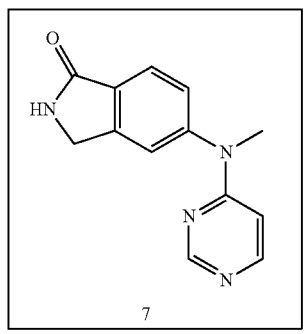

7

Synthesis of 2-(4-methoxybenzyl)-5-(pyrimidin-4-ylamino)isoindolin-1-one (3)

The synthesis of intermediate 3 was carried out as described above using the general protocol of Procedure A. Yield: 0.25 g, 80%; MS (ESI) m/z 347 [M+1]$^+$.

Synthesis of 2-(4-methoxybenzyl)-5-(methyl(pyrimidin-4-yl)amino)isoindolin-1-one (4)

To a solution of 2-(4-methoxybenzyl)-5-(pyrimidin-4-ylamino)isoindolin-1-one (3, 0.3 g, 0.86 mmol) in dimethylformamide (5 mL) was added cesium carbonate (0.56 g, 1.73 mmol). The mixture was stirred for 10 min. Iodomethane (0.12 g, 0.86 mmol) was added and the reaction mixture was stirred at room temperature for 2 h. After completion of the reaction, it was diluted with water and extracted with ethyl acetate. Organic layer was dried over anhydrous sodium sulfate, filtered and concentrated under reduced pressure. The residue was purified by silica gel column chromatography using 3% methanol in dichloromethane as eluent to afford 2-(4-methoxybenzyl)-5-(methyl(pyrimidin-4-yl)amino)isoindolin-1-one (4). Yield: 0.14 g, 38%; MS (ESI) m/z 361 [M+1]$^+$.

Synthesis of 5-(methyl(pyrimidin-4-yl)amino)isoindolin-1-one (Cpd. No. 7)

The synthesis of compound 7 was carried out as described above using the general protocol of Procedure B. Light yellow solid; Yield: 0.045 g, 48%; MS (ESI) m/z 241 [M+1]$^+$; $^1$H NMR (400 MHz, DMSO-d$_6$) δ 8.60 (d, J=1.3 Hz, 2H), 8.16 (d, J=6.1 Hz, 1H), 7.75 (d, J=8.1 Hz, 1H), 7.57 (dd, J=1.8, 0.9 Hz, 1H), 7.44 (dd, J=8.1, 1.9 Hz, 1H), 6.52 (dd, J=6.2, 1.3 Hz, 1H), 4.39 (s, 2H), 3.45 (s, 3H).

Example 8

Synthesis of 3-methyl-5-(pyrimidin-4-ylamino)isoindolin-1-one (Cpd. No. 8)

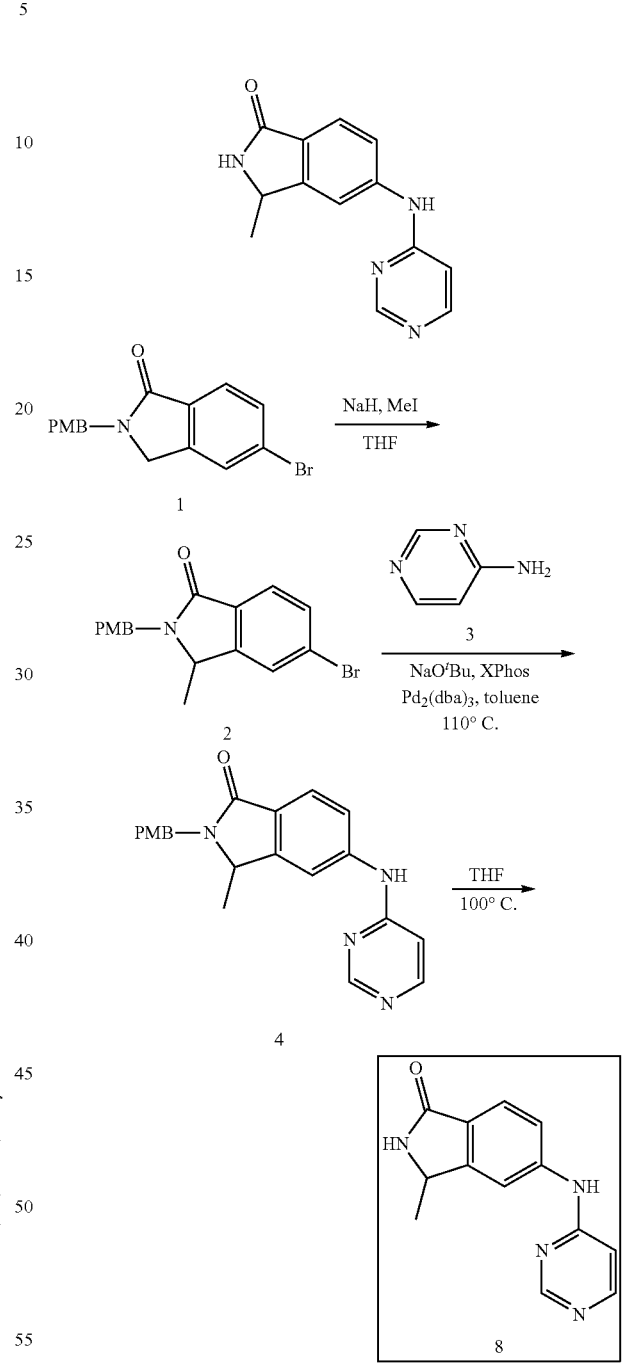

Synthesis of 5-bromo-2-(4-methoxybenzyl)-3-methylisoindolin-1-one (2)

To an ice cooled suspension of sodium hydride (0.072 g, 60% dispersion in mineral oil, 1.8 mmol) in dry tetrahydrofuran (5 mL) a solution of 5-bromo-2-(4-methoxybenzyl) isoindolin-1-one (1, 0.5 g, 1.5 mmol in dry tetrahydrofuran 5 mL) was added dropwise under nitrogen atmosphere. The reaction mixture was stirred for 1 h and iodomethane (0.14 mL, 2.2 mmol) was added. The reaction mixture was stirred at room temperature for 2 h. The reaction mixture was quenched with ice-water and extracted with ethyl acetate. The combined organic layer was dried over anhydrous sodium sulphate, filtered and concentrated under reduced pressure. The residue was purified by silica gel column chromatography using 0-8% of ethyl acetate in hexane as eluent to afford 5-bromo-2-(4-methoxybenzyl)-3-methyl-isoindolin-1-one (2). Yield: 0.29 g, 57%; MS (ESI) m/z 246, 248 [M+1]$^+$.

Synthesis of 2-(4-methoxybenzyl)-3-methyl-5-(py-rimidin-4-ylamino)isoindolin-1-one (4)

The synthesis of intermediate 4 was carried out as described above using the general protocol of Procedure A. Yield: 0.12 g, 58%; MS (ESI) m/z 361 [M+1]$^+$.

Synthesis of 3-methyl-5-(pyrimidin-4-ylamino)isoindolin-1-one (Cpd. No. 8)

The synthesis of compound 8 was carried out as described above using the general protocol of Procedure B. Off-white solid; Yield: 0.015 g, 19%; MS (ESI) m/z 241 [M+1]$^+$; $^1$H NMR (400 MHz, Methanol-d$_4$) δ 8.67 (s, 1H), 8.27 (d, J=6.1 Hz, 1H), 8.13 (s, 1H), 7.74-7.61 (m, 2H), 6.86 (d, J=6.0 Hz, 1H), 4.69 (q, J=6.8 Hz, 1H), 1.48 (d, J=6.7 Hz, 3H), 1.15 (d, J=6.2 Hz, 1H).

Example 9

Synthesis of 5-((5-oxo-2,5-dihydro-1H-pyrrol-3-yl)amino)isoindolin-1-one (Cpd. No. 9)

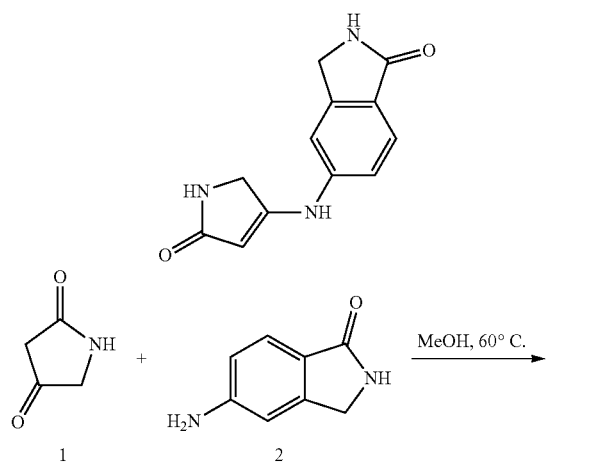

Synthesis of 5-((5-oxo-2,5-dihydro-1H-pyrrol-3-yl)amino)isoindolin-1-one (Cpd. No. 9)

A mixture of pyrrolidine-2,4-dione (1, 18 mg, 0.18 mmol) and 5-aminoisoindolin-1-one (2, 27 mg, 0.18 mmol) in methanol (1 mL) was stirred at 60° C. for 1 h. Upon cooling, the mixture was filtered, followed by rinsing with methanol. The solid was dried under vacuum to afford 5-((5-oxo-2,5-dihydro-1H-pyrrol-3-yl)amino)isoindolin-1-one (Cpd. No. 9) as an off-white solid. Yield: 23 mg, 55%; $^1$H NMR (300 MHz, DMSO-d$_6$) δ 9.44 (s, 1H), 8.28 (s, 1H), 7.57 (d, J=4.8 Hz, 1H), 7.32 (s, 1H), 7.19 (s, 1H), 7.15 (dd, J=1.2, 5.1 Hz, 1H), 5.40 (s, 1H), 4.32 (s, 2H), 4.01 (s, 2H).

Example 10

Synthesis of 6-(pyrimidin-4-ylamino)-3,4-dihy-droisoquinolin-1(2H)-one (Cpd. No. 10)

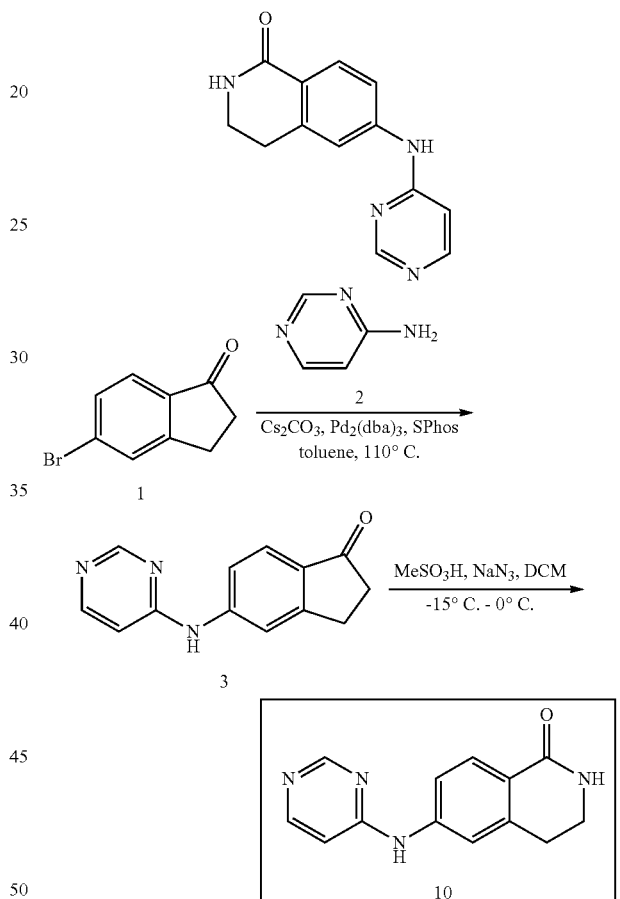

Synthesis of 5-(pyrimidin-4-ylamino)-2,3-dihydro-1H-inden-1-one (3)

The synthesis of intermediate 3 was carried out as described above using the general protocol of Procedure A. Yield: 0.48 g, 44.98%

Synthesis of 6-(pyrimidin-4-ylamino)-3,4-dihy-droisoquinolin-1 (2H)-one (Cpd. No. 10)

To a stirred solution of 5-(pyrimidin-4-ylamino)-2,3-dihydro-1H-inden-1-one (3, 0.48 g, 2.1 mmol) in dichloromethane (5 ml), methane sulfonic acid (1.01 ml, 15.5 mmol) was added at −15° C. over a period of 10 min. After stirring for 15 min, sodium azide (0.42 g, 6.39 mmol) was added portion wise over a period of 3 h at −15° C., and the reaction mixture was stirred at −15° C. for another 1 h. The reaction mixture was warmed to 0° C. and stirred at 0-5° C. for 2 h. The reaction was quenched with 4 M sodium hydroxide solution. The aqueous layer was extracted with ethyl acetate. The organic layer was dried over anhydrous sodium sulfate, filtered and concentrated under reduced pressure. The residue was purified by flash column chromatography to afford 6-(pyrimidin-4-ylamino)-3,4-dihydroisoquinolin-1(2H)-one (Cpd. No. 10) as light yellow solid. Yield: 0.075 g, 15%; MS (ESI) m/z 241 [M+1]$^+$; $^1$H NMR (400 MHz, Methanol-d$_4$) δ 8.66 (d, J=1.0 Hz, 1H), 8.26 (d, J=6.1 Hz, 1H), 7.89 (d, J=8.5 Hz, 1H), 7.79 (d, J=2.2 Hz, 1H), 7.61 (dd, J=8.5, 2.2 Hz, 1H), 6.86 (dd, J=6.1, 1.3 Hz, 1H), 3.51 (t, J=6.7 Hz, 2H), 3.35 (d, J=2.5 Hz, 1H), 3.28 (s, 1H), 2.99 (t, J=6.7 Hz, 2H).

Example 11

Synthesis of N-(6-((1-oxoisoindolin-5-yl)amino)pyrimidin-4-yl)acetamide (Cpd. No. 11)

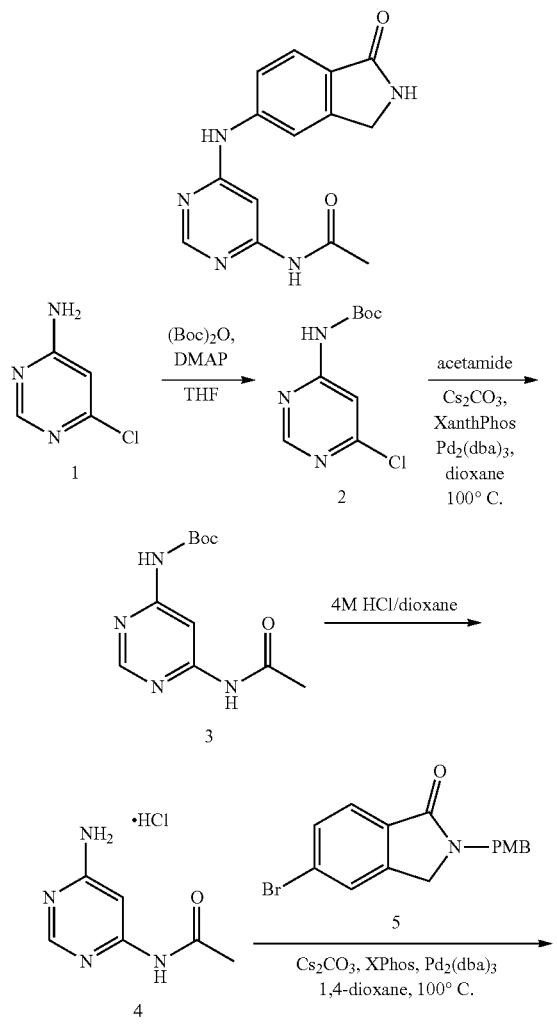

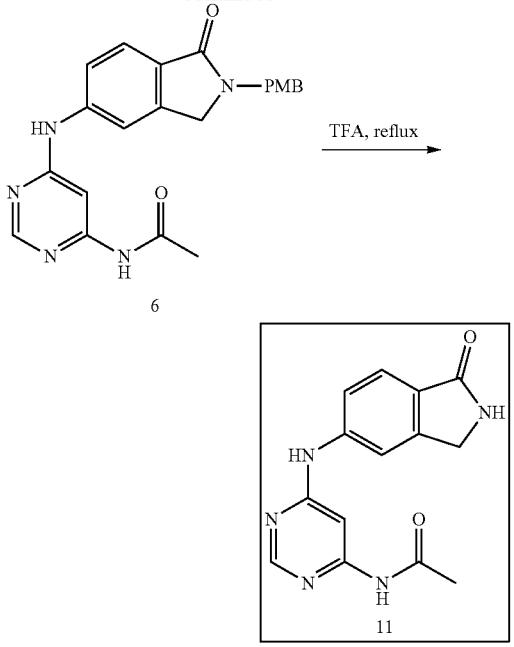

Synthesis of tert-butyl (6-chloropyrimidin-4-yl)carbamate (2)

To a stirred solution of 6-chloropyrimidin-4-amine (1, 2 g, 15.5 mmol) in tetrahydrofuran (40 mL), 4-(dimethylamino)pyridine (0.035 g, 0.78 mmol) and di-tert-butyl dicarbonate (7.1 g, 32.55 mmol) were added dropwise. The reaction mixture was stirred at room temperature for 16 h. After completion of the reaction (monitored by TLC), the reaction mixture was diluted with ethyl acetate and washed with water. The aqueous layer was re-extracted with ethyl acetate. Combined organic layer was washed with brine, dried over anhydrous sodium sulfate, filtered and concentrated under reduced pressure. The residue was triturated with diethyl ether to afford tert-butyl (6-chloropyrimidin-4-yl)carbamate (2) which was used for the next step without further purification. Yield: 2.4 g, 68%; MS (ESI) m/z 230 [M+1]$^+$.

Synthesis of tert-butyl (6-acetamidopyrimidin-4-yl)carbamate (3)

The synthesis of intermediate 3 was carried out as described above using the general protocol of Procedure A. Off-white solid; Yield: 0.81 g, 61%; MS (ESI) m/z 253 [M+1]$^+$.

Synthesis of N-(6-aminopyrimidin-4-yl)acetamide hydrochloride (4)

The synthesis of intermediate 4 was carried out as described above using the general protocol of Procedure C. Yield: 0.42 g, crude; MS (ESI) m/z 153 [M+1]$^+$.

Synthesis of N-(6-((2-(4-methoxybenzyl)-1-oxoisoindolin-5-yl)amino)pyrimidin-4-yl)acetamide (6)

The synthesis of intermediate 6 was carried out as described above using the general protocol of Procedure A. Off-white solid; Yield: 0.38 g, 44%; MS (ESI) m/z 404 [M+1]$^+$.

Synthesis of N-(6-((1-oxoisoindolin-5-yl)amino)pyrimidin-4-yl)acetamide (Cpd. No. 11)

The synthesis of compound 11 was carried out as described above using the general protocol of Procedure B. Off-white solid; Yield: 0.086 g, 33%; MS (ESI) m/z 284 [M+1]$^+$; $^1$H NMR (400 MHz, DMSO-d$_6$) δ 10.58 (s, 1H), 9.94 (s, 1H), 8.46 (s, 1H), 8.32 (s, 1H), 8.10 (s, 1H), 7.70-7.53 (m, 3H), 4.34 (s, 2H), 2.11 (s, 3H).

Example 12

Synthesis of N-(6-((1-oxoisoindolin-5-yl)amino)pyrimidin-4-yl)cyclopropanecarboxamide (Cpd. No. 12)

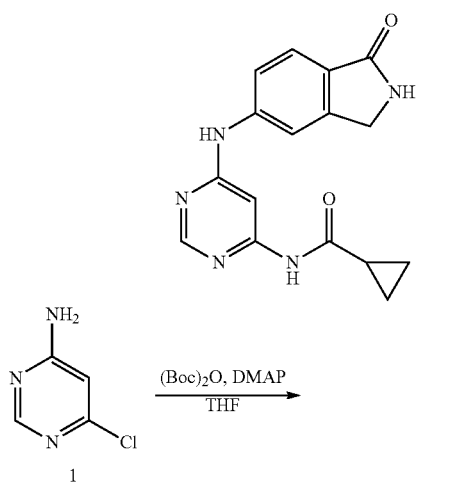

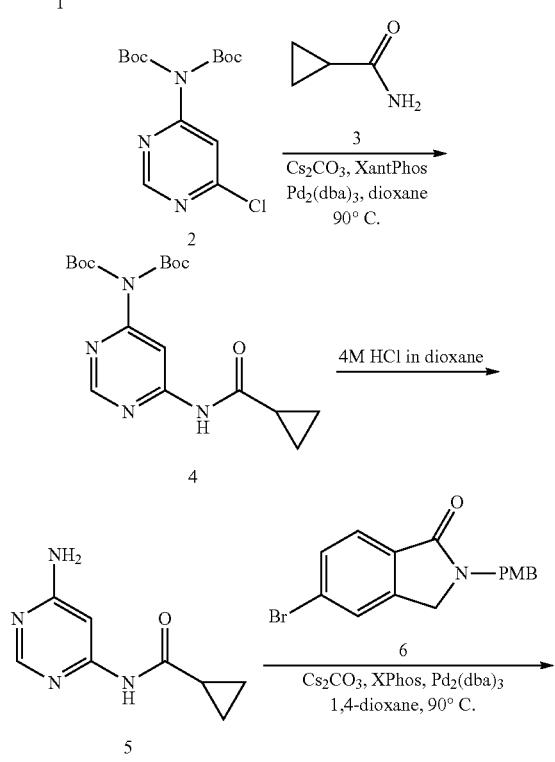

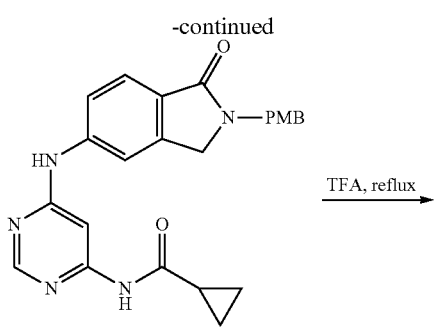

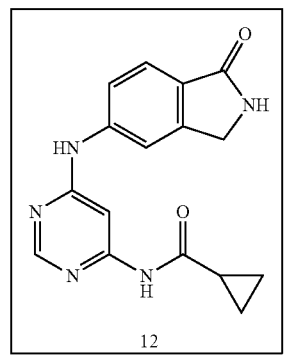

12

Synthesis of tert-butyl N-tert-butoxycarbonyl-N-(6-chloropyrimidin-4-yl)carbamate (2)

To a stirred solution of 6-chloropyrimidin-4-amine (1, 1 g, 7.75 mmol) in tetrahydrofuran (20 mL), 4-(dimethylamino)pyridine (0.047 g, 0.387 mmol) and di-tert-butyl dicarbonate (3.55 g, 16.27 mmol) were added dropwise. The reaction mixture was stirred at room temperature for 16 h. After completion of the reaction (monitored by TLC), the reaction mixture was diluted with water and extracted with ethyl acetate. Combined organic layer was washed with brine, dried over anhydrous sodium sulfate, filtered and concentrated under reduced pressure to afford tert-butyl N-tert-butoxycarbonyl-N-(6-chloropyrimidin-4-yl)carbamate (2) which was used for the next step without further purification. Yield: 1.3 g, 51%; MS (ESI) m/z 330 [M+1]$^+$.

Synthesis of tert-butyl N-tert-butoxycarbonyl-N-(6-(cyclopropanecarboxamido)pyrimidin-4-yl)carbamate (4)

The synthesis of intermediate 4 was carried out as described above using the general protocol of Procedure A. Yellow solid; Yield: 0.55 g, 96%; MS (ESI) m/z 379 [M+1]$^+$.

Synthesis of N-(6-aminopyrimidin-4-yl)cyclopropanecarboxamide (5)

The synthesis of intermediate 5 was carried out as described above using the general protocol of Procedure C. Yield: 0.3 g, crude; MS (ESI) m/z 179 [M+1]$^+$.

Synthesis of N-(6-((2-(4-methoxybenzyl)-1-ox-oisoindolin-5-yl)amino)pyrimidin-4-yl)cyclopropan-ecarboxamide (7)

The synthesis of intermediate 7 was carried out as described above using the general protocol of Procedure A. Yield: 0.3 g, 42%; MS (ESI) m/z 430 [M+1]$^+$.

Synthesis of N-(6-((1-oxoisoindolin-5-yl)amino)pyrimidin-4-yl)cyclopropanecarboxamide (Cpd. No. 12)

The synthesis of compound 12 was carried out as described above using the general protocol of Procedure B. Off-white solid; Yield: 0.066 g, 46%; MS (ESI) m/z 310 [M+1]$^+$; $^1$H NMR (400 MHz, DMSO-d$_6$) δ 10.88 (s, 1H), 9.91 (s, 1H), 8.47 (d, J=1.1 Hz, 1H), 8.32 (s, 1H), 8.10-8.05 (m, 1H), 7.69-7.53 (m, 3H), 4.34 (s, 2H), 2.03 (p, J=6.2 Hz, 1H), 1.23 (s, 1H), 0.84 (d, J=6.3 Hz, 4H).

Example 13

Synthesis of 3-isopropyl-5-(pyrimidin-4-ylamino)isoindolin-1-one (Cpd. No. 13)

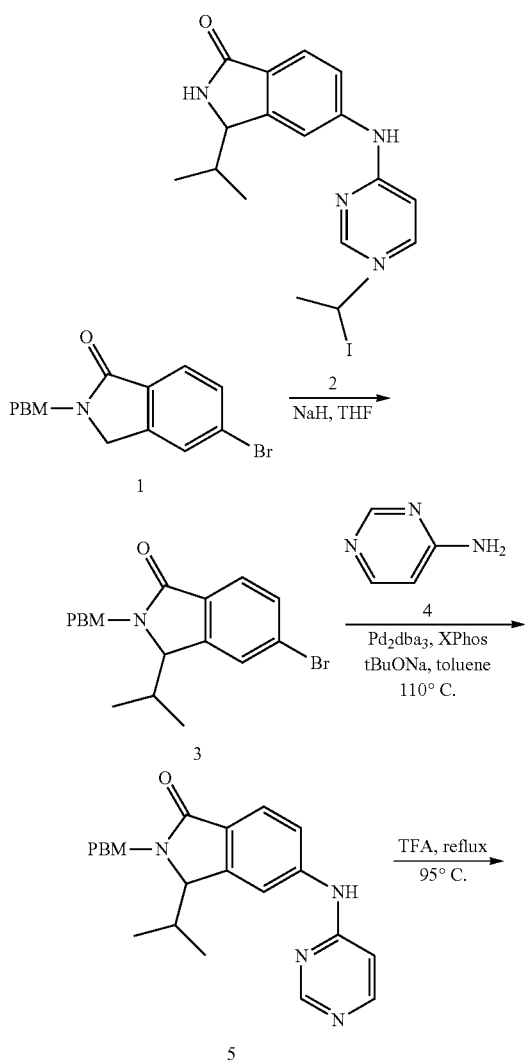

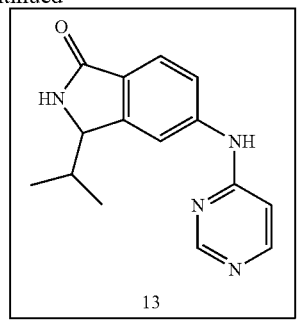

Synthesis of 5-bromo-3-isopropyl-2-(4-methoxybenzyl)isoindolin-1-one (3)

To a solution of 5-bromo-2-(4-methoxybenzyl)isoindolin-1-one (1, 2 g, 6 mmol) in tetrahydrofuran (20 mL) at 0° C., sodium hydride (0.29 g, 7.2 mmol) was added portion wise and the reaction mixture was allowed to stir at room temperature for 30 min. 2-iodopropane (2, 0.9 mL, 9 mmol) was added and the reaction mixture was allowed to stir at 90° C. for 16 h. The reaction mixture was quenched with water and the compound was extracted in ethyl acetate. The organic layer was separated, dried over sodium sulphate and concentrated under reduced pressure. The residue was purified by silica gel column chromatography using 30% ethyl acetate in hexanes as eluent to afford 5-bromo-3-isopropyl-2-(4-methoxybenzyl)isoindolin-1-one (3). Yield: 0.56 g, 25%; MS (ESI) m/z 375 [M+1]$^+$.

Synthesis of 3-isopropyl-2-(4-methoxybenzyl)-5-(pyrimidin-4-ylamino)isoindolin-1-one (5)

The synthesis of intermediate 5 was carried out as described above using the general protocol of Procedure A. Yield: 0.18 g, 30%; MS (ESI) m/z 389 [M+1]$^+$.

Synthesis of 3-isopropyl-5-(pyrimidin-4-ylamino)isoindolin-1-one (Cpd. No. 13)

The synthesis of compound 13 was carried out as described above using the general protocol of Procedure B. Yield: 0.11 g, 96%; MS (ESI) m/z 269 [M+1]$^+$; $^1$H NMR (400 MHz, DMSO-d$_6$) δ 11.06 (s, 1H), 8.94 (s, 1H), 8.63 (s, 1H), 8.41 (dd, J=6.8, 1.2 Hz, 1H), 7.96-7.91 (m, 1H), 7.75-7.64 (m, 2H), 7.04 (dd, J=6.9, 1.0 Hz, 1H), 4.55 (d, J=3.3 Hz, 1H), 2.2-2.18 (m, 1H), 1.00 (d, J=6.8 Hz, 3H), 0.62 (d, J=6.7 Hz, 3H).

Example 14

Synthesis of 5-(pyrimidin-4-ylamino)-2,3-dihydrobenzo[b]thiophene 1,1-dioxide (Cpd. No. 14)

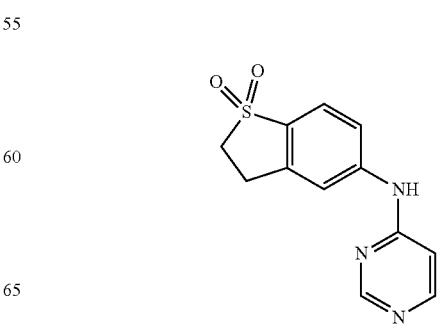

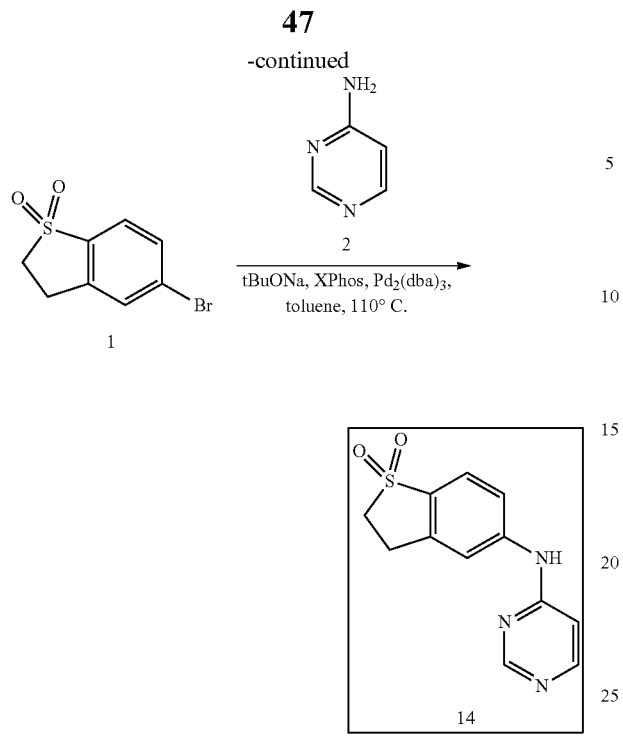

Synthesis of 5-(pyrimidin-4-ylamino)-2,3-dihydrobenzo[b]thiophene 1,1-dioxide (Cpd. No. 14)

The synthesis of compound 14 was carried out as described above using the general protocol of Procedure A. Yield: 0.044 g, 12%; MS (ESI) m/z 262 [M+1]$^+$; $^1$H NMR (400 MHz, DMSO-d$_6$) δ 10.04 (s, 1H), 8.73 (d, J=1.1 Hz, 1H), 8.38 (d, J=5.9 Hz, 1H), 8.00 (d, J=1.7 Hz, 1H), 7.79-7.62 (m, 2H), 6.90 (dd, J=5.9, 1.3 Hz, 1H), 3.55 (dd, J=7.5, 6.2 Hz, 2H), 3.40-3.27 (m, 2H).

Example 15

Synthesis of 3,3-dimethyl-5-(pyrimidin-4-ylamino) isoindolin-1-one (Cpd. No. 15)

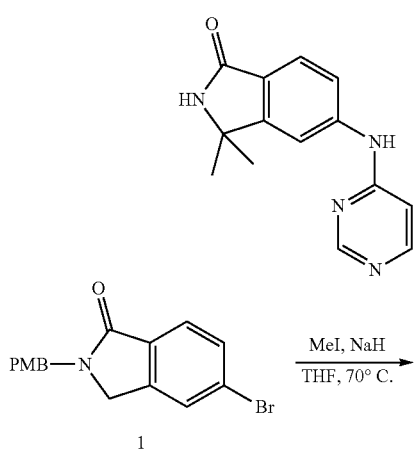

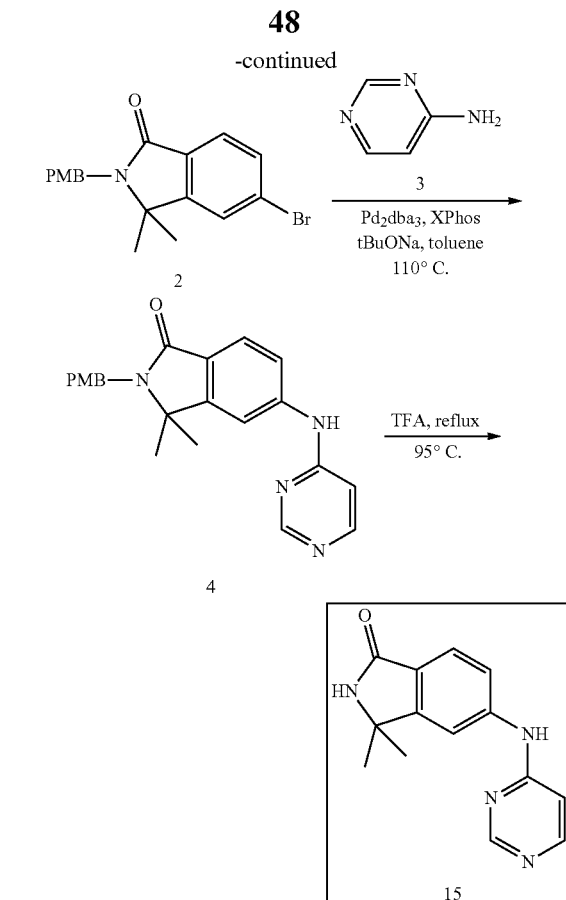

Synthesis of 5-bromo-2-(4-methoxybenzyl)-3,3-dimethylisoindolin-1-one (2)

To a solution of 5-bromo-2-(4-methoxybenzyl)isoindolin-1-one (1, 1 g, 3 mmol) in tetrahydrofuran (10 mL) at 0° C., sodium hydride (0.3 g, 7.5 mmol) was added portion wise and the reaction mixture was allowed to stir at room temperature for 30 min. Methyl iodide (0.57 mL, 9 mmol) was added and the reaction mixture was allowed to stir at 70° C. for 16 h. The reaction mixture was quenched with water and the compound was extracted in ethyl acetate. The organic layer was separated, dried over sodium sulphate and concentrated under reduced pressure. The residue was purified by silica gel column chromatography using 30% ethyl acetate in hexane as eluent to afford 5-bromo-2-(4-methoxybenzyl)-3,3-dimethylisoindolin-1-one (2). Yield: 0.4 g, 37%; MS (ESI) m/z 361 [M+1]$^+$.

Synthesis of 2-(4-methoxybenzyl)-3,3-dimethyl-5-(pyrimidin-4-ylamino)isoindolin-1-one (4)

The synthesis of intermediate 4 was carried out as described above using the general protocol of Procedure A. Yield: 0.2 g, 65%; MS (ESI) m/z 375 [M+1]$^+$.

Synthesis of 3,3-dimethyl-5-(pyrimidin-4-ylamino) isoindolin-1-one (Cpd. No. 15)

The synthesis of compound 15 was carried out as described above using the general protocol of Procedure B. Yield: 0.038 g, 22%; MS (ESI) m/z 255 [M+1]$^+$; $^1$H NMR (400 MHz, DMSO-d$_6$) δ 9.89 (s, 1H), 8.66 (s, 1H), 8.42 (s, 1H), 8.30 (d, J=5.9 Hz, 1H), 7.87 (d, J=1.9 Hz, 1H), 7.69 (dd, J=8.3, 1.9 Hz, 1H), 7.52 (d, J=8.3 Hz, 1H), 6.83 (dd, J=5.9, 1.3 Hz, 1H), 1.40 (s, 6H).

Example 16

Synthesis of 3-methyl-5-((6-(methylthio)pyrimidin-4-yl)amino)isoindolin-1-one (Cpd. No. 16)

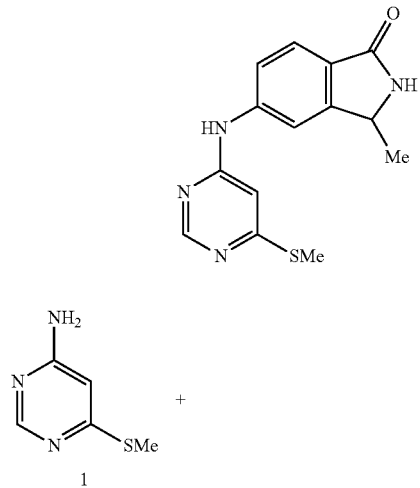

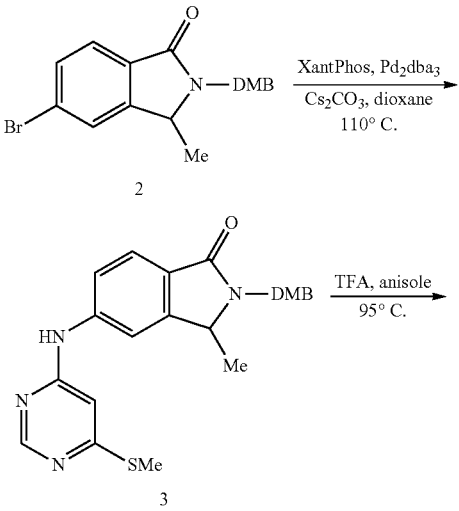

Synthesis of 2-(3,4-dimethylbenzyl)-3-methyl-5-((6-(methylthio)pyrimidin-4-yl)amino)isoindolin-1-one (3)

The synthesis of intermediate 3 was carried out as described above using the general protocol of Procedure A. Pale foamy yellow solid; Yield: 66 mg, 21%; MS (ESI) m/z 437 [M+1]$^+$.

Synthesis of 3-methyl-5-((6-(methylthio)pyrimidin-4-yl)amino)isoindolin-1-one (Cpd. No. 16)

To a solution of 2-(3,4-dimethylbenzyl)-3-methyl-5-((6-(methylthio)pyrimidin-4-yl)amino)isoindolin-1-one (3, 47 mg, 0.11 mmol) in anisole (3 mL) was added trifluoroacetic acid (2.0 mL, 26.1 mmol). The reaction was stirred at 95° C. for 16.5 h. The reaction mixture was concentrated at reduced pressure to produce a maroon residue. The residue was triturated with ether (5×2 mL) to provide a beige amorphous solid which was dried under high vacuum to provide 3-methyl-5-((6-(methylthio)pyrimidin-4-yl)amino)isoindolin-1-one (Cpd. No. 16) as a neat beige solid. Yield: 23 mg, 75%; MS (ESI) m/z 287 [M+1]$^+$; $^1$H NMR (500 MHz, DMSO-d$_6$) δ 9.87 (bs, 1H), 8.52 (s, 1H), 8.43 (s, 1H), 7.96 (s, 1H), 7.63 (dd, J=8.5, 2.0 Hz, 1H), 7.57 (d, J=8.0 Hz, 1H), 6.70 (d, J=1 Hz, 1H), 4.60 (q, J=6.5 Hz, 1H), 1.35 (d, J=7.0 Hz, 3H).

Example 17

Synthesis of N-(6-((3-methyl-1-oxoisoindolin-5-yl)amino)pyrimidin-4-yl)cyclopropanecarboxamide (Cpd. No. 17)

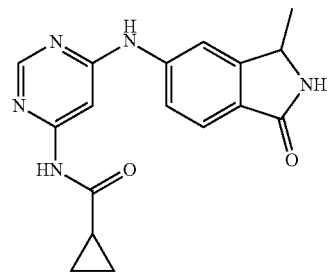

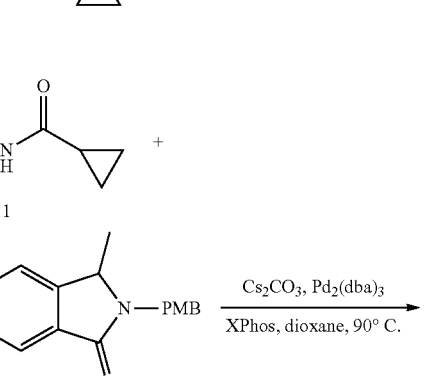

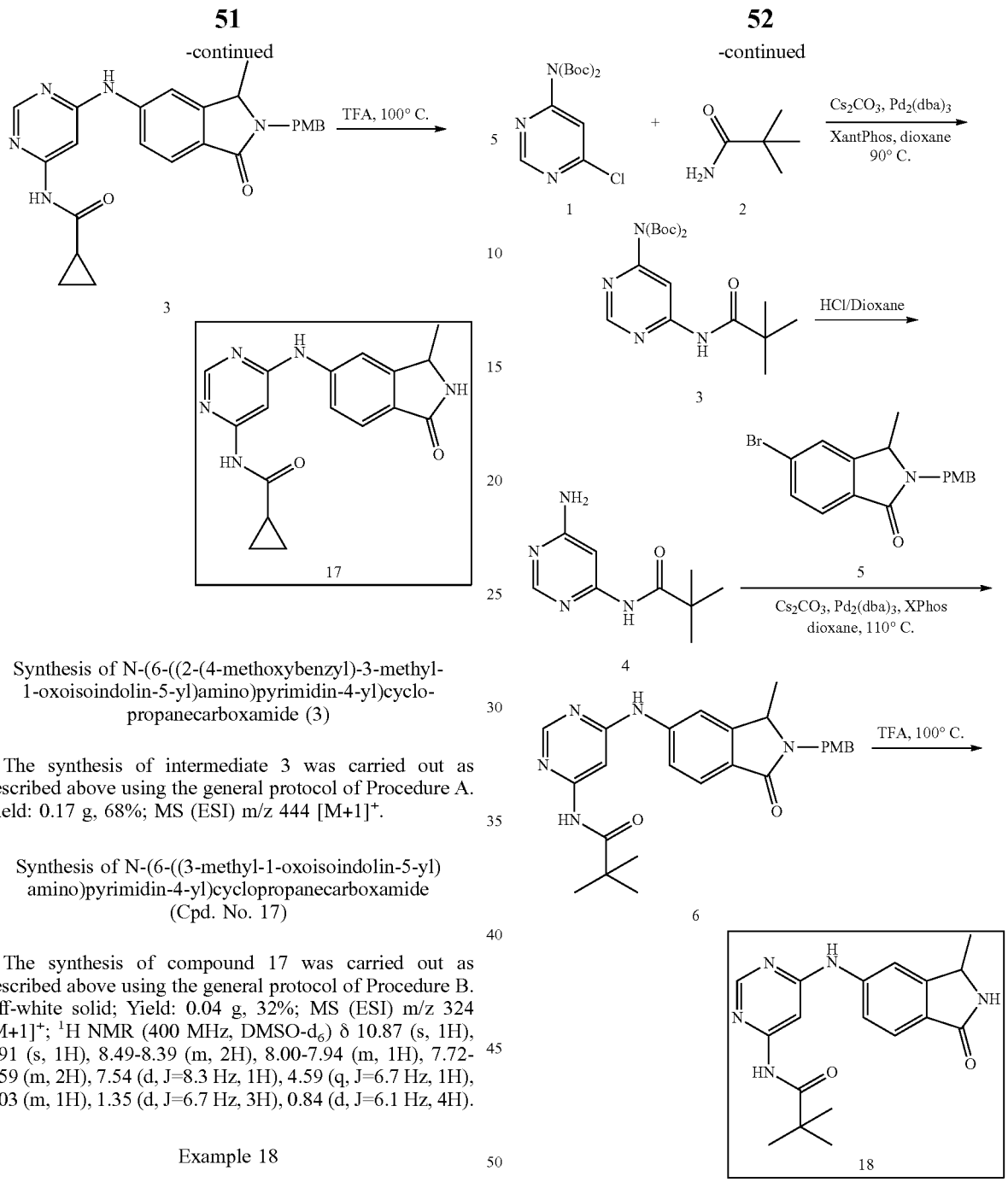

Synthesis of N-(6-((2-(4-methoxybenzyl)-3-methyl-1-oxoisoindolin-5-yl)amino)pyrimidin-4-yl)cyclopropanecarboxamide (3)

The synthesis of intermediate 3 was carried out as described above using the general protocol of Procedure A. Yield: 0.17 g, 68%; MS (ESI) m/z 444 [M+1]$^+$.

Synthesis of N-(6-((3-methyl-1-oxoisoindolin-5-yl)amino)pyrimidin-4-yl)cyclopropanecarboxamide (Cpd. No. 17)

The synthesis of compound 17 was carried out as described above using the general protocol of Procedure B. Off-white solid; Yield: 0.04 g, 32%; MS (ESI) m/z 324 [M+1]$^+$; $^1$H NMR (400 MHz, DMSO-d$_6$) δ 10.87 (s, 1H), 9.91 (s, 1H), 8.49-8.39 (m, 2H), 8.00-7.94 (m, 1H), 7.72-7.59 (m, 2H), 7.54 (d, J=8.3 Hz, 1H), 4.59 (q, J=6.7 Hz, 1H), 2.03 (m, 1H), 1.35 (d, J=6.7 Hz, 3H), 0.84 (d, J=6.1 Hz, 4H).

Example 18

Synthesis of N-(6-((3-methyl-1-oxoisoindolin-5-yl)amino)pyrimidin-4-yl)pivalamide (Cpd. No. 18)

Synthesis of tert-butyl N-tert-butoxycarbonyl-N-(6-pivalamidopyrimidin-4-yl)carbamate (3)

The synthesis of intermediate 3 was carried out as described above using the general protocol of Procedure A. Yield: 0.5 g, 84%; MS (ESI) m/z 395 [M+1]$^+$.

Synthesis of N-(6-aminopyrimidin-4-yl)pivalamide (4)

The synthesis of intermediate 4 was carried out as described above using the general protocol of Procedure C. Yield: 0.3 g, crude: MS (ESI) m/z 195 [M+1]$^+$.

Synthesis of N-(6-((2-(4-methoxybenzyl)-3-methyl-1-oxoisoindolin-5-yl)amino)pyrimidin-4-yl)pivalamide (6)

The synthesis of intermediate 6 was carried out as described above using the general protocol of Procedure A. Yield: 0.18 g, 54%; MS (ESI) m/z 460 [M+1]$^+$.

Synthesis of N-(6-((3-methyl-1-oxoisoindolin-5-yl)amino)pyrimidin-4-yl)pivalamide (Cpd. No. 18)

The synthesis of compound 18 was carried out as described above using the general protocol of Procedure B. Off-white solid; Yield: 0.055 g, 42%; MS (ESI) m/z 340 [M+1]$^+$; $^1$H NMR (400 MHz, DMSO-d$_6$) δ 9.92 (d, J=3.1 Hz, 2H), 8.48 (s, 1H), 8.41 (s, 1H), 7.99 (s, 1H), 7.72-7.64 (m, 2H), 7.55 (d, J=8.3 Hz, 1H), 4.59 (q, J=6.9 Hz, 1H), 3.17 (s, 1H), 1.35 (d, J=6.6 Hz, 3H), 1.24 (s, 9H).

Example 19

Synthesis of N-(6-((3-methyl-1-oxo-2,3-dihydro-1H-inden-5-yl)amino)pyrimidin-4-yl)cyclopropanecarboxamide (Cpd. No. 19)

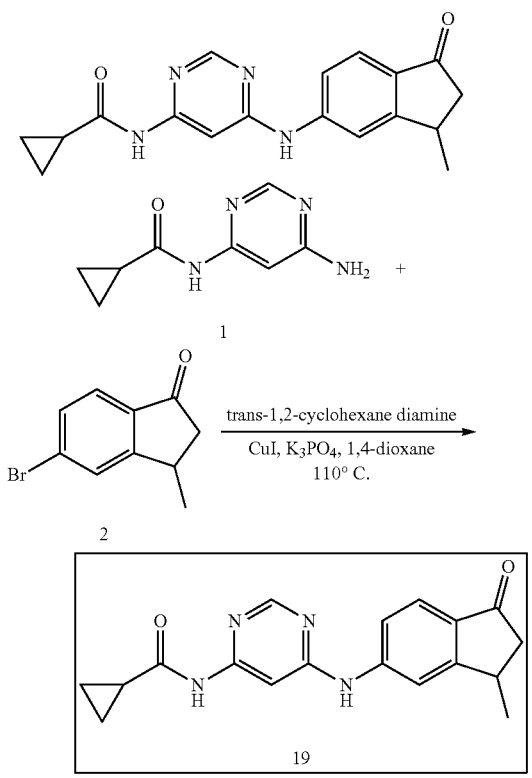

Synthesis of N-(6-((3-methyl-1-oxo-2,3-dihydro-1H-inden-5-yl)amino)pyrimidin-4-yl)cyclopropanecarboxamide (Cpd. No. 19)

To a stirred solution of N-(6-aminopyrimidin-4-yl)cyclopropanecarboxamide (1, 0.64 g, 3.5 mmol) in 1,4-dioxane (20 mL) were added 5-bromo-3-methyl-2,3-dihydro-1H-inden-1-one (2, 0.8 g, 3.5 mmol) and potassium phosphate (2.28 g, 10.7 mmol). The reaction mixture was degassed using argon balloon for 15 minutes. Then trans-1,2-cyclohexane diamine (0.34 g, 1.79 mmol) and copper(I) iodide (0.20 g, 1.79 mmol) was added to reaction mixture and the reaction was degassed for another 15 minutes. The reaction was stirred at 110° C. for 16 h. Progress of reaction was monitored by TLC. After the consumption of starting material, reaction mixture was cooled to room temperature, quenched with water and extracted with ethyl acetate. The organic layer was washed with brine solution, dried over anhydrous sodium sulfate, filtered and concentrated under reduced pressure. The resulting residue was purified using column chromatography on silica gel (100-200 mesh) using 2-5% methanol in dichloromethane. The desired fractions were concentrated to afford N-(6-((3-methyl-1-oxo-2,3-dihydro-1H-inden-5-yl)amino)pyrimidin-4-yl)cyclopropanecarboxamide (Cpd. No. 19) as a brown solid. Yield: 0.057 g, 4%; MS (ESI) m/z 323.09 [M+1]$^+$; $^1$H NMR (400 MHz, DMSO-d$_6$) δ 10.931 (s, 1H), 10.066 (s, 1H), 8.518 (s, 1H), 8.042 (s, 1H), 7.69-7.66 (m, 2H), 7.54 (d, J=8.4 Hz, 1H), 3.32 (m, 1H), 2.87 (m, 1H), 2.20-2.14 (m, 1H), 2.06-2.00 (m, 1H), 1.329-1.312 (d, J=6.8 Hz, 3H), 0.85 (s, 4H).

Example 20

Synthesis of 2,3-dimethyl-5-(pyrimidin-4-ylamino)isoindolin-1-one (Cpd. No. 20)

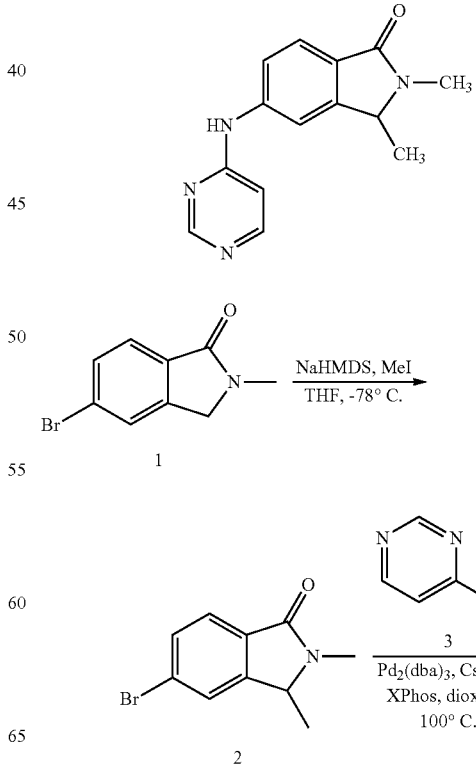

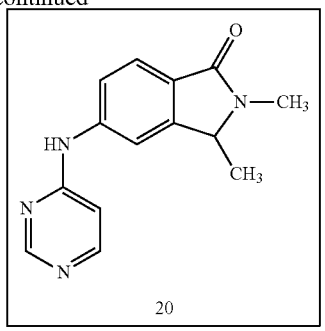

Synthesis of 5-bromo-2,3-dimethylisoindolin-1-one (2)

To a solution of 5-bromo-2-methylisoindolin-1-one (1, 1 g, 4.42 mmol) in tetrahydrofuran (20 mL) at −78° C., sodium hexamethyldisilazane (4.4 mL, 4.86 mmol 1M solution in tetrahydrofuran) was added and the reaction mixture was allowed to stir at the same temperature for 15 min. Methyl iodide (0.55 mL, 8.85 mmol) was added and the reaction mixture was stirred at −78° C. for 2 h. The reaction mixture was quenched with water and extracted with ethyl acetate. The organic layer was washed with brine, separated, dried over sodium sulphate and concentrated under reduced pressure. The residue was purified by silica gel column chromatography using 30% ethyl acetate in hexanes as eluent to afford 5-bromo-2,3-dimethylisoindolin-1-one (2). Yield: 0.1 g, 9%; MS (ESI) m/z 240 [M+1]$^+$.

Synthesis of 2,3-dimethyl-5-(pyrimidin-4-ylamino) isoindolin-1-one (Cpd. No. 20)

The synthesis of compound 20 was carried out as described above using the general protocol of Procedure A. Yield: 0.07 g, 22%; MS (ESI) m/z 255 [M+1]$^+$; $^1$H NMR (400 MHz, DMSO-d$_6$) δ 9.93 (s, 1H), 8.70 (s, 1H), 8.34 (d, J=5.9 Hz, 1H), 8.02 (s, 1H), 7.70 (d, J=8.3 Hz, 1H), 7.60 (d, J=8.2 Hz, 1H), 6.87 (d, J=5.9 Hz, 1H), 4.54 (q, J=6.7 Hz, 1H), 2.98 (s, 3H), 1.41 (d, J=6.7 Hz, 3H).

Example 21

Synthesis of 3-methyl-6-(pyrimidin-4-ylamino)-3,4-dihydroquinolin-2(1H)-one (Cpd. No. 21)

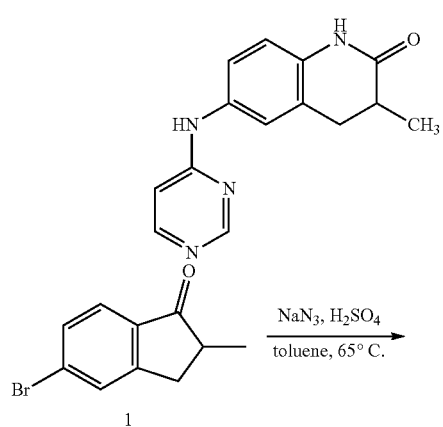

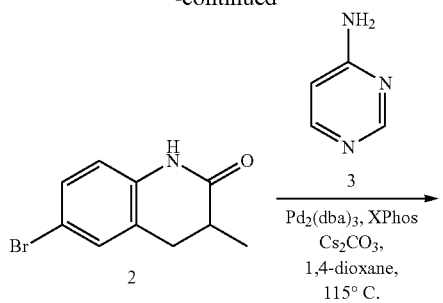

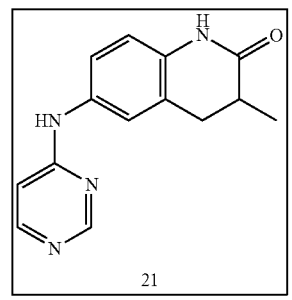

Synthesis of 6-bromo-3-methyl-3,4-dihydroquinolin-2(1H)-one (2)

To a solution of 5-bromo-2-methyl-2,3-dihydro-1H-inden-1-one (1, 5.0 g, 22.2 mmol) in toluene (50 mL) at 65° C. was added concentrated sulfuric acid (21.7 g, 222.0 mmol), followed by the lot wise addition of sodium azide (1.8 gm, 28.8 mmol). Heating was continued for 3 h at 65° C. Progress of the reaction was monitored by TLC. After completion, the reaction mass was quenched with cold water, basified with sodium carbonate and extracted with ethyl acetate. The organic layer was separated, dried over anhydrous sodium sulphate and concentrated under reduced pressure. The residue was purified via column chromatography using 18% ethyl acetate in hexane to afford 6-bromo-3-methyl-3,4-dihydroquinolin-2(1H)-one (2) as a yellow solid. Yield: 1.6 g, 30%; MS (ESI) m/z 240.95 [M+1]$^+$; $^1$H NMR (400 MHz, CDCl$_3$) δ 7.72 (bs, 1H), 7.29 (s, 1H), 7.27 (d, J=5.7 Hz, 1H), 6.62 (d, J=6.0 Hz, 1H), 2.97 (dd, J=5.2, 15.6 Hz, 1H), 2.73 (t, J=13.0 Hz, 1H), 2.63 (m, 1H), 1.28 (d, J=6.8 Hz, 3H).

Synthesis of 3-methyl-6-(pyrimidin-4-ylamino)-3,4-dihydroquinolin-2(1H)-one (Cpd. No. 21)

The synthesis of compound 21 was carried out as described above using the general protocol of Procedure A. Off-white solid. Yield: 0.035 g, 13%; MS (ESI) m/z 255.09 [M+1]$^+$; $^1$H NMR (400 MHz, DMSO-d$_6$) δ 10.01 (s, 1H), 9.42 (s, 1H), 8.54 (s, 1H), 8.19 (d, J=6.0 Hz, 1H), 7.45 (s, 1H), 7.34 (d, J=8.4 8 Hz, 1H), 6.80 (d, J=8.4 Hz, 1H), 6.69 (d, J=5.6 Hz, 1H), 2.91 (dd, J=5.6 Hz, J=15.6 Hz, 1H), 2.64 (m, 1H), 2.46 (bs, merged with solvent peak, 1H), 1.12 (d, J=6.8 Hz, 3H).

Example 22

Synthesis of 4-methyl-6-(pyrimidin-4-ylamino)-3,4-dihydroisoquinolin-1(2H)-one (Cpd. No. 22)

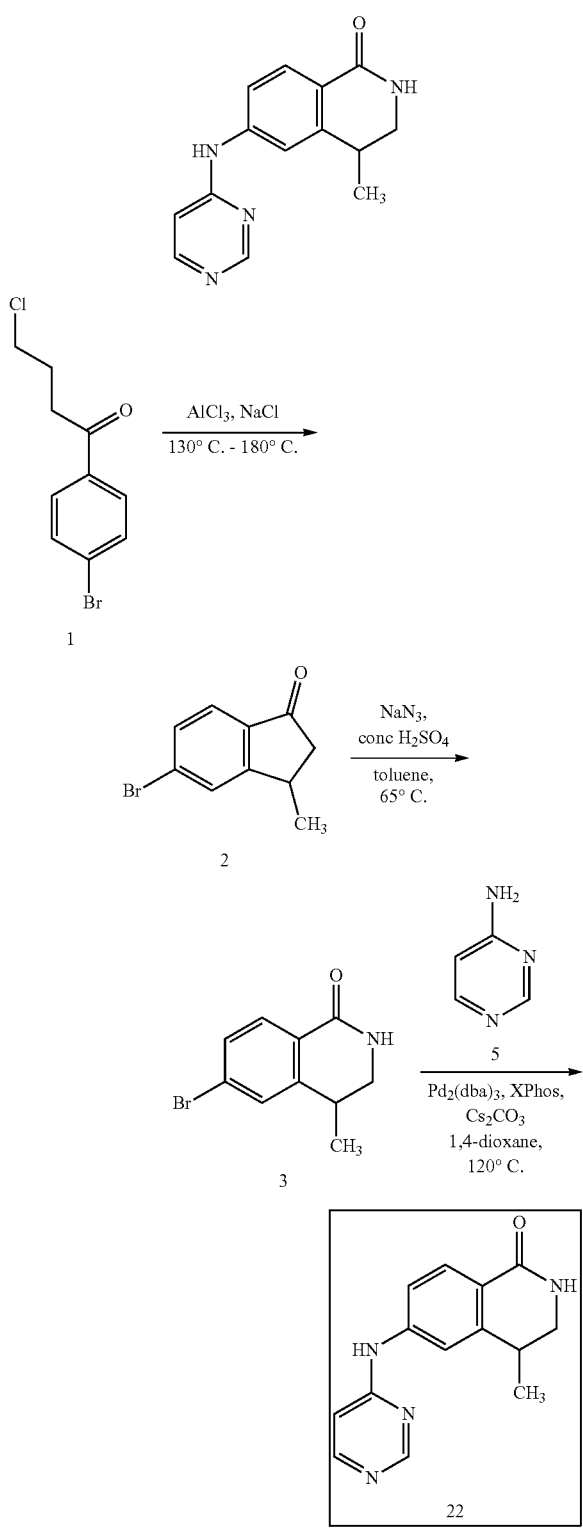

Synthesis of 5-bromo-3-methyl-2,3-dihydro-1H-inden-1-one (2)

Sodium chloride (22.33 g, 382.35 mmol) and aluminum chloride (101.93 g, 764.7 mmol) were mixed at room temperature and heated at 130° C. for 1 h. 1-(4-bromophenyl)-4-chloro-butan-1-one (1, 20.0 g, 76.47 mmol) was added and the reaction mixture was stirred at 180° C. for 30 min. Progress of the reaction was monitored by TLC. After completion, the reaction mixture was quenched with ice water and acidified with 1 M hydrochloric acid to pH=3-4. The resulting mixture was extracted with ethyl acetate. The organic layer was separated, dried over sodium sulphate and concentrated under reduced pressure. The residue was purified via column chromatography using 5% ethyl acetate in hexane to afford 5-bromo-3-methyl-2,3-dihydro-1H-inden-1-one (2) as light brown solid. Yield: 14.02 g, 83%; MS (ESI) m/z 224.82 [M+1]$^+$.

Synthesis of 6-bromo-4-methyl-3, 4-dihydroisoquinolin-1 (2H)-one (3)

To a stirred solution of 5-bromo-3-methyl-indan-1-one (2, 4.0 g, 17.77 mmol) in toluene at 65° C., sulfuric acid (17.42 g, 177.71 mmol) was added slowly. Then sodium azide (1.5 g, 23.1 mmol) was added portion wise. The reaction was allowed to run at 65° C. for 2 h. Progress of the reaction was monitored by TLC. After completion, the reaction mass was quenched with saturated aqueous sodium bicarbonate solution. The mixture was extracted with ethyl acetate twice. The organic layer was separated, dried over sodium sulphate and concentrated under reduced pressure. The residue was purified via column chromatography using 20% ethyl acetate in hexane to afford 6-bromo-4-methyl-3, 4-dihydroisoquinolin-1(2H)-one (3) as white solid. Yield: 0.5 g, 12%; MS (ESI) m/z 240.02 [M+1]$^+$.

Synthesis of 4-methyl-6-(pyrimidin-4-ylamino)-3,4-dihydroisoquinolin-1 (2H)-one (Cpd. No. 22)

The synthesis of compound 22 was carried out as described above using the general protocol of Procedure A. White solid; Yield: 0.045 g, 13%; MS (ESI) m/z 255.09 [M+1]$^+$; $^1$H NMR (400 MHz, DMSO-d$_6$) δ 9.87 (s, 1H), 8.69 (s, 1H), 8.33 (s, 1H), 7.72 (m, 4H), 6.87 (s, 1H), 3.44 (s, 1H), 3.07 (m, 2H), 1.25 (s, 3H).

Example 23

Synthesis of 3-methyl-6-(pyrimidin-4-ylamino)-3,4-dihydroisoquinolin-1(2H)-one (Cpd. No. 23)

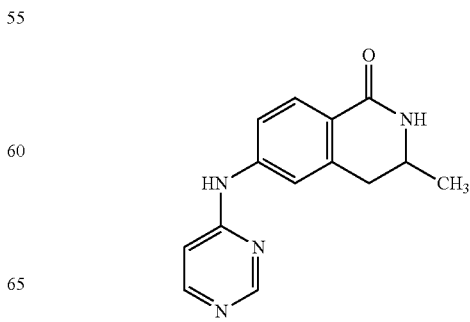

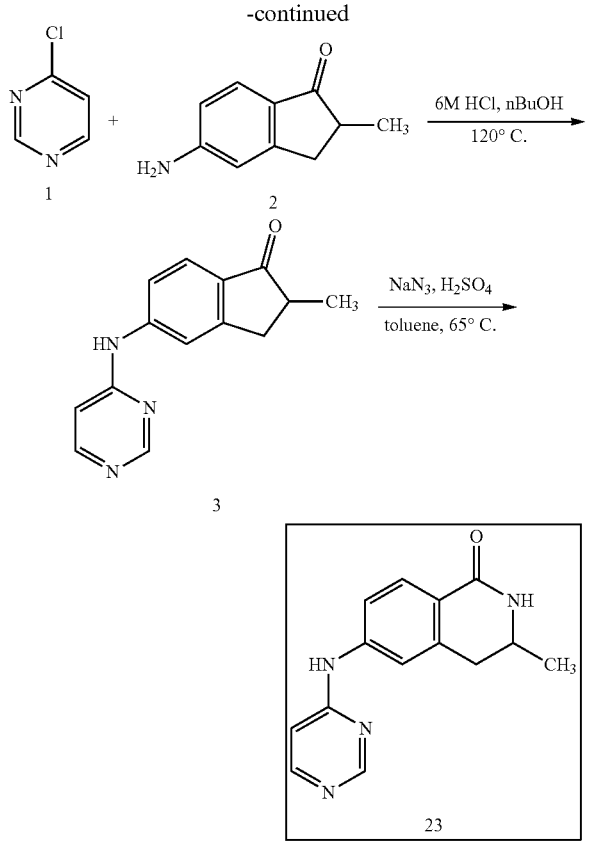

Synthesis of 2-methyl-5-(pyrimidin-4-ylamino)-2,3-dihydro-1H-inden-1-one (3)

To a solution of 4-chloropyrimidine (1, 0.83 g, 7.31 mmol) and 5-amino-2-methyl-2, 3-dihydro-1H-inden-1-one (2, 0.98 g, 6.09 mmol) in n-butanol at room temperature was added 6 M hydrochloric acid (0.1 mL). The reaction mixture was stirred at room temperature for 10 min, then at 120° C. in microwave for 0.5 h. Progress of the reaction was monitored by TLC. After completion, the reaction mass was quenched with saturated aqueous sodium bicarbonate solution and extracted with ethyl acetate. The organic layer was separated, dried over sodium sulphate, filtered and concentrated under reduced pressure to afford 2-methyl-5-(pyrimidin-4-ylamino)-2,3-dihydro-1H-inden-1-one (3) as a brown solid. The residue obtained was used for next step without any purification. Yield: 0.6 g, 41%; Mass m/z 240.3 [M+1]$^+$.

Synthesis of 3-methyl-6-(pyrimidin-4-ylamino)-3,4-dihydroisoquinolin-1(2H)-one (Cpd. No. 23)

To a solution of 2-methyl-5-(pyrimidin-4-ylamino)-2,3-dihydro-1H-inden-1-one (3, 0.5 g, 2.09 mmol) in toluene at 65° C. was added concentrated sulfuric acid (2.05 g, 20.9 mmol) followed by the lot wise addition of sodium azide (0.18 g, 2.72 mmol). Heating was continued for 3 h at 65° C. Progress of the reaction was monitored by TLC. After completion, the reaction mass was quenched with cold water, basified with sodium carbonate and extracted with ethyl acetate. The organic layer was separated, dried over sodium sulphate, filtered and concentrated under reduced pressure. The residue was purified via column chromatography using 18% ethylacetate in hexane to afford 3-methyl-6-(pyrimidin-4-ylamino)-3, 4-dihydroisoquinolin-1(2H)-one (Cpd. No. 23) as a white solid. Yield: 0.018 g, 4%; MS (ESI) m/z 255.09 [M+1]$^+$; $^1$H NMR (400 MHz, DMSO-d$_6$) δ 9.89 (s, 1H), 8.70 (s, 1H), 8.33 (d, J=6.0 Hz, 1H), 7.79 (d, J=8.4 Hz, 1H), 7.73 (s, 1H), 7.66 (s, 1H), 7.63 (d, J=9.6 Hz, 1H), 6.87 (d, J=6.0 Hz, 1H), 3.68 (bs, 1H), 2.92 (d, J=12.4 Hz, 1H), 2.69 (t, J=9.2 Hz, 1H), 1.19 (d, J=6.4 Hz, 3H).

Example 24

Synthesis of N-(4-((3-methyl-1-oxoisoindolin-5-yl)amino) pyridin-2-yl) cyclopropane carboxamide (Cpd. No. 24)

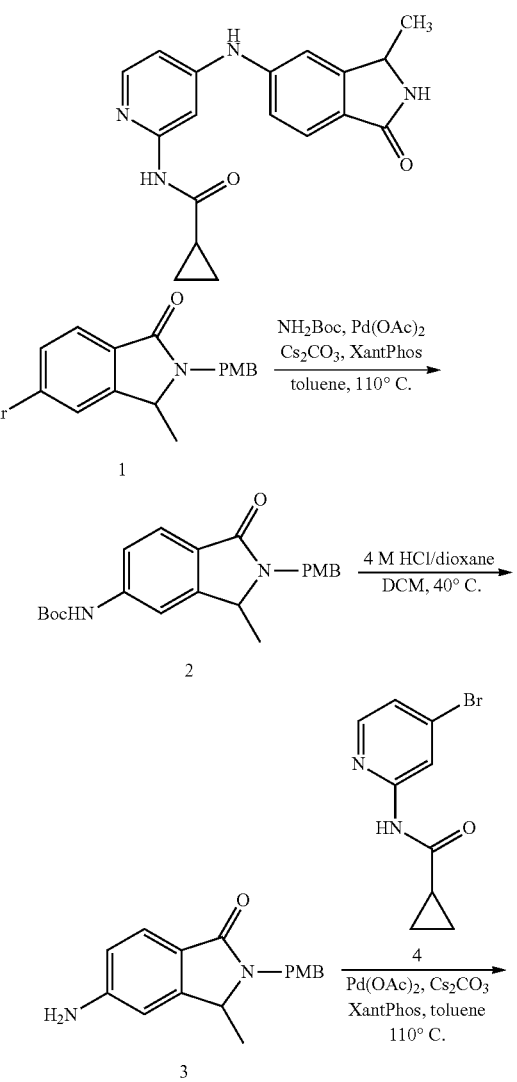

-continued

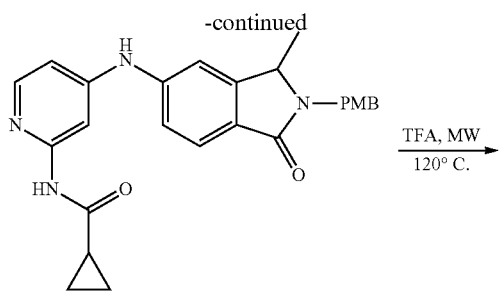

5

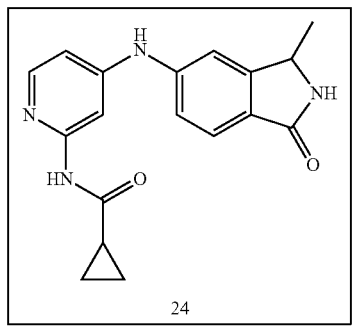 [SMILES: CC1NC(=O)c2ccc(Nc3ccnc(NC(=O)C4CC4)c3)cc21]

24

Synthesis of tert-butyl (2-(4-methoxybenzyl)-3-methyl-1-oxoisoindolin-5-yl)carbamate (2)

A solution of 5-bromo-2-(4-methoxybenzyl)-3-methyl-isoindolin-1-one (1, 0.6 g, 1.74 mmol), tert-butyl carbamate (0.30 g, 2.61 mmol) and cesium carbonate (1.6 g, 5.22 mmol) in toluene (12 ml) was degassed with argon for 15 min. Then palladium acetate (0.039 g, 0.17 mmol) and XantPhos (0.1 g, 0.17 mmol) were added under nitrogen atmosphere and purging was continued for another 10 min. The reaction was refluxed at 110° C. for 16 h. Progress of the reaction was monitored by TLC. After completion, the reaction mass was quenched with water and extracted with ethyl acetate. The organic layer was further washed with brine, separated, dried over sodium sulphate, filtered and concentrated under reduced pressure. The resulting residue was purified using column chromatography on silica gel (100-200 mesh) using 10-20% Ethyl acetate in hexane to afford tert-butyl (2-(4-methoxybenzyl)-3-methyl-1-oxoisoindolin-5-yl)carbamate (2) as yellow solid. Yield: 0.36 g, 54%; MS (ESI) m/z 383.08 [M+1]$^+$.

Synthesis of 5-amino-2-(4-methoxybenzyl)-3-methylisoindolin-1-one (3)

Tert-butyl (2-(4-methoxybenzyl)-3-methyl-1-oxoisoindolin-5-yl)carbamate (2, 0.31 g, 0.81 mmol) was dissolved in dichloromethane (10 ml) and 4 M hydrogen chloride in dioxane (3.1 ml) was added. The reaction mixture was refluxed at 40° C. for 3 h. Progress of the reaction was monitored by TLC. After completion, solvent was removed and the reaction mass was diluted with water. The resulting aqueous layer was basified with saturated aqueous sodium bicarbonate and extracted with ethyl acetate thrice. The combined organic layer was dried over sodium sulphate, filtered and concentrated under reduced pressure to get 5-amino-2-(4-methoxybenzyl)-3-methylisoindolin-1-one (3) as brown solid. Yield: 0.22 g, crude; MS (ESI) m/z 283.13 [M+1]$^+$.

Synthesis of N-(4-((2-(4-methoxybenzyl)-3-methyl-1-oxoisoindolin-5-yl) amino) pyridin-2-yl) cyclopropanecarboxamide (5)

The synthesis of intermediate 5 was carried out as described above using the general protocol of Procedure A. Yellow solid; Yield: 0.18 g, 50%; MS (ESI) m/z 443.14 [M+1]$^+$.

Synthesis of N-(4-((3-methyl-1-oxoisoindolin-5-yl) amino) pyridin-2-yl) cyclopropane carboxamide (Cpd. No. 24)

The synthesis of compound 24 was carried out as described above using the general protocol of Procedure B. White solid. Yield: 0.03 g, 24%; MS (ESI) m/z 323.10 [M+1]$^+$; $^1$H NMR (400 MHz, DMSO-d$_6$) δ 10.55 (s, 1H), 9.19 (s, 1H), 8.41 (s, 1H), 8.00 (d, J=5.6 Hz, 1H), 7.89 (s, 1H), 7.54 (d, J=8.4 Hz, 1H), 7.32 (s, 1H), 7.20 (d, J=8.8 Hz, 1H), 6.75 (t, J=5.6 Hz, 1H), 4.56 (m, 1H), 1.98 (bs, 1H), 1.35 (d, J=6.4 Hz, 3H), 0.78 (bs, 4H).

Example 25

Synthesis of 3-methyl-5-((2-(methyl amino) pyridin-4-yl) amino) isoindolin-1-one (Cpd. No. 25)

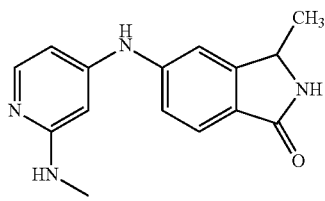

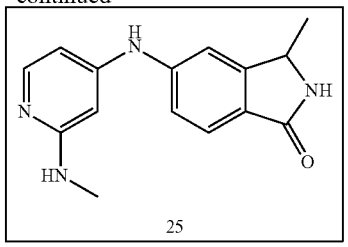

Synthesis of 2-(4-methoxybenzyl)-3-methyl-5-((2-(methylamino) pyridin-4-yl) amino) isoindolin-1-one (3)

The synthesis of intermediate 3 was carried out as described above using the general protocol of Procedure A. Yellow solid; Yield: 0.22 gm, 25%; MS (ESI) m/z 389.30 [M+1]$^+$.

Synthesis of 3-methyl-5-((2-(methyl amino) pyridin-4-yl) amino) isoindolin-1-one (Cpd. No. 25)

The synthesis of compound 25 was carried out as described above using the general protocol of Procedure B. White solid. Yield: 0.042 g, 27%; MS (ESI) m/z 269.13 [M+1]$^+$; NMR (400 MHz, DMSO-d$_6$) δ 8.86 (s, 1H), 8.37 (s, 1H), 7.75 (d, J=5.6 Hz, 1H), 7.52 (d, J=8.4 Hz, 1H), 7.26 (s, 1H), 7.16 (d, J=7.2 Hz, 1H), 6.34 (s, 1H), 6.27 (d, J=5.6 Hz, 1H), 6.14 (s, 1H), 4.55 (m, 1H), 2.73 (d, J=4.8 Hz, 3H), 1.35 (d, J=6.4 Hz, 3H).

Example 26

Synthesis of 3-methyl-5-((6-methylpyrimidin-4-yl) amino)isoindolin-1-one (Cpd. No. 26)

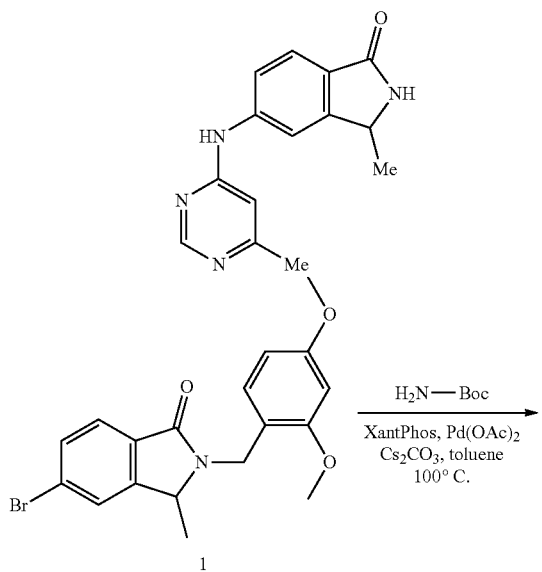

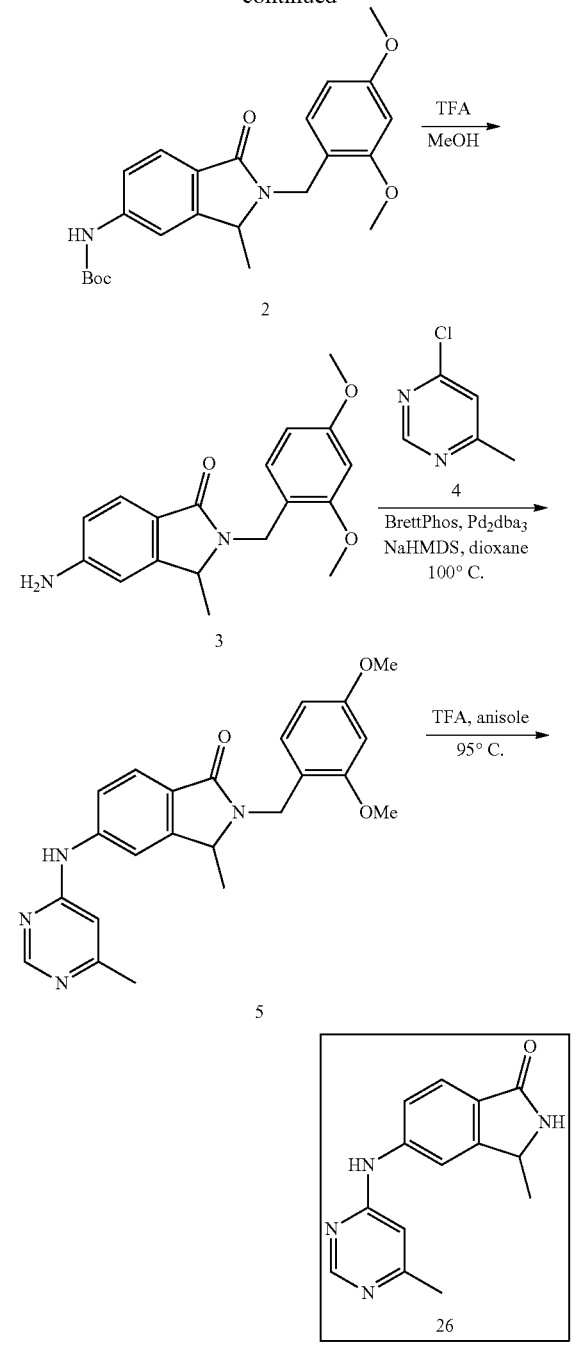

Synthesis of tert-butyl (2-(2,4-dimethoxybenzyl)-3-methyl-1-oxoisoindolin-5-yl)carbamate (2)

A suspension of 5-bromo-2-(2,4-dimethoxybenzyl)-3-methylisoindolin-1-one (1, 643 mg, 1.71 mmol), tert-butyl carbamate (200 mg, 1.71 mmol) and cesium carbonate (1.11 g, 3.41 mmol) was sparged with argon for 30 min at room temperature. Palladium acetate (26 mg, 0.11 mmol) and XantPhos (66 mg, 0.11 mmol) were added and the reaction mixture was sparged with argon for another 10 min. The reaction was stirred at 100° C. for 16 h. After cooling to ambient temperature, the reaction mixture was diluted with water and extracted with ethyl acetate. The combined organic layers were then dried with sodium sulfate, decanted and concentrated under reduced pressure. The subsequent yellow-orange crude solid was then purified via silica gel chromatography, eluting the desired product utilizing a gradient (ISCO Gold Series—24 g silica; 20-60% ethyl acetate/hexanes), providing tert-butyl (2-(2,4-dimethoxybenzyl)-3-methyl-1-oxoisoindolin-5-yl)carbamate (2) as a pale-orange solid. Yield: 112 mg, 24%.

Synthesis of 5-amino-2-(2,4-dimethoxybenzyl)-3-methylisoindolin-1-one (3)

To a solution of tert-butyl (2-(2,4-dimethoxybenzyl)-3-methyl-1-oxoisoindolin-5-yl)carbamate (2, 112 mg, 0.27 mmol) in methanol (1.4 mL) was added trifluoroacetic acid (0.1 mL, 1.36 mmol). After the starting material was consumed by TLC, the reaction mixture was concentrated to provide a neat residue. The residue was further dried under reduced pressure and used without further purification.

Synthesis of 2-(2,4-dimethoxybenzyl)-3-methyl-5-((6-methylpyrimidin-4-yl)amino)isoindolin-1-one (5)

The synthesis of intermediate 5 was carried out as described above using the general protocol of Procedure A. Yield: 15 mg, 48%. MS (ESI) m/z 405 [M+1]$^+$.

Synthesis of 3-methyl-5-((6-methylpyrimidin-4-yl)amino)isoindolin-1-one (Cpd. No. 26)

To a solution of 2-(2,4-dimethoxybenzyl)-3-methyl-5-((6-methylpyrimidin-4-yl)amino)isoindolin-1-one (5, 15 mg, 0.04 mmol) in anisole (1 mL) was added trifluoroacetic acid (0.7 mL, 9.14 mmol). The reaction was stirred at 95° C. overnight. The reaction mixture was concentrated under reduced pressure. The reddish-brown residue thus obtained was then triturated with ether (5×3 mL) to provide 3-methyl-5-((6-methylpyrimidin-4-yl)amino)isoindolin-1-one (Cpd. No. 26) as a beige-brown solid. Yield: 6.3 mg, 66%; MS (ESI) m/z 255 [M+1]$^+$; $^1$H NMR (300 MHz, CD$_3$OD) δ 8.74 (s, 1H), 7.92 (s, 1H), 7.75 (d, J=8.1 Hz, 1H), 7.64 (dd, J=8.1, 1.5 Hz, 1H), 6.86 (s, 1H), 4.68 (q, J=6.6 Hz, 1H), 2.49 (s, 3H), 1.43 (d, J=6.6 Hz, 3H).

Example 27

Synthesis of 6-(pyrimidin-4-ylamino)benzo[d]isothiazol-3(2H)-one (Cpd. No. 27)

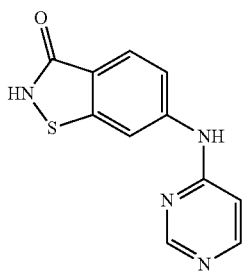

Synthesis of 6-bromobenzo[d]isothiazol-3(2H)-one (3)

To a solution of phenylmethanethiol (2, 1.29 g, 10.0 mmol) in tetrahydrofuran (26 mL) at 0° C., sodium hydride (0.48 g, 12.0 mmol) was added portion wise and the reaction mixture was stirred at room temperature for 1 h. A solution of 4-bromo-2-fluorobenzamide (1, 2.38 g, 10.0 mmol) in tetrahydrofuran (10 mL) was added and the reaction mixture was heated at 70° C. for 4 h. The reaction was quenched with water and extracted in ethyl acetate. The organic layer was separated, dried over sodium sulphate, decanted and concentrated under reduced pressure. The residue was dissolved in dichloromethane (85 mL) and cooled to 0° C. To this solution was added sulfuryl chloride (1 mL). The reaction was stirred at room temperature for 1 h. The reaction mixture was diluted with pentane (64 mL), filtered and dried to afford 6-bromobenzo[d]isothiazol-3(2H)-one (3). The crude compound was used as such for the next step without purification. Yield: 1.2 g, 47%; MS (ESI) m/z 231 [M+1]$^+$.

Synthesis of 6-(pyrimidin-4-ylamino)benzo[d]isothiazol-3(2H)-one (Cpd. No. 27)

The synthesis of compound 27 was carried out as described above using the general protocol of Procedure A. Yield: 0.042 g, 6%; MS (ESI) m/z 245.10 [M+1]$^+$; $^1$H NMR (400 MHz, DMSO-d$_6$) δ 11.0 (brs, 1H), 10.06 (s, 1H), 8.72 (s, 1H), 8.51 (d, J=1.7 Hz, 1H), 8.36 (d, J=5.9 Hz, 1H), 7.79 (d, J=8.6 Hz, 1H), 7.55 (dd, J=8.7, 1.9 Hz, 1H), 6.92 (dd, J=6.0, 1.2 Hz, 1H).

Example 28

Synthesis of 3-amino-5-(pyrimidin-4-ylamino)-2,3-dihydro-1H-inden-1-one (Cpd. No. 28)

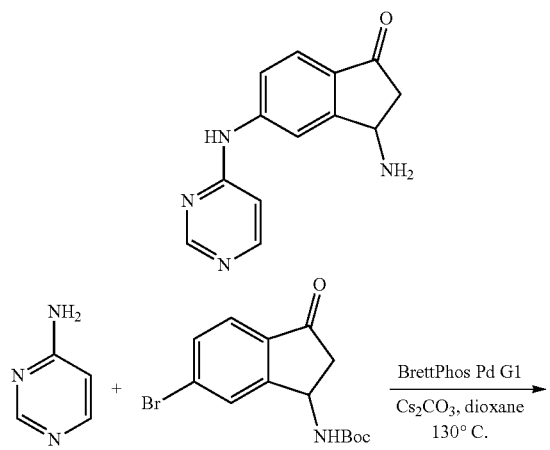

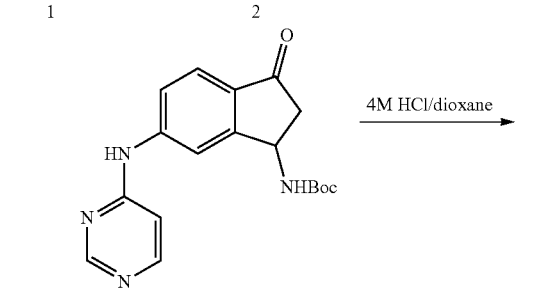

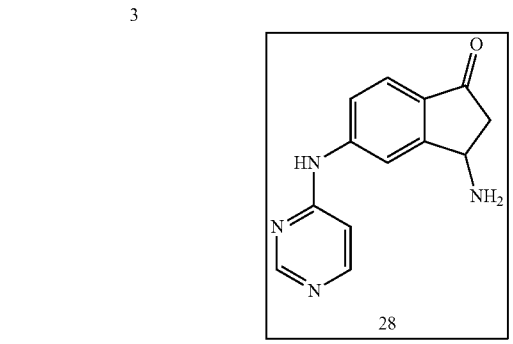

Synthesis of tert-butyl (3-oxo-6-(pyrimidin-4-ylamino)-2,3-dihydro-1H-inden-1-yl)carbamate (3)

The synthesis of intermediate 3 was carried out as described above using the general protocol of Procedure A. Yield: 0.27 g, 64%; MS (ESI) m/z 341 [M+1]$^+$.

Synthesis of 3-amino-5-(pyrimidin-4-ylamino)-2,3-dihydro-1H-inden-1-one (Cpd. No. 28)

The synthesis of compound 28 was carried out as described above using the general protocol of Procedure C. Yield: 0.093 g, 51%; MS (ESI) m/z 241 [M+1]$^+$; $^1$H NMR (400 MHz, DMSO-d$_6$) δ 10.09 (s, 1H), 8.74 (d, J=1.2 Hz, 1H), 8.39 (d, J=5.9 Hz, 1H), 8.20-8.14 (m, 1H), 7.72 (dd, J=8.4, 1.9 Hz, 1H), 7.56 (d, J=8.4 Hz, 1H), 6.94 (dd, J=5.9, 1.3 Hz, 1H), 4.41 (dd, J=7.1, 3.5 Hz, 1H), 2.93 (dd, J=18.4, 7.1 Hz, 1H), 2.58-2.51 (m, 1H), 2.46-2.40 (m, 1H), 2.28 (dd, J=18.4, 3.6 Hz, 1H).

Example 29

Synthesis of 6-(pyrimidin-4-ylamino)-1,1a,2,7b-tetrahydro-3H-cyclopropa[c]isoquinolin-3-one (Cpd. No. 29)

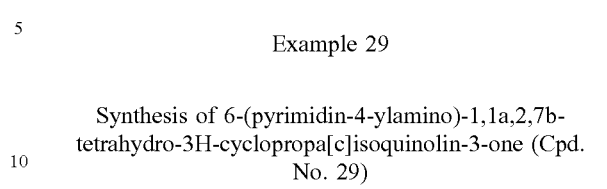

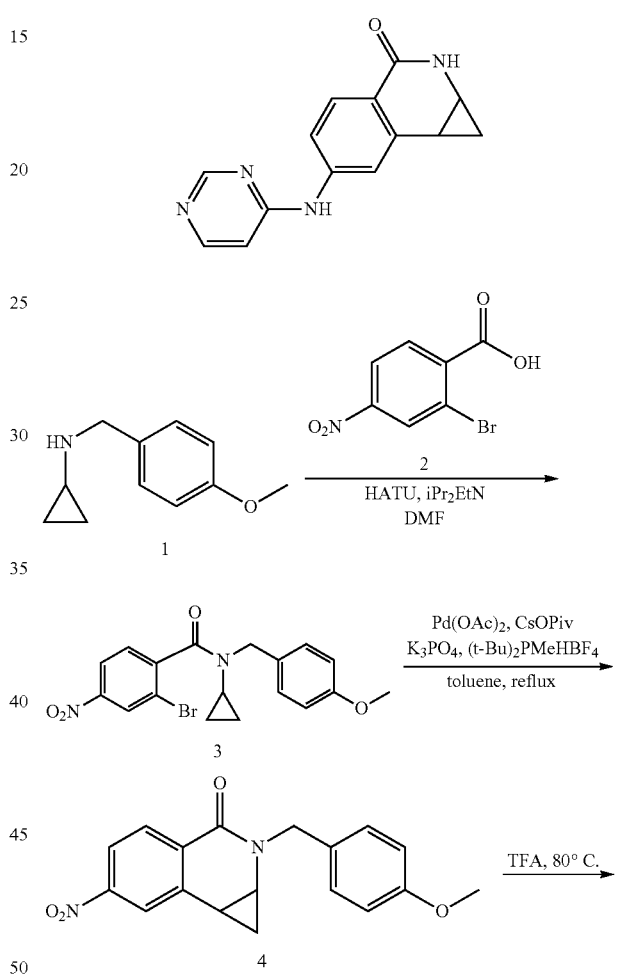

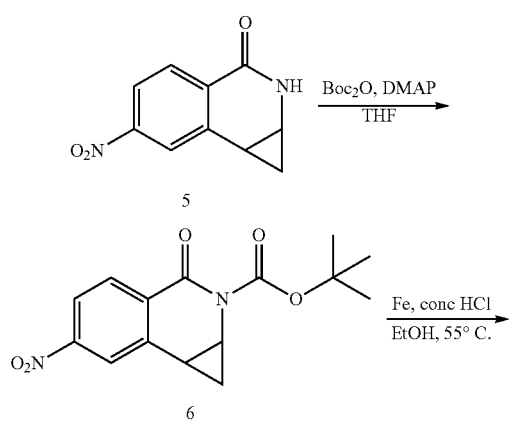

-continued

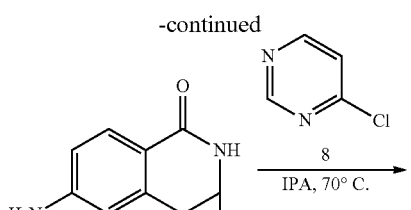

7

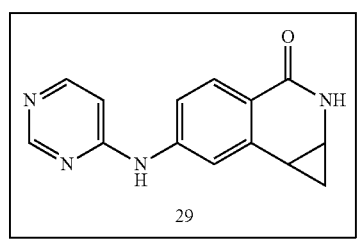 [SMILES: O=C1NC2CC2c2cc(Nc3ccncn3)ccc21]

29

Synthesis of 2-bromo-N-cyclopropyl-N-(4-methoxybenzyl)-4-nitrobenzamide (3)

9-91: To a solution of N-[(4-methoxyphenyl)methyl]cyclopropanamine (1, 0.72 g, 4.06 mmol), 2-bromo-4-nitrobenzoic acid (2, 1 g, 4.06 mmol) and HATU (1.7 g, 4.47 mmol) in N,N-dimethylformamide (10 mL) was added N,N-diisopropylethylamine (0.71 mL, 4.06 mmol). The reaction was stirred at room temperature for 2 h. The reaction mixture was diluted with ethyl acetate and washed sequentially with saturated aqueous sodium bicarbonate solution, 1 M hydrochloric acid and brine. The organics were combined, dried over magnesium sulfate, filtered and concentrated. The crude was purified via column chromatography (silica, ethyl acetate/Hexanes=5-50%) to afford 2-bromo-N-cyclopropyl-N-(4-methoxybenzyl)-4-nitrobenzamide (3). Yield: 1.30 g, 79%.

Synthesis of 2-(4-methoxybenzyl)-6-nitro-1,1a,2,7b-tetrahydro-3H-cyclopropa[c]isoquinolin-3-one (4)

To a solution of 2-bromo-N-cyclopropyl-N-[(4-methoxyphenyl)methyl]-4-nitrobenzamide (3, 1 g, 2.47 mmol) in toluene was added palladium(II) acetate (28 mg, 0.12 mmol), di-tert-butyl(methyl)phosphonium tetrafluoroborate (61 mg, 0.25 mmol), potassium phosphate tribasic (786 mg, 3.7 mmol) and cesium pivalate (173 mg, 0.74 mmol). The reaction was purged with nitrogen for 5 min and stirred at reflux for 16 h. Upon cooling, the mixture was diluted with ethyl acetate and passed through a pad of celite. The filtrate was concentrated and purified via column chromatography (silica, ethyl acetate/hexanes=0-40%) to afford 2-(4-methoxybenzyl)-6-nitro-1,1a,2,7b-tetrahydro-3H-cyclopropa[c]isoquinolin-3-one (4) as an off-white powder. Yield: 110 mg, 14%.

Synthesis of 6-nitro-1,1a, 2,7b-tetrahydro-3H-cyclopropa[c]isoquinolin-3-one (5)

The synthesis of intermediate 5 was carried out as described above using the general protocol of Procedure B. Yield: 189 mg, 100%.

Synthesis of tert-butyl 6-nitro-3-oxo-1,1a, 3,7b-tetrahydro-2H-cyclopropa[c]isoquinoline-2-carboxylate (6)

To a solution of 2-(4-methoxybenzyl)-6-nitro-1,1a,2,7b-tetrahydro-3H-cyclopropa[c]isoquinolin-3-one (5, 250 mg, 1.22 mmol) in tetrahydrofuran (15 mL) was added di-tert-butyl dicarbonate (267 mg, 1.22 mmol) and 4-(dimethylamino)pyridine (150 mg, 1.22 mmol). The reaction was stirred at room temperature until all solids dissolved. The crude was concentrated and purified via column chromatography (silica, ethyl acetate/hexanes=0-100%) to afford tert-butyl 6-nitro-3-oxo-1,1a,3,7b-tetrahydro-2H-cyclopropa[c]isoquinoline-2-carboxylate (6). Yield: 242 mg, 65%; MS (ESI) m/z 305.2 [M+1]$^+$.

Synthesis of 6-amino-1,1a,2,7b-tetrahydro-3H-cyclopropa[c]isoquinolin-3-one (7)

To a suspension of tert-butyl 6-nitro-3-oxo-1,1a,3,7b-tetrahydro-2H-cyclopropa[c]isoquinoline-2-carboxylate (6, 124 mg, 0.41 mmol) in ethanol (10 mL) was added iron (750 mg, 0.41 mmol) and concentrated hydrochloric acid (0.5 mL). The reaction was stirred at 55° C. for 20 min. Upon cooling, the mixture was diluted with ethyl acetate, washed with saturated aqueous sodium bicarbonate solution and brine (25 mL). The organics were combined, dried over magnesium sulfate, filtered and concentrated. The crude was purified via column chromatography (silica, methanol/dichloromethane=0-5%) to afford 6-amino-1,1a,2,7b-tetrahydro-3H-cyclopropa[c]isoquinolin-3-one (7). Yield: 68 mg, 96%.

Synthesis of 6-(pyrimidin-4-ylamino)-1,1a,2,7b-tetrahydro-3H-cyclopropa[c]isoquinolin-3-one (Cpd. No. 29)

To a solution of 6-amino-1,1a,2,7b-tetrahydro-3H-cyclopropa[c]isoquinolin-3-one (7, 35 mg, 0.20 mmol) in 2-propanol (2.5 mL) was added 4-chloropyrimidine hydrochloride (30 mg, 0.20 mmol). The reaction was stirred at 70° C. for 1 h. Upon cooling, the mixture was diluted with ethyl acetate and washed with saturated aqueous sodium bicarbonate solution. The organic layer was dried over magnesium sulfate, filtered and concentrated. The crude was purified via column chromatography (silica, methanol/dichloromethane=0-8%). The solid obtained was further triturated with dichloromethane to afford 6-(pyrimidin-4-ylamino)-1,1a,2,7b-tetrahydro-3H-cyclopropa[c]isoquinolin-3-one (Cpd. No. 29). Yield: 20 mg, 39%; MS (ESI) m/z 253.1 [M+1]$^+$; $^1$H NMR (300 MHz, DMSO-d$_6$) δ 9.88 (s, 1H), 8.72 (s, 1H), 8.34 (dd, J=0.6, 6.0 Hz, 1H), 8.31 (d, J=3.0 Hz, 1H), 7.97 (d, J=2.4 Hz, 1H), 7.85 (d, J=8.4 Hz, 1H), 7.54 (dd, J=2.4, 8.4 Hz, 1H), 6.88 (dd, J=1.2, 6.0 Hz, 1H), 3.19-3.12 (m, 1H), 2.34-2.27 (m, 1H), 1.36-1.29 (m, 1H), 0.13-0.09 (m, 1H).

Example 30

Synthesis of 3-amino-3-methyl-5-(pyrimidin-4-ylamino)-2,3-dihydro-1H-inden-1-one (Cpd. No. 30)

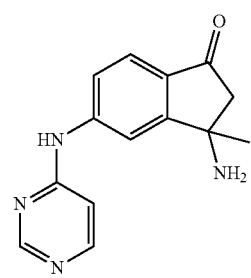

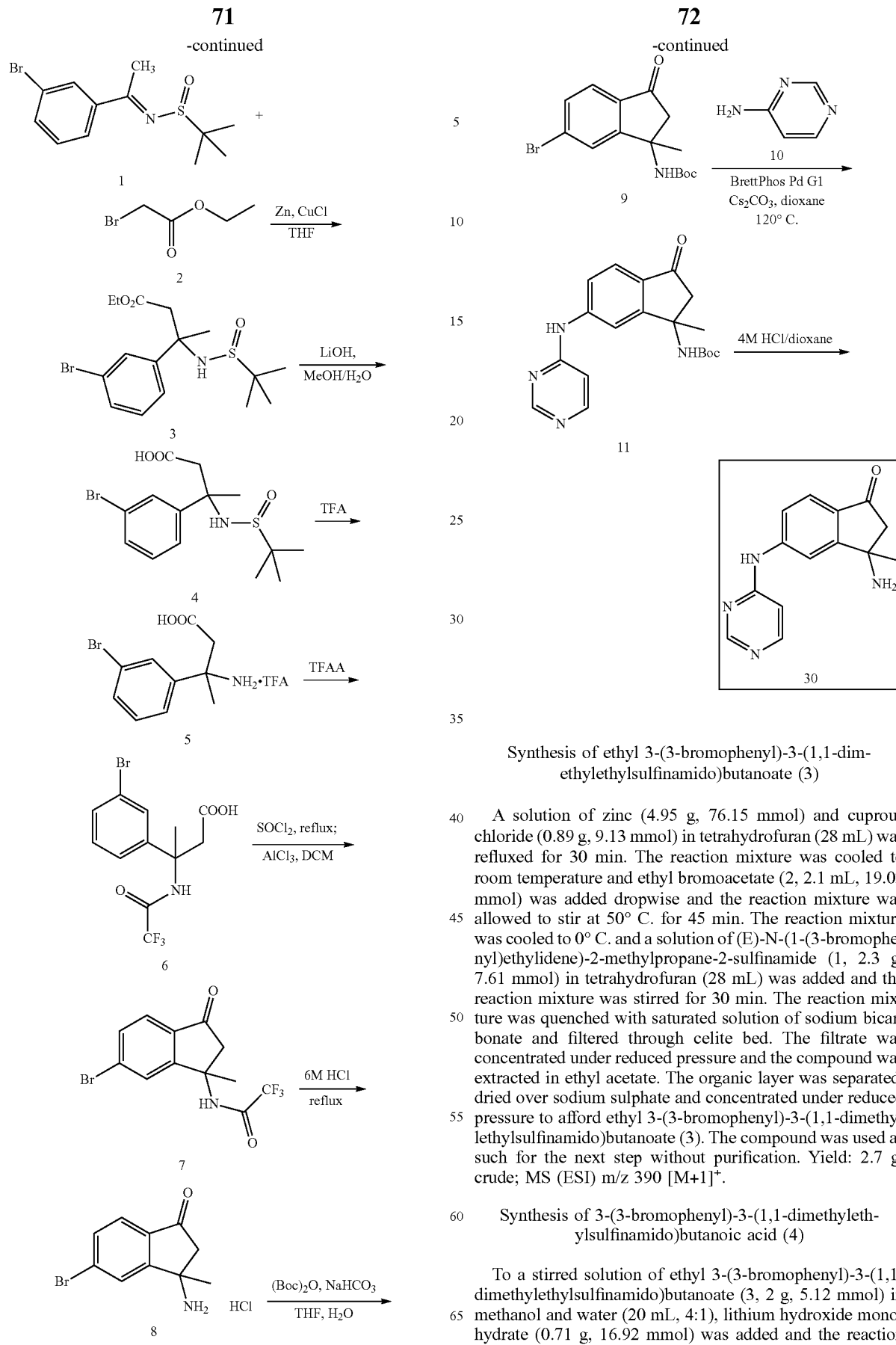

Synthesis of ethyl 3-(3-bromophenyl)-3-(1,1-dimethylethylsulfinamido)butanoate (3)

A solution of zinc (4.95 g, 76.15 mmol) and cuprous chloride (0.89 g, 9.13 mmol) in tetrahydrofuran (28 mL) was refluxed for 30 min. The reaction mixture was cooled to room temperature and ethyl bromoacetate (2, 2.1 mL, 19.03 mmol) was added dropwise and the reaction mixture was allowed to stir at 50° C. for 45 min. The reaction mixture was cooled to 0° C. and a solution of (E)-N-(1-(3-bromophenyl)ethylidene)-2-methylpropane-2-sulfinamide (1, 2.3 g, 7.61 mmol) in tetrahydrofuran (28 mL) was added and the reaction mixture was stirred for 30 min. The reaction mixture was quenched with saturated solution of sodium bicarbonate and filtered through celite bed. The filtrate was concentrated under reduced pressure and the compound was extracted in ethyl acetate. The organic layer was separated, dried over sodium sulphate and concentrated under reduced pressure to afford ethyl 3-(3-bromophenyl)-3-(1,1-dimethylethylsulfinamido)butanoate (3). The compound was used as such for the next step without purification. Yield: 2.7 g, crude; MS (ESI) m/z 390 [M+1]$^+$.

Synthesis of 3-(3-bromophenyl)-3-(1,1-dimethylethylsulfinamido)butanoic acid (4)

To a stirred solution of ethyl 3-(3-bromophenyl)-3-(1,1-dimethylethylsulfinamido)butanoate (3, 2 g, 5.12 mmol) in methanol and water (20 mL, 4:1), lithium hydroxide monohydrate (0.71 g, 16.92 mmol) was added and the reaction mixture was stirred at room temperature for 2 h. The reaction mixture was concentrated under reduced pressure and quenched with saturated solution of ammonium chloride. The reaction mixture was acidified with 1 M aqueous hydrochloric acid and the precipitated solid was filtered, washed with water and dried to afford 3-(3-bromophenyl)-3-(1,1-dimethylethylsulfinamido)butanoic acid (4). The compound was used as such for the next step without purification. Yield: 1.6 g, crude; MS (ESI) m/z 362 [M+1]$^+$.

Synthesis of 3-amino-3-(3-bromophenyl)butanoic acid trifluoroacetate salt (5)

A solution of 3-(3-bromophenyl)-3-(1,1-dimethylethylsulfinamido)butanoic acid (4, 1 g, 2.76 mmol) in trifluoroacetic acid (20 mL) was allowed to stir at room temperature for 16 h. The reaction mixture was concentrated under reduced pressure to afford 3-amino-3-(3-bromophenyl)butanoic acid trifluoroacetate salt (5) as sticky oil. The compound was used as such for the next step without purification. Yield: 1.1 g, crude; MS (ESI) m/z 258 [M+1]$^+$.

Synthesis of 3-(3-bromophenyl)-3-(2,2,2-trifluoroacetamido)butanoic acid (6)

A solution of 3-amino-3-(3-bromophenyl)butanoic acid trifluoroacetate salt (5, 1.1 g, 2.95 mmol) in trifluoroacetic anhydride (20 mL) was allowed to stir at room temperature for 1 h. The reaction mixture was concentrated under reduced pressure and the residue was purified by silica gel (100:200 mesh) column chromatography using 50% ethyl acetate in hexanes as eluent to afford 3-(3-bromophenyl)-3-(2,2,2-trifluoroacetamido)butanoic acid (6). Yield: 0.85 g, 81%.

Synthesis of N-(6-bromo-1-methyl-3-oxo-2,3-dihydro-1H-inden-1-yl)-2,2,2-trifluoroacetamide (7)

A solution of 3-(3-bromophenyl)-3-(2,2,2-trifluoroacetamido)butanoic acid (6, 0.85 g, 2.4 mmol) in thionyl chloride (20 mL) was refluxed for 3 h. The reaction mixture was concentrated under reduced pressure and the residue was dissolved in dichloromethane and cooled to 0° C.-5° C. Aluminium trichloride (0.64 g, 4.8 mmol) was added portion wise and the reaction mixture was refluxed for 2 h. The reaction mixture was quenched with ice and the organic layer was separated. The organic layer was dried over sodium sulphate, concentrated under reduced pressure and the residue was purified by flash column chromatograph to afford N-(6-bromo-1-methyl-3-oxo-2,3-dihydro-1H-inden-1-yl)-2,2,2-trifluoroacetamide (7). Yield: 0.35 g, 43%.

Synthesis of 3-amino-5-bromo-3-methyl-2,3-dihydro-1H-inden-1-one hydrochloride (8)

A solution of N-(6-bromo-1-methyl-3-oxo-2,3-dihydro-1H-inden-1-yl)-2,2,2-trifluoroacetamide (7, 0.35 g, 1.04 mmol) in 6 M aqueous hydrochloric acid (20 mL) was refluxed for 12 h. The reaction mixture was concentrated to dryness and the residue was triturated with diethyl ether. The residue was filtered and dried to afford 3-amino-5-bromo-3-methyl-2,3-dihydro-1H-inden-1-one hydrochloride (8) as a white solid. The compound was used as such for the next step without purification. Yield: 0.28 g, crude; MS (ESI) m/z 240 [M+1]$^+$.

Synthesis of tert-butyl (6-bromo-1-methyl-3-oxo-2,3-dihydro-1H-inden-1-yl)carbamate (9)

To a solution of 3-amino-5-bromo-3-methyl-2,3-dihydro-1H-inden-1-one hydrochloride (8, 0.28 g, 1.01 mmol) in tetrahydrofuran and water (5 mL, 4:1), sodium bicarbonate (0.34 g, 4.05 mmol) and di-tert-butyl dicarbonate (0.35 mL, 1.52 mmol) were added at 0° C. and the reaction mixture was allowed to stir at room temperature for 8 h. The reaction mixture was diluted with water and the compound was extracted in ethyl acetate. The organic layer was separated, dried over sodium sulphate and concentrated under reduced pressure. The residue was purified by silica gel column chromatography using 5% methanol in dichloromethane as eluent to afford tert-butyl (6-bromo-1-methyl-3-oxo-2,3-dihydro-1H-inden-1-yl)carbamate (9). Yield: 0.26 g, 76%.

Synthesis of tert-butyl (1-methyl-3-oxo-6-(pyrimidin-4-ylamino)-2,3-dihydro-1H-inden-1-yl)carbamate (11)

The synthesis of intermediate 11 was carried out as described above using the general protocol of Procedure A. Yield: 0.19 g, 92%; MS (ESI) m/z 355 [M+1]$^+$.

Synthesis of 3-amino-3-methyl-5-(pyrimidin-4-ylamino)-2,3-dihydro-1H-inden-1-one (Cpd. No. 30)

The synthesis of compound 30 was carried out as described above using the general protocol of Procedure C. Yield: 0.08 g, 56%; MS (ESI) m/z 255 [M+1]$^+$; $^1$H NMR (400 MHz, DMSO-d$_6$) δ 10.08 (s, 1H), 8.74 (s, 1H), 8.38 (d, J=5.9 Hz, 1H), 8.04 (d, J=1.9 Hz, 1H), 7.78 (dd, J=8.4, 1.9 Hz, 1H), 7.53 (d, J=8.4 Hz, 1H), 6.93 (dd, J=5.9, 1.3 Hz, 1H), 2.71-2.51 (m, 2H), 2.48 (s, 1H), 1.43 (s, 3H).

Example 31

Synthesis of 5-(pyrrolo[1,2-b]pyridazin-5-ylamino)isoindolin-1-one (Cpd. No. 31)

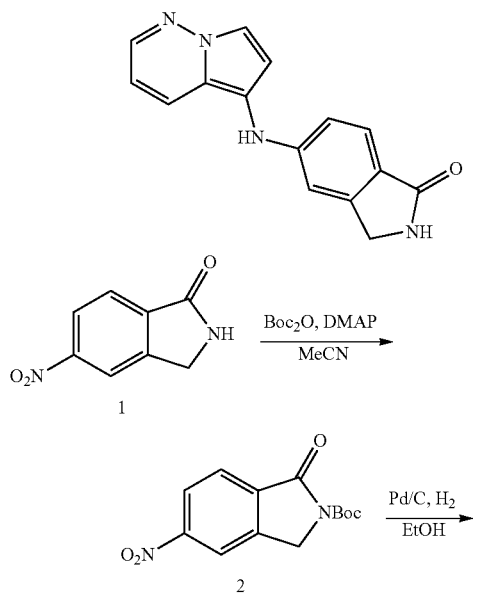

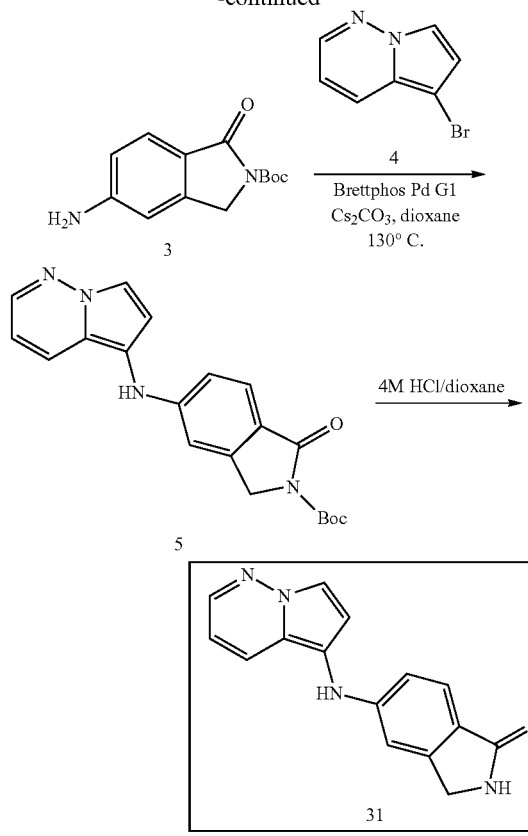

Synthesis of tert-butyl 5-nitro-1-oxoisoindoline-2-carboxylate (2)

To a stirred solution of 5-nitroisoindolin-1-one (1, 0.4 g, 2.24 mmol) in acetonitrile (20 mL), N,N-dimethylaminopyridine (0.41 g, 3.37 mmol) followed by di-tert-butyl dicarbonate (0.75 mL, 3.37 mmol) were added. The reaction mixture was allowed to stir at room temperature for 12 h. The reaction mixture was quenched with water and extracted with ethyl acetate. The organic layer was washed with brine, separated, dried over sodium sulphate and concentrated under reduced pressure. The crude was purified by silica gel column chromatography using 25% ethyl acetate in hexane to afford tert-butyl 5-nitro-1-oxoisoindoline-2-carboxylate (2). Yield: 0.36 g, 57%; MS (ESI) m/z 279 [M+1]$^+$.

Synthesis of tert-butyl 5-amino-1-oxoisoindoline-2-carboxylate (3)

To a stirred solution of tert-butyl 5-nitro-1-oxoisoindoline-2-carboxylate (2, 0.36 g, 1.29 mmol) in ethanol (30 mL), 10% palladium on carbon (0.07 g) was added and the reaction mixture was stirred at room temperature under hydrogen atmosphere for 2 h. The reaction mixture was filtered through celite bed and washed with methanol. The filtrate was concentrated under reduced pressure to afford tert-butyl 5-amino-1-oxoisoindoline-2-carboxylate (3). Yield: 0.3 g, 93%; MS (ESI) m/z 249 [M+1]$^+$.

Synthesis of tert-butyl 1-oxo-5-(pyrrolo[1,2-b]pyridazin-5-ylamino)isoindoline-2-carboxylate (5)

The synthesis of intermediate 5 was carried out as described above using the general protocol of Procedure A. Yield: 0.24 g, 54%; MS (ESI) m/z 365 [M+1]$^+$.

Synthesis of 5-(pyrrolo[1,2-b]pyridazin-5-ylamino)isoindolin-1-one (Cpd. No. 31)

The synthesis of compound 31 was carried out as described above using the general protocol of Procedure C. Yield: 0.032 g, 29%; MS (ESI) m/z 265 [M+1]$^+$; $^1$H NMR (400 MHz, DMSO-d$_6$) δ 8.17 (s, 1H), 8.09 (dd, J=4.4, 1.8 Hz, 1H), 7.95 (s, 1H), 7.86-7.74 (m, 2H), 7.39 (d, J=8.3 Hz, 1H), 6.88-6.74 (m, 3H), 6.55 (dd, J=9.1, 4.4 Hz, 1H), 4.18 (s, 2H).

Example 32

Synthesis of 4-amino-4-methyl-6-(pyrimidin-4-ylamino)-3,4-dihydroisoquinolin-1(2H)-one (Cpd. No. 32)

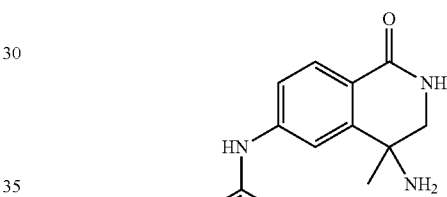

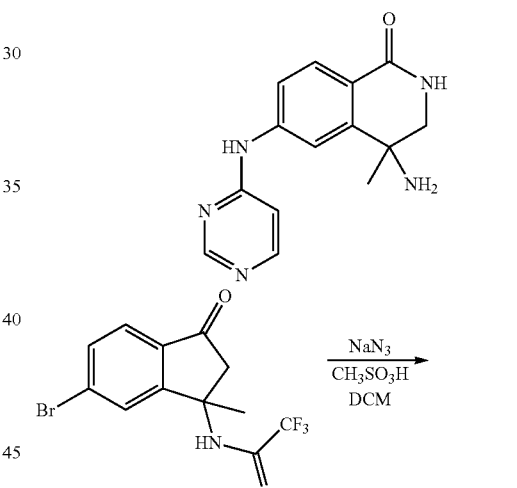

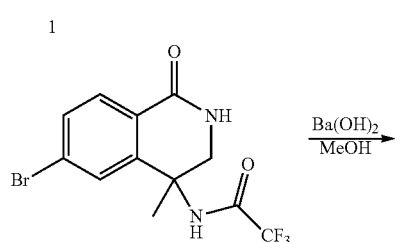

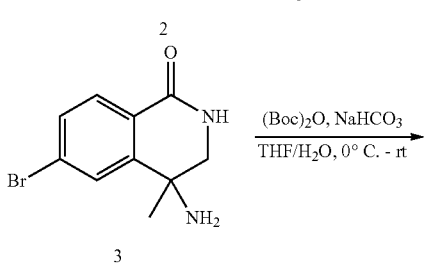

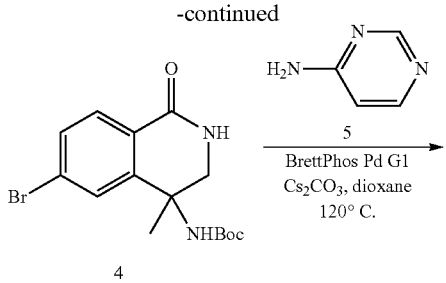

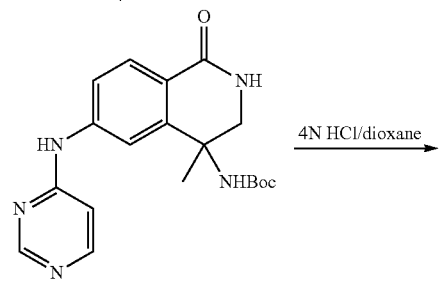

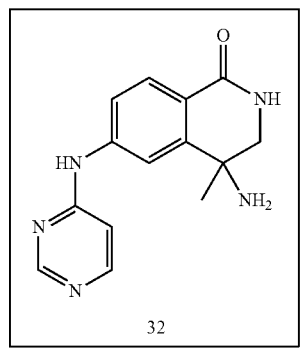 [SMILES: CC1(N)CNC(=O)c2ccc(Nc3ccncn3)cc21]

32

Synthesis of N-(6-bromo-4-methyl-1-oxo-1,2,3,4-tetrahydroisoquinolin-4-yl)-2,2,2-trifluoro-acetamide (2)

To a solution of N-(6-bromo-1-methyl-3-oxo-2,3-dihydro-1H-inden-1-yl)-2,2,2-trifluoroacetamide (1, 0.8 g, 2.38 mmol) in dichloromethane (20 mL), methane sulphonic acid (1.54 mL, 23.80 mmol) was added and reaction was cooled to 0° C. followed by portion wise addition of sodium azide (0.46 g, 7.14 mmol). The reaction was stirred at room temperature for 16 h. The reaction was basified with 2 M sodium hydroxide solution and extracted with dichloromethane. The organic layer was separated, washed with brine, dried over anhydrous sodium sulphate and concentrated under reduced pressure. The crude product was purified by combi-flash chromatography using 2% methanol in chloroform as eluent to afford N-(6-bromo-4-methyl-1-oxo-1,2,3,4-tetrahydroisoquinolin-4-yl)-2,2,2-trifluoro-acetamide (2). Yield: 0.7 g, 84%.

Synthesis of 4-amino-6-bromo-4-methyl-3,4-dihydroisoquinolin-(2H)-one (3)

To a solution of N-(6-bromo-4-methyl-1-oxo-1,2,3,4-tetrahydroisoquinolin-4-yl)-2,2,2-trifluoro-acetamide (2, 0.3 g, 0.85 mmol) in methanol (10 mL), barium hydroxide (4.39 g, 25.64 mmol) was added and the reaction was allowed to stir at room temperature for 16 h. The reaction mixture was diluted with water and the compound was extracted with ethyl acetate. The aqueous layer was separated, extracted with 10% methanol in dichloromethane, dried over sodium sulphate and concentrated under reduced pressure. The crude product was purified by combi-flash column chromatography using 5% methanol in chloroform as eluent to afford 4-amino-6-bromo-4-methyl-3,4-dihydroisoquinolin-1(2H)-one (3). Yield: 0.16 g, 74%.

Synthesis of tert-butyl (6-bromo-4-methyl-1-oxo-1,2,3,4-tetrahydroisoquinolin-4-yl)carbamate (4)

To a solution of 4-amino-6-bromo-4-methyl-3,4-dihydroisoquinolin-1(2H)-one (3, 0.16 g, 0.63 mmol) in tetrahydrofuran and water (6 mL, 2:1), sodium bicarbonate (0.26 g, 3.13 mmol) was added followed by addition of di-tert-butyl dicarbonate (0.27 g, 1.25 mmol) at 0° C. The reaction was allowed to stir at room temperature for 16 h. The reaction mixture was diluted with water and the compound was extracted with dichloromethane. The organic layer was separated, dried over sodium sulphate and concentrated under reduced pressure. The crude product was purified by combi-flash column chromatography using 3% methanol in chloroform as eluent to afford tert-butyl (6-bromo-4-methyl-1-oxo-1,2,3,4-tetrahydroisoquinolin-4-yl)carbamate (4). Yield: 0.14 g, 63%.

Synthesis of tert-butyl (4-methyl-1-oxo-6-(pyrimidin-4-ylamino)-1,2, 3,4-tetrahydroisoquinolin-4-yl)carbamate (6)

The synthesis of intermediate 6 was carried out as described above using the general protocol of Procedure A. Yield: 0.12 g, 83%; MS (ESI) m/z 370 [M+1]$^+$.

Synthesis of 4-amino-4-methyl-6-(pyrimidin-4-ylamino)-3,4-dihydroisoquinolin-(2H)-one (Cpd. No. 32)

The synthesis of compound 32 was carried out as described above using the general protocol of Procedure C. Yield: 0.043 g, 50%; MS (ESI) m/z 270 [M+1]$^+$; $^1$H NMR (400 MHz, DMSO-d$_6$) δ 9.89 (s, 1H), 8.68 (s, 1H), 8.32 (d, J=5.9 Hz, 1H), 7.86 (d, J=7.8 Hz, 2H), 7.77 (d, J=7.4 Hz, 2H), 6.88 (d, J=5.9 Hz, 1H), 3.28 (dd, J=12.1, 4.3 Hz, 1H), 3.11 (dd, J=12.1, 4.3 Hz, 1H), 2.14 (s, 2H), 1.29 (s, 3H).

Example 33

Synthesis of 3,7-dimethyl-5-(pyrimidin-4-ylamino) isoindolin-1-one (Cpd. No. 33)

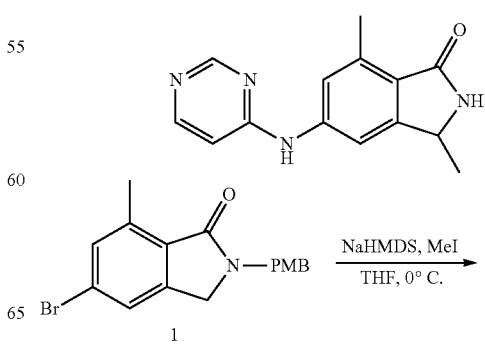

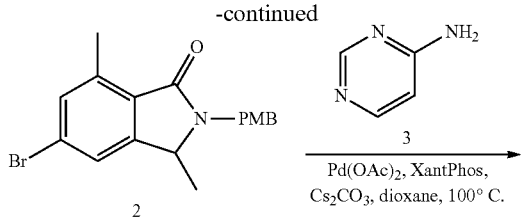

Synthesis of 5-bromo-2-(4-methoxybenzyl)-3,7-dimethylisoindolin-1-one (2)

To a stirred solution of methyl 5-bromo-2-(4-methoxybenzyl)-7-methylisoindolin-1-one (1, 2.2 g, 6.30 mmol) in tetrahydrofuran (20 mL) under nitrogen atmosphere were added sodium bis(trimethylsilyl)amide (1.39 g, 7.60 mmol) and iodomethane (1.17 g, 8.20 mmol) at 0° C. The reaction mixture was stirred at 0° C. for 4 h. Progress of reaction was monitored by TLC. After consumption of the starting material, the reaction mixture was diluted with water and the compound was extracted in ethyl acetate. The organic layer was washed with brine solution, dried over anhydrous sodium sulfate, filtered and concentrated under reduced pressure. The resulting residue was purified using combi-flash column chromatography using 0-20% ethyl acetate in hexane and desired fractions were concentrated to afford 5-bromo-2-(4-methoxybenzyl)-3,7-dimethylisoindolin-1-one (2) as white solid. Yield: 1.0 g, 44%. MS (ESI) m/z 360.16 [M+1]+.

Synthesis of 2-(4-methoxybenzyl)-3,7-dimethyl-5-(pyrimidin-4-ylamino)isoindolin-1-one (4)

The synthesis of intermediate 4 was carried out as described above using the general protocol of Procedure A. White solid; Yield: 0.27 g, 58%. MS (ESI) m/z 375.16 [M+1]+.

Synthesis of 3,7-dimethyl-5-(pyrimidin-4-ylamino)isoindolin-1-one (Cpd. No. 33)

The synthesis of compound 33 was carried out as described above using the general protocol of Procedure B. Off-white solid; Yield: 0.05 g, 30%; MS (ESI) m/z 253 [M−1]−; ¹H NMR (400 MHz, DMSO-d₆) δ 9.82 (s, 1H), 8.68 (s, 1H), 8.33-8.23 (m, 2H), 7.80 (s, 1H), 7.39 (s, 1H), 6.85 (d, J=5.6 Hz, 1H), 4.52 (m, 1H), 2.56 (s, 3H), 1.32 (d, J=6.4 Hz, 3H).

Example 34

Synthesis of 3-methyl-5-(pyrimidin-4-yloxy)isoindolin-1-one (Cpd. No. 34)

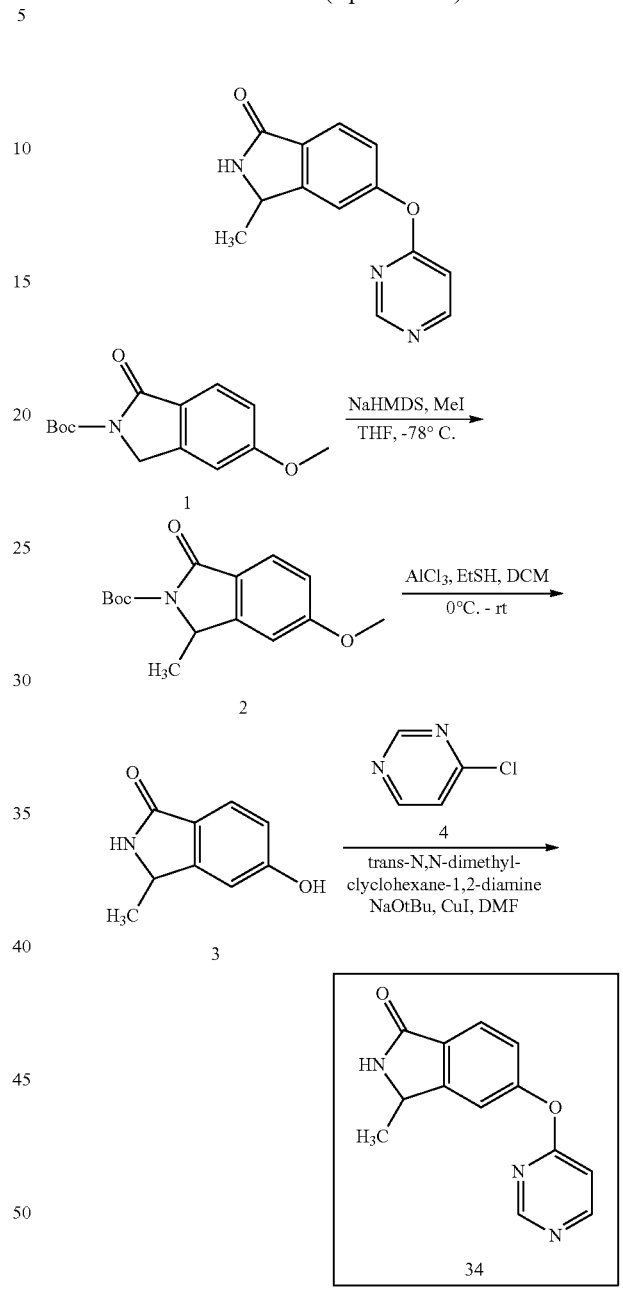

Synthesis of tert-butyl 5-methoxy-3-methyl-1-oxoisoindoline-2-carboxylate (2)

To a solution of tert-butyl 5-methoxy-1-oxoisoindoline-2-carboxylate (1, 1.7 g, 6.45 mmol) in tetrahydrofuran (30 mL) at −78° C., sodium bis(trimethylsilyl)amide (7.1 mL, 12.91 mmol) was added dropwise. The reaction was stirred for 15 min. Methyl iodide (1.83 g, 12.91 mmol) was added and the reaction mixture was allowed to stir at room temperature for 3 h. The reaction mixture was quenched with water and the compound was extracted in ethyl acetate. The organic layer was separated, dried over sodium sulphate and concentrated under reduced pressure. The residue was purified by silica gel column chromatography using 8% ethyl acetate in hexane as eluent to afford tert-butyl 5-methoxy-3-methyl-1-oxoisoindoline-2-carboxylate (2). Yield: 1.6 g, 89%; MS (ESI) m/z 278 [M+1]+.

Synthesis of 5-hydroxy-3-methylisoindolin-1-one (3)

To a solution of tert-butyl 5-methoxy-3-methyl-1-oxoisoindoline-2-carboxylate (2, 1 g, 3.60 mmol) in dichloromethane (50 mL) at –0° C., aluminium chloride (3.8 g, 28.8 mmol) was added and the reaction was stirred for 15 min. Ethanthiol (1.79 g, 28.8 mmol) was added and the reaction mixture was allowed to stir at room temperature for 16 h. The reaction mixture was quenched with water followed by sodium bicarbonate and the compound was extracted with n-butanol. The organic layer was separated, dried over sodium sulphate and concentrated under reduced pressure to afford 5-hydroxy-3-methylisoindolin-1-one (3). Yield: 0.3 g, crude; MS (ESI) m/z 164 [M+1]+.

Synthesis of 3-methyl-5-(pyrimidin-4-yloxy)isoindolin-1-one (Cpd. No. 34)

To a solution of 5-hydroxy-3-methylisoindolin-1-one (3, 0.12 g, 0.73 mmol) in N,N-dimethylforamide (2.5 mL), 4-chloropyrimidine (0.13 g, 0.88 mmol), sodium tert-butoxide (0.177 g, 1.83 mmol) and trans-N,N dimethylcyclohexane-1,2-diamine (0.052 g, 0.36 mmol) were added and the reaction mixture was degassed with argon for 15 min. Copper(I) iodide (0.028 g, 0.15 mmol) was added and the reaction mixture was heated at 120° C. for 18 h. The reaction mixture was concentrated under reduced pressure and diluted with ethyl acetate. The reaction mixture was filtered through a bed of celite. The filtrate was concentrated under reduced pressure and the residue was purified by prep HPLC to afford 3-methyl-5-(pyrimidin-4-yloxy)isoindolin-1-one (Cpd. No. 34). Yield: 0.072 g, 29%; MS (ESI) m/z 242 [M+1]+; 1H NMR (400 MHz, DMSO-d6) δ 8.79 (d, J=1.1 Hz, 1H), 8.75-8.66 (m, 2H), 7.70 (d, J=8.2 Hz, 1H), 7.50 (d, J=2.1 Hz, 1H), 7.31 (dd, J=8.2, 2.1 Hz, 1H), 7.23 (dd, J=5.9, 1.2 Hz, 1H), 4.64 (q, J=6.7 Hz, 1H), 1.37 (d, J=6.7 Hz, 3H).

Example 35

Synthesis of 7-chloro-3-methyl-5-(pyrimidin-4-ylamino)isoindolin-1-one (Cpd. No. 35)

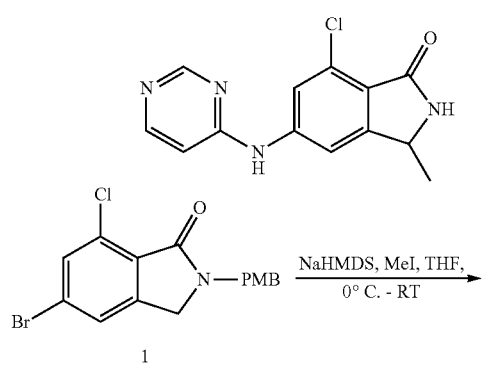

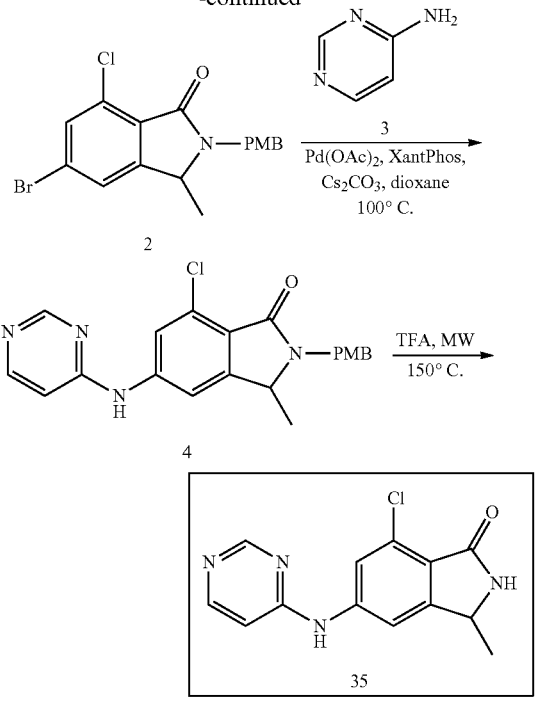

Synthesis of 5-bromo-7-chloro-2-(4-methoxybenzyl)-3-methylisoindolin-1-one (2)

To a stirred solution of 5-bromo-7-chloro-2-(4-methoxybenzyl)isoindolin-1-one (1, 1.6 g, 4.38 mmol) in tetrahydrofuran (44 mL) under nitrogen atmosphere was added sodium bis(trimethylsilyl)amide (0.95 g, 5.19 mmol) and iodomethane (2.7 mL, 43.80 mmol) at 0° C. The reaction mixture was stirred at 0° C. for 3 h. Progress of the reaction was monitored by TLC. After consumption of the starting material, the reaction mixture was diluted with water and extracted in ethyl acetate. The organic layer was washed with brine, dried over anhydrous sodium sulfate, filtered and concentrated under reduced pressure. The resulting residue was purified using combiflash column chromatography using 0-30% ethyl acetate in hexane and desired fractions were concentrated to afford 5-bromo-7-chloro-2-(4-methoxybenzyl)-3-methylisoindolin-1-one (2) as a yellow solid. Yield: 0.72 g, crude; MS (ESI) m/z 380 [M+1]+.

Synthesis of 7-chloro-2-(4-methoxybenzyl)-3-methyl-5-(pyrimidin-4-ylamino)isoindolin-1-one (4)

The synthesis of intermediate 4 was carried out as described above using the general protocol of Procedure A. Off-white solid; Yield: 0.32 g, crude; MS (ESI) m/z 395.1 [M+1]+.

Synthesis of 7-chloro-3-methyl-5-(pyrimidin-4-ylamino)isoindolin-1-one (Cpd. No. 35)

The synthesis of compound 35 was carried out as described above using the general protocol of Procedure B. Yield: 0.028 g, 50%; MS (ESI) m/z 275.03 [M+1]+; 1H NMR (400 MHz, DMSO-d6) δ 10.08 (s, 1H), 8.75 (s, 1H), 8.56 (s, 1H), 8.38 (d, J=8.0 Hz, 1H), 7.88 (s, 1H), 7.83 (s, 1H), 6.88 (d, 1H), 4.57 (q, 1H), 1.34 (d, 3H).

Example 36

Synthesis of 7-chloro-3,3-dimethyl-5-(pyrimidin-4-ylamino)isoindolin-1-one (Cpd. No. 36)

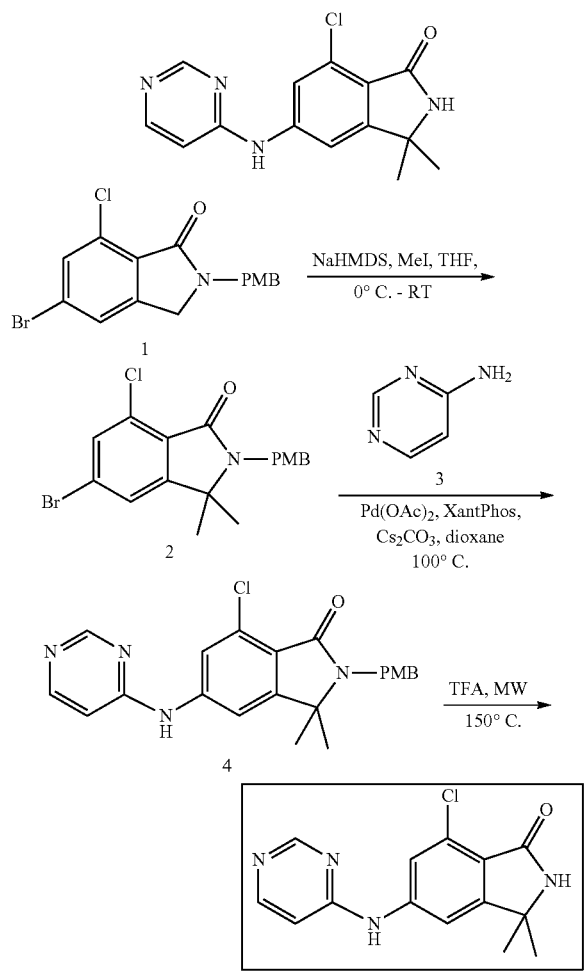

Synthesis of 5-bromo-7-chloro-2-(4-methoxybenzyl)-3,3-dimethylisoindolin-1-one (2)

To a stirred solution of 5-bromo-7-chloro-2-(4-methoxybenzyl)isoindolin-1-one (1, 1.6 g, 4.38 mmol) in tetrahydrofuran (44 mL) under nitrogen atmosphere was added sodium bis(trimethylsilyl)amide (0.95 g, 5.19 mmol) and iodomethane (2.7 mL, 43.80 mmol) at 0° C. The reaction mixture was stirred at 0° C. for 3 h. Progress of the reaction was monitored by TLC. After consumption of the starting material, the reaction mixture was diluted with water and extracted in ethyl acetate. The organic layer was washed with brine, dried over anhydrous sodium sulfate, filtered and concentrated under reduced pressure. The resulting residue was purified using combiflash column chromatography using 0-30% ethyl acetate in hexane and desired fractions were concentrated to afford 5-bromo-7-chloro-2-(4-methoxybenzyl)-3,3-dimethylisoindolin-1-one (2) as a yellow solid. Yield: 0.72 g, crude; MS (ESI) m/z 396 [M+1]$^+$.

Synthesis of 7-chloro-2-(4-methoxybenzyl)-3,3-dimethyl-5-(pyrimidin-4-ylamino)isoindolin-1-one (4)

The synthesis of intermediate 4 was carried out as described above using the general protocol of Procedure A. Off-white solid; Yield: 0.16 g, crude; MS (ESI) m/z 409.1 [M+1]$^+$.

Synthesis of 7-chloro-3,3-dimethyl-5-(pyrimidin-4-ylamino)isoindolin-1-one (Cpd. No. 35)

The synthesis of compound 35 was carried out as described above using the general protocol of Procedure B. Yield: 0.015 g, 35%; MS (ESI) m/z 289.03 [M+1]$^+$; $^1$H NMR (400 MHz, DMSO-d$_6$): δ 10.83 (s, 1H), 8.75 (s, 1H), 8.58 (s, 1H), 8.38 (d, J=8.0 Hz, 1H), 7.92 (d, 1H), 7.72 (d, 1H), 6.88 (d, 1H), 1.42 (s, 6H).

Example 37

Synthesis of 5-(pyrimidin-4-ylamino)-3-(thiophen-3-yl)isoindolin-1-one (Cpd. No. 37)

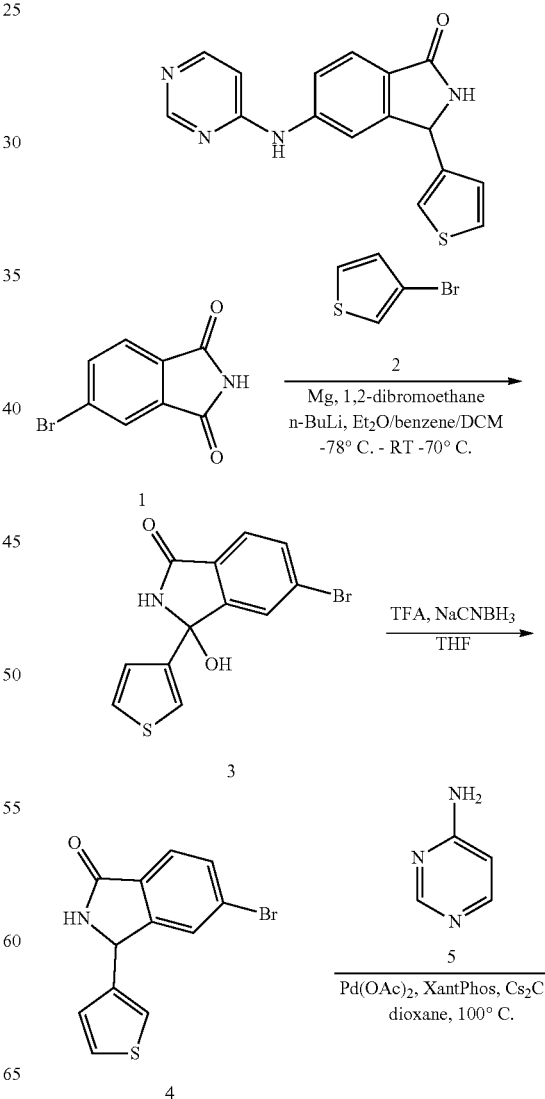

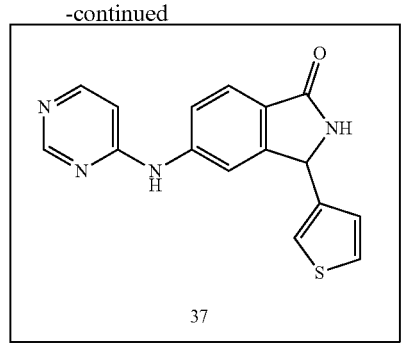

Synthesis of 5-bromo-3-hydroxy-3-(thiophen-3-yl) isoindolin-1-one (3)

A solution of 1, 2-dibromoethane (20 ml, 230.35 mmol) in ether/benzene (270 ml/100 ml) was added to a stirred suspension of magnesium turning (8.64 g, 355.6 mmol) in ether (100 ml). The reaction was stirred at room temperature for 2 h. To this was added a solution of n-butyllithium (110 ml, 177.6 mmol) and 3-bromothiophene (2, 29 g, 177.6 mmol) in tetrahydrofuran (200 ml) (prepared at −78° C.) and the reaction was stirred at room temperature for 1 h. Then a solution of 4-bromophthalimide (1, 4 g, 17.7 mmol) in dichloromethane (50 ml) was added and the reaction was stirred at room temperature for 1 h. Progress of the reaction was monitored by TLC. After completion, the reaction mixture was quenched with sat. ammonium chloride and extracted with dichloromethane. The organic layer was separated, dried over sodium sulphate and concentrated under reduced pressure. The residue was purified on combiflash using 25% ethyl acetate in hexane to afford mixture of 5-bromo-3-hydroxy-3-(thiophen-3-yl) isoindolin-1-one (3) as a yellow solid. Yield: 0.97 g, crude; MS (ESI) m/z 307.95 [M−1]$^-$.

Synthesis of 5-bromo-3-(thiophen-3-yl) isoindolin-1-one (4)

To a stirred solution of 5-bromo-3-hydroxy-3-(thiophen-3-yl) isoindolin-1-one (3, 0.97 g, 3.13 mmol) in dichloromethane (20 mL), sodium cyanoborohydride (0.43 g, 6.89 mmol) was added slowly. Then trifluoroacetic acid (2 ml) was added and the reaction was allowed to run at room temperature for 48 h. Progress of the reaction was monitored by TLC. After completion, the reaction mass was quenched with saturated solution of sodium bicarbonate and extracted with ethyl acetate twice. The organic layer was separated, dried over sodium sulphate and concentrated under reduced pressure. The residue was purified on combiflash using 20% ethyl acetate in hexane to afford 5-bromo-3-(thiophen-3-yl) isoindolin-1-one (4) as off-white solid. Yield: 368 mg, 40%; MS (ESI) m/z 294.02 [M+1]$^+$.

Synthesis of 5-(pyrimidin-4-ylamino)-3-(thiophen-3-yl)isoindolin-1-one (Cpd. No. 37)

The synthesis of compound 37 was carried out as described above using the general protocol of Procedure A. Yield: 0.16 g, 31%; MS (ESI) m/z 309.23 [M+1]$^+$; $^1$H NMR (400 MHz, DMSO-d$_6$) δ 9.91 (s, 1H), 8.86 (s, 1H), 8.65 (s, 1H), 8.31 (d, J=8.4 Hz, 1H), 7.84 (s, J=4 Hz, 1H), 7.73 (s, 1H), 7.64 (s, J=8 Hz, 1H), 7.53 (m, J=8 Hz, 2H), 6.90 (d, J=4 Hz, 1H), 6.81 (d, J=4 Hz, 1H), 5.80 (s, 1H).

Example 38

Synthesis of 5-(7,8-dihydro-6H-pyrimido[5,4-b][1,4]oxazin-4-ylamino)-3-methyl-isoindolin-1-one (Cpd. No. 38)

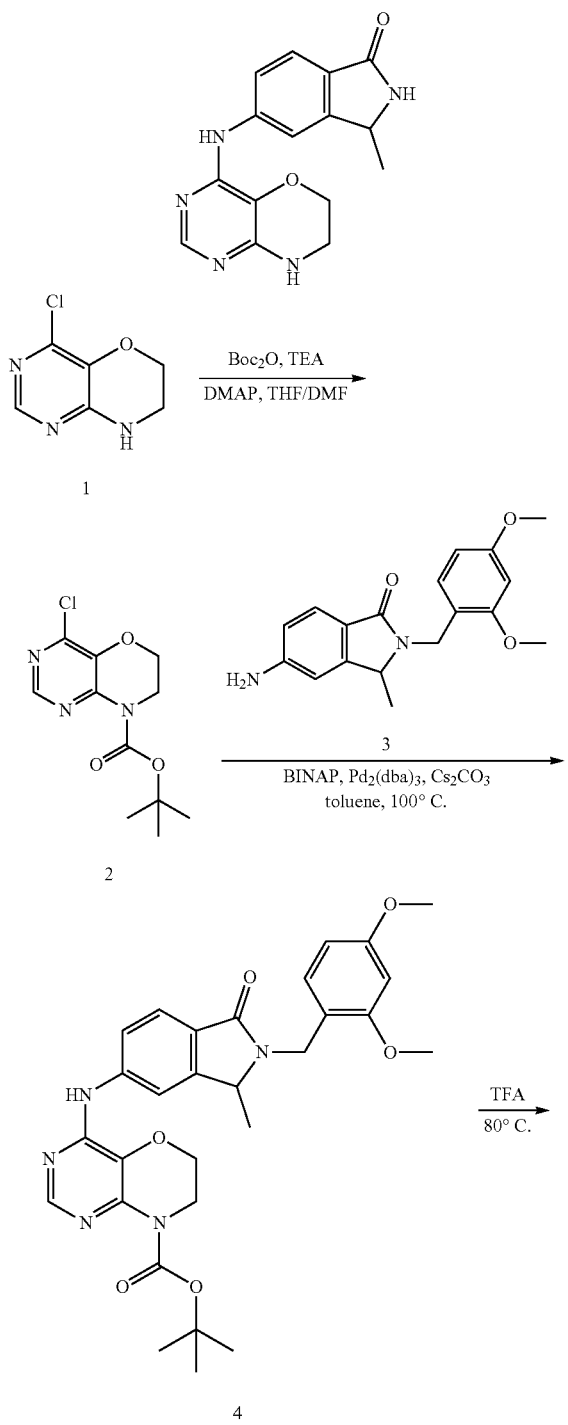

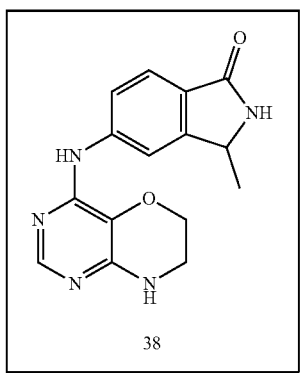

Synthesis of tert-butyl 4-chloro-6,7-dihydropyrimido[5,4-b][1,4]oxazine-8-carboxylate (2)

To a mixture containing 4-chloro-7,8-dihydro-6H-pyrimido[5,4-b][1,4]oxazine (1, 560 mg, 3.26 mmol) and tert-butoxycarbonyl tert-butyl carbonate (1.07 g, 4.9 mmol) in N,N-dimethylformamide (1 mL) and tetrahydrofuran (4 mL) was added 4-(dimethylamino)pyridine (199 mg, 1.63 mmol) and triethylamine (1.0 mL, 7.18 mmol). Gas evolved from the reaction and the reaction was allowed to stir at room temperature overnight. The reaction was then concentrated in vacuo, then partitioned between ethyl acetate and 1 M hydrochloric acid. The organic layer was dried with magnesium sulfate, filtered and concentrated. The crude was purified by flash column chromatography to afford tert-butyl 4-chloro-6,7-dihydropyrimido[5,4-b][1,4]oxazine-8-carboxylate (2). Yield: 632 mg, 71%; MS (ESI) m/z 272 [M+1]$^+$.

Synthesis of tert-butyl 4-[[2-[(2,4-dimethoxyphenyl)methyl]-3-methyl-1-oxo-isoindolin-5-yl]amino]-6,7-dihydropyrimido[5,4-b][1,4]oxazine-8-carboxylate (4)

The synthesis of intermediate 4 was carried out as described above using the general protocol of Procedure A. Yield: 15 mg, 35%; MS (ESI) m/z 548 [M+1]$^+$.

Synthesis of 5-(7,8-dihydro-6H-pyrimido[5,4-b][1,4]oxazin-4-ylamino)-3-methyl-isoindolin-1-one (Cpd. No. 38)

The synthesis of compound 38 as its trifluoroacetic acid salt was carried out as described above using the general protocol of Procedure B. Yield: 9 mg, 62%; MS (ESI) m/z 297 [M+1]$^+$; $^1$H NMR (400 MHz, CD$_3$OD-d$_4$) δ 8.04 (bs, 1H), 7.83 (m, 1H), 7.74-7.63 (m, 2H), 4.69 (q, 1H), 4.37 (t, 2H), 3.69 (t, 2H), 1.47 (d, 3H).

Example 39

Synthesis of 5-(6,7-dihydro-5H-pyrrolo[2,3-d]pyrimidin-4-ylamino)-3-methyl-isoindolin-1-one (Cpd. No. 39)

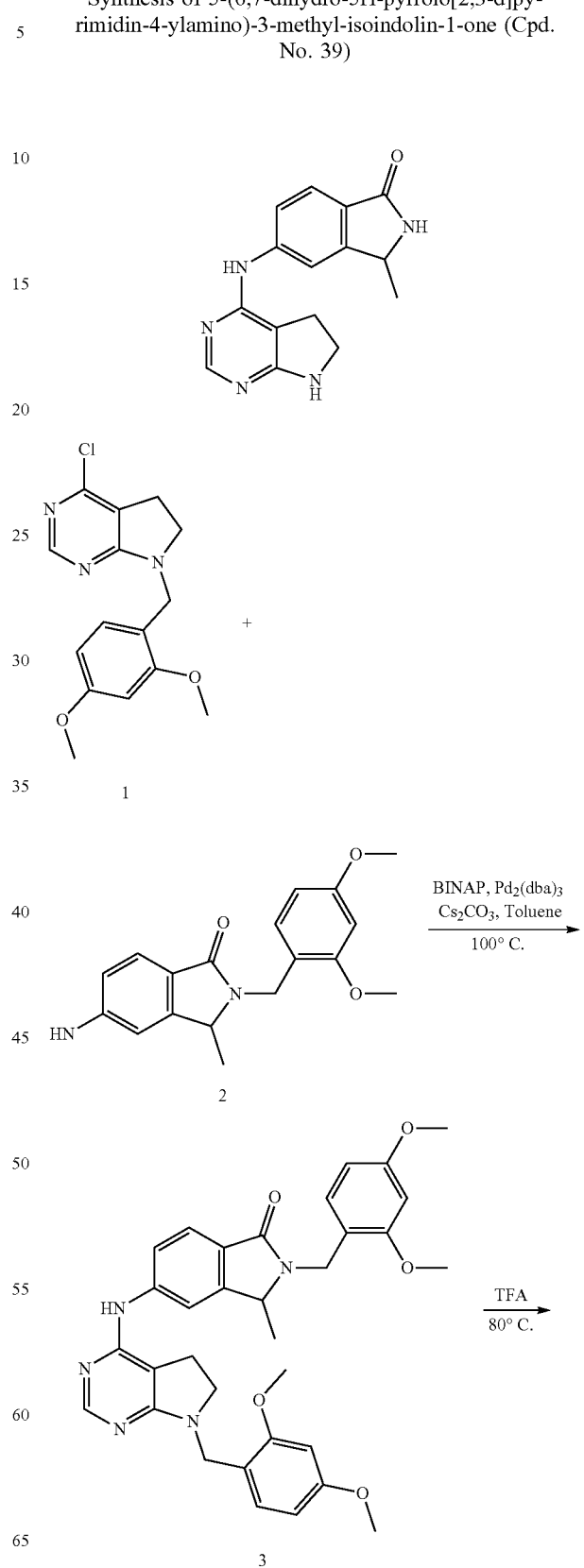

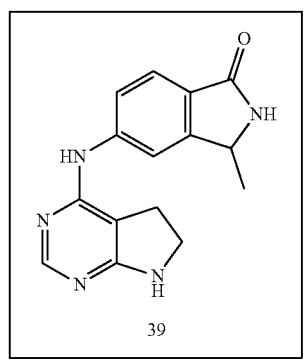

Synthesis of 2-(2,4-dimethoxybenzyl)-5-((7-(2,4-dimethoxybenzyl)-6,7-dihydro-5H-pyrrolo[2,3-d]pyrimidin-4-yl)amino)-3-methylisoindolin-1-one (3)

The synthesis of intermediate 3 was carried out as described above using the general protocol of Procedure A. Yield: 25 mg, 52%; MS (ESI) m/z 582 [M+1]$^+$.

Synthesis of 5-(6,7-dihydro-5H-pyrrolo[2,3-d]pyrimidin-4-ylamino)-3-methyl-isoindolin-1-one (Cpd. No. 39)

The synthesis of compound 39 was carried out as described above using the general protocol of Procedure B. Yield: 13 mg, 100%; MS (ESI) m/z 282 [M+1]$^+$; $^1$H NMR (400 MHz, CD$_3$OD-d$_4$) δ 8.16 (s, 1H), 7.75-7.70 (m, 2H), 7.45 (dd, 1H), 4.70 (q, 1H), 3.90 (t, 2H), 3.08 (t, 2H), 1.47 (d, 3H).

Example 40

Synthesis of 3-(aminomethyl)-3-methyl-5-(pyrimidin-4-ylamino)isoindolin-1-one hydrochloride salt (Cpd. No. 40)

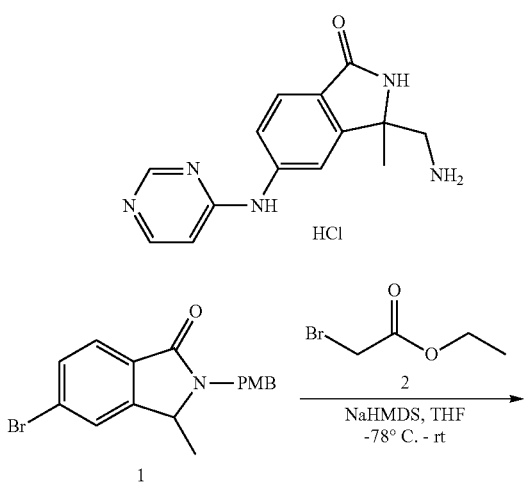

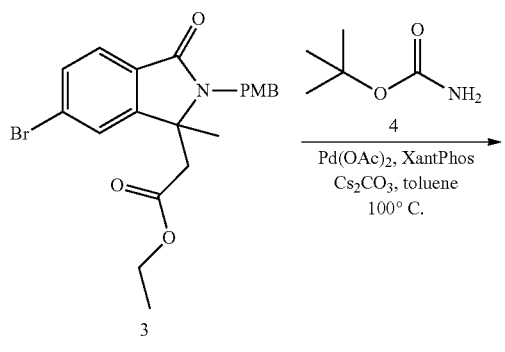

-continued

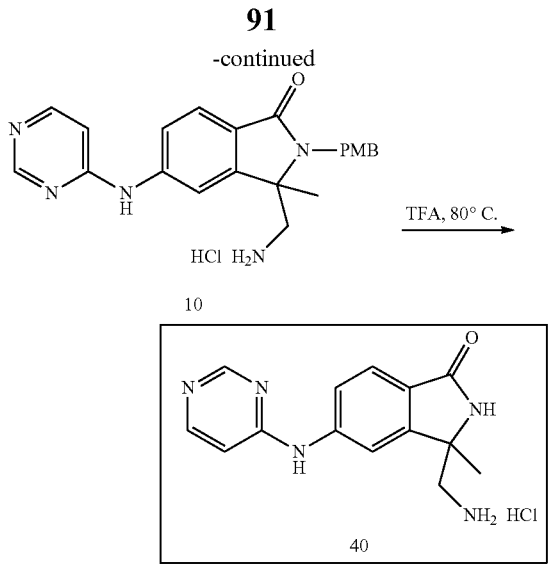

Synthesis of ethyl 2-(6-bromo-2-(4-methoxybenzyl)-1-methyl-3-oxoisoindolin-1-yl)acetate (3)

To a solution of 5-bromo-2-(4-methoxybenzyl)-3-methylisoindolin-1-one (1, 1 g, 2.89 mmol) in tetrahydrofuran (42 mL) at −78° C. was added dropwise a solution of sodium bis(trimethylsilyl)amide (530 mg, 2.89 mmol) in tetrahydrofuran (15 mL). The reaction was stirred for 15 min, followed by the dropwise addition of ethyl 2-bromoacetate (2, 555 mg, 3.32 mmol) in tetrahydrofuran (10 mL). The reaction was stirred at −78° C. for 20 min before it was allowed to warm to room temperature slowly. The reaction mixture was poured into half saturated aqueous ammonium chloride solution and extracted with ethyl acetate. The organics were combined, washed with brine, dried over magnesium sulfate, filtered and concentrated. The crude was purified via column chromatography (silica, ethyl acetate/hexanes=0-10%) to afford ethyl 2-(6-bromo-2-(4-methoxybenzyl)-1-methyl-3-oxoisoindolin-1-yl)acetate (3). Yield: 0.52 g, 42%; MS (ESI) m/z 432.0 [M+1]$^+$.

Synthesis of ethyl 2-(6-(((tert-butoxycarbonyl)amino)-2-(4-methoxybenzyl)-1-methyl-3-oxoisoindolin-1-yl)acetate (5)

The synthesis of intermediate 5 was carried out as described above using the general protocol of Procedure A. Off-white brittle foam; Yield: 329 mg, 95%; MS (ESI) m/z 469.3 [M+1]$^+$.

Synthesis of ethyl 2-(6-amino-2-(4-methoxybenzyl)-1-methyl-3-oxoisoindolin-1-yl)acetate (6)

The synthesis of intermediate 6 was carried out as described above using the general protocol of Procedure C. Beige solid. Yield: 308 mg, 95%; MS (ESI) m/z 369.2 [M+1]$^+$.

Synthesis of ethyl 2-(2-(4-methoxybenzyl)-1-methyl-3-oxo-6-(pyrimidin-4-ylamino)isoindolin-1-yl)acetate (8)

A mixture of ethyl 2-(6-amino-2-(4-methoxybenzyl)-1-methyl-3-oxoisoindolin-1-yl)acetate (6, 300 mg, 0.81 mmol) and 4-chloropyrimidine hydrochloride (7, 123 mg, 0.81 mmol) in 2-propanol (10 mL) was stirred at 60° C. for 16 h. The resulting mixture was concentrated and re-dissolved in dichloromethane. The mixture was washed with saturated aqueous sodium bicarbonate solution and brine. The organic layer dried was dried over magnesium sulfate, filtered and concentrated. The crude was purified via column chromatography (silica, ethyl acetate/hexanes=0-40%) to afford ethyl 2-(2-(4-methoxybenzyl)-1-methyl-3-oxo-6-(pyrimidin-4-ylamino)isoindolin-1-yl)acetate (8). Yield: 156 mg, 43%; MS (ESI) m/z 447.2 [M+1]$^+$.

Synthesis of 2-(2-(4-methoxybenzyl)-1-methyl-3-oxo-6-(pyrimidin-4-ylamino)isoindolin-1-yl)acetic acid (9)

To a solution of ethyl 2-(2-(4-methoxybenzyl)-1-methyl-3-oxo-6-(pyrimidin-4-ylamino)isoindolin-1-yl)acetate (8, 150 mg, 0.34 mmol) in methanol (4 mL) and tetrahydrofuran (4 mL) was added 1 M lithium hydroxide (4 mL, 1.36 mmol) solution. The reaction was stirred at room temperature for 4 h, before it was neutralized by the addition of 1 M hydrogen chloride to pH~6.8. The resulting mixture was extracted with ethyl acetate. The organics were combined, dried over magnesium sulfate, filtered and concentrated to afford 2-(2-(4-methoxybenzyl)-1-methyl-3-oxo-6-(pyrimidin-4-ylamino)isoindolin-1-yl)acetic acid (9) as a white powder. Yield: 90 mg, 64%; MS (ESI) m/z 419.3 [M+1]$^+$.

Synthesis of 3-(aminomethyl)-2-(4-methoxybenzyl)-3-methyl-5-(pyrimidin-4-ylamino)isoindolin-1-one hydrochloride (10)

To a suspension of 2-(2-(4-methoxybenzyl)-1-methyl-3-oxo-6-(pyrimidin-4-ylamino)isoindolin-1-yl)acetic acid (9, 82 mg, 0.20 mmol) in toluene (18 mL) and tetrahydrofuran (4 mL) was added tert-butanol (290 mg, 3.92 mmol), triethylamine (51 mg, 0.39 mmol) and diphenyl phosphoryl azide (54 mg, 0.20 mmol). The reaction was stirred at 85° C. for 16 h. 4 M hydrochloric acid (8 mL) was added and the reaction was stirred vigorously for 2 h. The resulting mixture was diluted with methanol and concentrated. The crude was purified via reverse phase HPLC (C18, acetonitrile/water=5-60%) to afford 3-(aminomethyl)-2-(4-methoxybenzyl)-3-methyl-5-(pyrimidin-4-ylamino)isoindolin-1-one hydrochloride (10) as an oil. Yield: 40 mg, 42%; MS (ESI) m/z 390.2 [M+1]$^+$.

Synthesis of 3-(aminomethyl)-3-methyl-5-(pyrimidin-4-ylamino)isoindolin-1-one hydrochloride salt (Cpd. No. 40)

The synthesis of compound 40 was carried out as described above using the general protocol of Procedure B. Off-white solid; Yield: 9 mg, 29%; MS (ESI) m/z 270.1 [M+1]$^+$. $^1$H NMR (300 MHz, CD$_3$OD) δ 8.94 (s, 1H), 8.40 (s, 1H), 8.18 (s, 1H), 7.89-7.83 (m, 2H), 7.20 (d, J=6.0 Hz, 1H), 3.66 (d, J=13.8 Hz, 1H), 3.37 (d, J=13.5 Hz, 1H), 1.65 (s, 3H).

Example 41

Synthesis of 4-[(3-methyl-1-oxo-isoindolin-5-yl)amino]-5,7-dihydropyrrolo[2,3-d]pyrimidin-6-one (Cpd. No. 41)

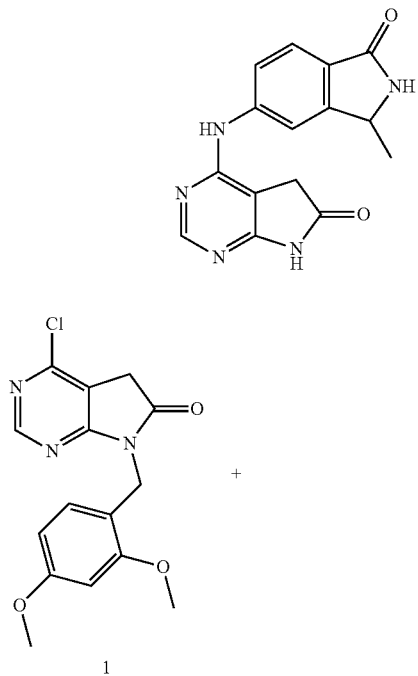

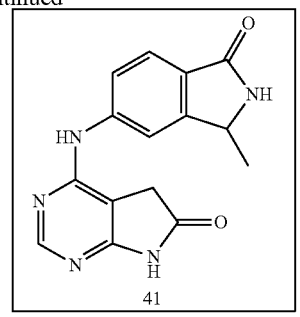

Synthesis of 7-[(2,4-dimethoxyphenyl)methyl]-4-[[2-[(2,4-dimethoxyphenyl)methyl]-3-methyl-1-oxo-isoindolin-5-yl]amino]-5H-pyrrolo[2,3-d]pyrimidin-6-one (3)

A solution of 5-amino-2-[(2,4-dimethoxyphenyl)methyl]-3-methyl-isoindolin-1-one (2, 50 mg, 0.16 mmol), 4-chloro-7-[(2,4-dimethoxyphenyl)methyl]-5H-pyrrolo[2,3-d]pyrimidin-6-one (1, 51 mg, 0.16 mmol) and p-toluenesulfonic acid monohydrate (15 mg, 0.08 mmol) in 1-methyl-2-pyrrolidinone (0.1 mL) and 1,2-dimethoxyethane (0.3 mL) was placed in a microwave reaction vial. The reaction was irradiated for 2 h at 200° C. The reaction was diluted with acetonitrile and purified by HPLC to afford 7-[(2,4-dimethoxyphenyl)methyl]-4-[[2-[(2,4-dimethoxyphenyl)methyl]-3-methyl-1-oxo-isoindolin-5-yl]amino]-5H-pyrrolo[2,3-d]pyrimidin-6-one (3). Yield: 15 mg, 95%; MS (ESI) m/z 596 [M+1]$^+$.

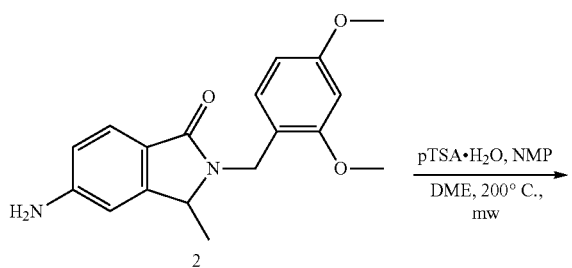

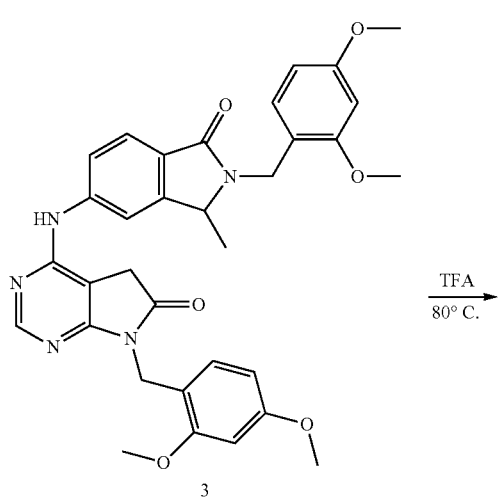

Synthesis of 4-[(3-methyl-1-oxo-isoindolin-5-yl)amino]-5,7-dihydropyrrolo[2,3-d]pyrimidin-6-one (Cpd. No. 41)

The synthesis of compound 41 was carried out as described above using the general protocol of Procedure B. Yield: 3 mg, 40%; MS (ESI) m/z 367 [M+1]$^+$; $^1$H NMR (400 MHz, CD$_3$OD-d$_4$) δ 8.37 (s, 1H), 8.04 (d, 1H), 7.68 (d, 1H), 4.69 (q, 1H), 3.56 (s, 2H), 1.48 (d, 3H).

Example 42

Synthesis of N-(4-((1-methyl-3-oxo-2,3-dihydro-1H-pyrrolo[3,4-c]pyridin-6-yl)amino)pyridin-2-yl)cyclopropanecarboxamide (Cpd. No. 42)

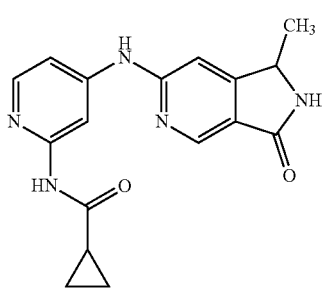

-continued

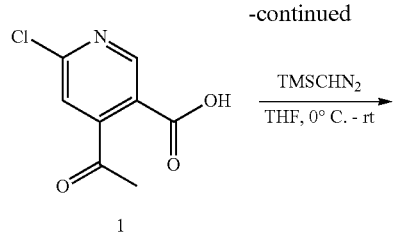

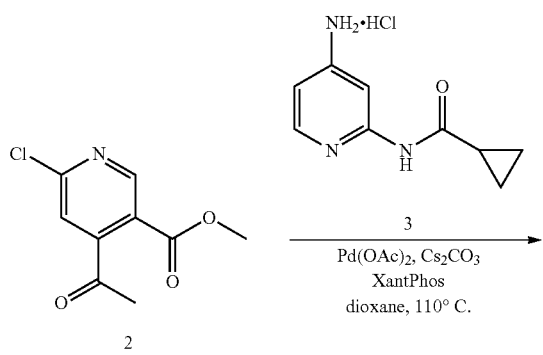

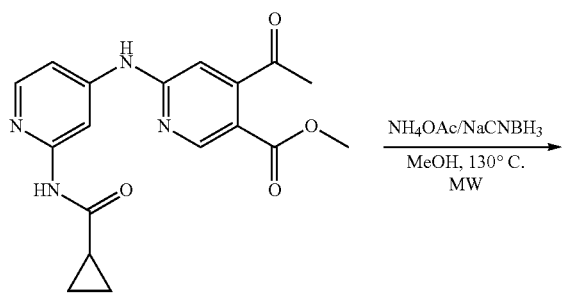

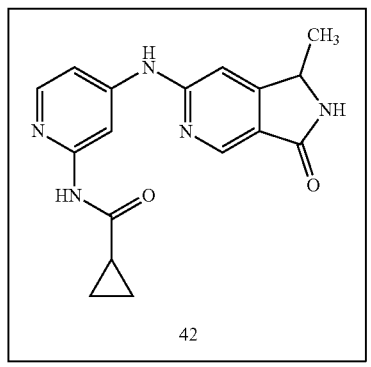

Synthesis of methyl 4-acetyl-6-chloronicotinate (2)

To a solution of 4-acetyl-6-chloronicotinic acid (1, 6.0 g, 301.01 mmol) in tetrahydrofuran (60 mL) at 0° C., trimethylsilyl diazomethane (6 mL) was added slowly. The reaction was allowed to stir at room temperature for 2 h. After completion, the reaction mixture was washed with water and brine, dried over anhydrous sodium sulfate, filtered and concentrated under reduced pressure to afford methyl 4-acetyl-6-chloronicotinate (2) as white solid. Yield: 4.3 g, 68%; $^1$H NMR (400 MHz, DMSO-d$_6$) δ: 8.87 (s, 1H), 7.83 (s, 1H), 3.85 (s, 3H), 2.52 (s, 3H).

Synthesis of methyl 4-acetyl-6-((2-(cyclopropanecarboxamido)pyridin-4-yl)amino)nicotinate (4)

The synthesis of intermediate 4 was carried out as described above using the general protocol of Procedure A. White solid; Yield: 0.32 g, 25%; MS (ESI) m/z 355.01 [M+1]$^+$.

Synthesis of N-(4-((1-methyl-3-oxo-2,3-dihydro-1H-pyrrolo[3,4-c]pyridin-6-yl)amino)pyridin-2-yl)cyclopropanecarboxamide (Cpd. No. 42)

Methyl 4-acetyl-6-((2-(cyclopropanecarboxamido)pyridin-4-yl)amino)nicotinate (4, 0.20 g, 0.56 mmol) was dissolved in methanol (4 mL) in a 10 mL microwave vial. Ammonium acetate (0.66 g, 8.40 mmol) was added followed by sodium cyanoborohydride (0.35 g, 5.60 mmol). The vial was irradiated under microwave at 130° C. for 30 min. After completion, solvent was removed under vacuum and water (5 mL) was added and the mixture was extracted with 10% methanol in dichloromethane (2×10 mL). The organics were dried over sodium sulfate and concentrated to dryness under vacuum. The crude was then purified by flash column chromatography eluting with 2% methanol in dichloromethane. The desired fractions were concentrated to dryness under vacuum to afford N-(4-((1-methyl-3-oxo-2,3-dihydro-1H-pyrrolo[3,4-c]pyridin-6-yl)amino)pyridin-2-yl)cyclopropanecarboxamide (Cpd. No. 42) as an off-white solid. Yield: 0.030 g, 16%; MS (ESI) m/z 324.32 [M+1]$^+$; $^1$H NMR (400 MHz, DMSO-d$_6$) δ 10.60 (s, 1H), 9.98 (s, 1H), 8.49 (m, 2H), 8.16 (m, 1H), 8.09 (m, 1H), 7.79 (d, J=4.4 Hz, 1H), 7.02 (s, 1H), 4.64 (m, 1H), 2.00 (m, 1H), 1.34 (d, J=6.4 Hz, 3H), 1.05 (m, 4H).

Example 43

Synthesis of 5-((6-aminopyrimidin-4-yl)amino)-7-chloro-3,3-dimethylisoindolin-1-one (Cpd. No. 43)

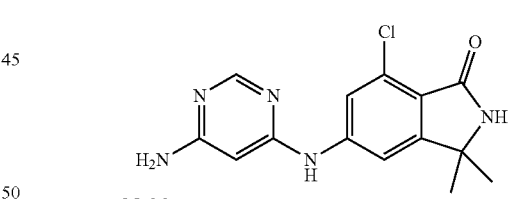

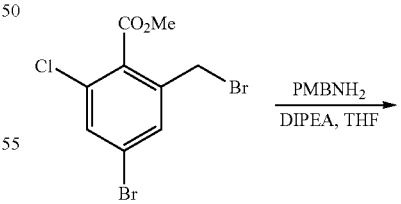

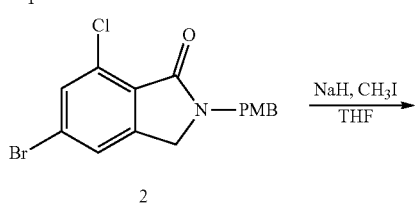

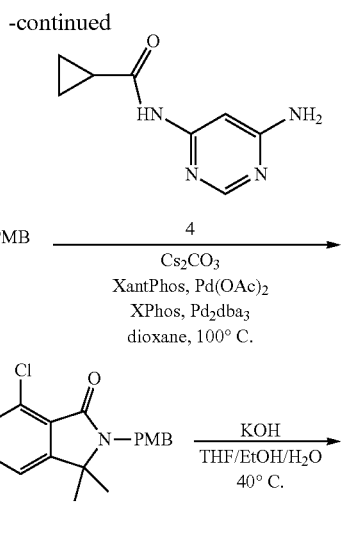

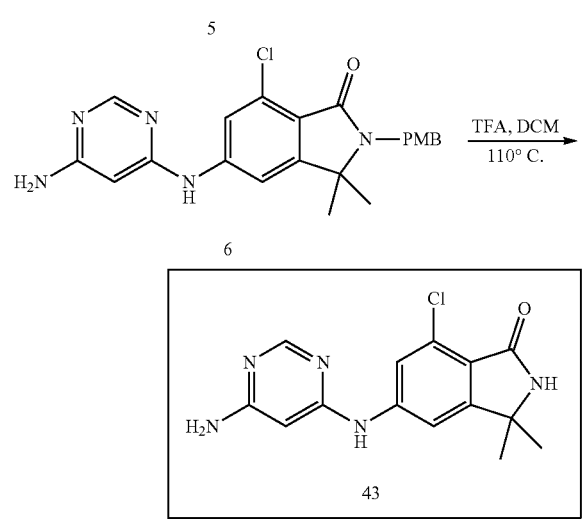

Synthesis of 5-bromo-7-chloro-2-[(4-methoxyphenyl)methyl]isoindolin-1-one (2)

A flask was charged with methyl 4-bromo-2-(bromomethyl)-6-chloro-benzoate (1, 5 g, 14.6 mmol) in tetrahydrofuran (35 mL) followed by the addition of 4-methoxybenzylamine (4.0 g, 29.2 mmol) and diisopropylethylamine (3.8 g, 29.2 mmol) at room temperature under nitrogen. The reaction mass was stirred at room temperature for 12 h. After completion, the solid precipitated was filtered and washed with cold n-pentane. The solid was dried to afford 5-bromo-7-chloro-2-[(4-methoxyphenyl)methyl]isoindolin-1-one (2) as a yellow solid. Yield: 3.3 g, 62%; MS (ESI) m/z 366 [M+1]$^+$; $^1$H NMR (400 MHz, DMSO-d$_6$) δ 7.88-7.80 (m, 2H), 7.23 (d, J=8.44 Hz, 2H), 6.89 (d, J=8.44 Hz, 2H), 4.63 (s, 2H), 4.36 (s, 2H), 3.79 (s, 3H).

Synthesis of 5-bromo-7-chloro-2-[(4-methoxyphenyl)methyl]-3,3-dimethyl-isoindolin-1-one (3)

A flask was charged with 5-bromo-7-chloro-2-[(4-methoxyphenyl)methyl]isoindolin-1-one (2, 2.5 g, 6.82 mmol) in tetrahydrofuran (25 mL) under nitrogen and sodium hydride (818 mg, 34.09 mmol) was added at room temperature. The suspension was stirred at room temperature for 30 min and then iodomethane (4839 mg, 34.09 mmol) was added. The reaction was further stirred at room temperature for 5 h. After completion, the reaction mass was quenched with saturated ammonium chloride solution at 0° C. The residue was dissolved in ethyl acetate (100 mL) and the organic layer was washed with water (2×10 mL), then with brine (10 mL). The organics were separated and dried (magnesium sulfate) before concentration to dryness. The crude was then purified by flash column chromatography eluting with 10% ethyl acetate in hexane. The desired fractions were concentrated to dryness under vacuum to afford 5-bromo-7-chloro-2-[(4-methoxyphenyl)methyl]-3,3-dimethyl-isoindolin-1-one (3) as a yellow solid. Yield: 1.8 g, 66%; MS (ESI) m/z 394.28 [M−1]$^−$; $^1$H NMR (400 MHz, DMSO-d$_6$) δ 8.01 (s, 1H), 7.76 (s, 1H), 7.31 (d, J=8.5 Hz, 2H), 6.87 (d, J=8.5 Hz, 2H), 4.58 (s, 2H), 3.72 (s, 3H), 1.36 (s, 6H).

Synthesis of N-[6-[[7-chloro-2-[(4-methoxyphenyl)methyl]-3,3-dimethyl-1-oxo-isoindolin-5-yl]amino]pyrimidin-4-yl]cyclopropanecarboxamide (5)

The synthesis of intermediate 5 was carried out as described above using the general protocol of Procedure A. Brown solid; Yield: 0.5 g, 33%; MS (ESI) m/z 492 [M+1]$^+$.

Synthesis of 5-[(6-aminopyrimidin-4-yl)amino]-7-chloro-2-[(4-methoxyphenyl)methyl]-3,3-dimethyl-isoindolin-1-one (6)

Procedure D: To a solution of N-[6-[[7-chloro-2-[(4-methoxyphenyl)methyl]-3,3-dimethyl-1-oxo-isoindolin-5-yl]amino]pyrimidin-4-yl]cyclopropanecarboxamide (5, 0.49 g, 1 mmol) in tetrahydrofuran (10 mL) and ethanol (10 mL) was added 3 M potassium hydroxide aqueous solution (8 mL). The reaction was stirred at 40° C. for 18 h. After completion the reaction mass was diluted with ethyl acetate. The organic layer was washed with brine, dried over sodium sulfate, filtered and concentrated. The crude obtained was further purified via column chromatography with 1-2% methanol in dichloromethane. The desired fractions were concentrated to obtain 5-[(6-aminopyrimidin-4-yl)amino]-7-chloro-2-[(4-methoxyphenyl)methyl]-3,3-dimethyl-isoindolin-1-one (6) as a light brown colored solid. Yield: 400 mg, 95%; MS (ESI) m/z 424.26 [M+1]$^+$; $^1$H NMR (400 MHz, DMSO-d$_6$) δ 8.14 (s, 1H), 7.86 (s, 1H), 7.65 (s, 1H), 7.30 (d, J=8.44 Hz, 2H), 6.87 (d, J=8.44 Hz, 2H), 6.57 (brs, 1H), 5.83 (s, 1H), 4.56 (s, 2H), 3.71 (s, 3H), 1.31 (s, 6H).

Synthesis of 5-[(6-aminopyrimidin-4-yl)amino]-7-chloro-3,3-dimethyl-isoindolin-1-one (Cpd. No. 43)

Procedure E: To a stirred solution of 5-[(6-aminopyrimidin-4-yl)amino]-7-chloro-2-[(4-methoxyphenyl)methyl]-3,3-dimethyl-isoindolin-1-one (6, 0.08 g, 0.19 mmol) in dichloromethane (2 mL), trifluoroacetic acid (215 mg, 1.89 mmol) was added under nitrogen. The vial was sealed and heated at 110° C. for 28 h. After completion, reaction mixture was cooled to room temperature and concentrated. The crude was co-evaporated with dichloromethane and then liquid ammonia was added to neutralize the reaction mass. The solid precipitated was filtered and dried to afford 5-[(6-aminopyrimidin-4-yl)amino]-7-chloro-3,3-dimethyl-isoindolin-1-one (Cpd. No. 43) as a brown-colored solid. Yield: 0.040 g, 69%; MS (ESI) m/z 304.3 [M+1]$^+$; $^1$H NMR (400 MHz, DMSO-$d_6$) δ 10.03 (s, 1H), 8.60 (s, 1H), 8.34 (s, 1H), 7.71 (s, 1H), 7.64 (s, 1H), 7.36 (brs, 2H), 5.90 (s, 1H), 1.41 (s, 6H).

Example 44

Synthesis of 5-((6-aminopyrimidin-4-yl)amino)-3,3, 7-trimethylisoindolin-1-one (Cpd. No. 44)

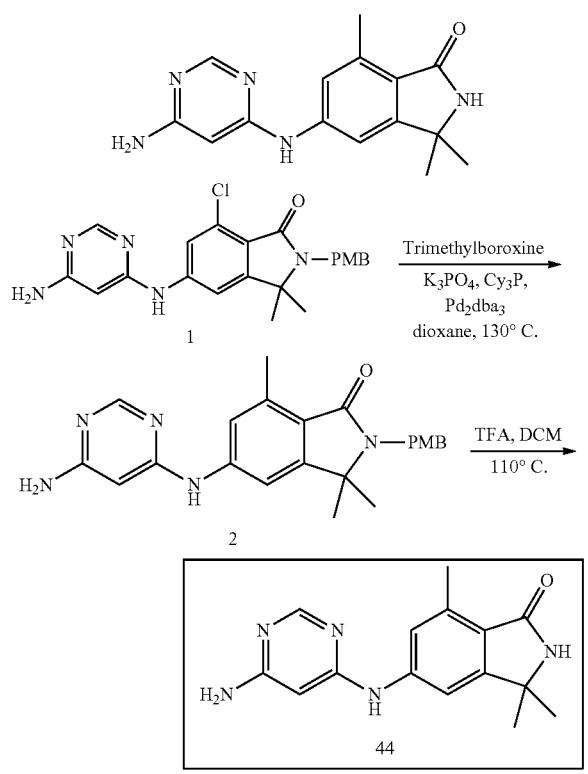

Synthesis of 5-[(6-aminopyrimidin-4-yl)amino]-2-[(4-methoxyphenyl)methyl]-3,3,7-trimethyl-isoindolin-1-one (2)

Procedure F: A vial containing 1,4-dioxane (15 mL) was charged with 5-[(6-aminopyrimidin-4-yl)amino]-7-chloro-2-[(4-methoxyphenyl)methyl]-3,3-dimethyl-isoindolin-1-one (1, 0.26 g, 0.61 mmol), trimethyl boroxine (380 mg, 3.04 mmol) and potassium phosphate (0.5 g, 1.52 mmol). The reaction was purged for 10 min with argon, then tris(dibenzylideneacetone)dipalladium(0) (55.7 mg, 0.06 mmol) and tricyclohexylphosphine (17.05 mg, 0.06 mmol) were added. Purging was continued for another 5 min. The vial was sealed and the reaction mixture was stirred at 130° C. for 16 h. After completion, the reaction was diluted with 10% methanol in dichloromethane (150 mL), filtered through a bed of celite and concentrated. The crude was triturated with dichloromethane and methanol and dried under high vacuum to afford 5-[(6-aminopyrimidin-4-yl)amino]-2-[(4-methoxyphenyl)methyl]-3,3,7-trimethyl-isoindolin-1-one (2) as a yellow solid. Yield: 0.21 g, 88%; MS (ESI) m/z 404.3 [M+1]$^+$.

Synthesis of 5-[(6-aminopyrimidin-4-yl)amino]-3,3, 7-trimethyl-isoindolin-1-one (Cpd. No. 44)

The synthesis of compound 44 was carried out as described above using the general protocol of Procedure E.

Off-white solid; Yield: 0.040 g, 28%; MS (ESI) m/z 284.03 [M+1]$^+$; $^1$H NMR (400 MHz, DMSO-$d_6$) δ 9.16 (s, 1H), 8.24 (s, 1H), 8.09 (s, 1H), 7.55 (s, 1H), 7.31 (s, 1H), 6.42 (brs, 2H), 5.83 (s, 1H), 1.33 (s, 6H).

Example 45

Synthesis of 5-(6-aminopyrimidin-4-yl)-2-naphthamide (Cpd. No. 45)

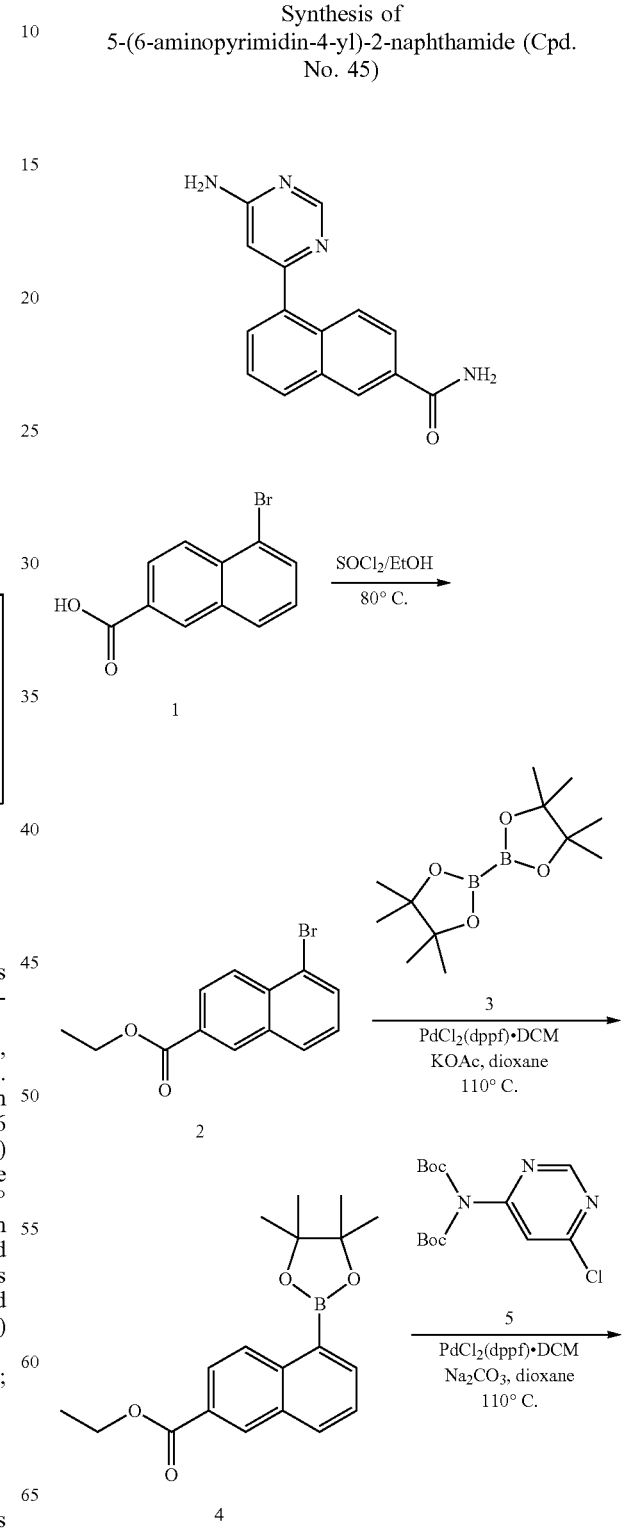

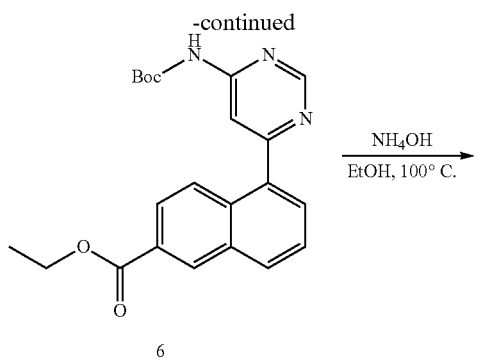

6

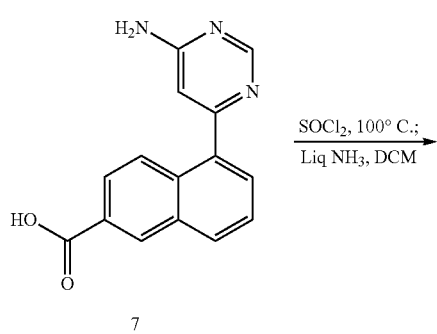

7

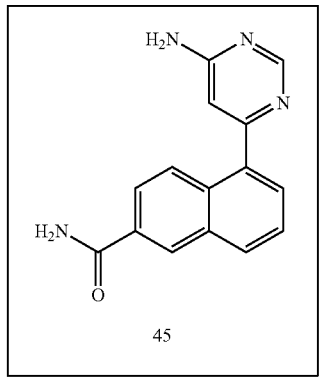

45

Synthesis of ethyl 5-bromo-2-naphthoate (2)

To a solution of 5-bromo-2-naphthoic acid (1, 2.0 g, 8.0 mmol) in ethanol (50 mL) was added thionyl chloride (5 mL) at 0° C. The reaction mixture was refluxed at 80° C. for 5 h. After completion, the reaction was basified with aqueous saturated sodium bicarbonate solution at 0° C. and diluted with Ethyl acetate. The organic layer was washed with brine, dried over sodium sulfate and concentrated to afford ethyl 5-bromo-2-naphthoate (2) as a white solid. Yield: 2.2 g, 98%; MS (ESI) m/z 279 [M+1]$^+$.

Synthesis of ethyl 5-(4,4,5,5-tetramethyl-1,3,2-dioxaborolan-2-yl)-2-naphthoate (4)

A mixture of ethyl 5-bromo-2-naphthoate (2, 2.0 g, 7.19 mmol), 4,4,4',4',5,5,5',5'-octamethyl-2,2'-bi(1,3,2-dioxaborolane) (3, 2.3 g, 9.3 mmol) and potassium acetate (1.7 g, 17.9 mmol) in 1,4-dioxane (10 mL) was purged with argon for 5 min. [1,1'-Bis(diphenylphosphino)ferrocene]dichloropalladium(II), complex with dichloromethane (293 mg, 0.36 mmol) was added and purging was continued for another 5 min. The vial was sealed and heated at 110° C. for 3 h. After completion, the solvents were removed under reduced pressure and water was added. The precipitated solid was filtered and washed with n-pentane and diethyl ether. The compound was dried under vacuum to afford ethyl 5-(4,4,5,5-tetramethyl-1,3,2-dioxaborolan-2-yl)-2-naphthoate (4) as a white solid. Yield: 1.2 g, 52%; MS (ESI) m/z 327.2 [M+1]$^+$.

Synthesis of ethyl 5-(6-((tert-butoxycarbonyl)amino)pyrimidin-4-yl)-2-naphthoate (6)

A mixture of ethyl 5-(4,4,5,5-tetramethyl-1,3,2-dioxaborolan-2-yl)-2-naphthoate (4, 1.0 g, 3.06 mmol), tert-butyl N-tert-butoxycarbonyl-N-(6-chloropyrimidin-4-yl)carbamate (5, 1.5 g, 4.6 mmol) and sodium carbonate (0.81 g, 7.60 mmol) in 1,4-dioxane (10 mL) was purged with argon for 5 min. [1,1'-Bis(diphenylphosphino)ferrocene]dichloropalladium(II), complex with dichloromethane (124 mg, 0.15 mmol) was added and purging was continued for another 5 min. The vial was sealed and heated at 110° C. for 3 h. After completion, solvent was removed under reduced pressure and water was added. The precipitated solid was filtered and washed with n-pentane and diethyl ether. The compound was dried under vacuum to afford ethyl 5-(6-((tert-butoxycarbonyl)amino)pyrimidin-4-yl)-2-naphthoate (6) as a brown solid. Yield: 1.0 g, 83%; MS (ESI) m/z 394.1 [M+1]$^+$.

Synthesis of 5-(6-aminopyrimidin-4-yl)-2-naphthoic acid (7)

A sealed tube containing ethanol (50 mL) was charged with ethyl 5-(6-((tert-butoxycarbonyl)amino)pyrimidin-4-yl)-2-naphthoate (6, 1.0 g, 2.53 mmol) and ammonium hydroxide (20 mL) at 0° C. The reaction mixture was refluxed at 100° C. for 8 h. Solvent was removed under reduced pressure to afford 5-(6-aminopyrimidin-4-yl)-2-naphthoic acid (7) as a brown solid. Yield: 0.5 g, 74%; MS (ESI) m/z 266.6 [M+1]$^+$.

Synthesis of 5-(6-aminopyrimidin-4-yl)-2-naphthamide (Cpd. No. 45)

A flask was charged with 5-(6-aminopyrimidin-4-yl)-2-naphthoic acid (7, 0.5 g, 1.88 mmol) and thionyl chloride (10 mL) at 0° C. The reaction mixture was refluxed at 100° C. for 3 h. After completion, thionyl chloride was removed under reduced pressure. The crude was diluted with dichloromethane and liquid ammonia was added at 0° C. The reaction was stirred at room temperature for 18 h. After completion, solvent was removed under reduced pressure to get the crude. The crude was purified by prep HPLC to afford 5-(6-aminopyrimidin-4-yl)-2-naphthamide (Cpd. No. 45) as a white solid. Yield: 0.15 g, 30%; MS (ESI) m/z 265.30 [M+1]$^+$; $^1$H NMR (400 MHz, DMSO-d$_6$) δ 8.55 (d, J=1.4 Hz, 1H), 8.52 (s, 1H), 8.19 (d, J=8.9 Hz, 1H), 8.16 (brs, 1H), 8.10 (dd, J=7.2, 2.4 Hz, 1H), 7.96 (dd, J=9.2, 1.8 Hz, 1H), 7.68-7.63 (m, 2H), 7.50 (brs, 1H), 7.02 (s, 2H), 6.65 (s, 1H).

Example 46

Synthesis of 4'-chloro-6'-(pyrimidin-4-ylamino)spiro[cyclohexane-1,1'-isoindolin]-3'-one (Cpd. No. 46)

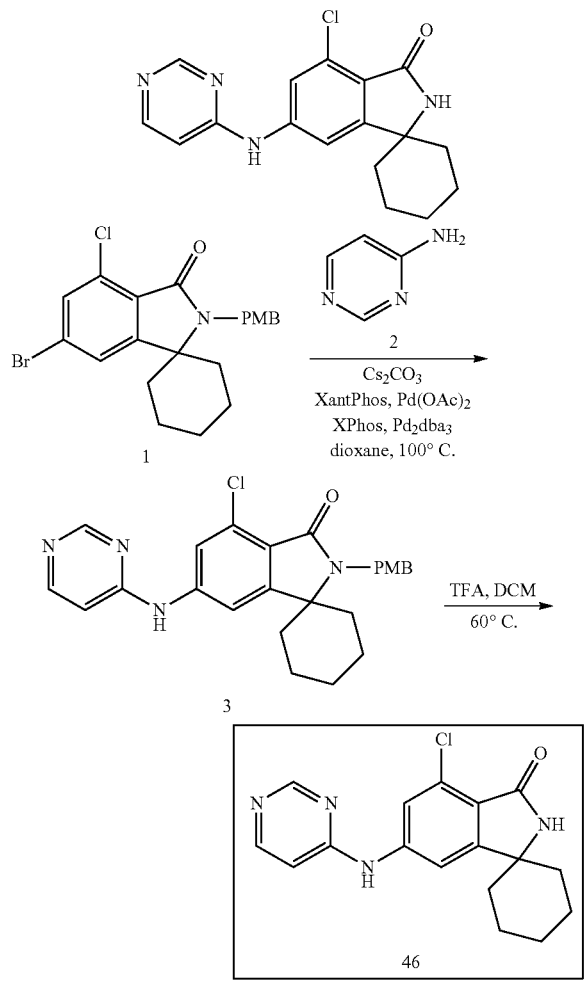

Synthesis of 7'-chloro-2'-[(4-methoxyphenyl)methyl]-5'-(pyrimidin-4-ylamino) spiro[cyclohexane-1,3'-isoindoline]-1'-one (3)

The synthesis of intermediate 3 was carried out as described above using the general protocol of Procedure A. Off-white solid; Yield: 0.05 g, 19%; MS (ESI) m/z 447.43 [M+1]$^+$.

Synthesis of 4'-chloro-6'-(pyrimidin-4-ylamino)spiro[cyclohexane-1,1'-isoindolin]-3'-one (Cpd. No. 46)

The synthesis of compound 46 was carried out as described above using the general protocol of Procedure E. Off-white solid; Yield: 0.025 g, 43%; MS (ESI) m/z 329.19 [M+1]$^+$; $^1$H NMR (400 MHz, DMSO-d$_6$) δ 10.07 (s, 1H), 9.09 (s, 1H), 8.75 (s, 1H), 8.39 (d, J=5.7 Hz, 1H), 7.89 (d, J=1.5 Hz, 1H), 7.76 (d, J=1.5 Hz, 1H), 6.88 (d, J=3.8 Hz, 1H), 1.83-1.76 (m, 2H), 1.68 (m, 4H), 1.43-1.35 (m, 2H).

Example 47

Synthesis of 6'-((6-aminopyrimidin-4-yl)amino)-4'-methylspiro[cyclopentane-1,1'-isoindolin]-3'-one (Cpd. No. 47)

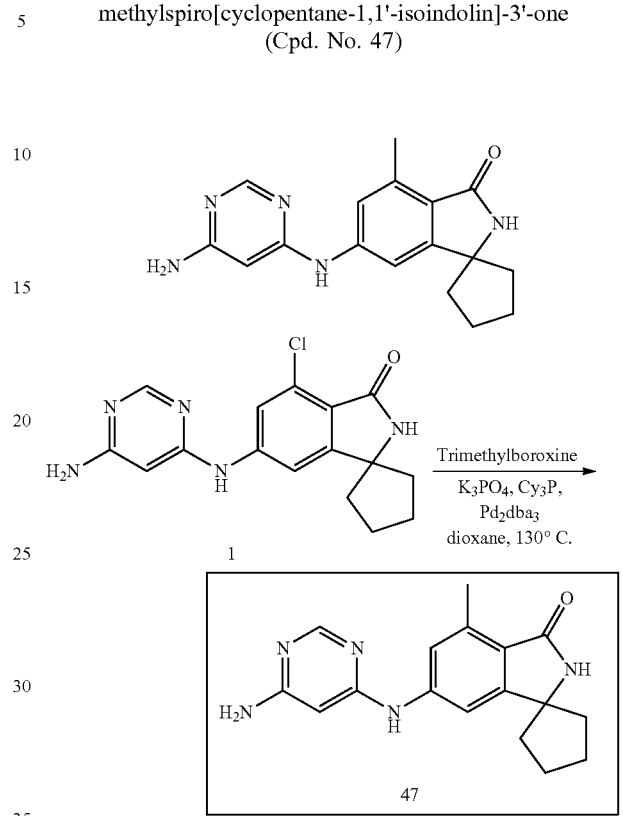

Synthesis of 6'-((6-aminopyrimidin-4-yl)amino)-4'-methylspiro[cyclopentane-1,1'-isoindolin]-3'-one (Cpd. No. 47)

The synthesis of compound 47 was carried out as described above using the general protocol of Procedure F. White solid; Yield: 0.015 g, 46%; MS (ESI) m/z 310.34 [M+1]$^+$; $^1$H NMR (400 MHz, DMSO-d$_6$) δ 9.13 (s, 1H), 8.49 (s, 1H), 8.08 (s, 1H), 7.56 (s, 1H), 7.30 (s, 1H), 6.42 (s, 2H), 5.82 (s, 1H), 2.55 (s, 3H), 1.91-1.87 (m, 8H).

Example 48

Synthesis of 6'-((6-aminopyrimidin-4-yl)amino)-4'-chlorospiro[cyclohexane-1,1'-isoindolin]-3'-one (Cpd. No. 48)

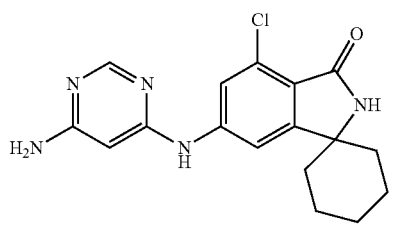

-continued

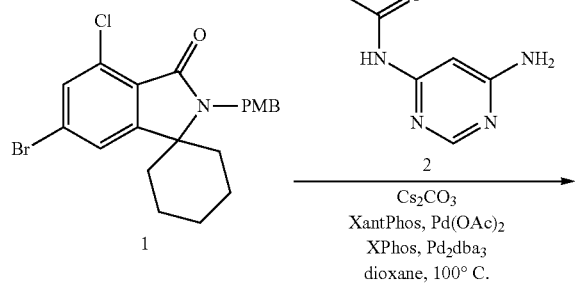

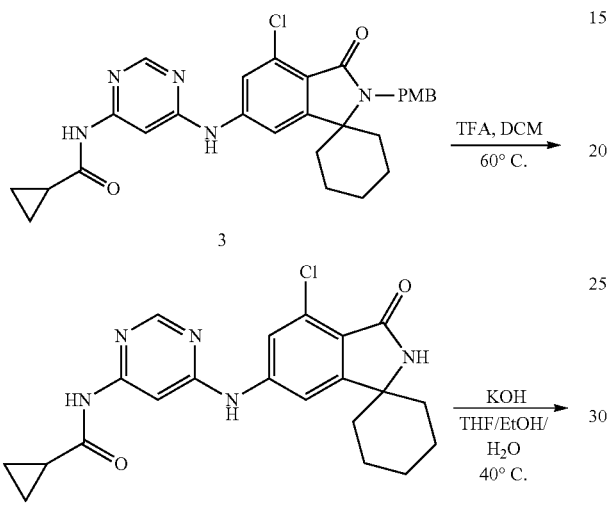

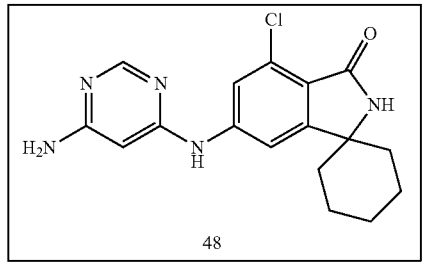

Synthesis of N-(6-((4'-chloro-2'-(4-methoxybenzyl)-3'-oxospiro[cyclohexane-1,1'-isoindolin]-6'-yl)amino)pyrimidin-4-yl)cyclopropanecarboxamide (3)

The synthesis of intermediate 3 was carried out as described above using the general protocol of Procedure A. Brown solid. Yield: 0.53 g, crude; MS (ESI) m/z 532.4 [M+1]$^+$.

Synthesis of N-(6-((4'-chloro-3'-oxospiro[cyclohexane-1,1'-isoindolin]-6'-yl)amino)pyrimidin-4-yl)cyclopropanecarboxamide (4)

The synthesis of intermediate 4 was carried out as described above using the general protocol of Procedure E. Brown solid; Yield: 85 mg, crude; MS (ESI) m/z 412.34 [M+1]$^+$.

Synthesis of 6'-((6-aminopyrimidin-4-yl)amino)-4'-chlorospiro[cyclohexane-1,1'-isoindolin]-3'-one (Cpd. No. 48)

The synthesis of compound 48 was carried out as described above using the general protocol of Procedure D. Off-white solid; Yield: 17 mg, 33%; MS (ESI) m/z 344.04 [M+1]$^+$; $^1$H NMR (400 MHz, DMSO-d$_6$) δ 9.44 (s, 1H), 8.98 (s, 1H), 8.14 (s, 1H), 7.81 (s, 1H), 7.63 (s, 1H), 6.54 (s, 2H), 5.83 (s, 1H), 1.75-1.68 (m, 8H), 1.42 (m, 2H).

Example 49

Synthesis of 1-(6-aminopyrimidin-4-yl)-1H-benzo[d]imidazole-5-carboxamide (Cpd. No. 49)

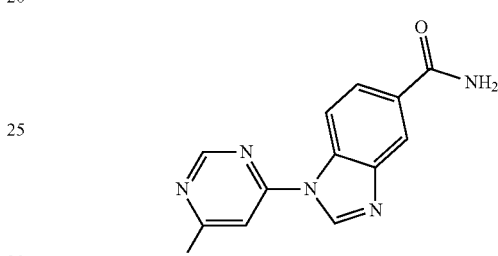

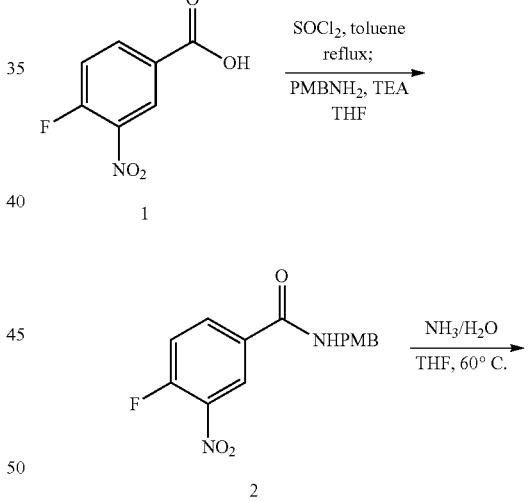

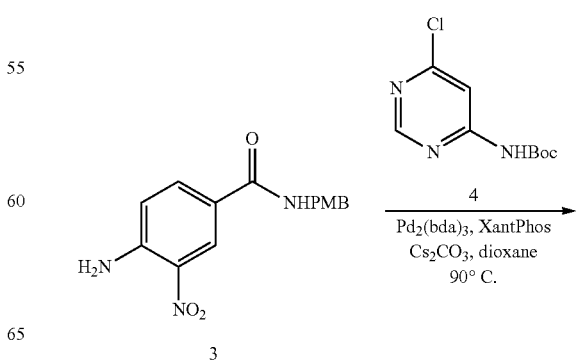

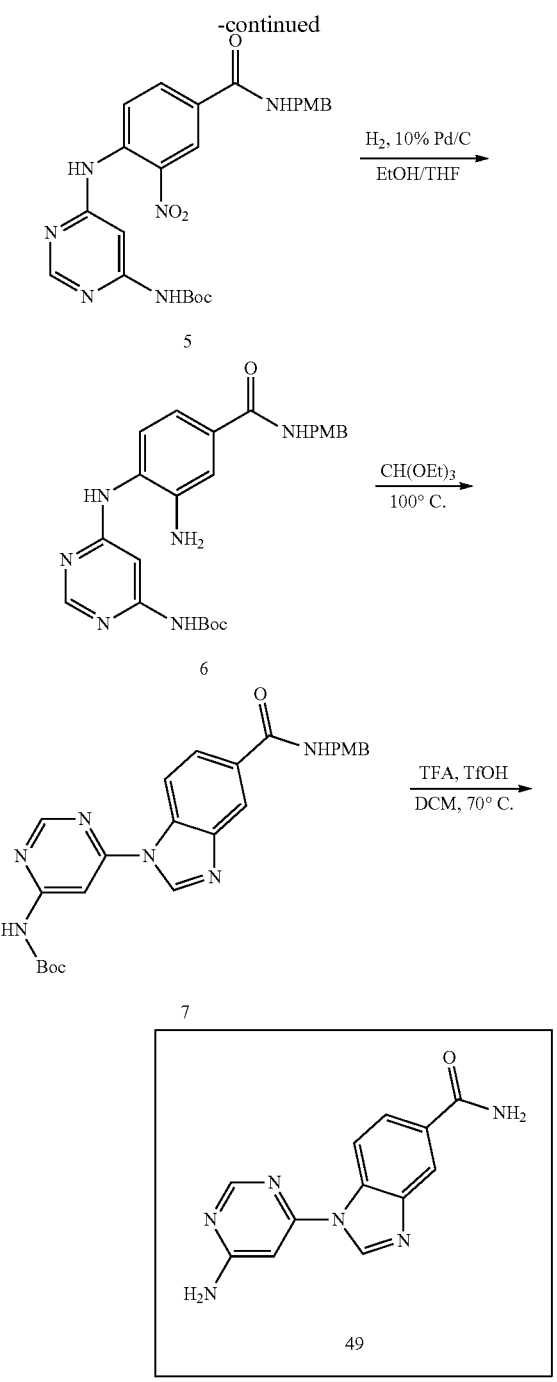

Synthesis of 4-fluoro-N-(4-methoxybenzyl)-3-nitrobenzamide (2)

Thionyl chloride (15.9 g, 135.1 mmol) was added to a solution of 4-fluoro-3-nitrobenzoic acid (1, 5 g, 27.0 mmol) in toluene (100 mL) at 0° C. under nitrogen. The reaction mixture was refluxed for 5 h and then volatiles were removed under reduced pressure. The crude was taken up in tetrahydrofuran (100 mL) and cooled to 0° C. Triethylamine (8.1 g, 80.1 mmol) was added followed by p-methoxybenzyl amine (5.5 g, 40.1 mmol). Stirring was continued for 16 h. After completion of reaction, water (50 mL) was added and the mixture was extracted with ethyl acetate (250 mL). The organic layer was separated, dried over sodium sulfate, filtered and concentrated to dryness to afford 4-fluoro-N-(4-methoxybenzyl)-3-nitrobenzamide (2). Yield: 6.5 g, crude; MS (ESI) m/z 304.28 [M+1]$^+$.

Synthesis 4-amino-N-(4-methoxybenzyl)-3-nitrobenzamide (3)

A solution of 4-fluoro-N-(4-methoxybenzyl)-3-nitrobenzamide (2, 6.5 g, 21.38 mmol) in tetrahydrofuran (100 mL) was treated with aqueous ammonia at ambient temperature. The reaction mixture was heated at 60° C. for 16 h. After completion of reaction, half of the solvent was evaporated and the crude mixture was triturated with ice water. The solid was washed with water (50 mL) and dried under vacuum to afforded 4-amino-N-(4-methoxybenzyl)-3-nitrobenzamide (3) as a yellow solid. Yield: 3.0 g, crude; MS (ESI) m/z 302.21 [M+1]$^+$.

Synthesis of tert-butyl (6-((4-((4-methoxybenzyl)carbamoyl)-2-nitrophenyl)amino) pyrimidin-4-yl) carbamate (5)

The synthesis of intermediate 5 was carried out as described above using the general protocol of Procedure A. Yellow solid; Yield: 2.1 g, 64%; MS (ESI) m/z 495.37 [M+1]$^+$.

Synthesis of tert-butyl (6-((2-amino-4-((4-methoxybenzyl)carbamoyl)phenyl)amino) pyrimidin-4-yl) carbamate (6)

To a solution of tert-butyl (6-((4-((4-methoxybenzyl)carbamoyl)-2-nitrophenyl)amino)pyrimidin-4-yl)carbamate (5, 1.38 g, 2.80 mmol) in ethanol and tetrahydrofuran (2:1, 60 mL) at room temperature was added 10% palladium on carbon (138 mg). The reaction was purged and filled with hydrogen and stirred for 16 h. After completion of reaction, the reaction mixture was filtered through a bed of celite. The celite bed was washed with 10% methanol in dichloromethane (100 mL). The filtrate was concentrated and dried under vacuo to get tert-butyl (6-((2-amino-4-((4-methoxybenzyl)carbamoyl)phenyl)amino)pyrimidin-4-yl)carbamate (6) which was forwarded to next step without further purification. Yield: 1.3 g, crude; MS (ESI) m/z 465.12 [M+1]$^+$.

Synthesis of tert-butyl (6-(5-((4-methoxybenzyl)carbamoyl)-1H-benzo[d]imidazol-1-yl)pyrimidin-4-yl)carbamate (7)

A solution of tert-butyl (6-((2-amino-4-((4-methoxybenzyl)carbamoyl)phenyl)amino) pyrimidin-4-yl)carbamate (6, 1.2 g, 2.58 mmol) in triethyl orthoformate (4.3 mL, 25.8 mmol) was stirred at 100° C. for 2 h. After completion, the mixture was diluted with 10% methanol in dichloromethane (200 mL) and washed with cold water (50 mL) and brine (50 mL). The organic layer was dried over sodium sulfate, filtered and concentrated. The crude was triturated with methanol and pentane to afford tert-butyl (6-(5-((4-methoxybenzyl)carbamoyl)-1H-benzo[d]imidazol-1-yl)pyrimidin-4-yl)carbamate (7) as a brown solid. Yield: 0.81 g, 66%; MS (ESI) m/z 475.39 [M+1]$^+$.

Synthesis of 1-(6-aminopyrimidin-4-yl)-1H-benzo[d]imidazole-5-carboxamide (Cpd. No. 49)

To a suspension of tert-butyl (6-(5-((4-methoxybenzyl)carbamoyl)-1H-benzo[d]imidazol-1-yl)pyrimidin-4-yl)carbamate (7, 0.60 g, 1.26 mmol) in dichloromethane (5 mL) at 0° C., trifluoroacetic acid (10 mL) was added followed by the addition of triflic acid (3 mL). The reaction was brought to room temperature and heated at 70° C. for 2 h. After completion, the reaction mixture was poured on ice cooled aqueous ammonia under stirring. The precipitate formed was filtered and washed with water and dried to get the crude. The crude was finally purified by flash column chromatography eluting with 10% methanol in dichloromethane. The desired fractions were concentrated to and triturated with diethyl ether and pentane to afford 1-(6-aminopyrimidin-4-yl)-1H-benzo[d]imidazole-5-carboxamide as an off-white solid. Yield: 0.22 g, 70%; MS (ESI) m/z 255.03 [M+1]$^+$; $^1$H NMR (400 MHz, DMSO-d$_6$) δ 8.96 (s, 1H), 8.45 (s, 1H), 8.33 (s, 1H), 8.22 (d, J=8.8 Hz, 1H), 8.08 (brs, 1H), 7.95 (d, J=8.8 Hz, 1H), 7.39 (brs, 1H), 7.26 (brs, 2H), 6.82 (s, 1H).

Example 50

Synthesis of 5-((6-amino-5-chloropyrimidin-4-yl) amino)-7-chloro-3,3-dimethylisoindolin-1-one (Cpd. No. 50)

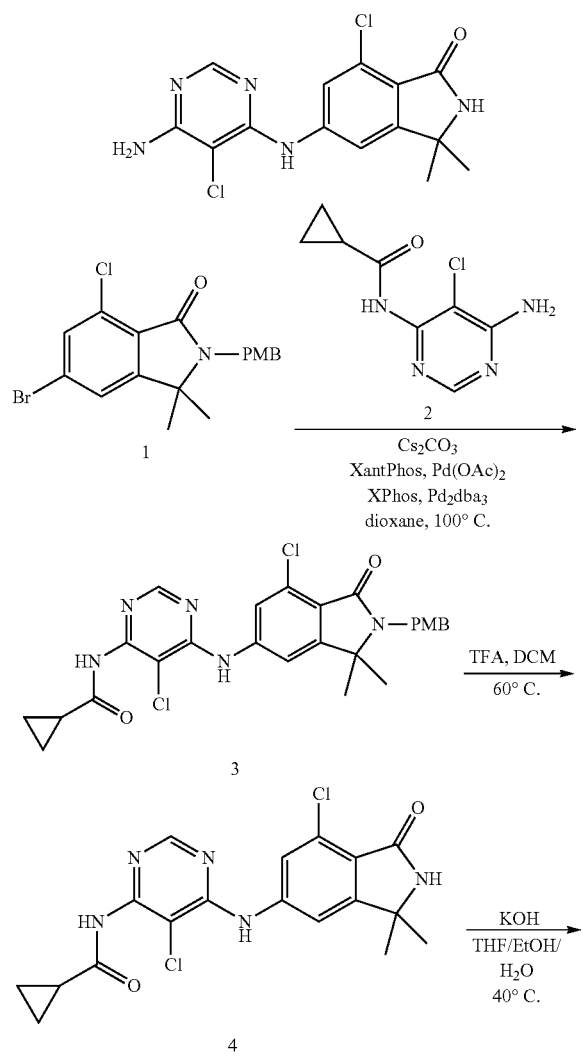

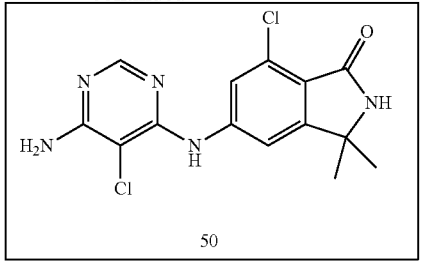

Synthesis of N-(5-chloro-6-((7-chloro-2-(4-methoxybenzyl)-3,3-dimethyl-1-oxoisoindolin-5-yl) amino)pyrimidin-4-yl)cyclopropanecarboxamide (3)

The synthesis of intermediate 3 was carried out as described above using the general protocol of Procedure A. Brown solid. Yield: 0.19 g, crude; MS (ESI) m/z 526 [M+1]$^+$.

Synthesis of N-(5-chloro-6-((7-chloro-3,3-dimethyl-1-oxoisoindolin-5-yl)amino)pyrimidin-4-yl)cyclopropanecarboxamide (4)

The synthesis of intermediate 4 was carried out as described above using the general protocol of Procedure E. Brown solid; Yield: 80 mg, 58%; MS (ESI) m/z 406 [M+1]$^+$.

Synthesis of 5-((6-amino-5-chloropyrimidin-4-yl) amino)-7-chloro-3,3-dimethylisoindolin-1-one (Cpd. No. 50)

The synthesis of compound 50 was carried out as described above using the general protocol of Procedure D. Off-white solid; Yield: 23 mg, 40%; MS (ESI) m/z 338.04 [M+1]$^+$; $^1$H NMR (400 MHz, DMSO-d$_6$) δ 8.82 (s, 1H), 8.55 (s, 1H), 8.06 (s, 1H), 7.91 (s, 1H), 7.79 (s, 1H), 6.98 (s, 2H), 1.4 (s, 6H).

Example 51

Synthesis of 6'-((6-aminopyrimidin-4-yl)amino)-4'-methylspiro[cyclohexane-1,1'-isoindolin]-3'-one (Cpd. No. 51)

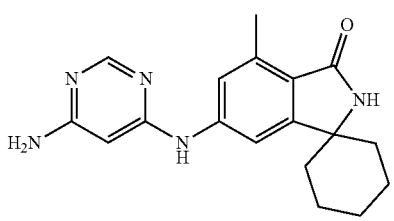

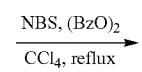

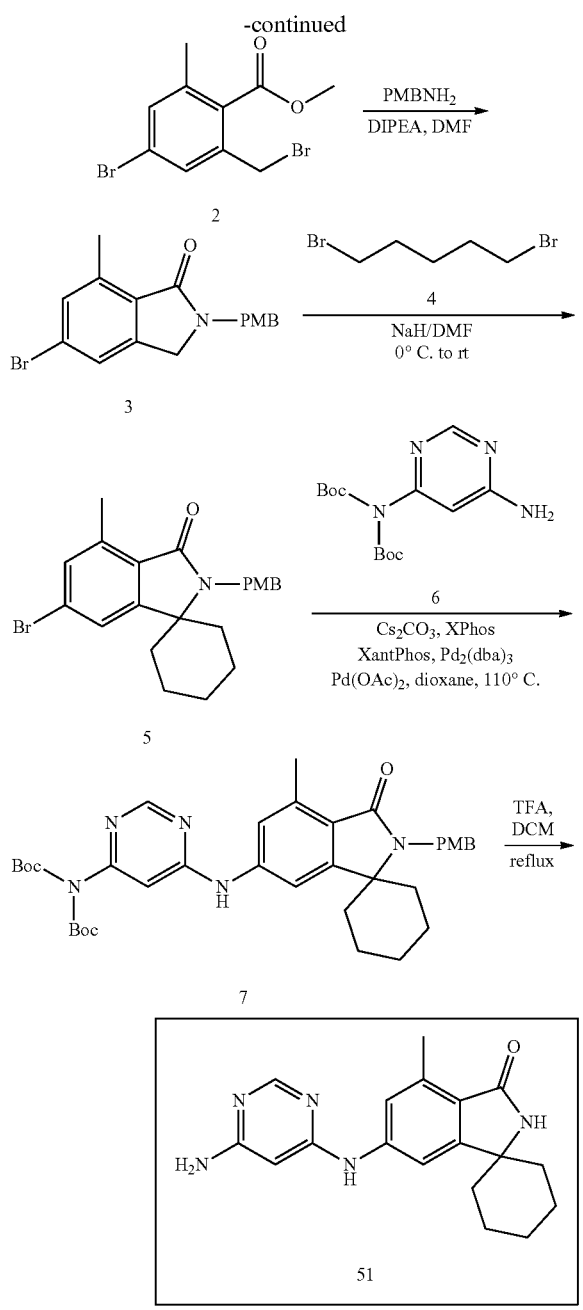

Synthesis of methyl 4-bromo-2-(bromomethyl)-6-methylbenzoate (2)

To a solution of methyl 4-bromo-2,6-dimethylbenzoate (1, 5.5 g, 22.63 mmol) in carbon tetrachloride at room temperature was add N-bromosuccinamide (4.4 g, 24.89 mmol) and benzoyl peroxide (0.5 g, 2.23 mmol). The reaction was refluxed for 16 h. After completion of the reaction as monitored by TLC, the mixture was cooled to room temperature, filtered and washed with carbon tetrachloride (30 mL). The filtrate was concentrated under reduced pressure to dryness to get methyl 4-bromo-2-(bromomethyl)-6-methylbenzoate (2) as a brown liquid. Yield: 7.5 g, crude; MS (ESI) m/z 322.12 [M+1]$^+$.

Synthesis of 5-bromo-2-(4-methoxybenzyl)-7-methylisoindolin-1-one (3)

To a solution of methyl 4-bromo-2-(bromomethyl)-6-methylbenzoate (2, 7.5 g, 23.29 mmol) in dimethylformamide (70 mL) at 0° C. was added diisopropylethylamine (9.0 g, 69.87 mmol) and p-methoxybenzylamine (4.7 g, 34.93 mmol). The reaction was stirred at room temperature for 16 h. After completion of the reaction as monitored by TLC, water (150 mL) was added and the mixture was extracted with ethyl acetate (2×200 mL). The organic layer was dried over anhydrous sodium sulfate, filtered and concentrated. The crude was purified by flash column chromatography eluting with 15% ethyl acetate in hexane. The desired fractions were concentrated and dried under vacuum to afford 5-bromo-2-(4-methoxybenzyl)-7-methylisoindolin-1-one (3) as a pale yellow solid. Yield: 3.5 g, 38%; MS (ESI) m/z 346.19 [M+1]$^+$.

Synthesis of 6'-bromo-2'-(4-methoxybenzyl)-4'-methylspiro[cyclohexane-1,1'-isoindolin]-3'-one (5)

To a solution of 5-bromo-2-(4-methoxybenzyl)-7-methylisoindolin-1-one (3, 1.5 g, 4.34 mmol) in dimethylformamide (15 mL) at 0° C. was added sodium hydride (0.5 g, 10.86 mmol). The reaction was stirred at room temperature for 30 min. 1,5-Dibromopentane (4, 1.29 g, 5.65 mmol) was added and the reaction was stirred for 16 h at room temperature. After completion of the reaction as monitored by TLC, water was added to quench the reaction and the mixture was extracted with ethyl acetate (2×150 mL). The organics were combined, dried over anhydrous sodium sulfate, filter and concentrate. The crude was purified by flash column chromatography eluting with 20% ethyl acetate in hexane. The desire fractions were concentrated to dryness under vacuum to afford 6'-bromo-2'-(4-methoxybenzyl)-4'-methylspiro[cyclohexane-1,1'-isoindolin]-3'-one (5) as a pale yellow solid. Yield: 0.45 g, 25%; MS (ESI) m/z 414.04 [M+1]$^+$.

Synthesis of tert-butyl N-tert-butoxycarbonyl-N-(6-((2'-(4-methoxybenzyl)-4'-methyl-3'-oxospiro[cyclohexane-1,1'-isoindolin]-6'-yl)amino)pyrimidin-4-yl)carbamate (7)

The synthesis of intermediate 7 was carried out as described above using the general protocol of Procedure A. Pale yellow solid; Yield: 0.2 g, 26%; MS (ESI) m/z 644.43 [M+1]$^+$.

Synthesis of 6'-((6-aminopyrimidin-4-yl)amino)-4'-methylspiro[cyclohexane-1,1'-isoindolin]-3'-one (Cpd. No. 51)

The synthesis of compound 51 was carried out as described above using the general protocol of Procedure E. Pale yellow solid; Yield: 0.05 g, 26%; MS (ESI) m/z 324.36 [M+1]$^+$; NMR (400 MHz, DMSO-d$_6$) δ 9.16 (s, 1H), 8.74 (s, 1H), 8.09 (s, 1H), 7.57 (s, 1H), 7.30 (s, 1H), 6.42 (s, 2H), 5.83 (s, 1H), 2.48 (s, 3H), 1.67 (m, 7H), 1.35 (m, 3H).

Example 52

Synthesis of 5-((6-aminopyrimidin-4-yl)amino)-4-chloro-3,3-dimethylisoindolin-1-one (Cpd. No. 52)

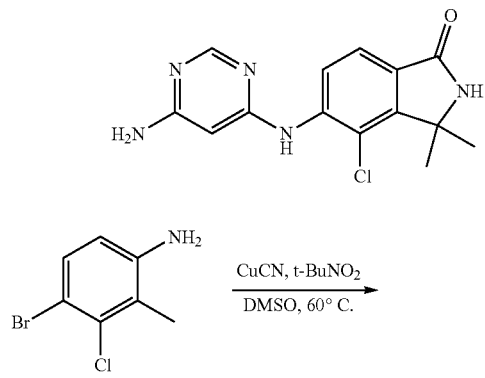

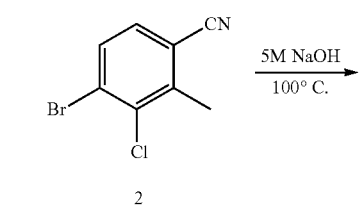

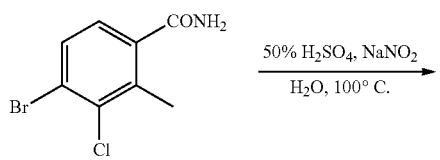

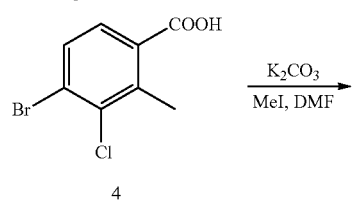

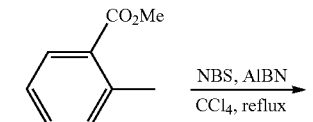

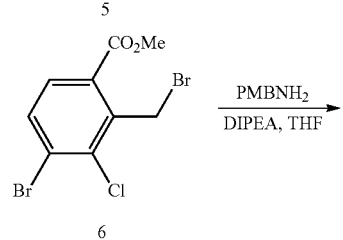

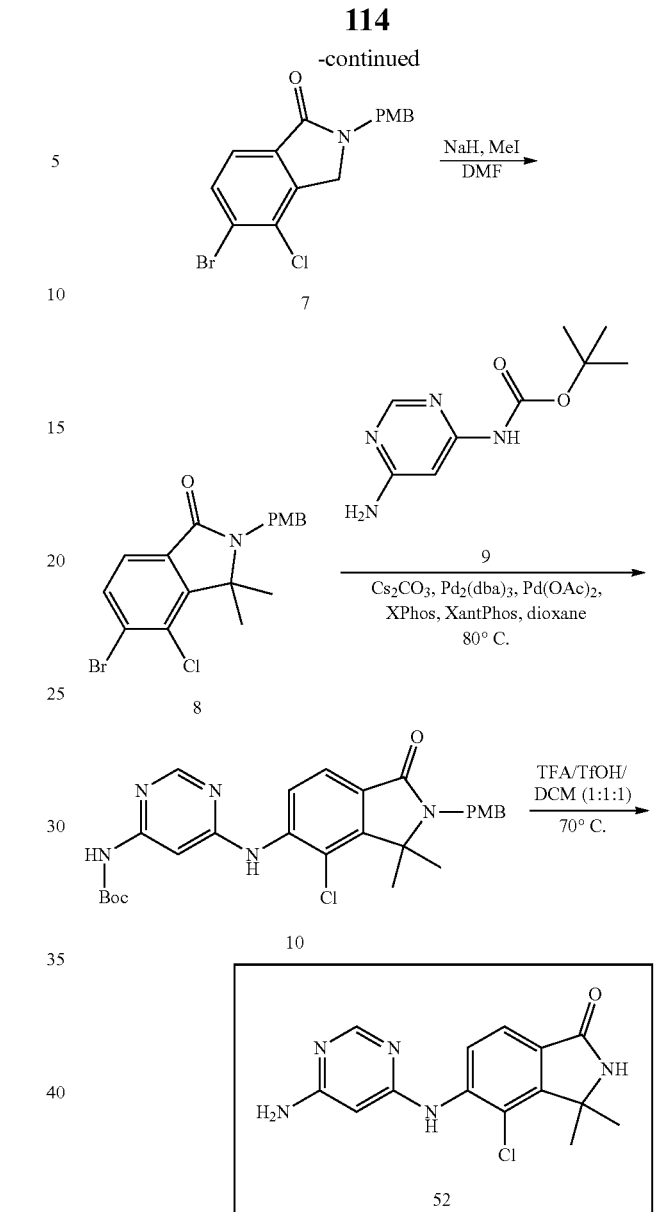

Synthesis of 4-bromo-3-chloro-2-methylbenzonitrile (2)

A solution of copper(I) cyanide (5.28 g, 59.0 mmol) and tert-butyl nitrite (14 g, 136.1 mmol) in dimethyl sulfoxide (100 mL) was stirred at 60° C. for 30 min. To this mixture was added a solution of 4-bromo-3-chloro-2-methylaniline (1, 10.0 g, 45.4 mmol) in DMSO dropwise over a period of 30 min. The reaction was stirred at 60° C. for 1 h. After completion, the reaction was quenched with 6 M hydrochloric acid and extracted with ethyl acetate (2×100 mL). The organics were dried over sodium sulfate, filtered and concentrated. The crude was purified by silica gel column chromatography eluting with 5-10% ethyl acetate in hexane to afford 4-bromo-3-chloro-2-methylbenzonitrile (2) as a yellow solid. Yield: 4.5 g, 43%; $^1$H NMR (400 MHz, DMSO-$d_6$) δ 7.84 (d, J=8.4 Hz, 1H), 7.72 (d, J=6.4 Hz, 1H), 2.62 (s, 3H).

Synthesis of 4-bromo-3-chloro-2-methylbenzamide (3)

4-Bromo-3-chloro-2-methylbenzonitrile (2, 4.4 g, 19.08 mmol) was mixed with 5 M sodium hydroxide in water (25 mL). The mixture was heated at 100° C. for 16 h. After completion, the reaction was quenched with aqueous solution of citric acid till pH 8. Off-white solid precipitated out. It was filtered, washed with water and dried under vacuum to afford 4-bromo-3-chloro-2-methylbenzamide (3) as an off-white solid. Yield: 3.5 g, 74%; MS (ESI) m/z 250.16 [M+1]$^+$.

Synthesis of 4-bromo-3-chloro-2-methylbenzoic acid (4)

To a mixture of 4-bromo-3-chloro-2-methylbenzamide (3, 2.5 g, 10.0 mmol) in 50% sulfuric acid (50 mL) at 0° C. was added a saturated aqueous solution of sodium nitrite (2.0 g, 27.0 mmol). The reaction was stirred at 100° C. for 16 h. After completion, the reaction was cooled and ice cold water was added. The precipitated white solid was filtered, washed with cold n-pentane and dried under vacuum to afford 4-bromo-3-chloro-2-methylbenzoic acid (4) as a white solid. Yield: 2.0 g, 61%; MS (ESI) m/z 248.88 [M−1]$^-$.

Synthesis of methyl 4-bromo-3-chloro-2-methylbenzoate (5)

To a mixture of 4-bromo-3-chloro-2-methylbenzoic acid (4, 4.5 g, 18.03 mmol) and potassium carbonate (4.97 g, 36.07 mmol) in dimethylformamide (100 mL) at room temperature was add iodomethane (3.83 g, 27.0 mmol) slowly. The reaction was stirred at room temperature for 1 h and quenched with ice cold water. The mixture was extracted with ethyl acetate. The organic layer was dried over sodium sulfate, filtered and concentrated. The crude was purified by silica gel column chromatography eluting with 2-5% ethyl acetate in hexane to afford methyl 4-bromo-3-chloro-2-methylbenzoate (5) as a brown liquid. Yield: 2.2 g, 38%.

Synthesis of methyl 4-bromo-2-(bromomethyl)-3-chlorobenzoate (6)

To a solution of methyl 4-bromo-3-chloro-2-methylbenzoate (5, 2.0 g, 7.59 mmol) in carbon tetrachloride (50 mL) was added N-bromosuccinimide (1.35 g, 7.59 mmol) and azobisisobutyronitrile (125 mg, 0.75 mmol). The reaction was heated at 100° C. for 24 h. After completion, the reaction was cooled to room temperature and filtered. The filtrate was concentrate and dried to afford methyl 4-bromo-2-(bromomethyl)-3-chlorobenzoate (6) as a colorless liquid. Yield: 2.2 g, 84%.

Synthesis of 5-bromo-4-chloro-2-(4-methoxybenzyl) isoindolin-1-one (7)

To a solution of methyl 4-bromo-2-(bromomethyl)-3-chlorobenzoate (6, 2.2 g, 6.42 mmol) in tetrahydrofuran (35 mL) was added 4-methoxybenzylamine (1.05 g, 7.71 mmol) and diisopropylethylamine (2.49 g, 19.27 mmol). The mixture was stirred at room temperature for 16 h. After completion, the precipitated solid was filtered, washed with cold n-pentane and dried to afford 5-bromo-4-chloro-2-(4-methoxybenzyl)isoindolin-1-one (7) as a yellow solid. Yield: 1.45 g, 61%; MS (ESI) m/z 366.2 [M+1]$^+$.

Synthesis of 5-bromo-4-chloro-2-(4-methoxybenzyl)-3,3-dimethylisoindolin-1-one (8)

To a solution of 5-bromo-4-chloro-2-(4-methoxybenzyl)isoindolin-1-one (7, 1.4 g, 3.81 mmol) in dimethylformamide (25 mL) was added sodium hydride (0.45 g, 19.09 mmol). The suspension was stirred at room temperature for 30 min followed by the addition of iodomethane (5.95 g, 38.18 mmol). The reaction was stirred for another 2 h. After completion, the reaction was quenched with aqueous saturated ammonium chloride solution at 0° C. The mixture was extracted with ethyl acetate (100 mL). The organic layer was washed with water (2×50 mL) and brine (50 mL). The organic layer was dried over magnesium sulfate, filtered and concentrated. The crude was purified by flash column chromatography eluting with 5 to 50% ethyl acetate in hexane to afford 5-bromo-4-chloro-2-(4-methoxybenzyl)-3,3-dimethylisoindolin-1-one (8) as a yellow solid. Yield: 0.5 g, 33%; MS (ESI) m/z 394.28 [M+1]$^+$.

Synthesis of tert-butyl (6-((4-chloro-2-(4-methoxybenzyl)-3,3-dimethyl-1-oxoisoindolin-5-yl)amino)pyrimidin-4-yl)carbamate (10)

The synthesis of intermediate 10 was carried out as described above using the general protocol of Procedure A. Brown solid; Yield: 0.2 g, 50%; MS (ESI) m/z 252 [M+1]$^+$.

Synthesis of 5-((6-aminopyrimidin-4-yl)amino)-4-chloro-3,3-dimethylisoindolin-1-one (Cpd. No. 52)

To a stirred solution of tert-butyl (6-((4-chloro-2-(4-methoxybenzyl)-3,3-dimethyl-1-oxoisoindolin-5-yl)amino)pyrimidin-4-yl)carbamate (10, 0.3 g, 0.57 mmol) in dichloromethane (2 mL) was added trifluoroacetic acid (2 mL) and triflic acid (2 mL). The vial was sealed and heat at 70° C. for 48 h. After completion, the reaction was cooled to room temperature and concentrated. The crude was co-evaporated with dichloromethane and liquid ammonia was added to neutralize the reaction mass. The solid precipitate was filtered and purified by Prep HPLC to afford 5-((6-aminopyrimidin-4-yl)amino)-4-chloro-3,3-dimethylisoindolin-1-one (Cpd. No. 52) as a yellow solid. Yield: 0.018 g, 10%; MS (ESI) m/z 304.09 [M+1]$^+$; $^1$H NMR (400 MHz, DMSO-$d_6$) δ 8.72 (s, 1H), 8.60 (s, 1H), 8.01 (s, 1H), 7.90-7.89 (m, 1H), 7.52 (m, 1H), 6.46 (brs, 2H), 5.87 (s, 1H), 1.58 (s, 6H).

Example 53

Synthesis of 6'-((6-amino-5-ethylpyrimidin-4-yl)amino)-4'-methylspiro[cyclohexane-1,1'-isoindolin]-3'-one (Cpd. No. 53)

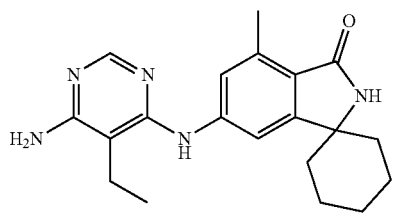

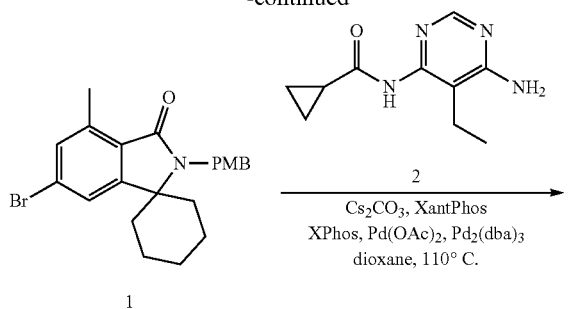

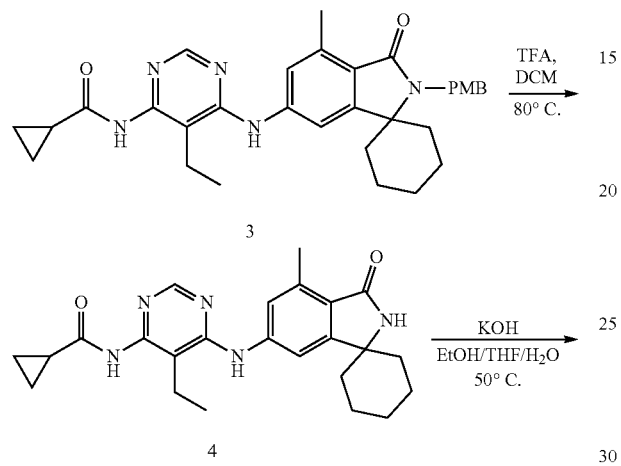

Synthesis of N-(5-ethyl-6-((2'-(4-methoxybenzyl)-4'-methyl-3'-oxospiro[cyclohexane-1,1'-isoindolin]-6'-yl)amino)pyrimidin-4-yl)cyclopropanecarboxamide (3)

The synthesis of intermediate 3 was carried out as described above using the general protocol of Procedure A. Pale yellow solid; Yield: 0.25 g, 38%; MS (ESI) m/z 540.5 [M+1]$^+$.

Synthesis of N-(5-ethyl-6-((4'-methyl-3'-oxospiro[cyclohexane-1,1'-isoindolin]-6'-yl)amino)pyrimidin-4-yl)cyclopropanecarboxamide (4)

The synthesis of intermediate 4 was carried out as described above using the general protocol of Procedure E. Pale yellow solid; Yield: 0.16 g, 84%; MS (ESI) m/z 418.17 [M+1]$^+$.

Synthesis 6'-((6-amino-5-ethylpyrimidin-4-yl)amino)-4'-methylspiro[cyclohexane-1,1'-isoindolin]-3'-one (Cpd. No. 53)

The synthesis of compound 53 was carried out as described above using the general protocol of Procedure D. Pale yellow solid; Yield: 0.03 g, 25%; MS (ESI) m/z 352.28 [M+1]$^+$; $^1$H NMR (400 MHz, DMSO-d$_6$) δ 8.73 (s, 1H), 8.10 (s, 1H), 7.95 (s, 1H), 7.58 (s, 1H), 7.43 (s, 1H), 6.26 (s, 2H), 2.50 (m, 5H), 1.80-1.62 (m, 6H), 1.40-1.30 (m, 4H), 1.01 (t, J=7.6 Hz, 3H).

Example 54

Synthesis of 6'-((5-methoxypyrimidin-4-yl)amino)-4'-methylspiro[cyclohexane-1,1'-isoindolin]-3'-one (Cpd. No. 54)

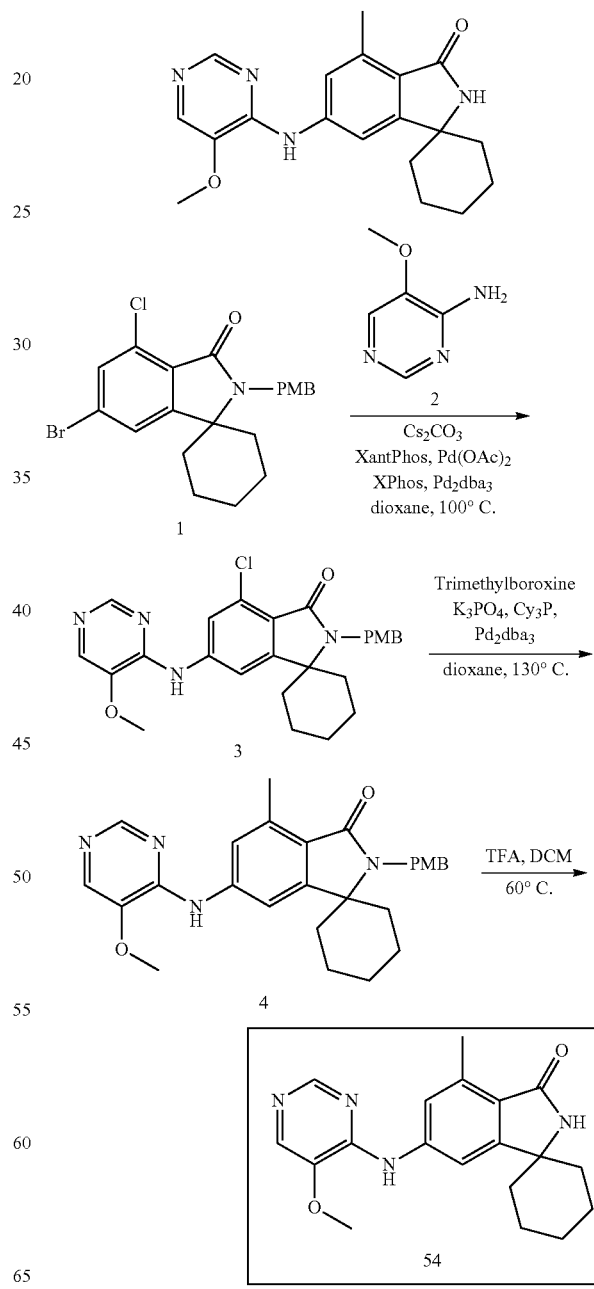

Synthesis of 4'-chloro-2'-(4-methoxybenzyl)-6'-((5-methoxypyrimidin-4-yl)amino)spiro[cyclohexane-1,1'-isoindolin]-3'-one (3)

The synthesis of intermediate 3 was carried out as described above using the general protocol of Procedure A. Brown solid; Yield: 0.47 g, crude; MS (ESI) m/z 479.4 [M+1]$^+$.

Synthesis of 2'-(4-methoxybenzyl)-6'-((5-methoxypyrimidin-4-yl)amino)-4'-methylspiro[cyclohexane-1,1'-isoindolin]-3'-one (4)

The synthesis of intermediate 4 was carried out as described above using the general protocol of Procedure F. Yellow solid; Yield: 0.42 g, crude; MS (ESI) m/z 459.3 [M+1]$^+$.

Synthesis of 6'-((5-methoxypyrimidin-4-yl)amino)-4'-methylspiro[cyclohexane-1,1'-isoindolin]-3'-one (Cpd. No. 54)

The synthesis of compound 54 was carried out as described above using the general protocol of Procedure E. Brown solid; Yield: 0.13 g, 28%; MS (ESI) m/z 337.01 [M−1]$^−$; $^1$H NMR (400 MHz, DMSO-d$_6$) δ 9.04 (s, 1H), 8.83 (s, 1H), 8.35 (s, 1H), 8.12 (s, 1H), 7.87 (s, 1H), 7.70 (s, 1H), 3.95 (s, 3H), 2.55 (s, 3H), 1.76-1.69 (m, 7H), 1.40-1.34 (m, 3H).

Example 55

Synthesis of 6'-((6-amino-5-methylpyrimidin-4-yl)amino)-4'-methylspiro[cyclohexane-1,1'-isoindolin]-3'-one (Cpd. No. 55)

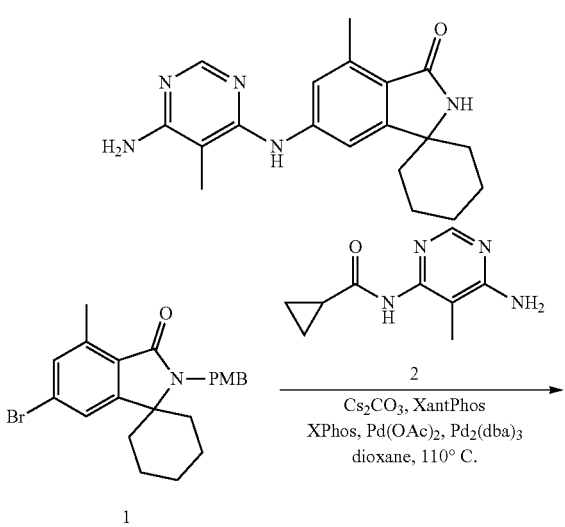

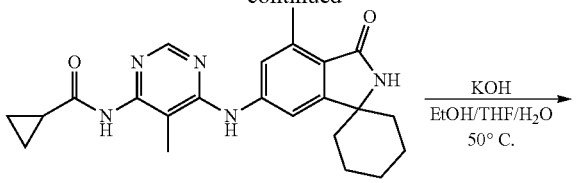

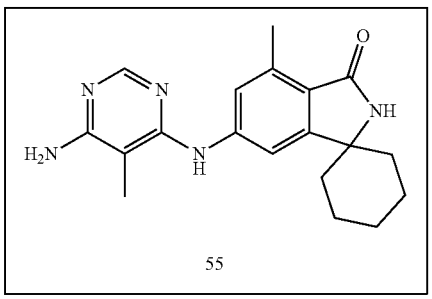

Synthesis of N-(6-((2'-(4-methoxybenzyl)-4'-methyl-3'-oxospiro[cyclohexane-1,1'-isoindolin]-6'-yl)amino)-5-methylpyrimidin-4-yl)cyclopropanecarboxamide (3)

The synthesis of intermediate 3 was carried out as described above using the general protocol of Procedure A. Pale yellow solid; Yield: 0.5 g, 79%; MS (ESI) m/z 526.62 [M+1]$^+$.

Synthesis of N-(5-methyl-6-((4'-methyl-3'-oxospiro[cyclohexane-1,1'-isoindolin]-6'-yl)amino)pyrimidin-4-yl)cyclopropanecarboxamide (4)

The synthesis of intermediate 4 was carried out as described above using the general protocol of Procedure E. Pale yellow solid; Yield: 0.15 g, 39%; MS (ESI) m/z 406.43 [M+1]$^+$.

Synthesis of 6'-((6-amino-5-methylpyrimidin-4-yl)amino)-4'-methylspiro[cyclohexane-1,1'-isoindolin]-3'-one (Cpd. No. 55)

The synthesis of compound 55 was carried out as described above using the general protocol of Procedure D. Pale yellow solid; Yield: 0.03 g, 14%; MS (ESI) m/z 338.40 [M+1]$^+$; $^1$H NMR (400 MHz, DMSO-d$_6$) δ 8.72 (s, 1H), 8.14 (s, 1H), 7.98 (s, 1H), 7.54 (s, 1H), 7.39 (s, 1H), 6.25 (s, 2H), 5.83 (s, 1H), 2.48 (s, 3H), 1.96 (s, 3H), 1.68 (m, 7H), 1.36 (m, 3H).

Example 56

Synthesis of 6'-((5-ethylpyrimidin-4-yl)amino)-4'-methylspiro[cyclohexane-1,1'-isoindolin]-3'-one (Cpd. No. 56)

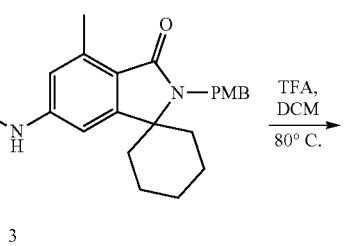

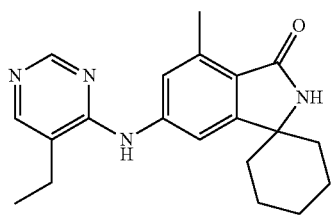

[M−1]−; 1H NMR (400 MHz, DMSO-d6) δ 8.86 (s, 1H), 8.61 (s, 1H), 8.52 (s, 1H), 8.20 (s, 1H), 7.71 (s, 1H), 7.55 (s, 1H), 2.66 (q, J=7.6 Hz, 2H), 1.82-1.69 (m, 7H), 1.40-1.34 (m, 3H), 1.20 (t, J=7.6 Hz, 3H).

Example 57

Synthesis of 6'-((6-amino-5-methoxypyrimidin-4-yl)amino)-4'-methylspiro[cyclohexane-1,1'-isoindolin]-3'-one (Cpd. No. 57)

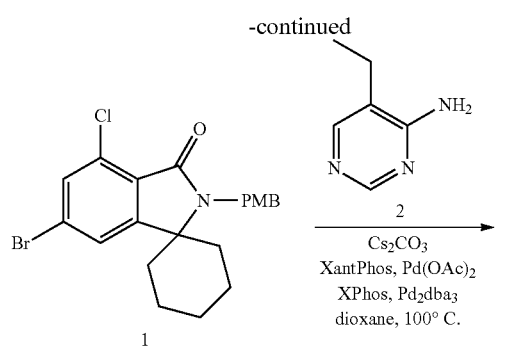

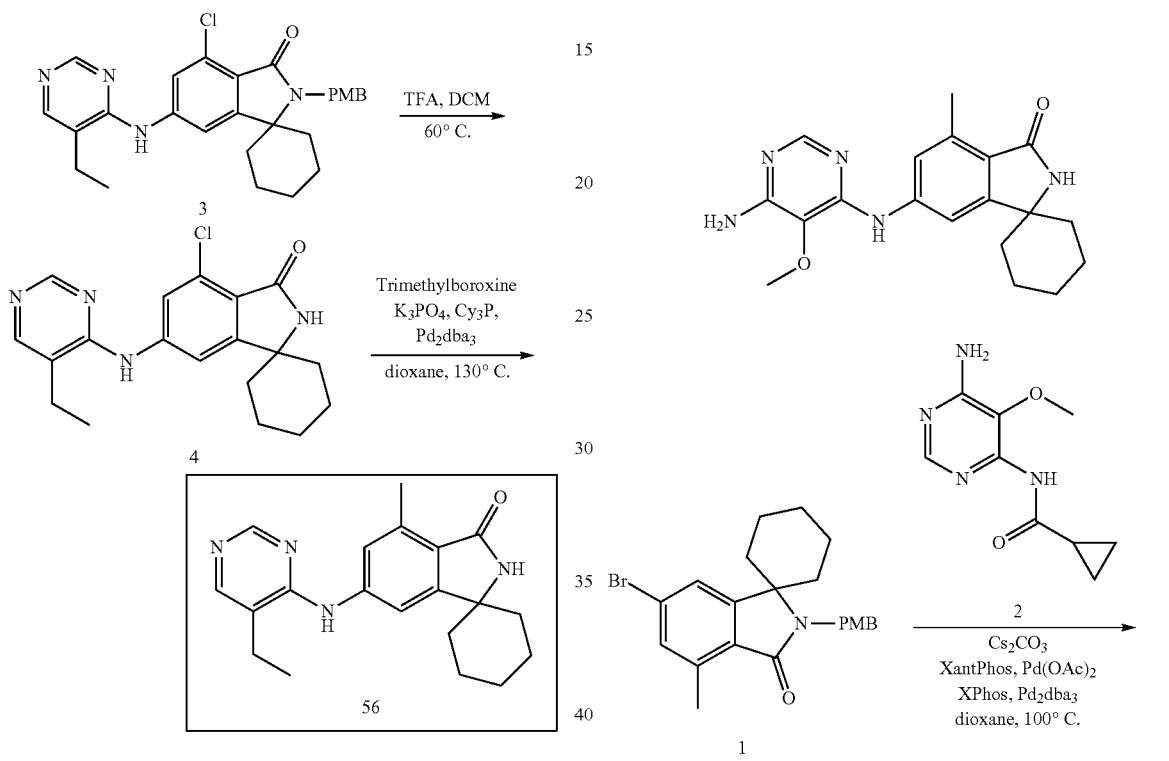

Synthesis of 4'-chloro-6'-((5-ethylpyrimidin-4-yl)amino)-2'-(4-methoxybenzyl)spiro[cyclohexane-1,1'-isoindolin]-3'-one (3)

The synthesis of intermediate 3 was carried out as described above using the general protocol of Procedure A. Brown solid; Yield: 0.45 g, crude; MS (ESI) m/z 477.12 [M+1]+.

Synthesis of 4'-chloro-6'-((5-ethylpyrimidin-4-yl)amino)spiro[cyclohexane-1,1'-isoindolin]-3'-one (4)

The synthesis of intermediate 4 was carried out as described above using the general protocol of Procedure E. Yellow solid; Yield: 0.35 g, crude; MS (ESI) m/z 357.23 [M+1]+.

Synthesis of 6'-((5-ethylpyrimidin-4-yl)amino)-4'-methylspiro[cyclohexane-1,1'-isoindolin]-3'-one (Cpd. No. 56)

The synthesis of compound 56 was carried out as described above using the general protocol of Procedure F. Yellow solid; Yield: 0.050 g, 18%; MS (ESI) m/z 337.01

-continued

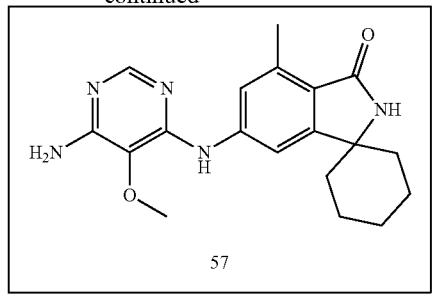

57

Synthesis of N-(5-methoxy-6-((2'-(4-methoxybenzyl)-4'-methyl-3'-oxospiro[cyclohexane-1,1'-isoindolin]-6'-yl)amino)pyrimidin-4-yl)cyclopropanecarboxamide (3)

The synthesis of intermediate 3 was carried out as described above using the general protocol of Procedure A. Brown solid; Yield: 0.35 g, crude; MS (ESI) m/z 542.46 [M+1]⁺.

Synthesis of N-(5-methoxy-6-((4'-methyl-3'-oxospiro[cyclohexane-1,1'-isoindolin]-6'-yl)amino)pyrimidin-4-yl)cyclopropanecarboxamide (4)

The synthesis of intermediate 4 was carried out as described above using the general protocol of Procedure E. Brown solid; Yield: 195 mg, crude; MS (ESI) m/z 422.46 [M+1]⁺.

Synthesis of 6'-((6-amino-5-methoxypyrimidin-4-yl)amino)-4'-methylspiro[cyclohexane-1,1'-isoindolin]-3'-one (Cpd. 57)

The synthesis of compound 57 was carried out as described above using the general protocol of Procedure D. Off-white solid; Yield: 50 mg, 31%; MS (ESI) m/z 354.21 [M+1]⁺; ¹H NMR (400 MHz, DMSO-d₆) δ 8.74 (s, 1H), 8.56 (s, 1H), 7.89 (s, 1H), 7.76 (s, 1H), 7.60 (s, 1H), 6.44 (s, 2H), 3.62 (s, 3H), 2.55 (s, 1H), 1.75-1.68 (m, 7H), 1.34 (m, 3H).

Example 58

Synthesis of 6'-((6-amino-5-chloropyrimidin-4-yl)amino)-4'-methylspiro[cyclohexane-1,1'-isoindolin]-3'-one (Cpd. No. 58)

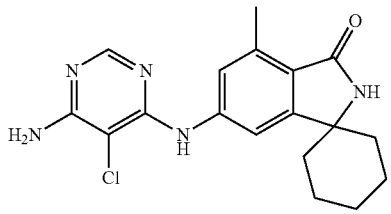

-continued

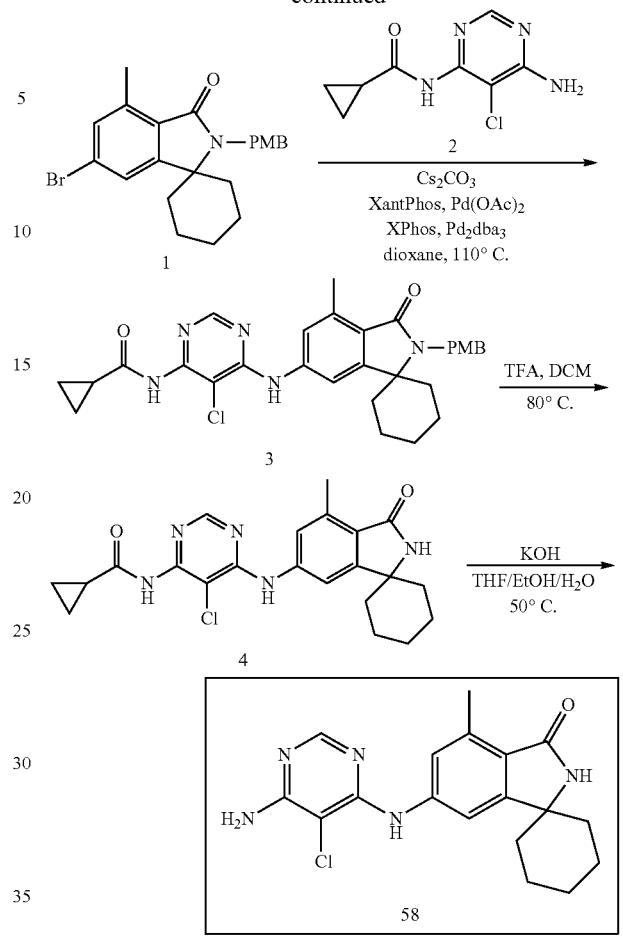

58

Synthesis of N-(5-chloro-6-((2'-(4-methoxybenzyl)-4'-methyl-3'-oxospiro[cyclohexane-1,1'-isoindolin]-6'-yl)amino)pyrimidin-4-yl)cyclopropanecarboxamide (3)

The synthesis of intermediate 3 was carried out as described above using the general protocol of Procedure A. Pale yellow solid; Yield: 0.15 g, 23%; MS (ESI) m/z 546.41 [M+1]⁺.

Synthesis of N-(5-chloro-6-((4'-methyl-3'-oxospiro[cyclohexane-1,1'-isoindolin]-6'-yl)amino)pyrimidin-4-yl)cyclopropanecarboxamide (4)

The synthesis of intermediate 4 was carried out as described above using the general protocol of Procedure E. Pale yellow solid; Yield: 0.09 g, 81%; MS (ESI) m/z 426.14 [M+1]⁺.

Synthesis 6'-((6-amino-5-chloropyrimidin-4-yl)amino)-4'-methylspiro[cyclohexane-1,1'-isoindolin]-3'-one (Cpd. No. 58)

The synthesis of compound 58 was carried out as described above using the general protocol of Procedure D. White solid; Yield: 25 mg, 32%; MS (ESI) m/z 358.13 [M+1]⁺; ¹H NMR (400 MHz, DMSO-d₆) δ 8.82 (s, 1H), 8.55 (s, 1H), 8.00 (s, 1H), 7.63 (s, 1H), 7.49 (s, 1H), 6.87 (brs, 2H), 2.53 (s, 3H), 1.82-1.64 (m, 7H), 1.42-1.30 (m, 3H).

Example 59

Synthesis of 6'-((6-amino-5-chloropyrimidin-4-yl)amino)-4'-chlorospiro[cyclohexane-1,1'-isoindolin]-3'-one (Cpd. No. 59)

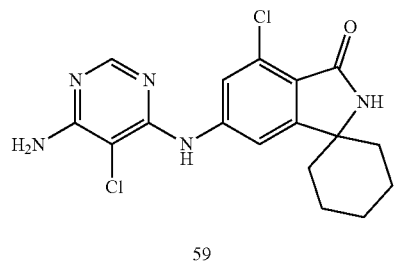

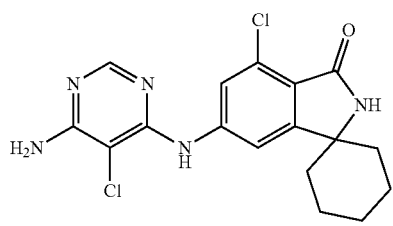

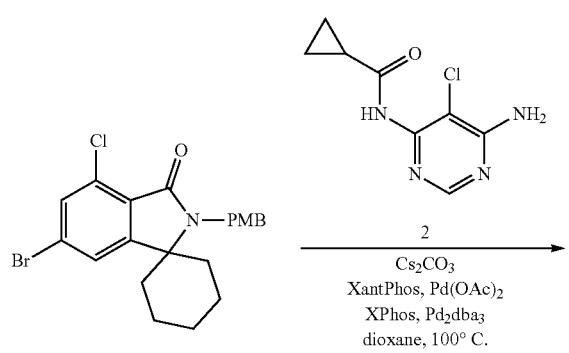

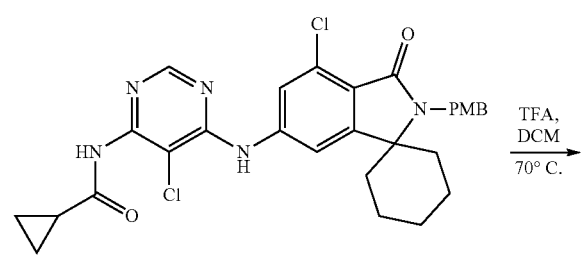

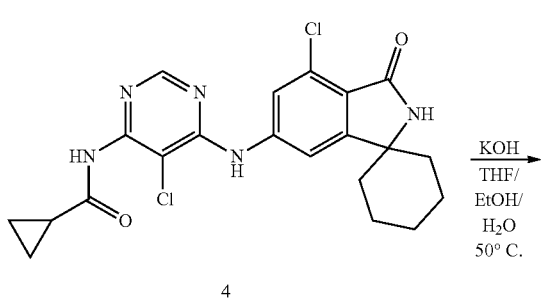

Synthesis of N-(5-chloro-6-((4'-chloro-2'-(4-methoxybenzyl)-3'-oxospiro[cyclohexane-1,1'-isoindolin]-6'-yl)amino)pyrimidin-4-yl)cyclopropanecarboxamide (3)

The synthesis of intermediate 3 was carried out as described above using the general protocol of Procedure A. Yellow solid; Yield: 0.21 g, crude; MS (ESI) m/z 566.4 [M+1]$^+$.

Synthesis of N-(5-chloro-6-((4'-chloro-3'-oxospiro[cyclohexane-1,1'-isoindolin]-6'-yl)amino)pyrimidin-4-yl)cyclopropanecarboxamide (4)

The synthesis of intermediate 4 was carried out as described above using the general protocol of Procedure E. Brown solid; Yield: 150 mg, crude.

Synthesis of 6'-((6-amino-5-chloropyrimidin-4-yl)amino)-4'-chlorospiro[cyclohexane-1,1'-isoindolin]-3'-one (Cpd. 59)

The synthesis of compound 59 was carried out as described above using the general protocol of Procedure D. MS (ESI) m/z 310.34 [M+1]$^+$; $^1$H NMR (400 MHz, DMSO-$d_6$) δ 9.06 (s, 1H), 8.85 (s, 1H), 8.07 (s, 1H), 7.90 (s, 1H), 7.81 (s, 1H), 7.02 (brs, 2H), 1.83-1.63 (m, 7H), 1.45-1.30 (m, 3H).

Example 60

Synthesis of 6-((5-methoxypyrimidin-4-yl)amino)-1',4-dimethylspiro[isoindoline-1,4'-piperidin]-3-one (Cpd. No. 60)

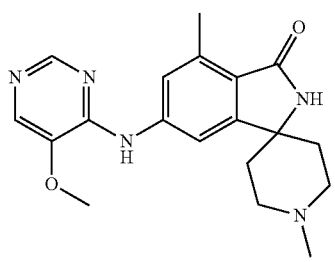

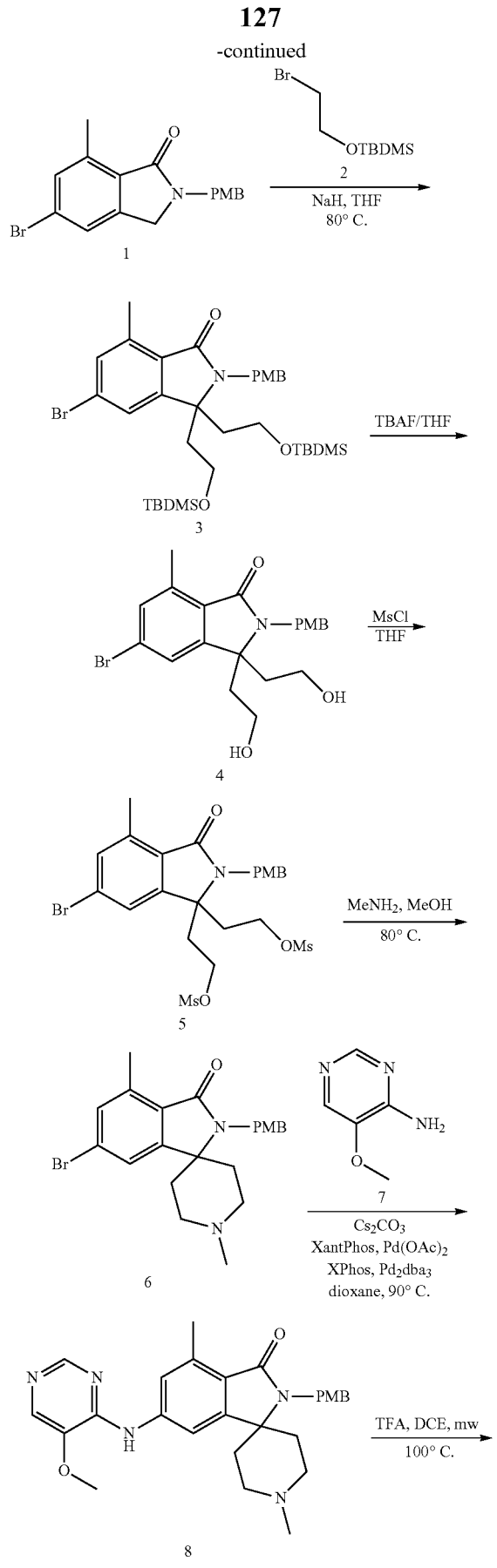

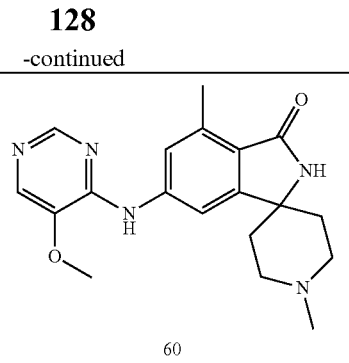

Synthesis of 5-bromo-3,3-bis(2-((tert-butyldimethylsilyl)oxy)ethyl)-2-(4-methoxybenzyl)-7-methylisoindolin-1-one (3)

To a solution of 5-bromo-2-(4-methoxybenzyl)-7-methylisoindolin-1-one (1, 3.0 g, 8.66 mmol) in tetrahydrofuran (25 mL) was added sodium hydride (694 mg, 17.32 mmol). The reaction was stirred at 40° C. for 30 min and then (2-bromoethoxy)-tert-butyldimethylsilane (2, 6.2 g, 25.92 mmol) was added. The reaction was stirred at 80° C. for 16 h. After completion, the reaction was cooled to 0° C. and quenched with aqueous saturated ammonium chloride solution. The mixture was extracted with ethyl acetate (100 mL). The organic layer was washed with water (2×20 mL) and brine (10 mL). The organic layer was dried over magnesium sulfate, filtered and concentrated. The crude was then purified by flash column chromatography eluting with 10% ethyl acetate in hexane. The desired fractions were concentrated to dryness under vacuum to afford 5-bromo-3,3-bis(2-((tert-butyldimethylsilyl)oxy)ethyl)-2-(4-methoxybenzyl)-7-methylisoindolin-1-one (3) as an off-white solid. Yield: 2.8 g, 24%; MS (ESI) m/z 584.5 $[M+1]^+$.

Synthesis of 5-bromo-3,3-bis(2-hydroxyethyl)-2-(4-methoxybenzyl)-7-methylisoindolin-1-one (4)

To a solution of 5-bromo-3,3-bis(2-((tert-butyldimethylsilyl)oxy) ethyl)-2-(4-methoxybenzyl)-7-methylisoindolin-1-one (3, 2.8 g, 4.22 mmol) in tetrahydrofuran (50 mL) at 0° C. was added tetra-n-butylammonium fluoride solution (1 M in tetrahydrofuran, 21.0 mL, 21.0 mmol). The reaction was stirred at room temperature for 1 h. After completion, the reaction was quenched with ice cold water and extracted with ethyl acetate. The organic layer was washed with brine, dried over magnesium sulfate, filtered and concentrated to afford 5-bromo-3,3-bis(2-hydroxyethyl)-2-(4-methoxybenzyl)-7-methylisoindolin-1-one (4) as a white solid. Yield: 1.7 g, 93%; MS (ESI) m/z 434.0 $[M+1]^+$.

Synthesis of (6-bromo-2-(4-methoxybenzyl)-4-methyl-3-oxoisoindoline-1,1-diyl)bis(ethane-2,1-diyl) dimethanesulfonate (5)

To a solution of 5-bromo-3,3-bis(2-hydroxyethyl)-2-(4-methoxybenzyl)-7-methylisoindolin-1-one (4, 1.7 g, 3.91 mmol) in tetrahydrofuran (50 mL) at 0° C. was added methanesulfonyl chloride (0.7 g, 8.61 mmol). The reaction was stirred at room temperature for 1 h. After completion, the reaction was quenched with ice cold water with dichloromethane. The organic layer was washed with brine, dried over magnesium sulfate, filtered and concentrated to afford (6-bromo-2-(4-methoxybenzyl)-4-methyl-3-oxoisoindoline- 1,1-diyl)bis(ethane-2,1-diyl) dimethanesulfonate (5) as a white solid. Yield: 2.1 g, 91%; MS (ESI) m/z 592.0 [M+1]⁺.

Synthesis of 6-bromo-2-(4-methoxybenzyl)-1',4-dimethylspiro[isoindoline-1,4'-piperidin]-3-one (6)

A sealed tube was charged with 6-bromo-2-(4-methoxybenzyl)-4-methyl-3-oxoisoindoline-1,1-diyl)bis(ethane-2,1-diyl) dimethanesulfonate (5, 1.0 g, 1.69 mmol) and methylamine in methanol (10 mL) at room temperature. The vial was sealed and heated to 80° C. 16 h. After completion, the reaction was cooled to room temperature and concentrated. The crude was then purified by flash column chromatography eluting with 10% ethyl acetate in hexane. The desired fractions were concentrated to dryness under vacuum to afford (6-bromo-2-(4-methoxybenzyl)-1',4-dimethylspiro[isoindoline-1,4'-piperidin]-3-one (6) as a white solid. Yield: 2.1 g, 91%; MS (ESI) m/z 592.0 [M+1]⁺.

Synthesis of 2-(4-methoxybenzyl)-6-((5-methoxypyrimidin-4-yl)amino)-1',4-dimethylspiro[isoindoline-1,4'-piperidin]-3-one (8)

The synthesis of intermediate 8 was carried out as described above using the general protocol of Procedure A. Yellow solid; Yield: 0.2 g, 90%; MS (ESI) m/z 354.2 [M+1]⁺.

Synthesis of 6-((5-methoxypyrimidin-4-yl)amino)-1',4-dimethylspiro[isoindoline-1,4'-piperidin]-3-one (Cpd. No. 60)

Procedure G: To a solution of 2-(4-methoxybenzyl)-6-((5-methoxypyrimidin-4-yl)amino)-1',4-dimethylspiro[isoindoline-1,4'-piperidin]-3-one (8, 0.2 g, 0.42 mmol) in 1,2-dichloroethane (5 mL) was added trifluoroacetic acid (5 mL). The vial was sealed and heated in a microwave at 100° C. for 1.5 h. After completion, the reaction was cooled to room temperature and concentrated. The crude was neutralized with aqueous ammonia and concentrated. The crude was purified via column chromatography eluting 5-6% methanol in dichloromethane. The desired fractions were concentrated to afford 6-((5-methoxypyrimidin-4-yl)amino)-1',4-dimethylspiro[isoindoline-1,4'-piperidin]-3-one (Cpd. No. 60) as a brown solid. Yield: 100 mg, 67%; MS (ESI) m/z 354.1 [M+1]⁺; ¹H NMR (400 MHz, DMSO-d₆) δ 9.03 (s, 1H), 8.87 (s, 1H), 8.35 (s, 1H), 8.13 (s, 1H), 7.96 (s, 1H), 7.69 (s, 1H), 3.95 (s, 3H), 2.78 (m, 2H), 2.55 (s, 3H), 2.30 (s, 3H), 2.05-2.03 (m, 2H), 1.42-1.39 (m, 2H).

Example 61

Synthesis of 4-((1',4-dimethyl-3-oxospiro[isoindoline-1,4'-piperidin]-6-yl)amino)pyrimidine-5-carbonitrile trifluoroacetic acid salt (Cpd. No. 61)

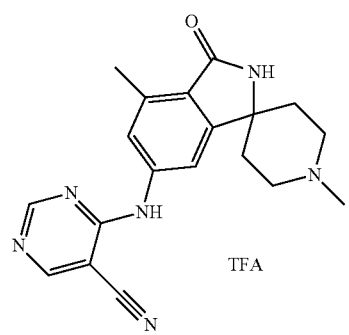

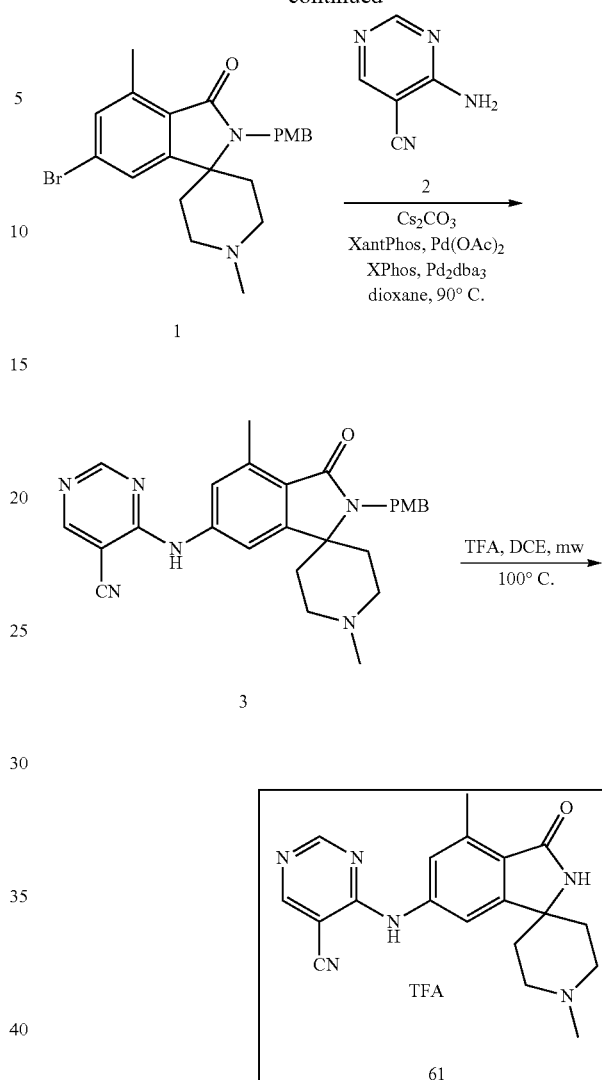

Synthesis of 4-((2-(4-methoxybenzyl)-1',4-dimethyl-3-oxospiro[isoindoline-1,4'-piperidin]-6-yl)amino)pyrimidine-5-carbonitrile (3)

The synthesis of intermediate 3 was carried out as described above using the general protocol of Procedure A. Yellow solid; Yield: 0.14 g, 66%; MS (ESI) m/z 469.45 [M+1]⁺.

Synthesis of 4-((1',4-dimethyl-3-oxospiro[isoindoline-1,4'-piperidin]-6-yl)amino)pyrimidine-5-carbonitrile trifluoroacetic acid salt (Cpd. No. 61)

The synthesis of compound 61 was carried out as described above using the general protocol of Procedure G. Brown solid; Yield: 4 mg, 38%; MS (ESI) m/z 349.1 [M+1]⁺; ¹H NMR (400 MHz, DMSO-d₆) δ 10.14 (s, 1H), 9.68 (s, 1H), 9.19 (s, 1H), 8.89 (s, 1H), 8.79 (s, 1H), 7.57 (s, 1H), 7.51 (s, 1H), 3.48-3.61 (m, 2H), 3.20 (m, 2H), 2.82 (s, 3H), 2.58 (s, 3H), 2.36-2.22 (m, 2H), 1.71-1.62 (m, 2H).

Example 62

Synthesis of 6-((6-amino-5-methylpyrimidin-4-yl)amino)-1',4-dimethylspiro[isoindoline-1,4'-piperidin]-3-one (Cpd. No. 62)

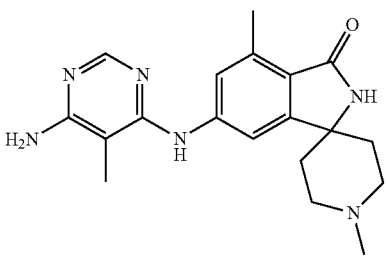

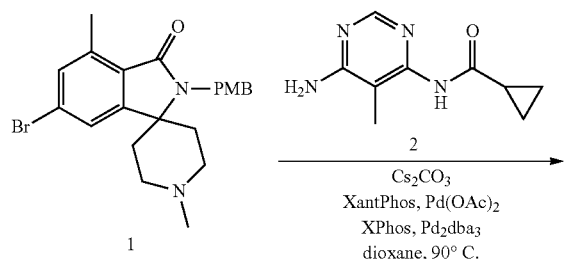

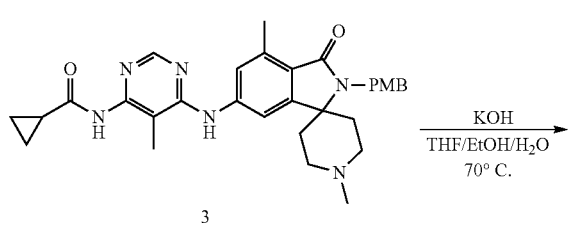

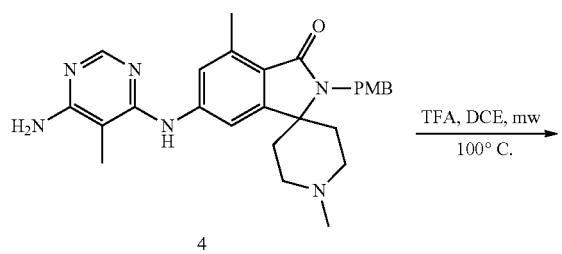

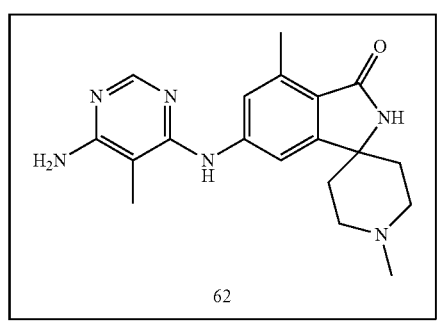

Synthesis of N-(6-((2-(4-methoxybenzyl)-1',4-dimethyl-3-oxospiro[isoindoline-1,4'-piperidin]-6-yl)amino)-5-methylpyrimidin-4-yl)cyclopropanecarboxamide (3)

The synthesis of intermediate 3 was carried out as described above using the general protocol of Procedure A. Brown solid; Yield: 0.60 g, crude; MS (ESI) m/z 541.2 [M+1]$^+$.

Synthesis of 6-((6-amino-5-methylpyrimidin-4-yl)amino)-2-(4-methoxybenzyl)-1',4-dimethylspiro[isoindoline-1,4'-piperidin]-3-one (4)

The synthesis of intermediate 4 was carried out as described above using the general protocol of Procedure D. Brown solid; Yield: 0.31 g, crude; MS (ESI) m/z 473.29 [M+1]$^+$.

Synthesis of 6-((6-amino-5-methylpyrimidin-4-yl)amino)-1',4-dimethylspiro[isoindoline-1,4'-piperidin]-3-one (Cpd. No. 62)

The synthesis of compound 62 was carried out as described above using the general protocol of Procedure G. Brown solid; Yield: 75 mg, 33%; MS (ESI) m/z 353.2 [M+1]$^+$; $^1$H NMR (400 MHz, DMSO-d$_6$) δ 8.76 (s, 1H), 8.19 (s, 1H), 7.99 (s, 1H), 7.64 (s, 1H), 7.37 (s, 1H), 6.28 (s, 2H), 2.75-2.65 (m, 2H), 2.52 (s, 3H), 2.4 (m, 2H), 2.25 (s, 3H), 2.01 (m, 2H), 1.97 (s, 3H), 1.41-1.35 (m, 2H).

Example 63

Synthesis of 4-((4'-methyl-3'-oxospiro[cyclohexane-1,1'-isoindolin]-6'-yl)amino)pyrimidine-5-carbonitrile (Cpd. No. 63)

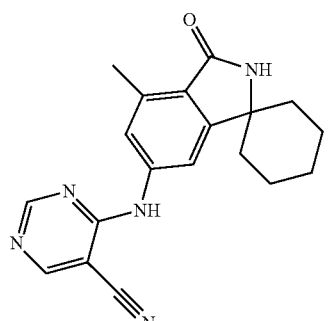

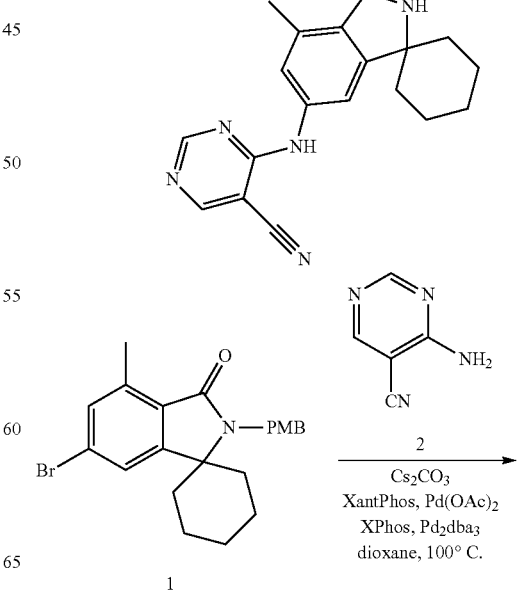

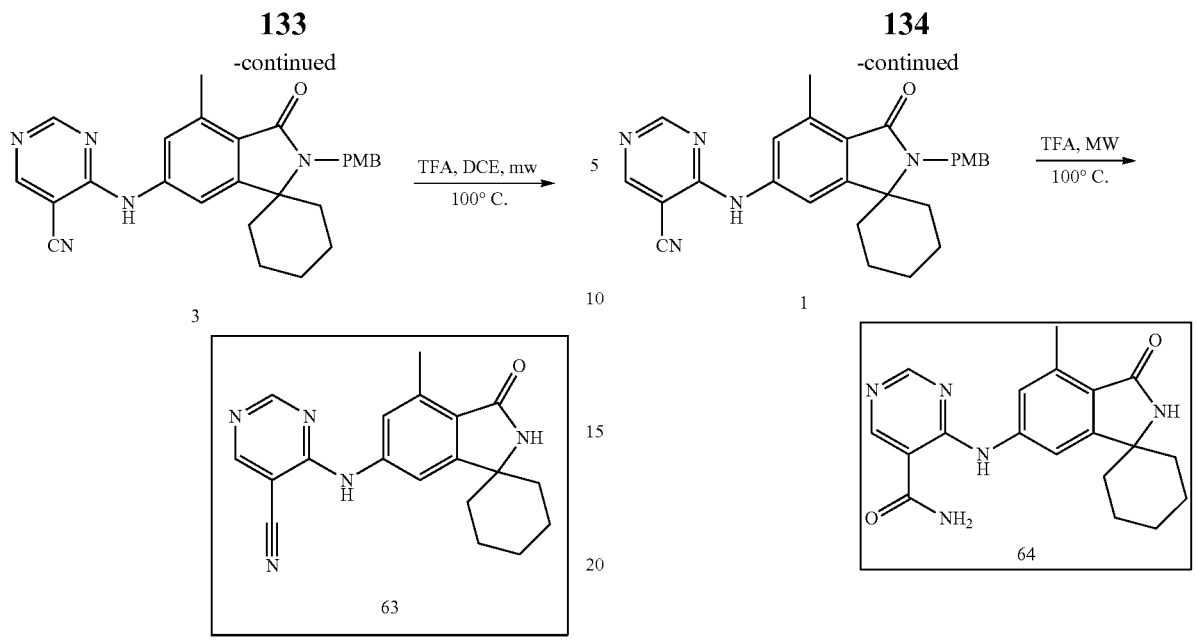

Synthesis of 4-((2'-(4-methoxybenzyl)-4'-methyl-3'-oxospiro[cyclohexane-1,1'-isoindolin]-6'-yl)amino)pyrimidine-5-carbonitrile (3)

The synthesis of intermediate 3 was carried out as described above using the general protocol of Procedure A. Yellow solid; Yield: 0.45 g, 41%; MS (ESI) m/z 454.24 [M+1]⁺.

Synthesis 4-((4'-methyl-3'-oxospiro[cyclohexane-1,1'-isoindolin]-6'-yl)amino)pyrimidine-5-carbonitrile (Cpd. No. 63)

The synthesis of compound 63 was carried out as described above using the general protocol of Procedure G. Pale yellow solid; Yield: 30 mg, 21%; MS (ESI) m/z 332.07 [M+1]⁺; $^1$H NMR (400 MHz, DMSO-d$_6$) δ 10.03 (s, 1H), 9.10 (s, 1H), 8.92 (s, 1H), 8.78 (s, 1H), 7.55 (s, 1H), 7.42 (s, 1H), 2.56 (s, 3H), 1.83-1.68 (m, 7H), 1.39-1.33 (m, 3H).

Example 64

Synthesis of 4-((4'-methyl-3'-oxospiro[cyclohexane-1,1'-isoindolin]-6'-yl)amino)pyrimidine-5-carboxamide (Cpd. No. 64)

A vial was charged with 4-((2'-(4-methoxybenzyl)-4'-methyl-3'-oxospiro[cyclohexane-1,1'-isoindolin]-6'-yl)amino)pyrimidine-5-carbonitrile (1, 0.1 g, 0.22 mmol) in trifluoroacetic acid (5 mL) under nitrogen. The vial was sealed and irradiated under microwave at 100° C. for 1 h. After completion, the reaction mixture was cooled to room temperature and concentrated. The crude was neutralized with aqueous saturated sodium bicarbonate solution and concentrated again. The crude was purified via column chromatography eluting with 5-6% methanol in dichloromethane. The desired fractions were concentrated to afford 4-((4'-methyl-3'-oxospiro[cyclohexane-1,1'-isoindolin]-6'-yl)amino)pyrimidine-5-carboxamide (Cpd. No. 64) as a pale yellow solid. Yield: 30 mg, 38%; MS (ESI) m/z 352.19 [M+1]⁺; $^1$H NMR (400 MHz, DMSO-d$_6$) δ 10.03 (s, 1H), 8.97 (s, 1H), 8.85 (s, 1H), 8.78 (s, 1H), 7.58 (s, 1H), 7.42 (s, 1H), 2.66 (s, 3H), 1.78-1.68 (m, 7H), 1.39-1.36 (m, 3H).

Example 65

Synthesis of 1'-(2,2-difluoroethyl)-6-((5-methoxypyrimidin-4-yl)amino)-4-methylspiro[isoindoline-1,4'-piperidin]-3-one (Cpd. No. 65)

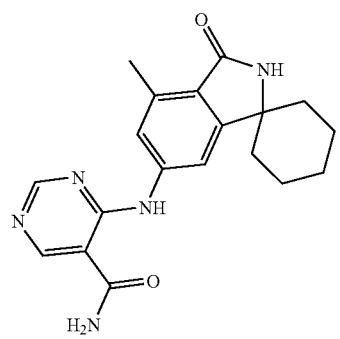
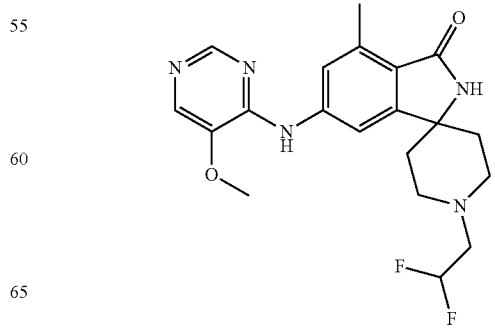

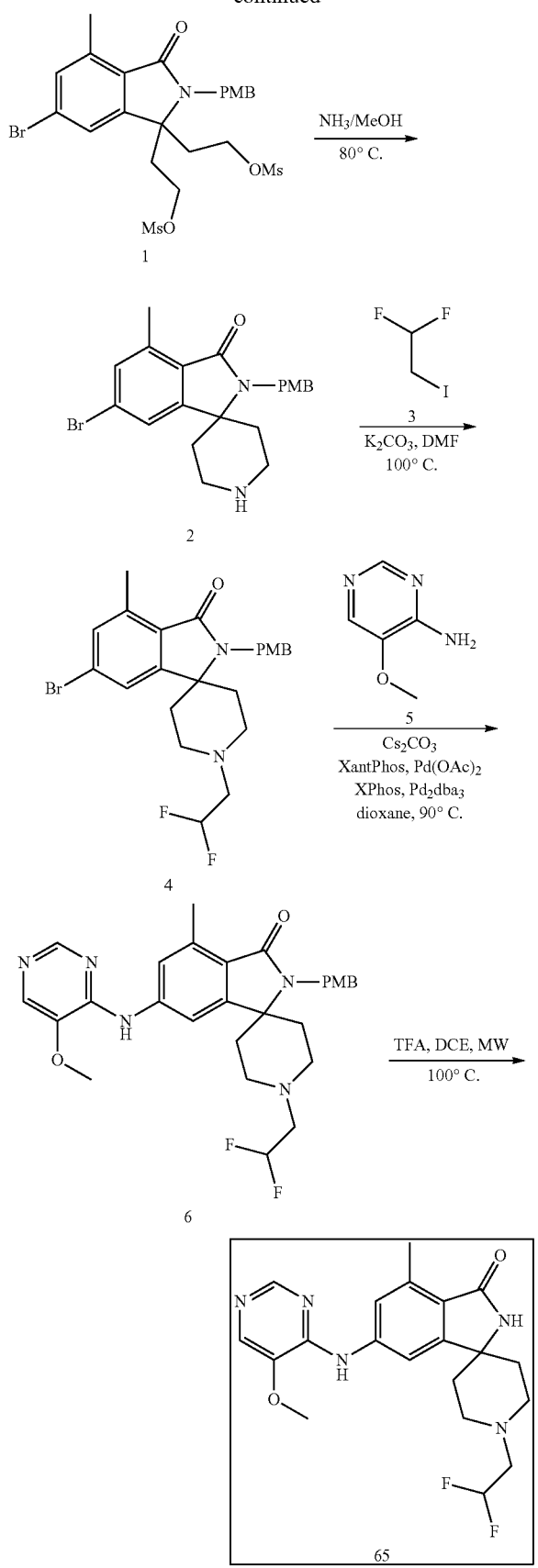

Synthesis of 6-bromo-2-(4-methoxybenzyl)-4-methylspiro[isoindoline-1,4'-piperidin]-3-one (2)

A sealed tube was charged with (6-bromo-2-(4-methoxybenzyl)-4-methyl-3-oxoisoindoline-1,1-diyl)bis(ethane-2,1-diyl) dimethanesulfonate (1, 1.0 g, 1.69 mmol) and ammonia in methanol (10 mL) at room temperature. The vial was sealed and heated to 80° C. 16 h. After completion, the reaction was cooled to room temperature and concentrated. The crude was then purified by flash column chromatography eluting with 10% methanol in dichloromethane. The desired fractions were concentrated to dryness under vacuum to afford 6-bromo-2-(4-methoxybenzyl)-4-methylspiro[isoindoline-1,4'-piperidin]-3-one (2) as a white solid. Yield: 0.5 g, 68%; MS (ESI) m/z 416 [M+1]$^+$.

Synthesis of 6-bromo-1'-(2,2-difluoroethyl)-2-(4-methoxybenzyl)-4-methylspiro[isoindoline-1,4'-piperidin]-3-one (4)

A sealed tube was charged with 6-bromo-2-(4-methoxybenzyl)-4-methylspiro[isoindoline-1,4'-piperidin]-3-one (2, 0.50 g, 1.2 mmol), potassium carbonate (0.50 g, 3.6 mmol) and 1,1-difluoro-2-iodoethane (3, 0.69 g, 3.6 mmol) in dimethylformamide at room temperature. The vial was sealed and heated to 100° C. 16 h. After completion, the reaction was quenched with ice cold water and extracted with ethyl acetate (100 mL). The organic layer was washed with water (2×20 mL) and brine (10 mL). It was then dried over magnesium sulfate, filtered and concentrated. The crude was then purified by flash column chromatography eluting with 20-30% ethyl acetate in hexane. The desired fractions were concentrated to afford 6-bromo-1'-(2,2-difluoroethyl)-2-(4-methoxybenzyl)-4-methylspiro[isoindoline-1,4'-piperidin]-3-one (4) as a white solid. Yield: 0.4 g, crude; MS (ESI) m/z 481.0 [M+1]$^+$.

Synthesis of 1'-(2,2-difluoroethyl)-2-(4-methoxybenzyl)-6-((5-methoxypyrimidin-4-yl)amino)-4-methylspiro[isoindoline-1,4'-piperidin]-3-one (6)

The synthesis of intermediate 6 was carried out as described above using the general protocol of Procedure A. Yellow solid; Yield: 0.2 g, crude; MS (ESI) m/z 524.2 [M+1]$^+$.

Synthesis of 1'-(2,2-difluoroethyl)-6-((5-methoxypyrimidin-4-yl)amino)-4-methylspiro[isoindoline-1,4'-piperidin]-3-one (Cpd. No. 65)

The synthesis of compound 65 was carried out as described above using the general protocol of Procedure G. Off-white solid; Yield: 50 mg, 33%; MS (ESI) m/z 404.2 [M+1]$^+$; $^1$H NMR (400 MHz, DMSO-d$_6$) δ 9.00 (s, 1H), 8.92 (s, 1H), 8.37 (s, 1H), 8.14 (brs, 1H), 7.99 (s, 1H), 7.69 (s, 1H), 6.34-6.04 (tt, J=55.6, 4.16 Hz, 1H), 3.96 (s, 1H), 2.95-2.76 (m, 4H), 2.7-2.64 (m, 2H), 2.56 (s, 3H), 2.01 (m, 2H), 1.43-1.36 (m, 2H).

Example 66

Synthesis of 6-((6-amino-5-methylpyrimidin-4-yl)amino)-1'-(2,2-difluoroethyl)-4-methylspiro[isoindoline-1,4'-piperidin]-3-one (Cpd. No. 66)

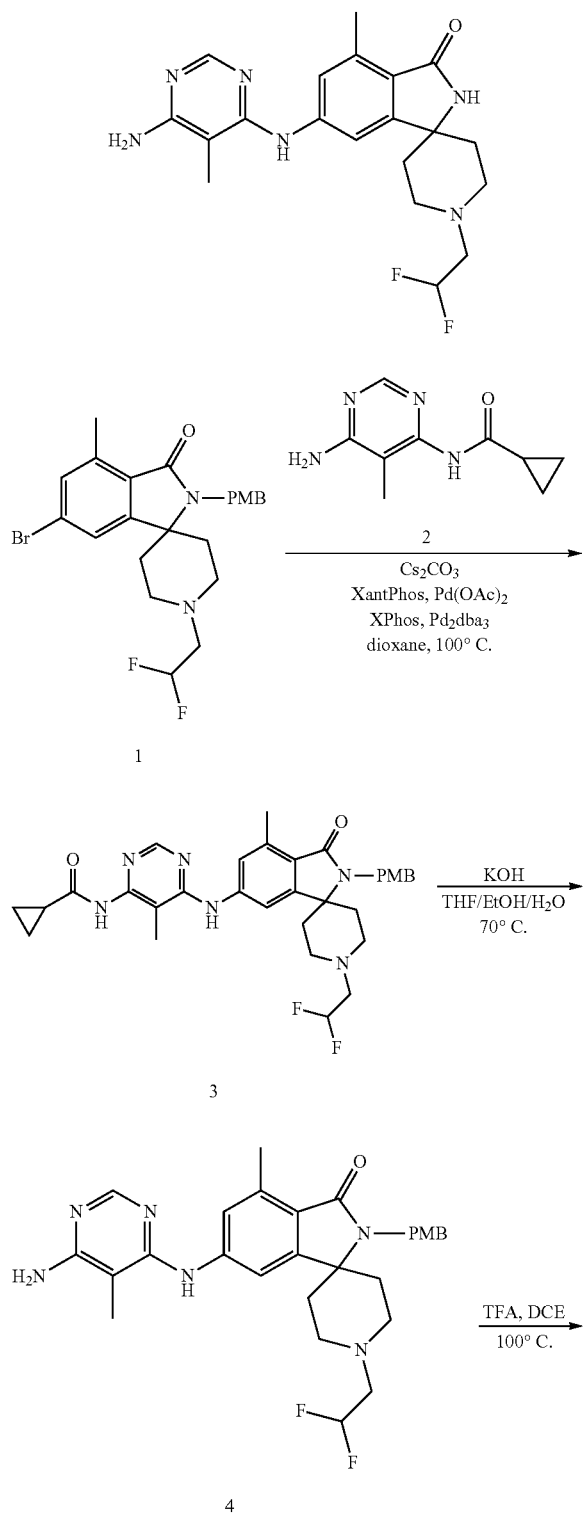

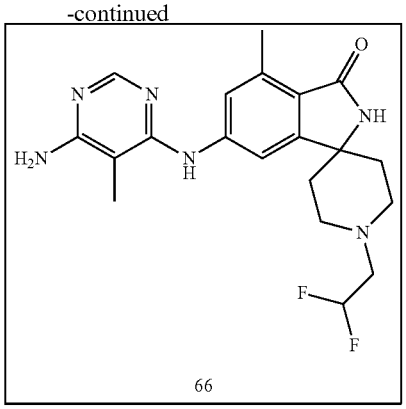

Synthesis of N-(6-((1'-(2,2-difluoroethyl)-2-(4-methoxybenzyl)-4-methyl-3-oxospiro [isoindoline-1,4'-piperidin]-6-yl)amino)-5-methylpyrimidin-4-yl)cyclopropanecarboxamide (3)

The synthesis of intermediate 3 was carried out as described above using the general protocol of Procedure A. Brown solid; Yield: 0.3 g, crude; MS (ESI) m/z 591.2 [M+1]$^+$.

Synthesis of 6-((6-amino-5-methylpyrimidin-4-yl)amino)-1'-(2,2-difluoroethyl)-2-(4-methoxybenzyl)-4-methylspiro[isoindoline-1,4'-piperidin]-3-one (4)

The synthesis of intermediate 4 was carried out as described above using the general protocol of Procedure D. Brown solid; Yield: 0.21 g, crude; MS (ESI) m/z 523.3 [M+1]$^+$.

Synthesis of 6-((6-amino-5-methylpyrimidin-4-yl)amino)-1'-(2,2-difluoroethyl)-4-methylspiro[isoindoline-1,4'-piperidin]-3-one (Cpd. No. 66)

The synthesis of compound 66 was carried out as described above using the general protocol of Procedure G. Off-white solid; Yield: 50 mg, 33%; MS (ESI) m/z 403.2 [M+1]$^+$; $^1$H NMR (400 MHz, DMSO-d$_6$) δ 8.79 (s, 1H), 8.15 (s, 1H), 8.01 (s, 1H), 7.68 (s, 1H), 7.37 (s, 1H), 6.26 (s, 2H), 6.33-6.02 (tt, J=55.72, 4.16 Hz, 1H), 2.19-2.79 (m, 4H), 2.68-2.60 (m, 3H), 2.53 (s, 3H), 2.01 (m, 2H), 1.97 (s, 3H), 1.40-1.32 (m, 2H).

Example 67

Synthesis of 4-((1'-(2,2-difluoroethyl)-4-methyl-3-oxospiro[isoindoline-1,4'-piperidin]-6-yl)amino)pyrimidine-5-carbonitrile (Cpd. No. 67)

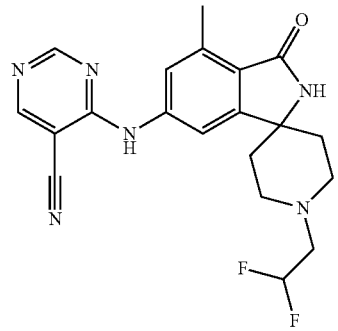

139

-continued

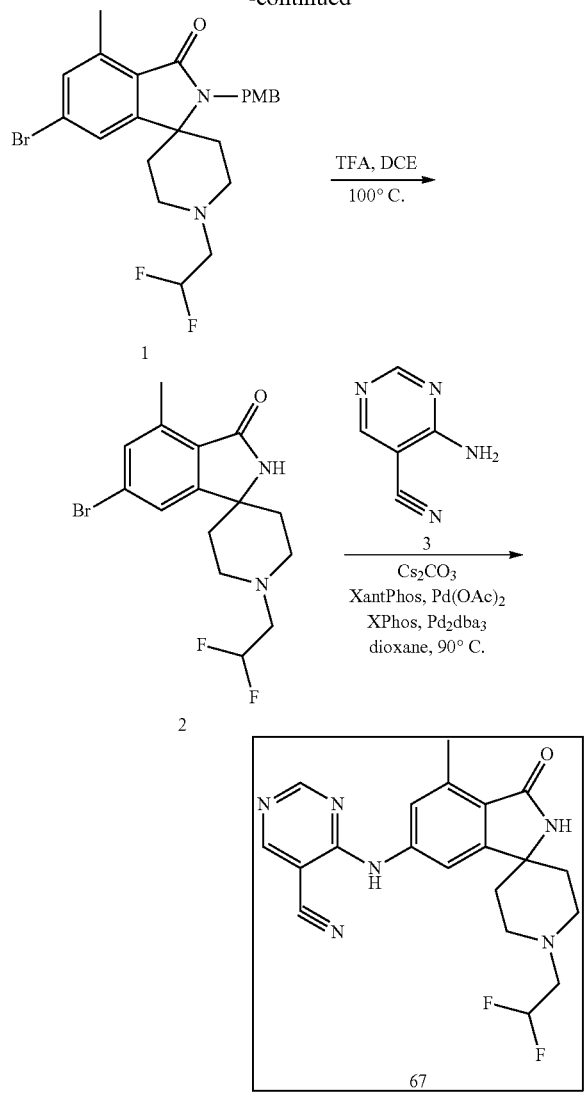

Synthesis of 6-bromo-1'-(2,2-difluoroethyl)-4-methylspiro[isoindoline-1,4'-piperidin]-3-one (2)

The synthesis of intermediate 2 was carried out as described above using the general protocol of Procedure G. Brown solid; Yield: 0.2 g, 89%; MS (ESI) m/z 359.0 [M+1]$^+$.

Synthesis of 4-((1'-(2,2-difluoroethyl)-4-methyl-3-oxospiro[isoindoline-1,4'-piperidin]-6-yl)amino)pyrimidine-5-carbonitrile (Cpd. No. 67)

The synthesis of compound 67 was carried out as described above using the general protocol of Procedure A. Yellow solid; Yield: 0.08 g, 36%; MS (ESI) m/z 399.1 [M+1]$^+$; $^1$H NMR (400 MHz, DMSO-d$_6$) δ 10.03 (s, 1H), 9.05 (s, 1H), 8.85 (s, 1H), 8.80 (s, 1H), 7.68 (s, 1H), 7.41 (s, 1H), 6.32-6.02 (m, 1H), 2.89-2.86 (m, 2H), 2.85-2.84 (m, 2H), 2.67-2.64 (m, 2H), 2.57 (s, 3H), 2.07-2.02 (m, 2H), 1.39-1.36 (m, 2H).

140

Example 68

Synthesis of 6-((6-amino-5-methoxypyrimidin-4-yl)amino)-1',4-dimethylspiro[isoindoline-1,4'-piperidin]-3-one (Cpd. No. 68)

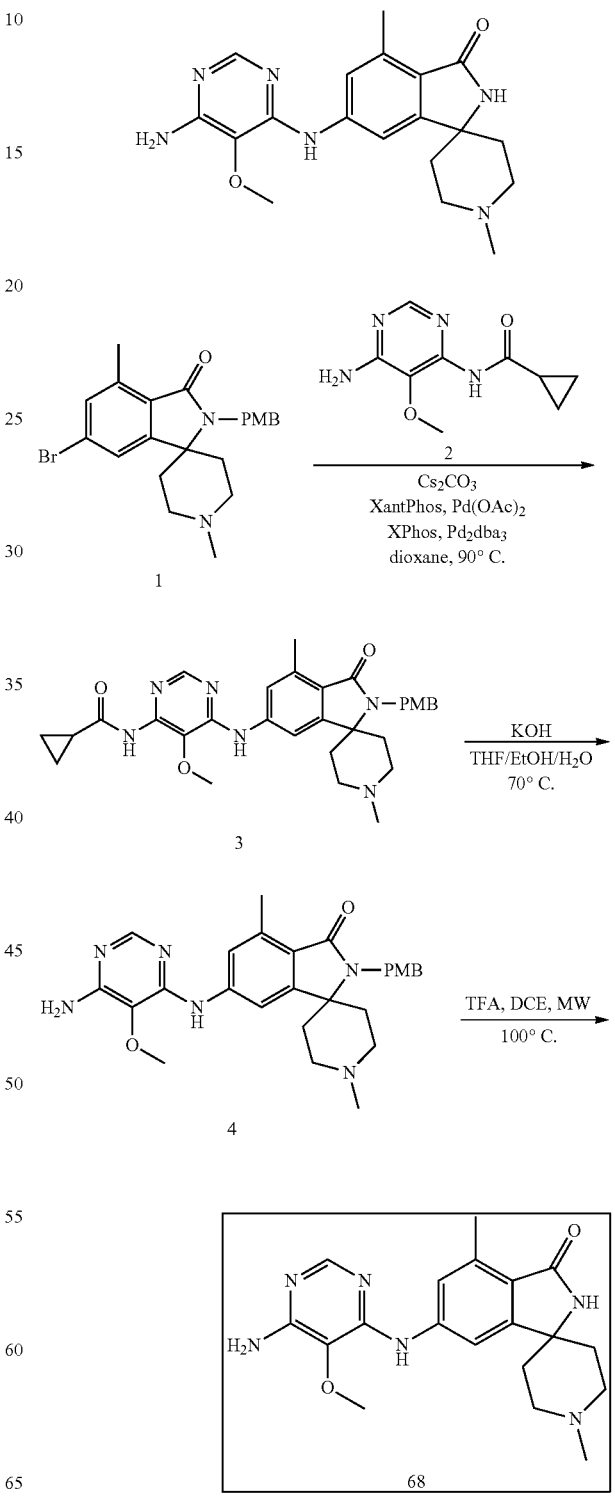

Synthesis of N-(5-methoxy-6-((2-(4-methoxybenzyl)-1',4-dimethyl-3-oxospiro[isoindoline-1,4'-piperidin]-6-yl)amino)pyrimidin-4-yl)cyclopropanecarboxamide (3)

The synthesis of intermediate 3 was carried out as described above using the general protocol of Procedure A. Brown solid; Yield: 0.60 g, crude; MS (ESI) m/z 557.2 [M+1]$^+$.

Synthesis of 6-((6-amino-5-methoxypyrimidin-4-yl)amino)-2-(4-methoxybenzyl)-1',4-dimethylspiro [isoindoline-1,4'-piperidin]-3-one (4)

The synthesis of intermediate 4 was carried out as described above using the general protocol of Procedure D. Yellow solid; Yield: 0.31 g, crude; MS (ESI) m/z 489.1 [M+1]$^+$.

Synthesis of 6-((6-amino-5-methoxypyrimidin-4-yl)amino)-1',4-dimethylspiro[isoindoline-1,4'-piperidin]-3-one (Cpd. No. 68)

The synthesis of compound 68 was carried out as described above using the general protocol of Procedure G. Yellow solid; Yield: 75 mg, 50%; MS (ESI) m/z 369.1 [M+1]$^+$; $^1$H NMR (400 MHz, DMSO-d$_6$) δ 8.78 (s, 1H), 8.61 (s, 1H), 7.90 (s, 1H), 7.88 (s, 1H), 7.56 (s, 1H), 6.45 (s, 2H), 3.63 (s, 3H), 2.8-2.69 (m, 2H), 2.52 (s, 3H), 2.49-2.35 (m, 2H), 2.27 (s, 3H), 2.05-1.95 (m, 2H), 1.42-1.35 (m, 2H).

Example 69

Synthesis of 6-((6-amino-5-methoxypyrimidin-4-yl)amino)-1'-(2,2-difluoroethyl)-4-methylspiro[isoindoline-1,4'-piperidin]-3-one (Cpd. No. 69)

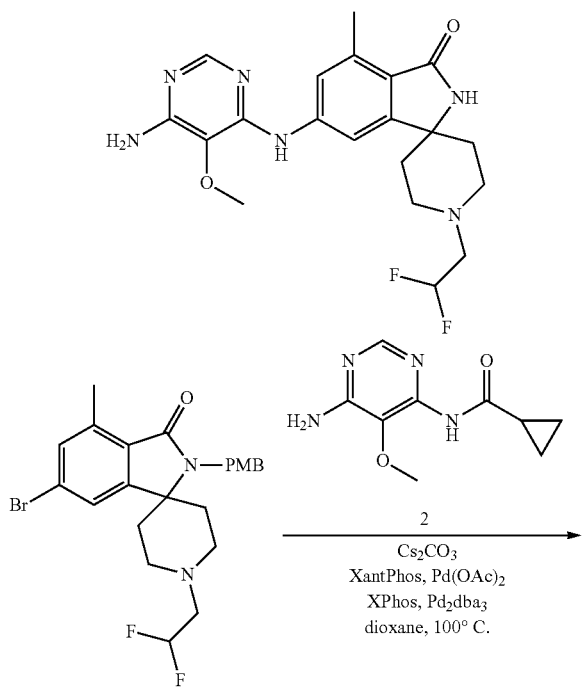

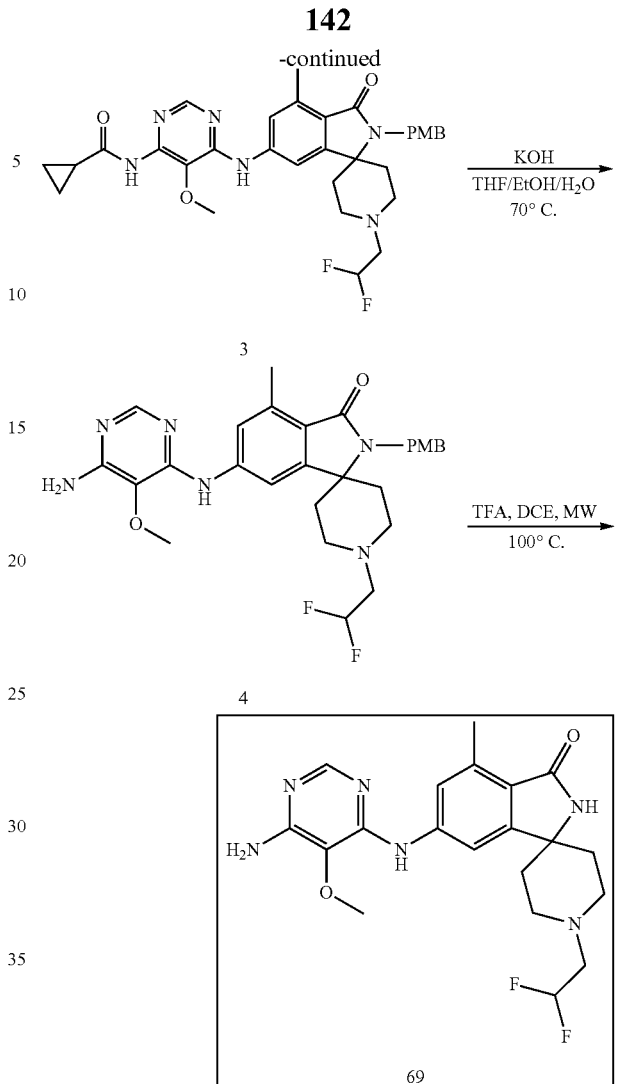

Synthesis of N-(6-((1'-(2,2-difluoroethyl)-2-(4-methoxybenzyl)-4-methyl-3-oxospiro [isoindoline-1,4'-piperidin]-6-yl)amino)-5-methoxypyrimidin-4-yl)cyclopropanecarboxamide (3)

The synthesis of intermediate 3 was carried out as described above using the general protocol of Procedure A. Yellow solid; Yield: 0.4 g, crude; MS (ESI) m/z 607.3 [M+1]$^+$.

Synthesis of 6-((6-amino-5-methoxypyrimidin-4-yl)amino)-1'-(2,2-difluoroethyl)-2-(4-methoxybenzyl)-4-methylspiro[isoindoline-1,4'-piperidin]-3-one (4)

The synthesis of intermediate 4 was carried out as described above using the general protocol of Procedure D. Brown solid; Yield: 0.3 g, 84%; MS (ESI) m/z 539.3 [M+1]$^+$.

Synthesis of 6-((6-amino-5-methoxypyrimidin-4-yl)amino)-1'-(2,2-difluoroethyl)-4-methylspiro[isoindoline-1,4'-piperidin]-3-one (Cpd. No. 69)

The synthesis of compound 69 was carried out as described above using the general protocol of Procedure G.

Off-white solid; Yield: 50 mg, 33%; MS (ESI) m/z 418.2 [M+1]+; 1H NMR (400 MHz, DMSO-d6) δ 8.82 (s, 1H), 8.57 (s, 1H), 7.92 (s, 1H), 7.90 (s, 1H), 7.56 (s, 1H), 6.45 (s, 2H), 6.31-6.04 (tt, J=55.6, 5.2 Hz, 1H), 3.63 (s, 3H), 2.89-2.79 (m, 4H), 2.66-2.60 (m, 2H), 2.52 (s, 3H), 1.99-1.90 (m, 2H), 1.39-1.36 (m, 2H).

Pink solid; Yield: 0.24 g, 97%, MS (ESI) m/z 345.2 [M+1]+; 1H NMR: (400 MHz, DMSO-d6) δ 9.84 (s, 1H), 8.88 (s, 1H), 8.10 (s, 1H), 7.28 (s, 1H), 6.99 (s, 2H), 6.63 (S, 2H), 2.50 (s, 3H), 2.02-1.96 (m, 2H), 1.70-1.62 (m, 5H), 1.44-1.42 (m, 1H), 1.34-1.31 (m, 2H).

Example 70

Synthesis of 2'-((6-aminopyrimidin-4-yl)amino)-4'-methylspiro[cyclohexane-1,7'-pyrrolo[3,4-b]pyridin]-5'(6'H)-one (Cpd. No. 70)

Example 71

Synthesis of 2'-((6-amino-5-methylpyrimidin-4-yl)amino)-4'-methylspiro[cyclohexane-1,7'-pyrrolo[3,4-b]pyridin]-5'(6'H)-one (Cpd. No. 71)

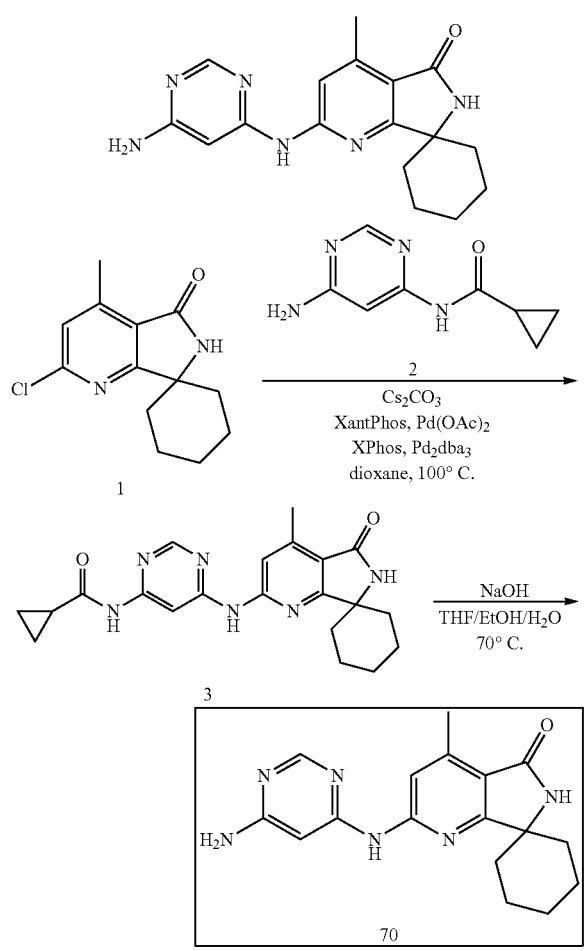

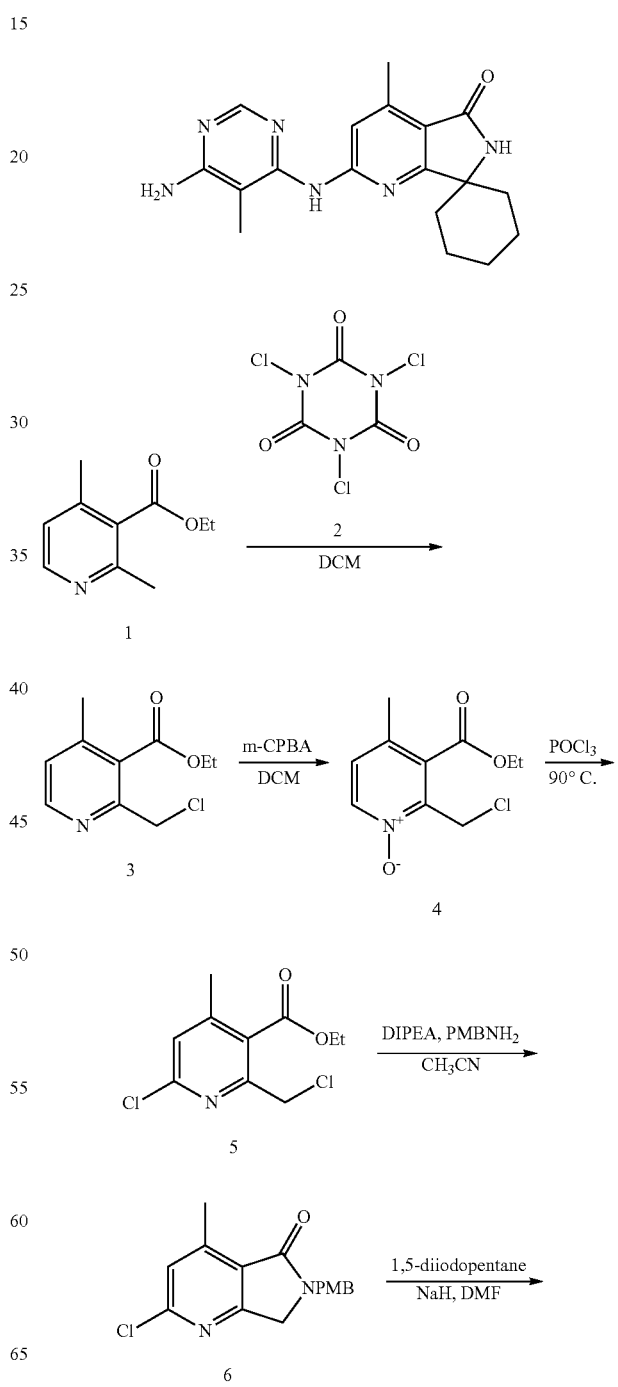

Synthesis of N-(6-(((4'-methyl-5'-oxo-5',6'-dihydrospiro[cyclohexane-1,7'-pyrrolo[3,4-b]pyridin]-2'-yl)amino)pyrimidin-4-yl)cyclopropanecarboxamide (3)

The synthesis of intermediate 3 was carried out as described above using the general protocol of Procedure A. Yellow solid; Yield: 0.3 g, 76%; MS (ESI) m/z 392.2 [M+1]+.

Synthesis of 2'-((6-aminopyrimidin-4-yl)amino)-4'-methylspiro[cyclohexane-1,7'-pyrrolo[3,4-b]pyridin]-5'(6'H)-one (Cpd. No. 70)

The synthesis of compound 70 was carried out as described above using the general protocol of Procedure D.

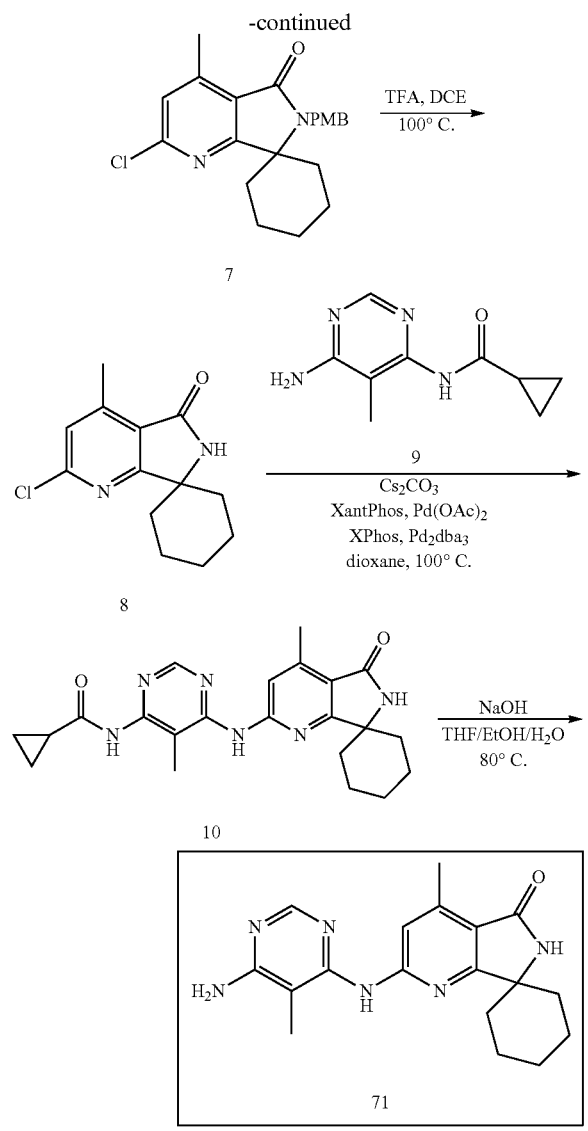

Synthesis of ethyl 2-(chloromethyl)-4-methylnicotinate (3)

To a stirred solution of ethyl 2,4-dimethylnicotinate (1, 10 g, 0.055 mol) in dichloromethane (200 mL), 1,3,5-trichloro-1,3,5-triazinane-2,4,6-trione (2, 19.35 g, 0.083 mol) was added. The reaction was stirred at room temperature overnight. After completion, the reaction mixture was concentrated and quenched with saturated aqueous solution of sodium carbonate till pH 8. The mixture was extracted with dichloromethane (2×150 mL). The organics were combined, dried over magnesium sulfate, filtered and concentrated to afford ethyl 2-(chloromethyl)-4-methylnicotinate (2) as a yellow oil. Yield: 10.0 g, 84%; MS (ESI) m/z 214.2 [M+1]$^+$.

Synthesis of ethyl 2-(chloromethyl)-4-methyl-1-(l1-oxidanyl)-l14-pyridine-3-carboxylate (4)

To a solution of ethyl 2-(chloromethyl)-4-methylnicotinate (3, 15 g, 0.070 mol) in dichloromethane (250 mL) at 0° C. was added portion wise 3-chloroperbenzoic acid (30.28 g, 0.18 mol). After the addition was complete, the reaction was stirred at room temperature for 16 h. After completion, the reaction mass was quenched with saturated aqueous solution of sodium carbonate and extracted with dichloromethane (2×150 mL). The combined organics was washed with brine (100 mL), dried over sodium sulfate and concentrated under reduced pressure to afford ethyl 2-(chloromethyl)-4-methylnicotinate n-oxide (4) as a brown liquid. Yield: 15 g, 85%; MS (ESI) m/z 230.1 [M+1]$^+$.

Synthesis of ethyl 6-chloro-2-(chloromethyl)-4-methylnicotinate (5)

A flask was charged with ethyl 2-(chloromethyl)-4-methyl-1-(l1-oxidanyl)-l14-pyridine-3-carboxylate (4, 15 g, 0.065 mol) and phosphoryl chloride (60 mL) was added dropwise at 0° C. After the addition was complete, the reaction was heated at 90° C. for 16 h. After completion, the reaction mixture was concentrated, diluted with water (200 mL) and extracted with dichloromethane (2×150 mL). The combined organic extract was washed with saturated aqueous solution of sodium bicarbonate (100 mL), dried over sodium sulfate and concentrated under reduced pressure to obtain the crude. The crude was purified by flash chromatography eluting with 0-5% methanol in dichloromethane to ethyl 6-chloro-2-(chloromethyl)-4-methylnicotinate (5) as a yellow liquid. Yield: 6 g, 38%; MS (ESI) m/z 248.2 [M+1]$^+$.

Synthesis of 2-chloro-6-(4-methoxybenzyl)-4-methyl-6,7-dihydro-5H-pyrrolo[3,4-b]pyridin-5-one (6)

A flask containing acetonitrile (50 mL) was charged with ethyl 6-chloro-2-(chloromethyl)-4-methylnicotinate (5, 5.0 g, 20.15 mmol), 4-methoxybenzylamine (4.15 g, 30.25 mmol) and diisopropylethylamine (7.86 g, 60.46 mmol). The reaction was stirred at room temperature for 16 h. After completion, the solvent was evaporated under reduced pressure and the crude was purified by flash column chromatography eluting with 2.5% methanol in dichloromethane to afford 2-chloro-6-(4-methoxybenzyl)-4-methyl-6,7-dihydro-5H-pyrrolo[3,4-b]pyridin-5-one (6) as a yellow solid. Yield: 6.1 g, 65%; MS (ESI) m/z 302.2 [M+1]$^+$.

Synthesis of 2'-chloro-6'-(4-methoxybenzyl)-4'-methylspiro[cyclohexane-1,7'-pyrrolo[3,4-b]pyridin]-5'(6'H)-one (7)

To a solution of 2-chloro-6-(4-methoxybenzyl)-4-methyl-6,7-dihydro-5H-pyrrolo[3,4-b]pyridin-5-one (6, 1.0 g, 3 mmol) in tetrahydrofuran (25 mL) was added slowly sodium hydride (240 mg, 6 mmol, 60%) and 1,5-diiodopentane (1.18 g, 3.4 mmol). The reaction was stirred at room temperature for 3 h. After completion, the reaction was quenched with saturated aqueous ammonium chloride solution at 0° C. and extracted with ethyl acetate (100 mL). The organic layer was washed with water (2×20 mL) and brine (10 mL). The organic layer was dried over magnesium sulfate, filtered and concentrated. The crude was then purified by flash column chromatography eluting with 10% ethyl acetate in hexane. The desired fractions were concentrated to dryness under vacuum to afford 2'-chloro-6'-(4-methoxybenzyl)-4'-methylspiro[cyclohexane-1,7'-pyrrolo[3,4-b]pyridin]-5'(6'H)-one (7) as a yellow solid. Yield: 0.4 g, 33%; MS (ESI) m/z 370.2 [M−1]$^−$.

Synthesis of 2'-chloro-4'-methylspiro[cyclohexane-1,7'-pyrrolo[3,4-b]pyridin]-5'(6'H)-one (8)

The synthesis of intermediate 8 was carried out as described above using the general protocol of Procedure G. Yellow solid; Yield: 40 mg, 30%; MS (ESI) m/z 250.7 [M+1]$^+$.

Synthesis of N-(5-methyl-6-((4'-methyl-5'-oxo-5',6'-dihydrospiro[cyclohexane-1,7'-pyrrolo[3,4-b]pyridin]-2'-yl)amino)pyrimidin-4-yl)cyclopropanecarboxamide (10)

The synthesis of intermediate 10 was carried out as described above using the general protocol of Procedure A. Yellow solid. Yield: 0.3 g, crude; MS (ESI) m/z 407.2 [M+1]$^+$.

Synthesis of 2'-((6-amino-5-methylpyrimidin-4-yl)amino)-4'-methylspiro[cyclohexane-1,7'-pyrrolo[3,4-b]pyridin]-5'(6'H)-one (Cpd. No. 71)

The synthesis of compound 71 was carried out as described above using the general protocol of Procedure D. Pink solid; Yield: 0.05 g, 24%; MS (ESI) m/z 339.2 [M+1]$^+$; $^1$H NMR (400 MHz, DMSO-d$_6$) δ 9.02 (brs, 1H), 8.98 (s, 1H), 8.17 (s, 1H), 7.46 (s, 1H), 6.80 (brs, 2H), 2.49 (s, 3H), 1.98 (s, 3H), 1.94-1.91 (m, 2H), 1.70-1.64 (m, 5H), 1.44-1.42 (m, 1H), 1.36-1.33 (m, 2H).

Example 72

Synthesis of 2'-((6-amino-5-methoxypyrimidin-4-yl)amino)-4'-methylspiro[cyclohexane-1,7'-pyrrolo[3,4-b]pyridin]-5'(6'H)-one (Cpd. No. 72)

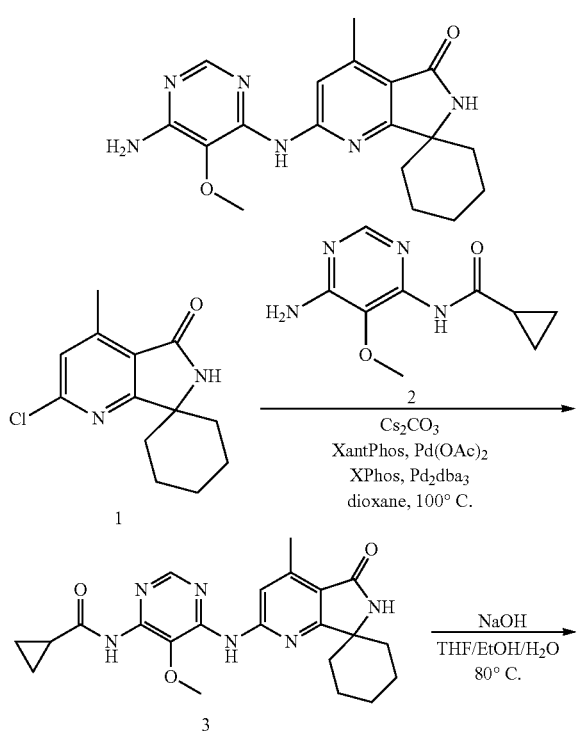

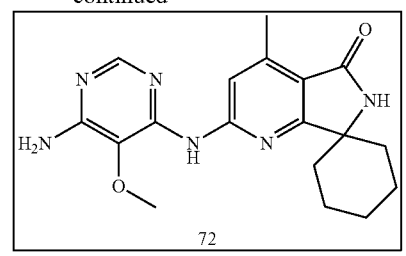

Synthesis of N-(5-methoxy-6-((4'-methyl-5'-oxo-5',6'-dihydrospiro[cyclohexane-1,7'-pyrrolo[3,4-b]pyridin]-2'-yl)amino)pyrimidin-4-yl)cyclopropanecarboxamide (3)

The synthesis of intermediate 3 was carried out as described above using the general protocol of Procedure A. Yellow solid; Yield: 0.3 g, 75%; MS (ESI) m/z 423.2 [M+1]$^+$.

Synthesis of 2'-((6-amino-5-methoxypyrimidin-4-yl)amino)-4'-methylspiro[cyclohexane-1,7'-pyrrolo[3,4-b]pyridin]-5'(6'H)-one (Cpd. No. 72)

The synthesis of compound 72 was carried out as described above using the general protocol of Procedure D. Pink solid; Yield: 0.24 g, 97%; MS (ESI) m/z 355.2 [M+1]$^+$; $^1$H NMR (400 MHz, DMSO-d$_6$) δ 8.92 (s, 1H), 8.30 (s, 1H), 8.08 (s, 1H), 7.97 (s, 2H), 6.67 (s, 1H), 3.73 (s, 3H), 2.55 (s, 3H), 1.93-1.92 (m, 2H), 1.72-1.60 (m, 5H), 1.37-1.30 (m, 2H).

Example 73

Synthesis of 2'-((6-amino-5-chloropyrimidin-4-yl)amino)-4'-methylspiro[cyclohexane-1,7'-pyrrolo[3,4-b]pyridin]-5'(6'H)-one (Cpd. No. 73)

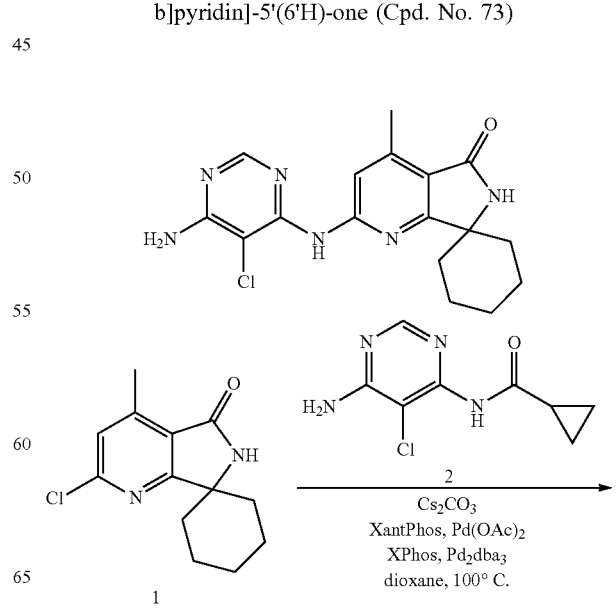

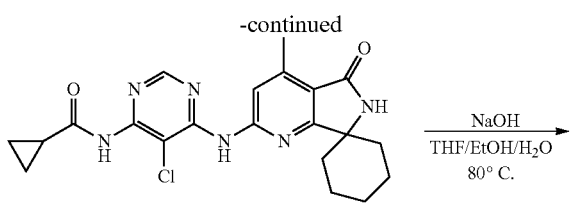

Synthesis of N-(5-chloro-6-(((4'-methyl-5'-oxo-5',6'-dihydrospiro[cyclohexane-1,7'-pyrrolo[3,4-b]pyridin]-2'-yl)amino)pyrimidin-4-yl)cyclopropanecarboxamide (3)

The synthesis of intermediate 3 was carried out as described above using the general protocol of Procedure A. Yellow solid; Yield: 0.2 g, 47%; MS (ESI) m/z 425.8 [M+1]$^+$.

Synthesis of 2'-((6-amino-5-chloropyrimidin-4-yl)amino)-4'-methylspiro[cyclohexane-1,7'-pyrrolo[3,4-b]pyridin]-5'(6'H)-one (Cpd. No. 73)

The synthesis of compound 73 was carried out as described above using the general protocol of Procedure D. Off-white solid; Yield: 0.24 g, 97%; MS (ESI) m/z 359.12 [M+1]$^+$; $^1$H NMR: (400 MHz, DMSO-$d_6$) δ 8.98 (s, 1H), 8.40 (s, 1H), 8.13 (s, 1H), 7.95 (s, 1H), 7.10 (brs, 2H), 2.56 (s, 3H), 1.94-1.91 (m, 2H), 1.72-1.66 (m, 5H), 1.37-1.30 (m, 3H).

Example 74

Synthesis of 6-((6-amino-5-methylpyrimidin-4-yl)amino)-4-methyl-2',3',5',6'-tetrahydrospiro[isoindoline-1,4'-pyran]-3-one (Cpd. No. 74)

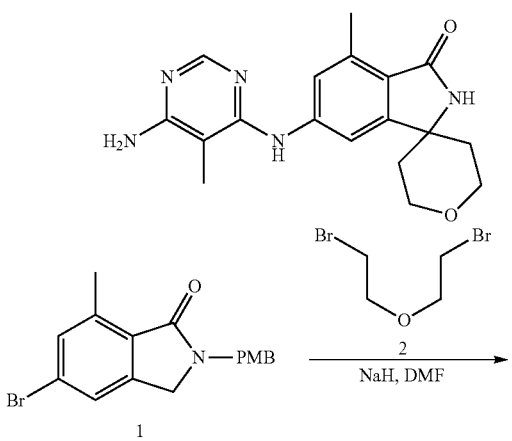

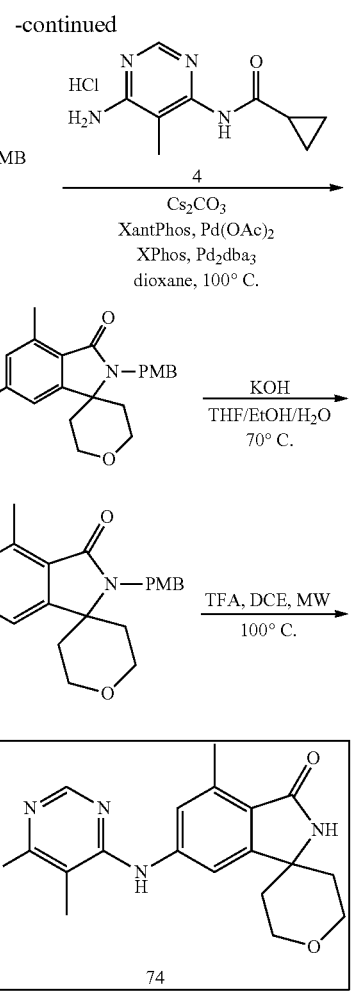

Synthesis of 6-bromo-2-(4-methoxybenzyl)-4-methyl-2',3',5',6'-tetrahydrospiro[isoindoline-1,4'-pyran]-3-one (3)

To a solution of 5-bromo-2-(4-methoxybenzyl)-7-methylisoindolin-1-one (1, 1.0 g, 2.89 mmol) in dimethylformamide (25 mL) was added sodium hydride (0.35 g, 8.66 mmol). The reaction was stirred for 15 min. 1-Bromo-2-(2-bromoethoxy)ethane (2, 0.871 mg, 3.75 mmol) was added and the reaction was stirred at room temperature for 16 h. After completion, the reaction was quenched with saturated aqueous ammonium chloride solution at 0° C. and extracted with ethyl acetate (100 mL). The organic layer was washed with water (2×20 mL) and brine (10 mL). The organic layer was separated, dried over magnesium sulfate, filtered and concentrated. The crude was then purified by flash column chromatography eluting with 10% ethyl acetate in hexane. The desired fractions were concentrated to dryness under vacuum to afford 6-bromo-2-(4-methoxybenzyl)-4-methyl-2',3',5',6'-tetrahydrospiro[isoindoline-1,4'-pyran]-3-one (3) as an off-white solid. Yield: 0.65 g, 54%; MS (ESI) m/z 418.0 [M+1]$^+$.

Synthesis of N-(6-((2-(4-methoxybenzyl)-4-methyl-3-oxo-2',3',5',6'-tetrahydrospiro[isoindoline-1,4'-pyran]-6-yl)amino)-5-methylpyrimidin-4-yl)cyclopropanecarboxamide (5)

The synthesis of intermediate 5 was carried out as described above using the general protocol of Procedure A. Yellow solid; Yield: 0.51 g; crude; MS (ESI) m/z 528.0 [M+1]$^+$.

Synthesis of 6-((6-amino-5-methylpyrimidin-4-yl)amino)-2-(4-methoxybenzyl)-4-methyl-2',3',5',6'-tetrahydrospiro[isoindoline-1,4'-pyran]-3-one (6)

The synthesis of intermediate 6 was carried out as described above using the general protocol of Procedure D. Yellow solid; Yield: 0.30 g, 70%; MS (ESI) m/z 458.2 [M+1]$^+$.

Synthesis of 6-((6-amino-5-methylpyrimidin-4-yl)amino)-4-methyl-2',3',5',6'-tetrahydrospiro[isoindoline-1,4'-pyran]-3-one (Cpd. No. 74)

The synthesis of compound 74 was carried out as described above using the general protocol of Procedure G. Brown solid; Yield: 43 mg, 19%; MS (ESI) m/z 344.04 [M+1]$^+$; $^1$H NMR (400 MHz, DMSO-d$_6$) δ 9.22 (s, 1H), 9.12 (s, 1H), 8.26 (s, 1H), 7.52 (s, 1H), 7.45 (brs, 2H), 7.29 (s, 1H), 3.90-3.80 (m, 2H), 3.80-3.70 (m, 2H), 2.57 (s, 3H), 2.15-2.07 (m, 2H), 2.04 (s, 3H), 1.37-1.29 (m, 2H).

Example 75

Synthesis of 6'-((7H-pyrrolo[2,3-d]pyrimidin-4-yl)amino)-4'-methylspiro[cyclohexane-1,1'-isoindolin]-3'-one (Cpd. No. 75)

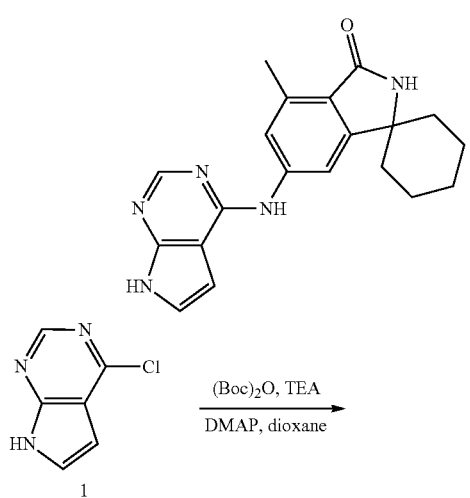

Synthesis of tert-butyl 4-chloro-7H-pyrrolo[2,3-d]pyrimidine-7-carboxylate (2)

A mixture of 4-chloro-7H-pyrrolo[2,3-d]pyrimidine (1, 0.5 g, 3.26 mmol), triethylamine (0.99 g, 9.80 mmol), di-tert-butyl dicarbonate (0.71 g, 3.26 mmol) and 4-dimethylaminopyridine (0.08 g, 0.65 mmol) in dioxane (15 mL) was stirred at room temperature for 16 h. After TLC showed completion, the reaction mixture was extracted with ethyl acetate (2×50 mL). The combined organic layer was washed with water and brine, dried over anhydrous sodium sulfate, filtered and concentrated. The crude was then purified by flash column chromatography eluting with 30-40% ethyl acetate in hexane. The desired fractions were concentrated to dryness under vacuum to afford tert-butyl 4-chloro-7H-pyrrolo[2,3-d]pyrimidine-7-carboxylate (2) as an off-white solid. Yield: 0.6 g, 73%; $^1$H NMR (400 MHz, DMSO-d6) δ 8.80 (s, 1H), 7.96-7.95 (d, J=4.0 Hz, 1H), 6.83-6.82 (d, J=4.0 Hz, 1H), 1.62 (s, 9H).

Synthesis of 6'-((7H-pyrrolo[2,3-d]pyrimidin-4-yl)amino)-4'-methylspiro[cyclohexane-1,1'-isoindolin]-3'-one (Cpd. No. 75)

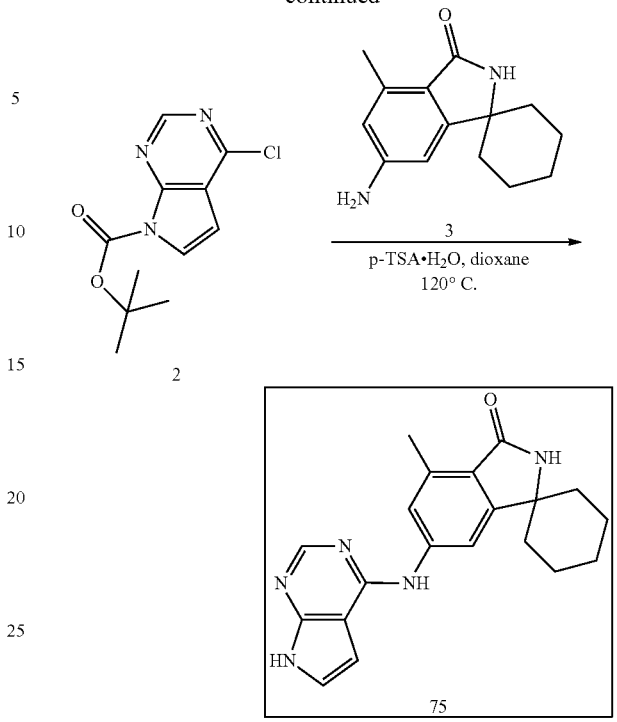

To a solution of tert-butyl 4-chloro-7H-pyrrolo[2,3-d]pyrimidine-7-carboxylate (2, 0.09 g, 0.36 mmol) and 6'-amino-4'-methylspiro[cyclohexane-1,1'-isoindolin]-3'-one (3, 0.095 g, 0.36 mmol) in 1,4-dioxane (12 mL), p-toluenesulfonic acid monohydrate (7 mg, 0.035 mmol) was added and the resulting mixture was stirred at 120° C. for 2 d. After completion, the reaction mixture was concentrated to dryness, quenched with saturated aqueous solution of sodium bicarbonate till pH 8 and extracted with 10% methanol in dichloromethane (2×10 mL). The combined organic layer was dried over magnesium sulfate and concentrated. The crude was purified by column chromatography using 0-5% methanol in dichloromethane to afford 6'-((7H-pyrrolo[2,3-d]pyrimidin-4-yl)amino)-4'-methyl-spiro[cyclohexane-1,1'-isoindolin]-3'-one (Cpd. No. 75) as an off-white solid. Yield: 0.07 g, 73%; MS (ESI) m/z 348.19 [M+1]$^+$; $^1$H NMR (400 MHz, DMSO-d$_6$) δ 11.81 (s, 1H), 9.46 (s, 1H), 8.81 (s, 1H), 8.34 (s, 1H), 7.92 (s, 1H), 7.73 (s, 1H), 7.27 (s, 1H), 6.82 (s, 1H), 2.58 (s, 3H), 1.86-1.74 (m, 2H), 1.73-1.65 (m, 5H), 1.46-1.32 (m, 3H).

Example 76

Synthesis of 6'-((6-amino-5-ethoxypyrimidin-4-yl)amino)-4'-methylspiro[cyclohexane-1,1'-isoindolin]-3'-one (Cpd. No. 76)

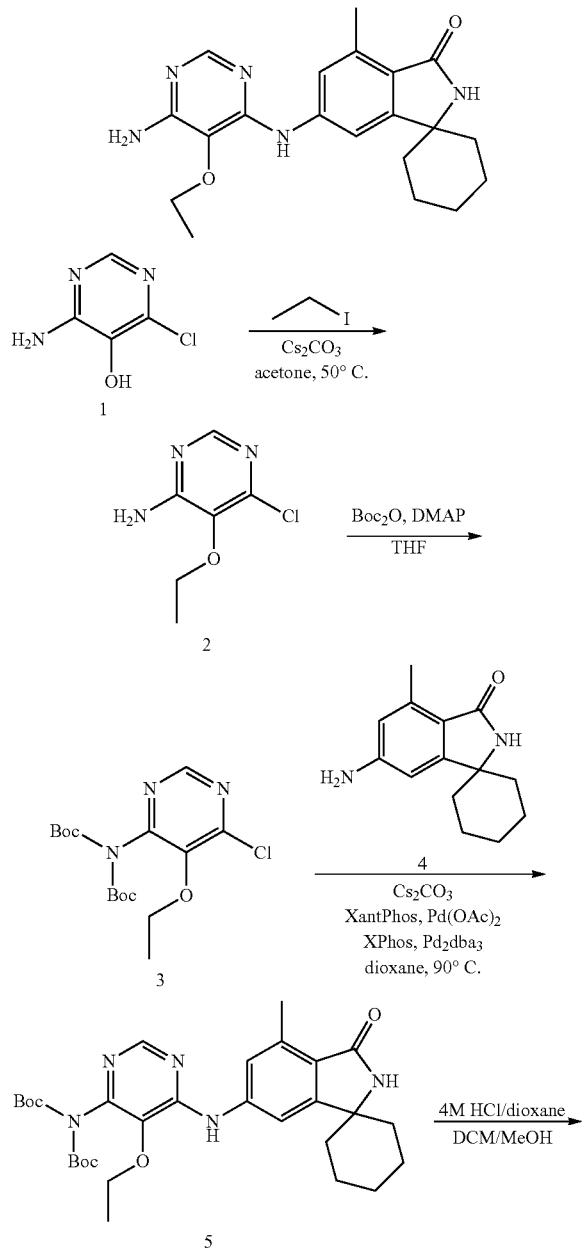

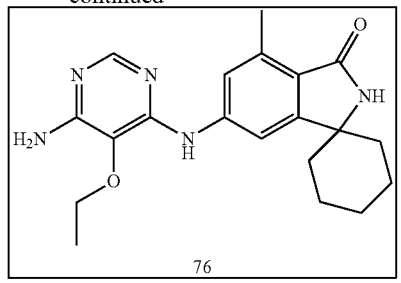

Synthesis of 6-chloro-5-ethoxypyrimidin-4-amine (2)

To a solution of 4-amino-6-chloropyrimidin-5-ol (1, 0.5 g, 3.43 mmol) and iodoethane (0.80 g, 5.15 mmol) in acetone (20 mL) was added cesium carbonate (3.35 g, 10.2 mmol). The reaction was heated at 50° C. for 16 h. After TLC showed completion, solvent was removed under reduced pressure to get crude, which was purified by flash column chromatography eluting with 20-30% ethyl acetate in hexane. The desired fractions were concentrated to dryness under vacuum to afford 6-chloro-5-ethoxypyrimidin-4-amine (2) as an off-white solid. Yield: 0.25 g, 42%; MS (ESI) m/z 173.88 [M+1]$^+$; $^1$H NMR (400 MHz, DMSO-d$_6$) δ 7.95 (s, 1H), 7.20 (brs, 2H), 3.96-3.90 (q, J=6.8 Hz, 2H), 1.34-1.30 (t, J=7.2 Hz, 3H).

Synthesis of tert-butyl N-tertbutoxy carbonyl-N-(6-chloro-5-ethoxypyrimidin-4-yl) carbamate (3)

To a solution of 6-chloro-5-ethoxypyrimidin-4-amine (2, 0.25 g, 1.44 mmol) in tetrahydrofuran (10 mL) were added di-tert-butyl dicarbonate (0.78 g, 3.60 mmol) and 4-dimethylaminopyridine (0.087 g, 0.72 mmol). The reaction mixture was stirred at room temperature for 16 h. After TLC showed completion, the reaction mass was extracted with ethyl acetate. The organic layer was washed with water and brine, dried over anhydrous sodium sulfate, filtered and concentrated. The crude was purified by flash column chromatography eluting with 20% ethyl acetate in hexane. The desired fractions were concentrated to dryness under vacuum to afford tert-butyl N-tertbutoxy carbonyl-N-(6-chloro-5-ethoxypyrimidin-4-yl) carbamate (3) as a light yellow solid. Yield: 0.20 g, 37%; MS (ESI) m/z 374.23 [M+1]$^+$.

Synthesis of tert-butyl N-tertbutoxy carbonyl-N-(5-ethoxy-6-((4'-methyl-3'-oxospiro[cyclohexane-1,1'-isoindolin]-6'-yl)amino)pyrimidin-4-yl)carbamate (5)

The synthesis of intermediate 5 was carried out as described above using the general protocol of Procedure A. Yellow solid; Yield: 0.080 g, 17%; MS (ESI) m/z 568.39 [M+1]$^+$.

Synthesis of 6'-((6-amino-5-ethoxypyrimidin-4-yl)amino)-4'-methylspiro [cyclohexane-1,1'-isoindolin]-3'-one (Cpd. No. 76)

To a solution of tert-butyl N-tert-butoxy carbonyl-N-(5-ethoxy-6-((4'-methyl-3'-oxospiro [cyclohexane-1,1'-isoindolin]-6'-yl)amino)pyrimidin-4-yl)carbamate (5, 80 mg, 0.14 mmol) in dichloromethane (10 mL) and methanol (2 mL) at 0° C. was added 4 M hydrogen chloride in dioxane (5 mL). The reaction was stirred for 16 h. After completion, solvent was removed under reduced pressure and the resulting residue was washed with diethyl ether and pentane to afford 6'-((6-amino-5-ethoxypyrimidin-4-yl)amino)-4'-methylspiro[cyclohexane-1,1'-isoindolin]-3'-one (Cpd. No. 76) as an off-white solid. Yield: 0.025 g, 48%; MS (ESI) m/z 368.17 [M+1]+; 1H NMR (400 MHz, DMSO-d6) δ 9.36 (s, 1H), 8.92 (s, 1H), 8.17 (s, 1H), 7.60 (brs, 2H), 7.53 (s, 1H), 7.36 (s, 1H), 3.91-3.86 (q, J=7.6 Hz, 2H), 2.55 (s, 3H), 1.79 (m, 2H), 1.67 (m, 5H), 1.39-13.2 (m, 6H).

Example 77

Synthesis of 4-amino-6-((4'-methyl-3'-oxospiro[cyclohexane-1,1'-isoindolin]-6'-yl)amino)pyrimidine-5-carbonitrile (Cpd. No. 77)

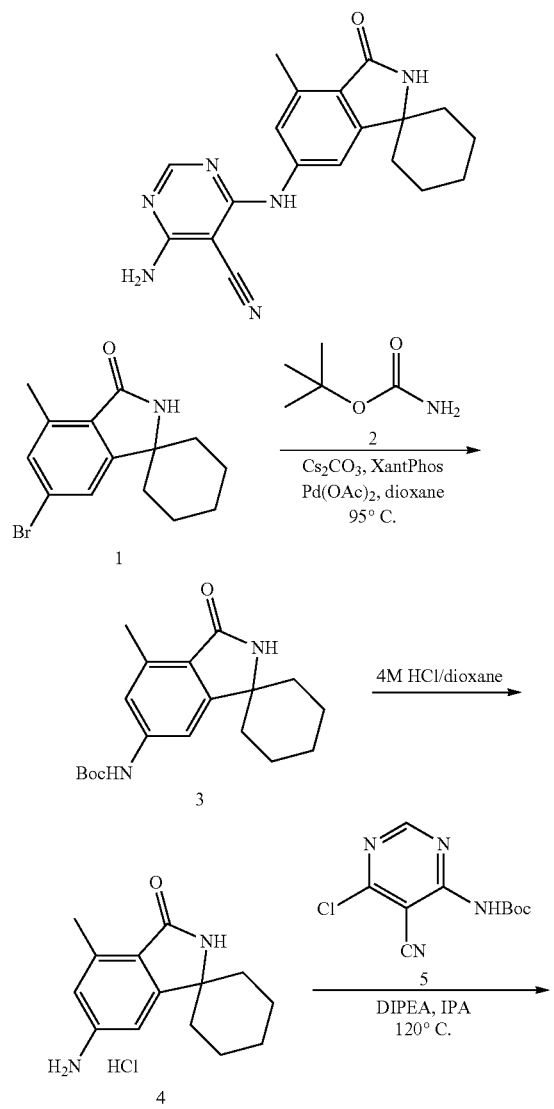

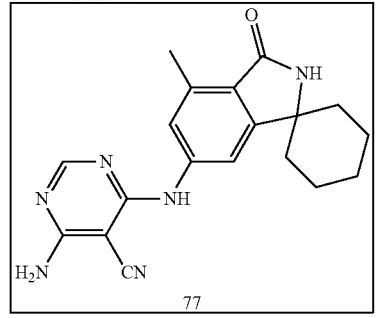

Synthesis of tert-butyl (4'-methyl-3'-oxospiro[cyclohexane-1,1'-isoindolin]-6'-yl)carbamate (3)

The synthesis of intermediate 3 was carried out as described above using the general protocol of Procedure A. Off-white solid; Yield: 2.0 g, 89%; MS (ESI) m/z 331.18 [M+1]+.

Synthesis of 6'-amino-4'-methylspiro[cyclohexane-1,1'-isoindolin]-3'-one (4)

The synthesis of intermediate 4 was carried out as described above using the general protocol of Procedure C. Brown solid; Yield: 1.5 g, 94%; MS (ESI) m/z 231.0 [M+1]+.

Synthesis of 4-amino-6-((4'-methyl-3'-oxospiro[cyclohexane-1,1'-isoindolin]-6'-yl)amino)pyrimidine-5-carbonitrile (Cpd. No. 77)

A vial was charged with 6'-amino-4'-methylspiro[cyclohexane-1,1'-isoindolin]-3'-one hydrochloride (4, 150 mg, 0.57 mmol), tert-butyl (6-chloro-5-cyanopyrimidin-4-yl)carbamate (5, 140 mg, 0.57 mmol) and 2-propanol (8 mL). To the above stirred mixture diisopropylethylamine (0.2 mL, 1.13 mmol) was added and the reaction mixture was heated at 100° C. for 24 h. TLC showed more starting material and again the reaction was heated for 48 h at 120° C. Solvent was removed. The residue was diluted with water and extracted with 10% methanol in dichloromethane. The crude was purified by silica gel column chromatography using 4.5% methanol in dichloromethane. Concentration of the appropriate fractions under reduced pressure afforded 4-amino-6-((4'-methyl-3'-oxospiro[cyclohexane-1,1'-isoindolin]-6'-yl)amino)pyrimidine-5-carbonitrile (Cpd. No. 77) as an off-white solid. Yield: 0.05 g, 19%; MS (ESI) m/z 349.20 [M+1]+; 1H NMR (400 MHz, DMSO-d6) δ 9.34 (s, 1H), 8.87 (s, 1H), 8.15 (s, 1H), 7.54 (s, 1H), 7.45-7.56 (brs, 2H), 7.39 (s, 1H), 2.54 (s, 3H), 1.80-1.62 (m, 7H), 1.41-1.30 (s, 3H).

Example 78

Synthesis of 6'-((6-amino-5-methylpyrimidin-4-yl)amino)-4'-methoxyspiro[cyclohexane-1,1'-isoindolin]-3'-one (Cpd. No. 78)

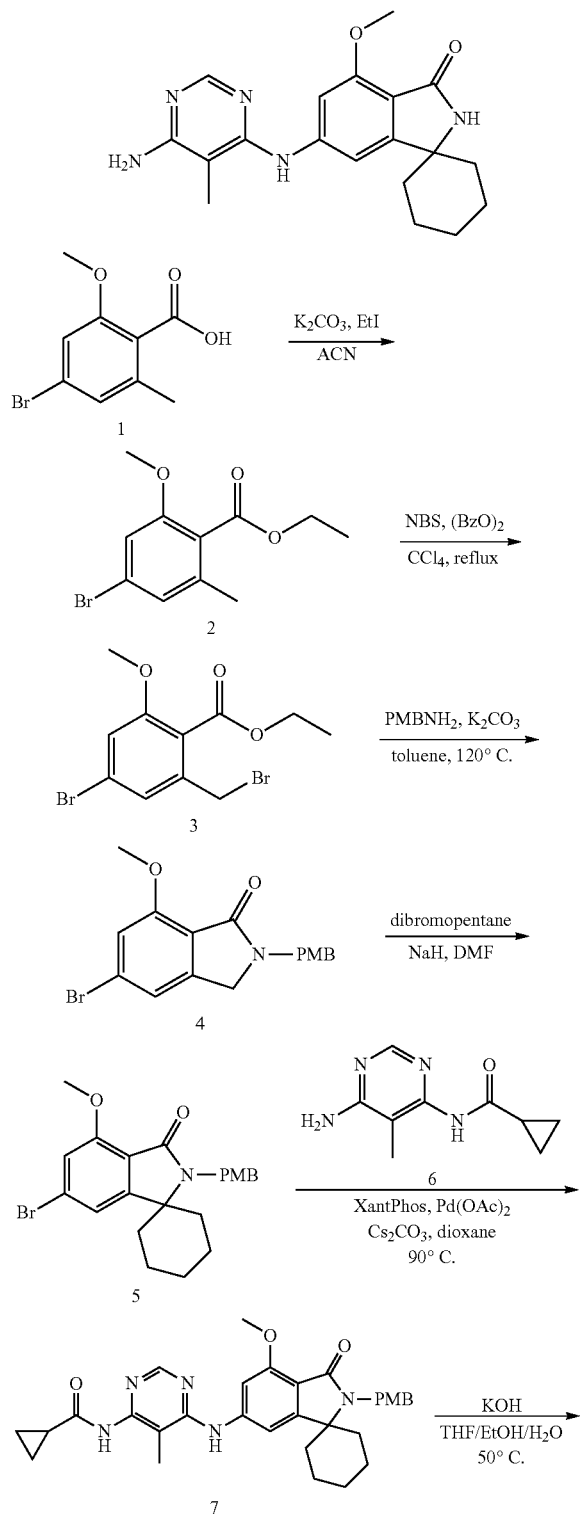

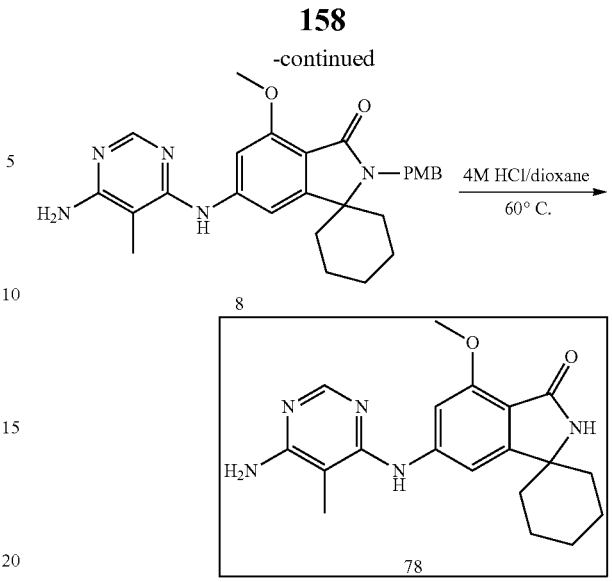

Synthesis of ethyl 4-bromo-2-methoxy-6-methylbenzoate (2)

To a solution of 4-bromo-2-methoxy-6-methylbenzoic acid (1, 5.0 g, 20.5 mmol) in acetonitrile (100 mL) was added potassium carbonate (7.8 g, 56.5 mmol) followed by ethyl iodide (3.2 g, 20.5 mmol). The reaction was stirred at room temperature for 16 h. The reaction was quenched with ice water and extracted with ethyl acetate. The organic layer was dried over sodium sulfate, filtered and concentrated to afford ethyl 4-bromo-2-methoxy-6-methylbenzoate (2) as a white solid. Yield: 3.3 g, 60%.

Synthesis of ethyl 4-bromo-2-(bromomethyl)-6-methoxybenzoate (3)

To a solution of ethyl 4-bromo-2-methoxy-6-methylbenzoate (2, 2.5 g, 9.19 mmol) in carbon tetrachloride (50 mL) were added N-bromosuccinimide (1.96 g, 11.9 mmol) and benzoylperoxide (220 mg, 0.92 mmol). The reaction was stirred at 90° C. for 12 h and then cooled to room temperature. The mixture was diluted with dichloromethane and washed with water and brine. The organic layer was dried over sodium sulfate, filtered and concentrated to afford ethyl 4-bromo-2-(bromomethyl)-6-methoxybenzoate (3) as light brown liquid. Yield: 2.8 g, crude.

Synthesis of 5-bromo-7-methoxy-2-(4-methoxybenzyl)isoindolin-1-one (4)

To a solution of ethyl 4-bromo-2-(bromomethyl)-6-methoxybenzoate (3, 2.5 g, 7.14 mmol) in toluene (30 mL) was added 4-methoxybenzylamine (1.4 g, 10.7 mmol) followed by potassium carbonate (3.05 g, 22.1 mmol). The mixture was then heated at 120° C. for 2 h. After completion, the solvent was evaporated and the crude was purified by silica gel column chromatography eluting with 20-30% ethyl acetate in hexane. Appropriate column fractions were concentrated under reduced pressure to afford 5-bromo-7-methoxy-2-(4-methoxybenzyl)isoindolin-1-one (4) as a yellow sticky solid. Yield: 2.0 g, 78%; MS (ESI) m/z 362.13 [M+1]$^+$.

Synthesis of 6'-bromo-4'-methoxy-2'-(4-methoxybenzyl)spiro[cyclohexane-1,1'-isoindolin]-3'-one (5)

To a solution of 5-bromo-7-methoxy-2-(4-methoxybenzyl)isoindolin-1-one (4, 1.3 g, 3.6 mmol) in dimethylformamide (18 mL) was added sodium hydride (0.55 g, 14.4 mmol). The suspension was stirred at room temperature for 30 min and then a solution of 1,5-dibromopentane (1.65 g, 7.2 mmol) in dimethylformamide (5 mL) was added. The reaction was stirred for another 12 h at room temperature, quenched with saturated aqueous ammonium chloride solution and extracted with ethyl acetate. The crude was purified by flash column chromatography eluting with 20-30% ethyl acetate in hexane. The desired fractions were concentrated to dryness under vacuum to afford 6'-bromo-4'-methoxy-2'-(4-methoxybenzyl)spiro[cyclohexane-1,1'-isoindolin]-3'-one (5) as a yellow solid. Yield: 1.15 g, 73%; MS (ESI) m/z 430.03 [M−1]$^-$.

Synthesis of N-(6-((4'-methoxy-2'-(4-methoxybenzyl)-3'-oxospiro[cyclohexane-1,1'-isoindolin]-6'-yl)amino)-5-methylpyrimidin-4-yl)cyclopropanecarboxamide (7)

The synthesis of intermediate 7 was carried out as described above using the general protocol of Procedure A. Brown solid; Yield: 370 mg, 28%; MS (ESI) m/z 542.19 [M+1]$^+$.

Synthesis of 6'-((6-amino-5-methylpyrimidin-4-yl)amino)-4'-methoxy-2'-(4-methoxybenzyl)spiro[cyclohexane-1,1'-isoindolin]-3'-one (8)

The synthesis of intermediate 8 was carried out as described above using the general protocol of Procedure D. Brown solid; Yield: 250 mg; MS (ESI) m/z 474.38 [M+1]$^+$.

Synthesis of 6'-((6-amino-5-methylpyrimidin-4-yl)amino)-4'-methoxyspiro[cyclohexane-1,1'-isoindolin]-3'-one (Cpd. No. 78)

A vial was charged with 6'-((6-amino-5-methylpyrimidin-4-yl)amino)-4'-methoxy-2'-(4-methoxybenzyl)spiro[cyclohexane-1,1'-isoindolin]-3'-one (8, 150 mg, 0.32 mmol) and 4 M hydrogen chloride in dioxane (5 mL). The reaction was then heated at 60° C. for 16 h. The mixture was concentrated, basified with aqueous ammonia and extracted with 10% 2-propanol in dichloromethane. The organic layer was concentrated and purified by prep HPLC to afford 6'-((6-amino-5-methylpyrimidin-4-yl)amino)-4'-methoxyspiro[cyclohexane-1,1'-isoindolin]-3'-one (Cpd. No. 78) as a yellow solid. Yield: 29 mg, 26%; MS (ESI) m/z 354.21 [M+1]$^+$; $^1$H NMR (400 MHz, DMSO-d$_6$) δ 9.19 (s, 1H), 8.72 (s, 1H), 8.27 (s, 1H), 7.62 (s, 2H), 7.21 (s, 1H), 7.10 (s, 1H), 3.80 (s, 3H), 2.05 (s, 3H) 1.76-1.73 (m, 2H), 1.68-1.64 (m, 5H), 1.37-1.29 (m, 3H).

Example 79

Synthesis of 6'-((6-amino-5-methylpyrimidin-4-yl)amino)-4'-(trifluoromethyl)spiro[cyclohexane-1,1'-isoindolin]-3'-one (Cpd. No. 79)

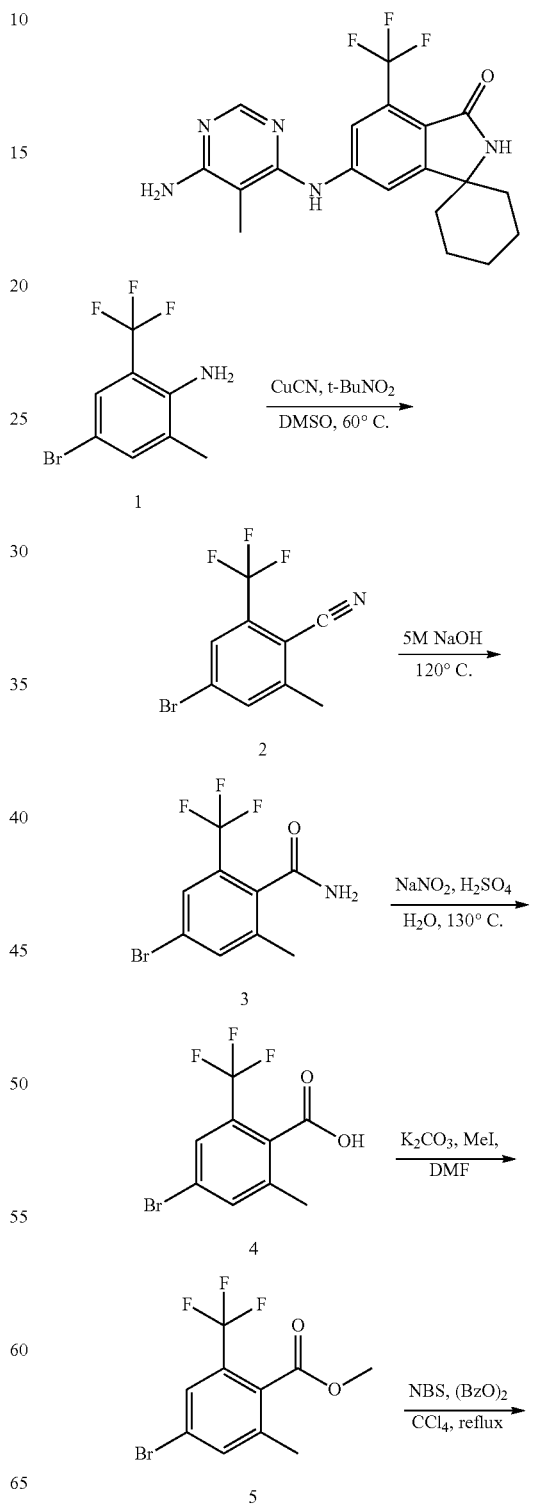

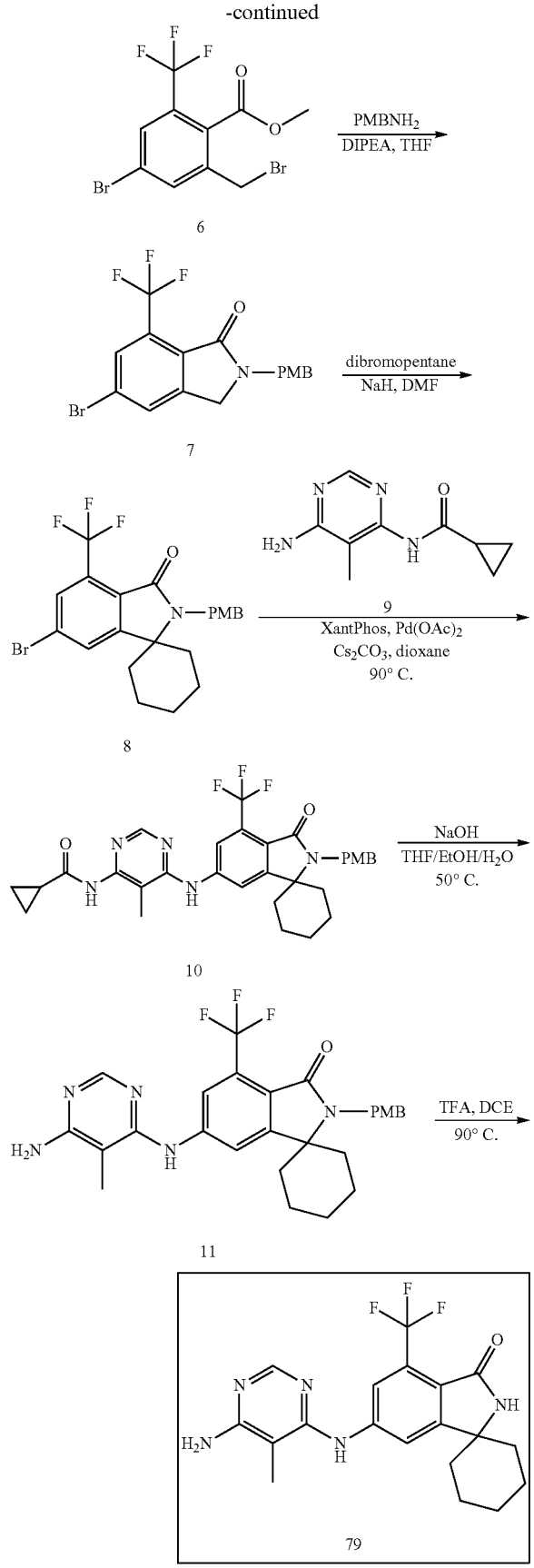

Synthesis of 4-bromo-2-methyl-6-(trifluoromethyl)benzonitrile (2)

A mixture of copper(I) cyanide (11.1 g, 123.9 mmol) and t-butyl nitrite (42.58 g, 413 mmol) in dimethyl sulfoxide (200 mL) was stirred at 60° C. for 30 min. To the above mixture was added dropwise a solution of 4-bromo-2-methyl-6-(trifluoromethyl)aniline (1, 21 g, 82.6 mmol) in dimethyl sulfoxide (100 mL) over a period of 30 min. The reaction was stirred at 60° C. for 30 min. After completion, the reaction was quenched with 6 M hydrochloric acid and extracted with ethyl acetate (3×100 mL). Combined organic layers was washed with water and brine, dried over sodium sulfate, filtered and concentrated. The crude was purified by silica gel column chromatography eluting with 10-20% ethyl acetate in hexane. Appropriate column fractions were concentrated under reduced pressure to afford 4-bromo-2-methyl-6-(trifluoromethyl)benzonitrile (2) as an off-white solid. Yield: 12 g, 55%; $^1$H NMR (400 MHz, DMSO-d$_6$) δ 7.76 (s, 1H), 7.72 (s, 1H), 2.62 (s, 3H).

Synthesis of 4-bromo-2-methyl-6-(trifluoromethyl)benzamide (3)

A mixture of 4-bromo-3-chloro-2-methylbenzonitrile (2, 12 g, 45.4 mmol) in 5 M sodium hydroxide in water (46 mL) was stirred at 120° C. for 48 h. The reaction was cooled to room temperature. The precipitate was filtered, washed with water and pentane and dried under vacuum to afford 4-bromo-2-methyl-6-(trifluoromethyl)benzamide (3) as a light brown solid. Yield: 12.05 g, 94%; MS (ESI) m/z 279.91 [M−1]$^-$.

Synthesis of 4-bromo-2-methyl-6-(trifluoromethyl)benzoic acid (4)

To a mixture of 4-Bromo-2-methyl-6-(trifluoromethyl) benzamide (3, 2.5 g, 10.0 mmol) in 50% sulfuric acid (50 mL) at 0° C. was added an aqueous solution of sodium nitrite (11.74 g, 170.18 mmol). The reaction was stirred at 130° C. for 16 h. After completion, the reaction mixture was cooled and ice cold water was added. The precipitated white solid was filtered and washed with water and n-pentane. The compound was dried under vacuum to afford 4-bromo-2-methyl-6-(trifluoromethyl)benzoic acid (4) as an off-white solid. Yield: 8.0 g, 66%; MS (ESI) m/z 280.82 [M−1]$^-$.

Synthesis of methyl 4-bromo-2-methyl-6-(trifluoromethyl)benzoate (5)

To a mixture of 4-bromo-2-methyl-6-(trifluoromethyl) benzoic acid (4, 8.0 g, 28.2 mmol) and potassium carbonate (7.8 g, 56.5 mmol) in dimethylformamide (500 mL) was added slowly iodomethane (6.0 g, 42.3 mmol). The reaction was stirred at room temperature for 1 h. The reaction was quenched with ice water and extracted with ethyl acetate. The organic layer was dried over sodium sulfate, filtered and concentrated to afford methyl 4-bromo-2-methyl-6-(trifluoromethyl)benzoate (5) as a thick brown liquid. Yield: 8.5 g, crude; $^1$H NMR (400 MHz, DMSO-d$_6$) δ 7.65 (s, 1H), 7.58 (s, 1H), 3.92 (s, 2H), 2.34 (s, 3H).

Synthesis of methyl 4-bromo-2-(bromomethyl)-6-(trifluoromethyl)benzoate (6)

To a solution of methyl 4-bromo-2-methyl-6-(trifluoromethyl)benzoate (5, 8.5 g, 28.6 mmol) in carbon tetrachloride (200 mL) were added N-bromosuccinimide (6.11 g, 34.3 mmol) and benzoylperoxide (692 mg, 2.86 mmol). The reaction was then heated at 90° C. for 16 h. After completion, the reaction was cooled to room temperature and diluted with dichloromethane. The organic layer was washed water and brine, dried over sodium sulfate, filtered and concentrated to afford 4-bromo-2-(bromomethyl)-6-(trifluoromethyl)benzoate (6) as a light brown liquid. Yield: 10.5 g, crude.

Synthesis of 5-bromo-2-(4-methoxybenzyl)-7-(trifluoromethyl)isoindolin-1-one (7)

To a solution of 4-bromo-2-(bromomethyl)-6-(trifluoromethyl)benzoate (6, 5.0 g, 13.2 mmol) in tetrahydrofuran (25 mL), 4-methoxybenzylamine (2.18 g, 15.9 mmol) was added followed by diisopropylethylamine (4.32 g, 33.1 mmol). The mixture was stirred at room temperature for 16 h. After completion, the solvent was evaporated and the crude was purified by silica gel column chromatography eluting with 20-30% ethyl acetate in hexane. Appropriate column fractions were concentrated under reduced pressure to afford 5-bromo-2-(4-methoxybenzyl)-7-(trifluoromethyl)isoindolin-1-one (7) as an off-white solid. Yield: 2.5 g, 47%; MS (ESI) m/z 401.11 [M+1]$^+$.

Synthesis of 6'-bromo-2'-(4-methoxybenzyl)-4'-(trifluoromethyl)spiro[cyclohexane-1,1'-isoindolin]-3'-one (8)

To a solution of 5-bromo-2-(4-methoxybenzyl)-7-(trifluoromethyl)isoindolin-1-one (7, 2.0 g, 3.81 mmol) in dimethylformamide (50 mL) was added sodium hydride (0.36 g, 15.0 mmol). The suspension was stirred at room temperature for 30 min and then a solution of dibromopentane (2.3 g, 10 mmol) in dimethylformamide (10 mL) was added. The reaction was stirred for another 3 h at room temperature. After completion, the reaction was quenched with saturated aqueous ammonium chloride solution and extracted with ethyl acetate. The organic layer was dried over sodium sulfate, filtered and concentrated. The crude was purified by flash column chromatography eluting with 20-30% ethyl acetate in hexane to afford 6'-bromo-2'-(4-methoxybenzyl)-4'-(trifluoromethyl)spiro[cyclohexane-1,1'-isoindolin]-3'-one (8) as a yellow solid. Yield: 0.65 g, 28%; MS (ESI) m/z 467.16 [M−1]$^-$.

Synthesis of N-(6-((2'-(4-methoxybenzyl)-3'-oxo-4'-(trifluoromethyl)spiro[cyclohexane-1,1'-isoindolin]-6'-yl)amino)-5-methylpyrimidin-4-yl)cyclopropanecarboxamide (10)

The synthesis of intermediate 10 was carried out as described above using the general protocol of Procedure A. Yellow solid; Yield: 450 mg, crude.

Synthesis of 6'-((6-amino-5-methylpyrimidin-4-yl)amino)-2'-(4-methoxybenzyl)-4'-(trifluoromethyl)spiro[cyclohexane-1,1'-isoindolin]-3'-one (11)

The synthesis of intermediate 11 was carried out as described above using the general protocol of Procedure D. Yellow solid; Yield: 300 mg, crude; MS (ESI) m/z 498.16 [M+1]$^+$.

Synthesis of 6'-((6-amino-5-methylpyrimidin-4-yl)amino)-4'-(trifluoromethyl)spiro [cyclohexane-1,1'-isoindolin]-3'-one (Cpd. No. 79)

The synthesis of compound 79 was carried out as described above using the general protocol of Procedure G. White solid; Yield: 5 mg, 3%; MS (ESI) m/z 378.15 [M+1]$^+$; $^1$H NMR (400 MHz, DMSO-d$_6$) δ 9.09 (s, 1H), 8.59 (s, 1H), 8.08 (s, 2H), 8.03 (s, 1H), 6.39 (s, 2H), 1.99 (s, 3H), 1.90 (s, 1H) 1.80-1.77 (m, 2H), 1.72-1.68 (m, 5H), 1.42-1.35 (m, 2H).

Example 80

Synthesis of 6'-((6-amino-5-(trifluoromethyl)pyrimidin-4-yl)amino)-4'-methylspiro[cyclohexane-1,1'-isoindolin]-3'-one (Cpd. No. 80)

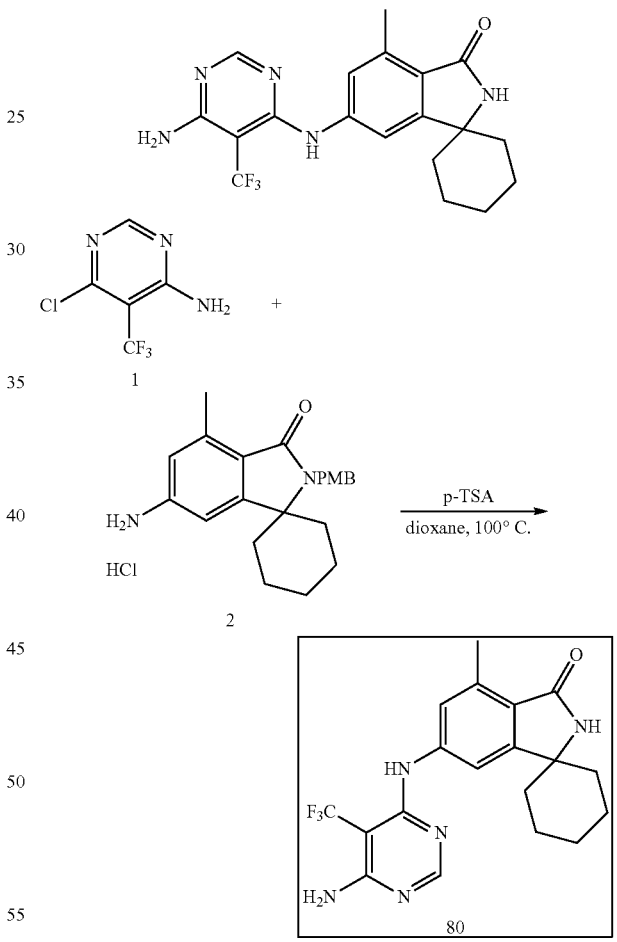

Synthesis of 6'-((6-amino-5-(trifluoromethyl)pyrimidin-4-yl)amino)-4'-methylspiro[cyclohexane-1,1'-isoindolin]-3'-one (Cpd. No. 80)

To a solution of 6-chloro-5-(trifluoromethyl)pyrimidin-4-amine (1, 0.10 g, 0.50 mmol) and 6'-amino-2'-(4-methoxybenzyl)-4'-methylspiro[cyclohexane-1,1'-isoindolin]-3'-one hydrochloride (2, 0.13 g, 0.50 mmol) in 1,4-dioxane (3.5 mL), p-toluenesulfonic acid monohydrate (20 mg, 0.10 mmol) was added and the resulting mixture was stirred at 100° C. for 30 h. After completion, the reaction was concentrated, quenched with saturated aqueous solution of sodium bicarbonate till pH 8 and extracted with 10% methanol in dichloromethane (2×10 mL). The organics were then dried over magnesium sulfate, filtered and concentrated. The crude was purified by column chromatography using 0-5% methanol in dichloromethane to afford 6'-((6-amino-5-(trifluoromethyl)pyrimidin-4-yl)amino)-4'-methylspiro[cyclohexane-1,1'-isoindolin]-3'-one (Cpd. No. 80) as a white solid. Yield: 0.05 g, 26%; MS (ESI) m/z 392.15 [M+1]$^+$; $^1$H NMR (400 MHz, DMSO-d$_6$) δ 8.85 (s, 1H), 8.41 (s, 1H), 8.06 (s, 1H), 7.43 (s, 1H), 7.26 (s, 1H), 6.9-7.1 (brs, 2H), 2.53 (s, 3H), 1.82-1.75 (m, 2H), 1.72-1.60 (m, 5H), 1.37-1.34 (m, 3H).

Example 81

Synthesis of 6'-((6-amino-5-(2-aminoethoxy)pyrimidin-4-yl)amino)-4'-methylspiro[cyclohexane-1,1'-isoindolin]-3'-one hydrochloride (Cpd. No. 81)

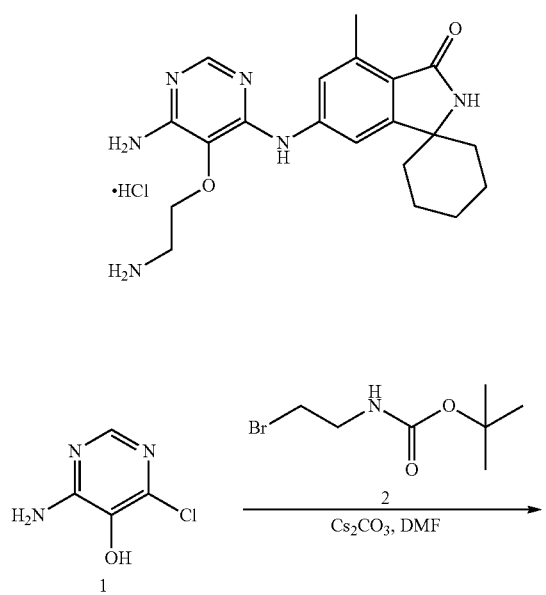

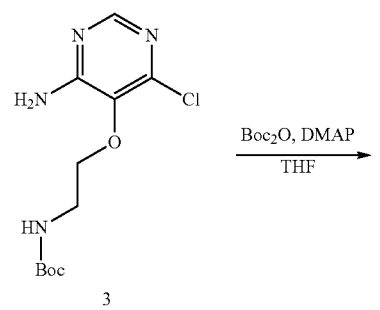

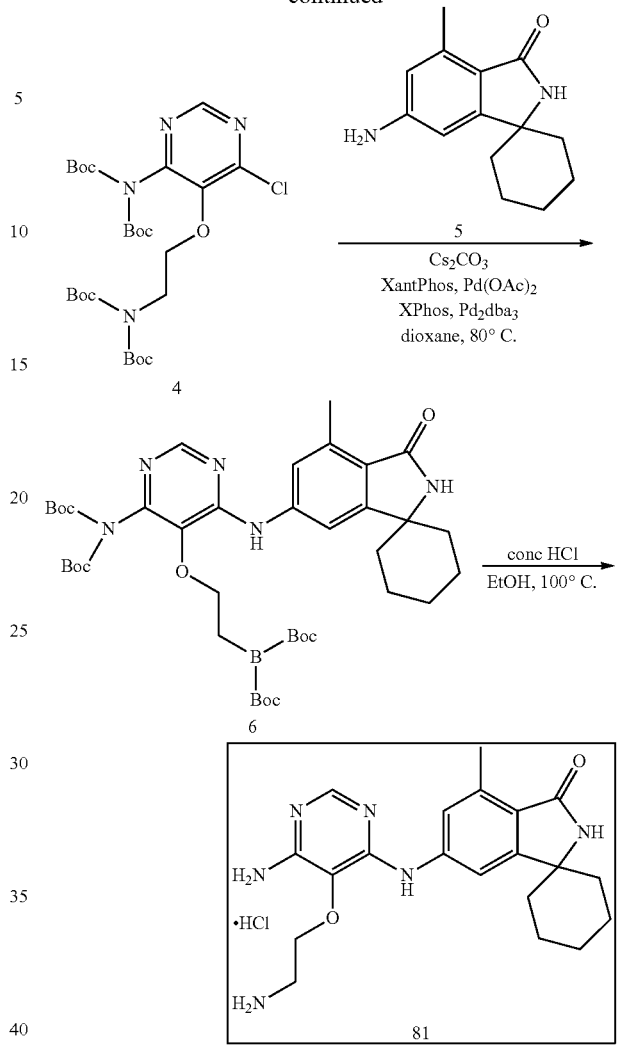

Synthesis of tert-butyl (2-((4-amino-6-chloropyrimidin-5-yl)oxy)ethyl)carbamate (3)

To a solution of 4-amino-6-chloropyrimidin-5-ol (1, 1.0 g, 6.87 mmol) and tert-butyl (2-bromoethyl)carbamate (2, 1.85 g, 8.24 mmol) in dimethylformamide (50 mL) was added cesium carbonate (4.48 g, 13.7 mmol). The mixture was stirred at room temperature for 16 h. After TLC showed completion, the solvent was evaporated and the crude was purified by column chromatography eluting with 30-35% ethyl acetate in hexane. The desired fractions were concentrated to dryness under vacuum to afford tert-butyl (2-((4-amino-6-chloropyrimidin-5-yl)oxy)ethyl)carbamate (3) as a colorless sticky solid. Yield: 210 mg, 11%; MS (ESI) m/z 289.09 [M+1]$^+$.

Synthesis of tert-butyl-N-tert butoxycarbonyl-N-(2-((4-((ditert-butoxycarbonyl)amino)-6-chloropyrimidin-5-yl)oxy)ethyl)carbamate (4)

A solution of tert-butyl (2-((4-amino-6-chloropyrimidin-5-yl)oxy)ethyl)carbamate (3, 0.21 g, 0.73 mmol), di-tert-butyl dicarbonate (0.40 g, 0.18 mmol) and 4-dimethylaminopyridine (0.044 g, 0.36 mmol) in tetrahydrofuran (10 mL) was stirred at room temperature for 24 h. After TLC showed completion, the reaction was extracted with ethyl acetate (2×20 mL). The organics were washed with water and brine. The organic layer was dried over anhydrous sodium sulfate, filtered and concentrated. The crude was purified by flash column chromatography eluting with 20-30% ethyl acetate in hexane. The desired fractions were concentrated to dryness under vacuum to afford tert-butyl-N-tert butoxycarbonyl-N-(2-((4-((di-tert-butoxycarbonyl)amino)-6-chloropyrimidin-5-yl)oxy)ethyl)carbamate (4) as a colorless oil. Yield: 0.49 g, 59%; MS (ESI) m/z 487.24 [M−1]⁻.

Synthesis of tert-butyl (2-((4-((ditert-butoxycarbonyl)amino)-6-((4'-methyl-3'-oxospiro[cyclohexane-1,1'-isoindolin]-6'-yl)amino)pyrimidin-5-yl)oxy)ethyl)(tert-butoxycarbonyl)carbamate (6)

The synthesis of intermediate 6 was carried out as described above using the general protocol of Procedure A. Off-white solid; Yield: 0.20 g, 28%; MS (ESI) m/z 783.48 [M+1]⁺.

Synthesis of 6'-((6-amino-5-(2-amino ethoxy)pyrimidin-4-yl)amino)-4'-methylspiro[cyclohexane-1,1'-isoindolin]-3'-one hydrochloride (Cpd. No. 81)

To a solution of tert-butyl-tert-butoxycarbonyl-(5-(2-((di-tert-butoxycarbonyl)amino)ethoxy)-6-((2'-(4-methoxybenzyl)-4'-methyl-3'-oxospiro[cyclohexane-1,1'-isoindolin]-6'-yl)amino)pyrimidin-4-yl)carbamate (6, 200 mg, 0.22 mmol) in ethanol (3 mL) was added concentrated hydrochloric acid (8 mL). The reaction was heated at 100° C. for 18 h. After completion, the reaction was washed with 10% methanol in dichloromethane. The aqueous layer was concentrated. The obtained solid was washed with methanol (1 mL) followed by diethyl ether and dried under vacuum to afford 6'-((6-amino-5-(2-aminoethoxy)pyrimidin-4-yl)amino)-4'-methylspiro[cyclohexane-1,1'-isoindolin]-3'-one hydrochloride (Cpd. No. 81) as a white crystalline solid. Yield: 41 mg, 48%; MS (ESI) m/z 383.19 [M+1]⁺; ¹H NMR (400 MHz, DMSO-d₆) δ 8.84 (s, 1H), 8.92 (s, 1H), 8.26 (brs, 3H), 8.14 (s, 1H), 7.61 (s, 1H), 7.52 (s, 1H), 7.40 (s, 1H), 3.99-3.97 (m, 2H), 3.30-3.29 (m, 2H), 2.56 (s, 3H), 1.78-1.75 (m, 2H), 1.68 (m, 5H), 1.39-1.36 (m, 2H), 1.31-1.29 (m, 1H).

Example 82

Synthesis of 6'-((6-amino-5-(difluoromethyl)pyrimidin-4-yl)amino)-4'-methylspiro[cyclohexane-1,1'-isoindolin]-3'-one (Cpd. No. 82)

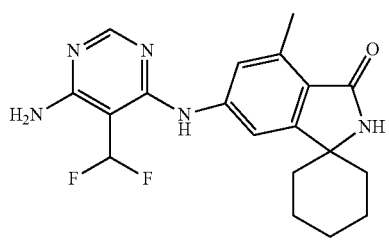

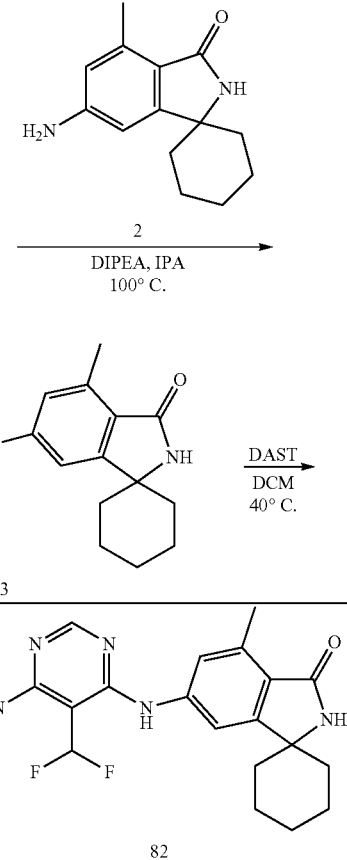

Synthesis of 4-amino-6-((4'-methyl-3'-oxospiro[cyclohexane-1,1'-isoindolin]-6'-yl)amino)pyrimidine-5-carbaldehyde (3)

To a solution of 4-amino-6-chloropyrimidine-5-carbaldehyde (1, 0.16 g, 1 mmol) and 6'-amino-4'-methylspiro[cyclohexane-1,1'-isoindolin]-3'-one (2, 0.23 g, 1 mmol) in 2-propanol at room temperature is added diisopropylethylamine (0.52 mL, 3 mmol). The reaction is stirred at 100° C. for 48 h. After completion of the reaction, the solvent is evaporated under reduced pressure. The crude is purified by prep HPLC to get 4-amino-6-((4'-methyl-3'-oxospiro[cyclohexane-1,1'-isoindolin]-6'-yl)amino)pyrimidine-5-carbaldehyde (3).

Synthesis of 6'-((6-amino-5-(difluoromethyl)pyrimidin-4-yl)amino)-4'-methylspiro[cyclohexane-1,1'-isoindolin]-3'-one (Cpd. No. 82)

To a solution of 4-amino-6-((4'-methyl-3'-oxospiro[cyclohexane-1,1'-isoindolin]-6'-yl)amino)pyrimidine-5-carbaldehyde (3, 0.35 g, 1 mmol) in dichloromethane (4 mL) at 0° C. is slowly added (diethylamino)sulfur trifluoride (1.32 mL, 10 mmol). The reaction is stirred at 40° C. for 16 h. After completion of the reaction, the reaction is quenched with saturated aqueous sodium bicarbonate solution and extract with 5% methanol in dichloromethane. The combined organic layer is dried over anhydrous sodium sulphate, filtered and concentrated. The crude is purified by flash column chromatography to afford 6'-((6-amino-5-(difluoromethyl)pyrimidin-4-yl)amino)-4'-methylspiro[cyclohexane-1,1'-isoindolin]-3'-one (Cpd. No. 82).

Example 83

Synthesis of 6'-((6-amino-5-(trifluoromethoxy)pyrimidin-4-yl)amino)-4'-methylspiro[cyclohexane-1,1'-isoindolin]-3'-one (Cpd. No. 83)

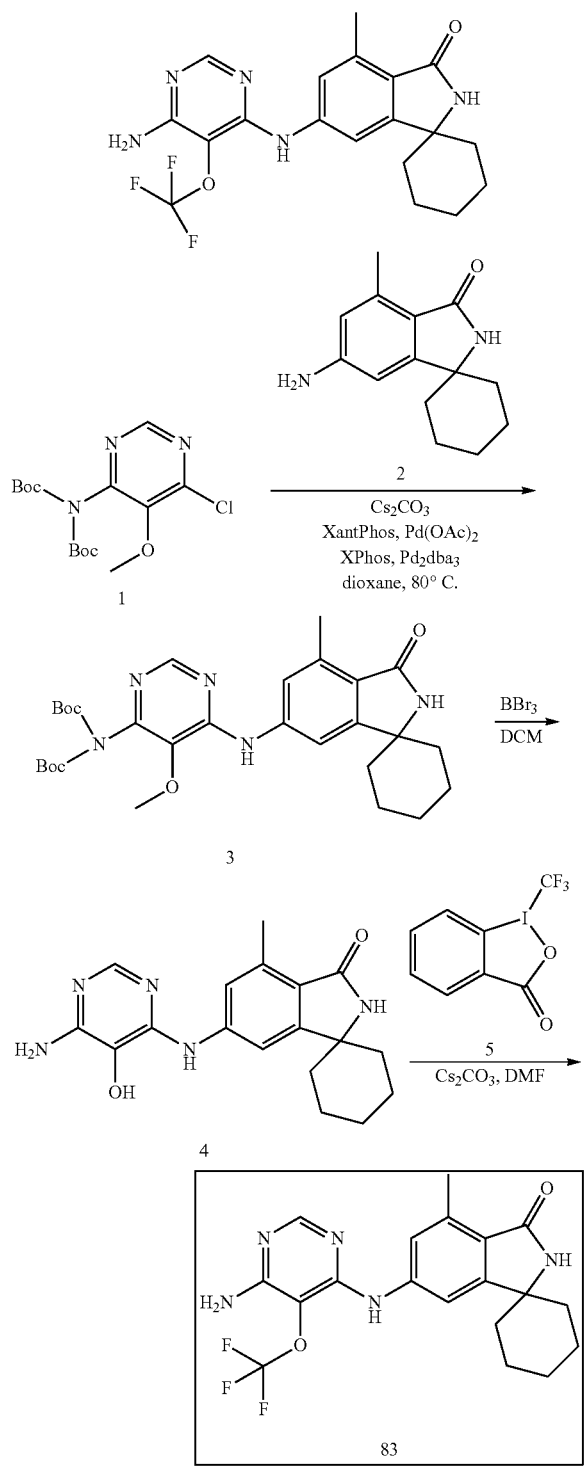

Synthesis of tert-butyl-tert-butoxycarbonyl-(5-methoxy-6-((4'-methyl-3'-oxospiro[cyclohexane-1,1'-isoindolin]-6'-yl)amino)pyrimidin-4-yl)carbamate (3)

The synthesis of intermediate 3 was carried out as described above using the general protocol of Procedure A. Off-white solid; Yield: 1.4 g, 58%; MS (ESI) m/z 554.57 [M+1]$^+$.

Synthesis of 6'-((6-amino-5-hydroxypyrimidin-4-yl)amino)-4'-methylspiro[cyclohexane-1,1'-isoindolin]-3'-one (4)

To a solution of tert-butyl-tert-butoxycarbonyl-(5-methoxy-6-((4'-methyl-3'-oxospiro[cyclohexane-1,1'-isoindolin]-6'-yl)amino)pyrimidin-4-yl)carbamate (3, 1.0 g, 1.81 mmol) in dichloromethane (30 mL) at 0° C. was added boron tribromide (1.36 g, 5.42 mmol). The reaction was stirred at room temperature for 16 h. After TLC showed completion, the reaction was cooled to −40° C. and quenched with methanol (2 mL). PH of the reaction was adjusted to 7 using ammonium hydroxide. The resulting mixture was extracted with 10% methanol in dichloromethane to afford 6'-((6-amino-5-hydroxypyrimidin-4-yl)amino)-4'-methylspiro[cyclohexane-1,1'-isoindolin]-3'-one (4) as a light brown solid. Yield: 0.20 g, 20%; MS (ESI) m/z 340.12 [M+1]$^+$.

Synthesis of 6'-((6-amino-5-(trifluoromethoxy)pyrimidin-4-yl)amino)-4'-methylspiro[cyclohexane-1,1'-isoindolin]-3'-one (Cpd. No. 83)

To a solution of 6'-((6-Amino-5-hydroxypyrimidin-4-yl)amino)-4'-methylspiro[cyclohexane-1,1'-isoindolin]-3'-one (4, 200 mg, 0.589 mmol) in dimethylformamide (10 mL) were added 1-(trifluoromethyl)-1l3-benzo[d][1,2]iodaoxol-3(1H)-one (223 mg, 0.71 mmol) and cesium carbonate (480 mg, 1.47 mmol). The reaction was stirred at room temperature for 16 h. After completion, the reaction mass was extracted with ethyl acetate (3×50 mL). Combined organic layer was washed with saturated aqueous ammonium chloride solution and brine solution, dried over sodium sulfate, filtered and concentrated. The crude was purified by silica gel column chromatography eluting with 50-70% ethyl acetate in hexane. Appropriate column fractions were concentrated under reduced pressure to afford a yellow solid which was further purified by prep HPLC to afford 6'-((6-amino-5-(trifluoromethoxy)pyrimidin-4-yl)amino)-4'-methylspiro[cyclohexane-1,1'-isoindolin]-3'-one (Cpd. No. 83) as a white solid. Yield: 7.5 mg, 3%; MS (ESI) m/z 408.21 [M+1]$^+$; $^1$H NMR (400 MHz, DMSO-$d_6$) δ 9.01 (s, 1H), 8.81 (s, 1H), 7.97 (s, 1H), 7.62 (s, 1H), 7.46 (s, 1H), 6.96 (s, 2H), 2.49 (s, 3H), 1.80-1.67 (m, 7H), 1.39-1.33 (s, 3H).

Example 84

Synthesis of 6'-((6-amino-5-(difluoromethoxy)pyrimidin-4-yl)amino)-4'-methylspiro[cyclohexane-1,1'-isoindolin]-3'-one (Cpd. No. 84)

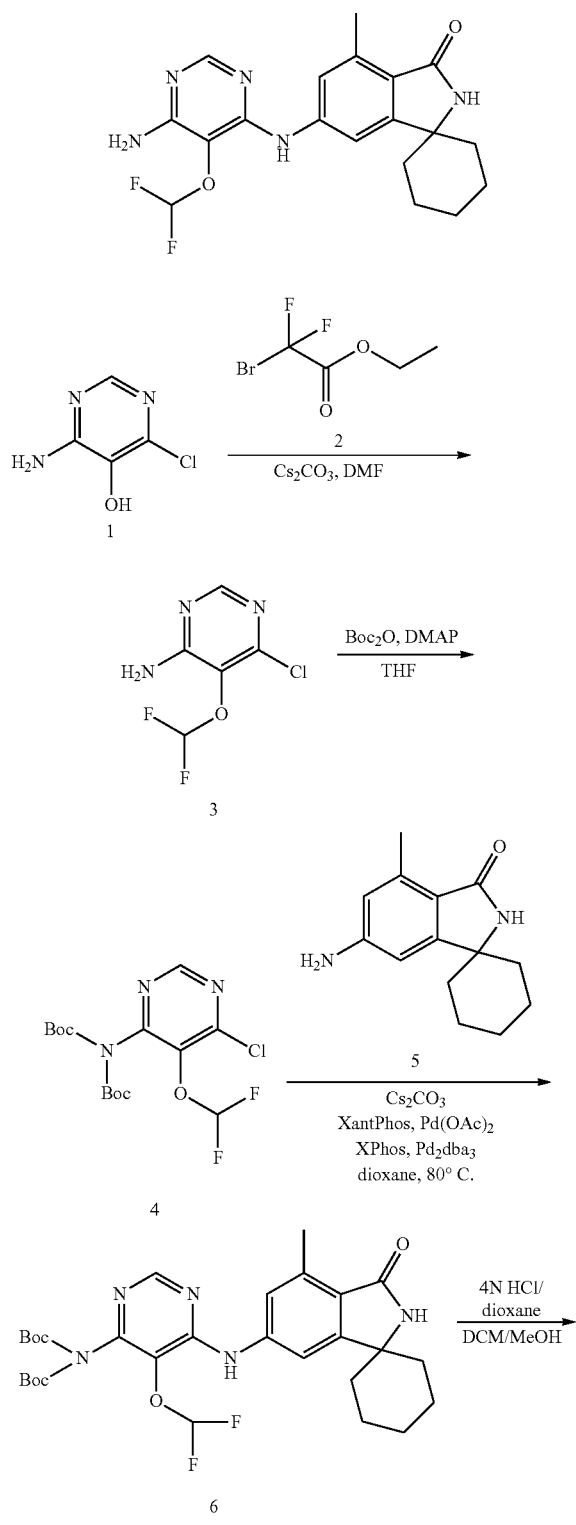

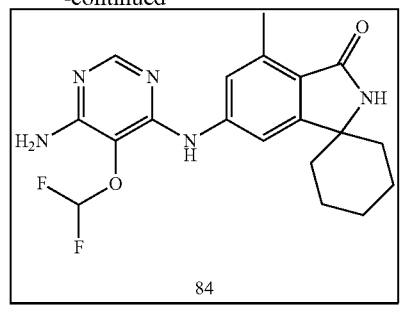

Synthesis of 6-chloro-5-(difluoromethoxy)pyrimidin-4-amine (3)

To a solution of 4-amino-6-chloropyrimidin-5-ol (1, 1.0 g, 6.87 mmol) and ethyl 2-bromo-2,2-difluoroacetate (2, 2.09 g, 10.3 mmol) in dimethylformamide (20 mL) was added cesium carbonate (4.48 g, 13.7 mmol). The reaction was stirred for 16 h at room temperature. After TLC showed completion, the reaction was quenched with ice water and extracted with ethyl acetate (2×20 mL). The combined organic layer was washed with saturated aqueous ammonium chloride solution, water and brine, dried over anhydrous sodium sulfate, filtered and concentrated to get 6-chloro-5-(difluoromethoxy)pyrimidin-4-amine (3) as a brown sticky mass. Yield: 1.2 g, crude.

Synthesis of tert-butyl-N-tertbutoxycarbonyl-N-(6-chloro-5-(difluoromethoxy)pyrimidin-4-yl)carbamate (4)

To a solution of 6-chloro-5-(difluoromethoxy)pyrimidin-4-amine (3, 1.2 g crude, 6.15 mmol) in tetrahydrofuran (25 mL) were added di-tert-butyl dicarbonate (3.35 g, 15.3 mmol) and 4-dimethylaminopyridine (0.075 g, 0.615 mmol). The reaction was stirred at room temperature for 16 h. After TLC showed completion, the mixture was extracted with ethyl acetate (2×50 mL). The organic layer was washed with water and brine, dried over anhydrous sodium sulfate, filtered and concentrated. The crude was then purified by flash column chromatography eluting with 30-40% ethyl acetate in hexane. The desired fractions were concentrated to dryness under vacuum to afford tert-butyl-N-tert-butoxycarbonyl-N-(6-chloro-5-(difluoromethoxy)pyrimidin-4-yl)carbamate (4) as a light yellow thick liquid. Yield: 0.52 g, 21%; $^1$H NMR (400 MHz, DMSO-$d_6$) δ 8.80 (s, 1H), 6.70-6.34 (t, J=72 Hz, 1H), 1.42 (s, 18H).

Synthesis of tert-butyl-N-tert-butoxycarbonyl-(5-(difluoromethoxy)-6-((4'-methyl-3'-oxospiro[cyclohexane-1,1'-isoindolin]-6'-yl)amino)pyrimidin-4-yl)carbamate (6)

The synthesis of intermediate 6 was carried out as described above using the general protocol of Procedure A. Off-white solid; Yield: 78 g, 26%. MS (ESI) m/z 590.43 [M+1]$^+$.

Synthesis of 6'-((6-amino-5-(difluoromethoxy)pyrimidin-4-yl)amino)-4'-methylspiro[cyclohexane-1,1'-isoindolin]-3'-one (Cpd. No. 84)

To a solution of tert-butyl-N-tert-butoxycarbonyl-(5-(difluoromethoxy)-6-((4'-methyl-3'-oxospiro[cyclohexane-1, 1'-isoindolin]-6'-yl)amino)pyrimidin-4-yl)carbamate (6, 75 mg, 0.13 mmol in methanol (3 mL) and dichloromethane (9 mL) was added 4 M hydrogen chloride in dioxane (3 mL). The reaction was stirred at room temperature for 18 h. After completion of reaction, solvent was distilled off. The obtained solid was washed with methanol (2 mL) followed by diethyl ether and pentane. The solid was dried under vacuum to afford 6'-((6-amino-5-(difluoromethoxy)pyrimidin-4-yl)amino)-4'-methylspiro[cyclohexane-1,1'-isoindolin]-3'-one (Cpd. No. 84) as a white solid. Yield: 32 mg, 65%; MS (ESI) m/z 390.17 [M+1]$^+$; $^1$H NMR (400 MHz, DMSO-d$_6$) δ 9.39 (s, 1H), 8.89 (s, 1H), 8.16 (s, 1H), 7.56 (s, 1H), 7.46 (s, 1H), 7.38 (s, 1H), 7.13-6.76 (t, J=72 Hz, 1H), 2.55 (s, 3H), 1.77-1.74 (m, 2H), 1.68-1.64 (m, 5H), 1.39-1.36 (m, 2H).

Example 85

Synthesis of 6'-((6-amino-5-(methylthio)pyrimidin-4-yl)amino)-4'-methylspiro[cyclohexane-1,1'-isoindolin]-3'-one trifluoroacetic acid salt (Cpd. No. 85)

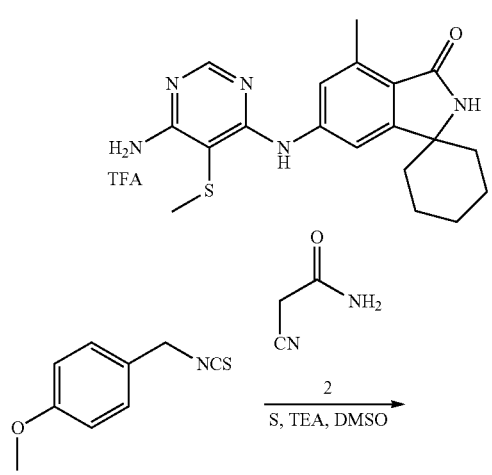

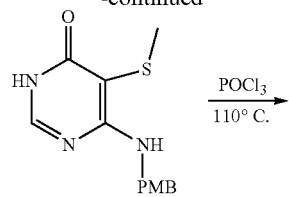

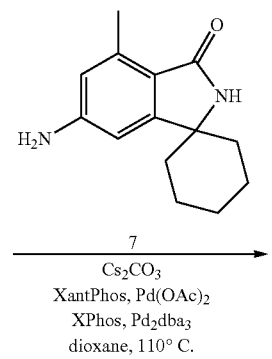

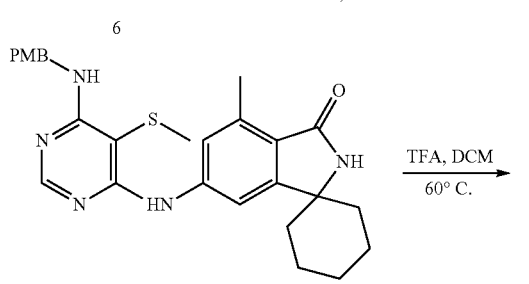

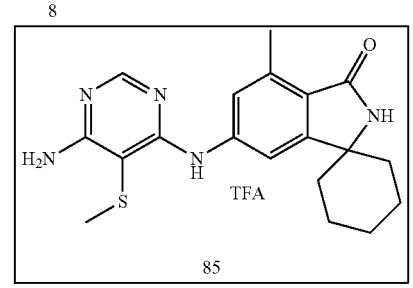

Synthesis of 4-amino-3-(4-methoxybenzyl)-2-thioxo-2,3-dihydrothiazole-5-carboxamide (3)

A solution of 1-(isothiocyanatomethyl)-4-methoxybenzene (1, 6.0 g, 33 mmol) in dimethylsulfoxide (30 mL) was charged with sulfur (1.07 g, 33 mmol), triethylamine (3.39 g, 33 mmol) and 2-cyanoacetamide (2, 3.81 g, 33 mmol). The reaction was stirred at room temperature for 16 h. After completion as monitored by TLC, the mixture was diluted with water (100 mL). The yellow solid precipitate was filtered, washed with methanol (20 mL) and diethyl ether (50 mL) and dried under reduced pressure to afford 4-amino-3-(4-methoxybenzyl)-2-thioxo-2,3-dihydrothiazole-5-carboxamide (3) as a yellow solid. Yield: 6.0 g, 60%; MS (ESI) m/z 296.29 [M+1]$^+$.

Synthesis of 3-(4-methoxybenzyl)-2-thioxo-2,3-dihydrothiazolo[4,5-d]pyrimidin-7(6H)-one (4)

To a mixture of triethyl orthoformate and acetic anhydride (1:1) (30 mL) was added 4-amino-3-(4-methoxybenzyl)-2- thioxo-2,3-dihydrothiazole-5-carboxamide (3, 5.0 g, 16.9 mmol) at room temperature. The reaction was stirred at 130° C. for 5 h. After completion, the mixture was cooled. The solid was filtered, washed with ethanol (30 mL) and diethyl ether (30 mL) and dried under reduced pressure to afford 3-(4-methoxybenzyl)-2-thioxo-2,3-dihydrothiazolo[4,5-d]pyrimidin-7(6H)-one (4) as an off-white solid. Yield: 4.5 g, 86%; MS (ESI) m/z 305.94 [M+1]$^+$.

Synthesis of 6-((4-methoxybenzyl)amino)-5-(methylthio)pyrimidin-4(3H)-one (5)

A mixture of 3-(4-methoxybenzyl)-2-thioxo-2,3-dihydrothiazolo[4,5-d]pyrimidin-7(6H)-one (4, 4.0 g, 13.1 mmol) in 4 M sodium hydroxide (25 mL) was stirred at 110° C. for 4 h. After completion the mixture was cooled to 0° C. and a solution of iodomethane (2.7 g, 19.1 mmol) in 1,4-dioxane (4 mL) was added slowly. The reaction mixture was stirred at room temperature for 16 h. After completion, the mixture was again cooled to 0° C. and pH was adjusted to 4 using concentrated HCl (3 mL). The resulting mixture was stirred for 10 min. The precipitated solid was filtered, washed with ice cold water (30 mL), diethyl ether (20 mL) and pentane (20 mL). It was finally dried under reduce pressure to afford 6-((4-methoxybenzyl)amino)-5-(methylthio)pyrimidin-4(3H)-one (5) as an off-white solid. Yield: 3.2 g, 88%; MS (ESI) m/z 278.01 [M+1]$^+$.

Synthesis of 6-chloro-N-(4-methoxybenzyl)-5-(methylthio) pyrimidin-4-amine (6)

To 6-((4-methoxybenzyl) amino)-5-(methylthio)pyrimidin-4(3H)-one (5, 1.0 g, 3.6 mmol) in a sealed tube at 0° C. was added phosphoryl chloride (10 mL). The reaction was heated at 110° C. for 2 h. After completion, phosphoryl chloride was removed under reduced pressure. The residue was diluted with ethyl acetate (10 mL) and washed with chilled water (10 mL). The aqueous layer was extracted with ethyl acetate (3×15 mL). The combined organic layers was washed with saturated aqueous sodium bicarbonate solution, dried over anhydrous sodium sulfate, filtered and concentrated. The residue was purified by column chromatography over silica gel (100 to 200 mesh) using 3% methanol/dichloromethane as eluent. The appropriate fractions were collected and concentrated under reduce pressure to afford 6-chloro-N-(4-methoxybenzyl)-5-(methylthio)pyrimidin-4-amine (6) as an off-white solid. Yield: 0.61 g, 57%; MS (ESI) m/z 296.20 [M+1]$^+$.

Synthesis of 6'-((6-((4-methoxybenzyl)amino)-5-(methylthio)pyrimidin-4-yl)amino)-4'-methylspiro[cyclohexane-1,1'-isoindolin]-3'-one (8)

The synthesis of intermediate 8 was carried out as described above using the general protocol of Procedure A. Off-white solid; Yield: 0.29 g, 29%; MS (ESI) m/z 490 [M+1]$^+$.

Synthesis of 6'-((6-amino-5-(methylthio)pyrimidin-4-yl)amino)-4'-methylspiro[cyclohexane-1,1'-isoindolin]-3'-one trifluoroacetic acid salt (Cpd. No. 85)

The synthesis of compound 85 was carried out as described above using the general protocol of Procedure E. Off-white solid; Yield: 0.17 g, 80%; MS (ESI) m/z 370.19 [M+1]$^+$; $^1$H NMR (400 MHz, DMSO-d$_6$) δ 9.19 (b, 1H), 8.91 (s, 1H), 8.18 (s, 1H), 7.61 (s, 1H), 7.49 (brs, 2H), 7.43 (s, 1H), 2.56 (s, 3H), 2.22 (s, 3H), 1.84-1.80 (m, 2H), 1.77-1.68 (s, 5H), 1.39-1.32 (s, 3H).

Example 86

Synthesis of 6'-((6-amino-5-(methylsulfonyl)pyrimidin-4-yl)amino)-4'-methylspiro[cyclohexane-1,1'-isoindolin]-3'-one (Cpd. No. 86)

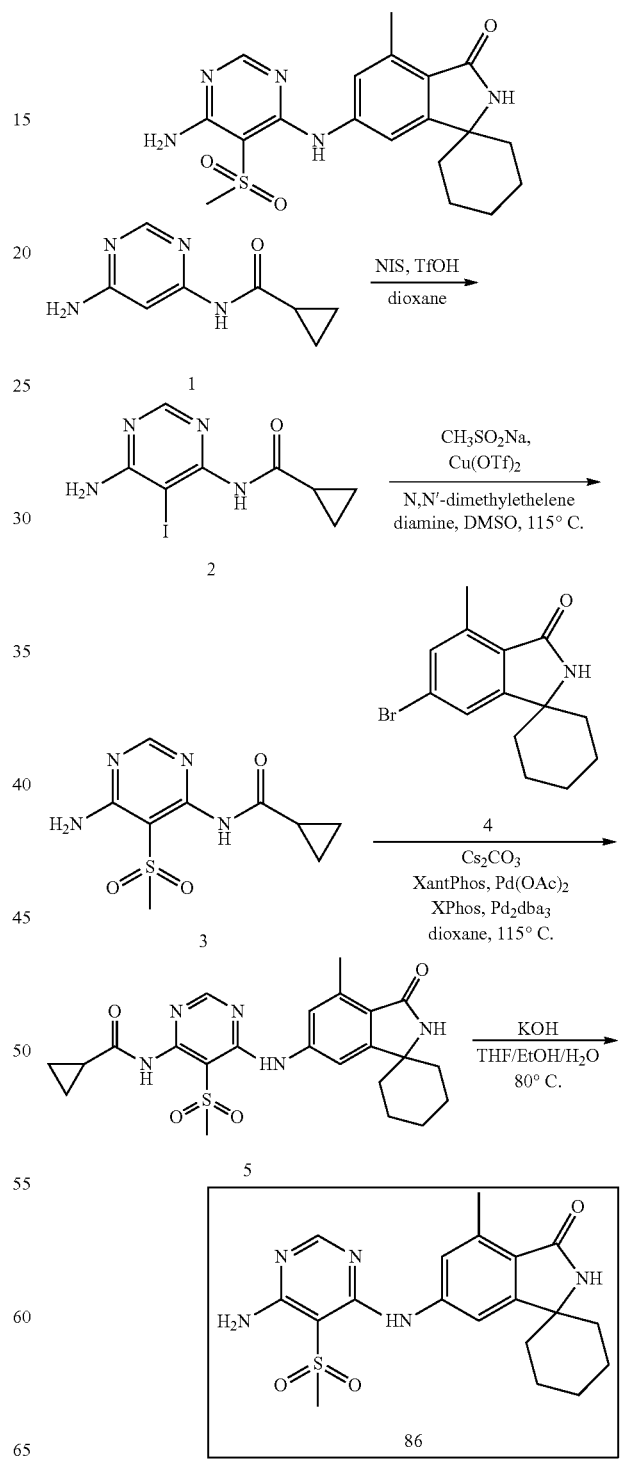

Synthesis of N-(6-amino-5-iodopyrimidin-4-yl)cyclopropanecarboxamide (2)

To a solution of N-(6-aminopyrimidin-4-yl)cyclopropanecarboxamide (1, 5.0 g, 28 mmol) in dioxane (40 mL) at 0° C. was added N-iodosuccinimide (7.58 g, 33 mmol) portion wise followed by triflic acid (4.2 g, 28 mmol). The reaction mixture was stirred at room temperature for 26 h. After completion of the reaction as monitored by TLC, the solvent was removed under reduce pressure. The residue was diluted with water (100 mL) and extracted with ethyl acetate (3×250 mL). The combined organic layers was dried over anhydrous sodium sulphate, filtered and concentrated. The crude was then purified by silica gel column chromatography using 2% methanol/dichloromethane as an eluent. Appropriate fractions were collected and concentrated under reduce pressure to give N-(6-amino-5-iodopyrimidin-4-yl)cyclopropanecarboxamide (2) as an off-white solid. Yield: 3.7 g, 43%; MS (ESI) m/z 304.91 $[M+1]^+$.

Synthesis of N-(6-amino-5-(methylsulfonyl)pyrimidin-4-yl)cyclopropanecarboxamide (3)

A mixture of N-(6-amino-5-iodopyrimidin-4-yl)cyclopropanecarboxamide (2, 2.0 g, 6.5 mmol), sodium methanesulfinate (1.6 g, 16 mmol), N,N'-dimethylehelene diamine and copper(II) triflate (0.23 g, 0.65 mmol) in dimethylsulfoxide was stirred at 115° C. for 16 h. After completion, the reaction mixture was diluted with ethyl acetate (50 mL) and filtered through a celite bed. Combined organic layer was washed with water (100 mL), brine (100 mL), dried over anhydrous sodium sulphate, filtered and concentrate. The residue was purified by silica gel column chromatography using 10% methanol/dichloromethane as eluent to afford N-(6-amino-5-(methylsulfonyl)pyrimidin-4-yl)cyclopropanecarboxamide (3) as an off-white solid. Yield: 0.77 g, crude.

Synthesis of N-(6-((4'-methyl-3'-oxospiro[cyclohexane-1,1'-isoindolin]-6'-yl)amino)-5-(methylsulfonyl)pyrimidin-4-yl)cyclopropanecarboxamide (5)

The synthesis of intermediate 5 was carried out as described above using the general protocol of Procedure A. Off-white solid; Yield: 1.18 g.

Synthesis of 6'-((6-amino-5-(methylsulfonyl)pyrimidin-4-yl)amino)-4'-methylspiro[cyclohexane-1,1'-isoindolin]-3'-one (Cpd. No. 86)

The synthesis of compound 86 was carried out as described above using the general protocol of Procedure D. Off-white solid; Yield: 0.11 g, 11%; MS (ESI) m/z 402.2 $[M+1]^+$; $^1$H NMR (400 MHz, DMSO-$d_6$) δ 9.49 (s, 1H), 8.92 (s, 1H), 8.17 (s, 1H), 7.61 (s, 1H), 7.46 (brs, 1H), 3.46 (s, 3H), 2.55 (s, 3H), 1.87-1.83 (m, 2H), 1.65-1.58 (m, 5H), 1.34-1.19 (s, 3H).

Example 87

Synthesis of 6'-((6-amino-5-(3-aminopropoxy)pyrimidin-4-yl)amino)-4'-methylspiro[cyclohexane-1,1'-isoindolin]-3'-one hydrochloride salt (Cpd. No. 87)

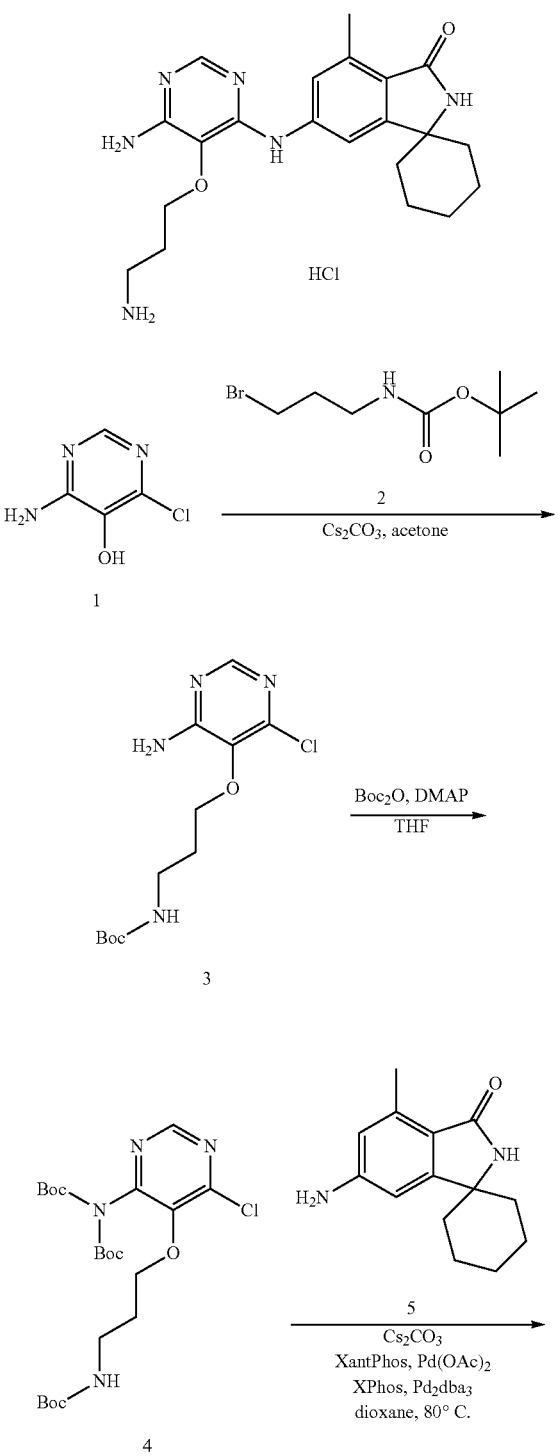

-continued

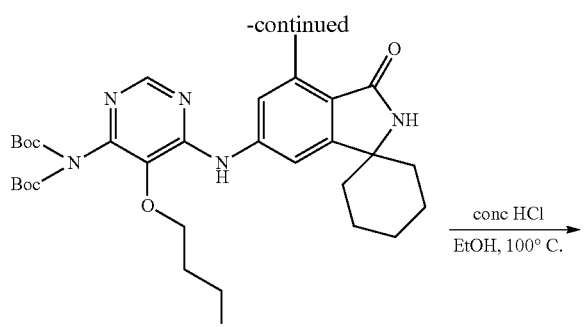

6

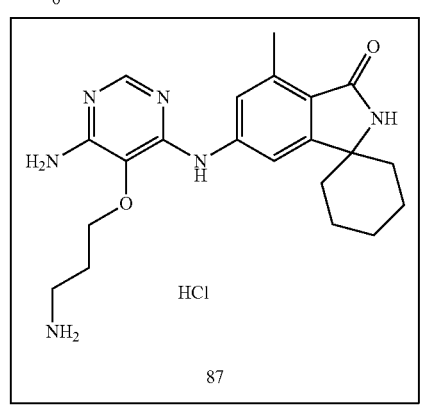

87

Synthesis of tert-butyl (3-((4-amino-6-chloropyrimidin-5-yl)oxy)propyl)carbamate (3)

To a solution of 4-amino-6-chloropyrimidin-5-ol (1, 500 mg, 3.44 mmol) and tert-butyl (3-bromopropyl)carbamate (2, 1.23 g, 5.17 mmol) in acetone (50 mL) was added cesium carbonate (2.25 g, 6.89 mmol). The reaction was stirred at room temperature for 16 h. After TLC showed completion, the solvent was evaporated. The crude was purified by column chromatography eluting with 30-35% ethyl acetate in hexane. The desired fractions were concentrated to dryness under vacuum to afford tert-butyl (3-((4-amino-6-chloropyrimidin-5-yl)oxy)propyl)carbamate (3) as an off-white solid. Yield: 300 mg, 29%; MS (ESI) m/z 303.35 [M+1]$^+$.

Synthesis of tert-butyl (tert-butoxycarbonyl)(5-(3-((tert-butoxycarbonyl)amino)propoxy)-6-chloropyrimidin-4-yl)carbamate (4)

A mixture of tert-butyl (3-((4-amino-6-chloropyrimidin-5-yl)oxy)propyl)carbamate (3, 0.30 g crude, 0.99 mmol), di-tert-butyl dicarbonate (0.64 mL, 2.98 mmol) and 4-dimethylaminopyridine (0.025 g, 0.20 mmol) in tetrahydrofuran (15 mL) was stirred at room temperature for 16 h. After TLC showed completion, the reaction was extracted with ethyl acetate (2×20 mL). The combined organic layer was washed with water and brine. The organic layer was dried over anhydrous sodium sulfate, filtered and concentrated to afford tert-butyl (tert-butoxycarbonyl)(5-(3-((tert-butoxycarbonyl)amino)propoxy)-6-chloropyrimidin-4-yl)carbamate (4) as a colorless oil. Yield: 0.48 g, 96%; MS (ESI) m/z 503.22 [M+1]$^+$.

Synthesis of tert-butyl (tert-butoxycarbonyl)(5-(3-((tert-butoxycarbonyl)amino)propoxy)-6-((4'-methyl-3'-oxospiro[cyclohexane-1,1'-isoindolin]-6'-yl)amino)pyrimidin-4-yl)carbamate (6)

The synthesis of intermediate 6 was carried out as described above using the general protocol of Procedure A. Off-white solid; Yield: 0.44 g, 60%; MS (ESI) m/z 817.73 [M+1]$^+$.

Synthesis of 6'-((6-amino-5-(3-aminopropoxy)pyrimidin-4-yl)amino)-4'-methylspiro[cyclohexane-1,1'-isoindolin]-3'-one hydrochloride salt (Cpd. No. 87)

To a solution of tert-butyl (tert-butoxycarbonyl)(5-(3-((tert-butoxycarbonyl)amino)propoxy)-6-((2'-(4-methoxybenzyl)-4'-methyl-3'-oxospiro[cyclohexane-1,1'-isoindolin]-6'-yl)amino)pyrimidin-4-yl)carbamate (6, 400 mg, 0.49 mmol) in ethanol (5 mL) was added concentrated hydrochloric acid (8 mL). The reaction was stirred at 100° C. for 36 h. After completion, the reaction mass was washed with 10% methanol in dichloromethane. The aqueous layer was concentrated and purified by prep HPLC purification to afford 6'-((6-amino-5-(2-aminoethoxy)pyrimidin-4-yl)amino)-4'-methylspiro[cyclohexane-1,1'-isoindolin]-3'-one hydrochloride (Cpd. No. 87) as a white solid. Yield: 50 mg, 23%; MS (ESI) m/z 397.23 [M+1]$^+$; $^1$H NMR (400 MHz, DMSO-d6) δ 8.84 (s, 1H), 8.68 (s, 1H), 8.01 (s, 1H), 7.68 (brs, 2H), 7.63 (s, 1H), 7.40 (s, 1H), 6.87 (brs, 2H), 3.87-3.84 (t, J=6.4 Hz, 2H), 3.00-2.96 (q, J=6.4 Hz, 2H), 2.54 (s, 3H), 2.09.2.02 (m, 2H), 1.82-1.68 (m, 7H), 1.39-1.32 (m, 3H).

Example 88

Synthesis of 6'-((6-amino-5-methylpyrimidin-4-yl)amino)-4'-(difluoromethyl)spiro[cyclohexane-1,1'-isoindolin]-3'-one (Cpd. No. 88)

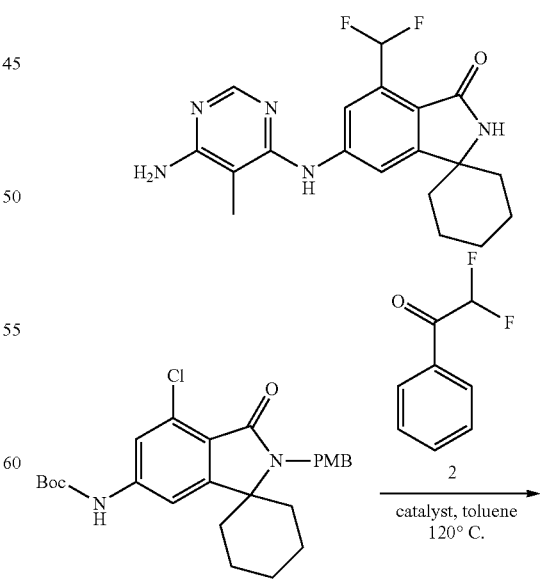

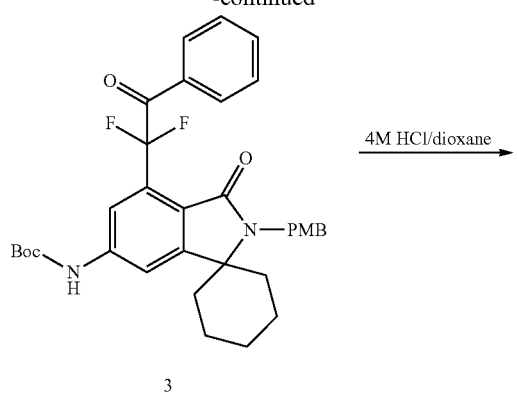

3

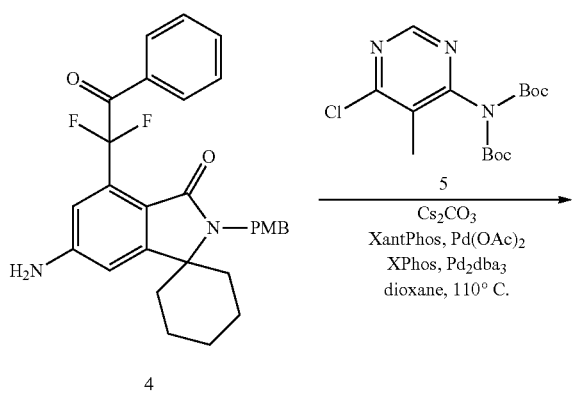

4

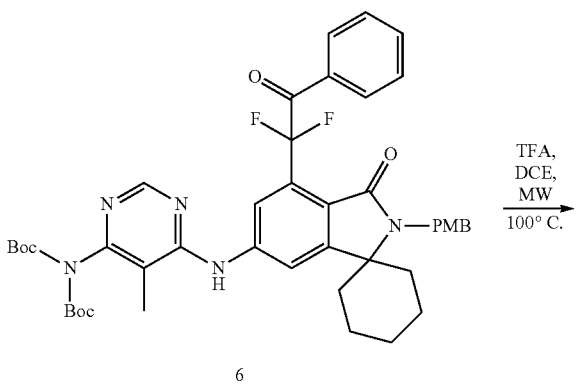

6

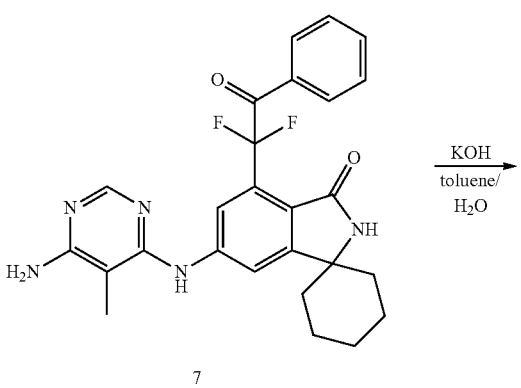

7

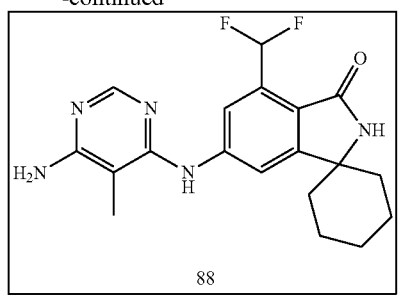

Synthesis of tert-butyl (4'-(1,1-difluoro-2-oxo-2-phenylethyl)-2'-(4-methoxybenzyl)-3'-oxospiro[cyclohexane-1,1'-isoindolin]-6'-yl)carbamate (3)

A mixture of catalyst (0.096 g, 0.17 mmol), tert-butyl (4'-chloro-2'-(4-methoxybenzyl)-3'-oxospiro[cyclohexane-1,1'-isoindolin]-6'-yl)carbamate (1, 0.8 g, 1.7 mmol), cesium carbonate (1.1 g, 3.4 mmol) and 2,2-difluoro-1-phenylethan-1-one (2, 0.53 g, 3.4 mmol) in toluene (12 mL) was purged with argon for 5 min. The reaction was heated at 120° C. for 72 h. After completion, the reaction was diluted with 5% methanol in dichloromethane (150 mL) and passed through an alumina bed. The filtrate was concentrated and purified by flash chromatography eluting at 20% ethyl acetate in hexane. The solvent was removed under reduced pressure to afford tert-butyl (4'-(1,1-difluoro-2-oxo-2-phenylethyl)-2'-(4-methoxybenzyl)-3'-oxospiro[cyclohexane-1,1'-isoindolin]-6'-yl)carbamate (3) as a brown solid; Yield: 0.15 g, crude; MS (ESI) m/z 591.76 [M+1]$^+$.

Synthesis of 6'-amino-4'-(1,1-difluoro-2-oxo-2-phenylethyl)-2'-(4-methoxybenzyl) spiro [cyclohexane-1,1'-isoindolin]-3'-one (4)

The synthesis of intermediate 4 was carried out as described above using the general protocol of Procedure C. Yellow solid; Yield: 0.12 g, 96%; MS (ESI) m/z 491 [M+1]$^+$.

Synthesis of 6'-((6-(ditert-butoxycarbonyl)amino-5-methylpyrimidin-4-yl)amino)-4'-(1,1-difluoro-2-oxo-2-phenylethyl)-2'-(4-methoxybenzyl)spiro[cyclohexane-1,1'-isoindolin]-3'-one (6)

The synthesis of intermediate 6 was carried out as described above using the general protocol of Procedure A. Yellow solid; Yield: 0.05 g, crude; MS (ESI) m/z 798 [M+1]$^+$.

Synthesis of 6'-((6-amino-5-methylpyrimidin-4-yl)amino)-4'-(1,1-difluoro-2-oxo-2-phenylethyl)spiro[cyclohexane-1,1'-isoindolin]-3'-one (7)

The synthesis of intermediate 7 was carried out as described above using the general protocol of Procedure G. Yellow solid; Yield: 40 mg, crude.

Synthesis of 6'-((6-amino-5-methylpyrimidin-4-yl) amino)-4'-(difluoromethyl)spiro [cyclohexane-1,1'-isoindolin]-3'-one (Cpd. No. 88)

The synthesis of compound 88 was carried out as described above using the general protocol of Procedure D. Brown solid; Yield: 1.8 mg, 6%; MS (ESI) m/z 374 [M+1]$^+$; $^1$H NMR (400 MHz, DMSO-d$_6$) δ 9.17 (s, 1H), 8.49 (s, 1H), 8.02 (s, 1H), 7.97 (s, 2H), 7.73 (t, J=55.6 Hz, 1H), 6.35 (s, 2H), 1.99 (s, 3H), 1.83-1.79 (m, 2H), 1.77-1.67 (m, 5H), 1.44-1.41 (m, 2H), 1.30-1.40 (m, 1H).

Example 89

Synthesis of 6'-((6-amino-5-methylpyrimidin-4-yl) amino)-4'-fluorospiro[cyclohexane-1,1'-isoindolin]-3'-one (Cpd. No. 89)

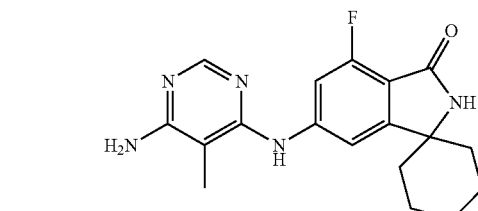

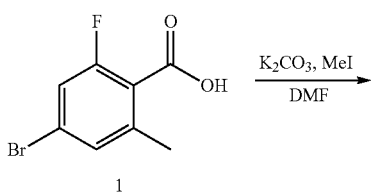

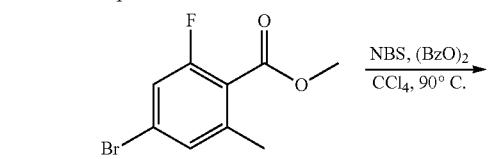

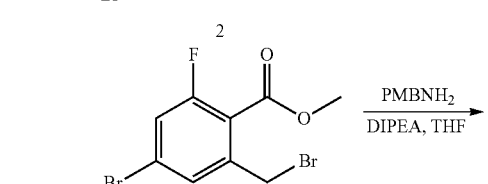

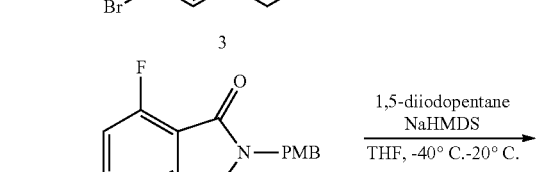

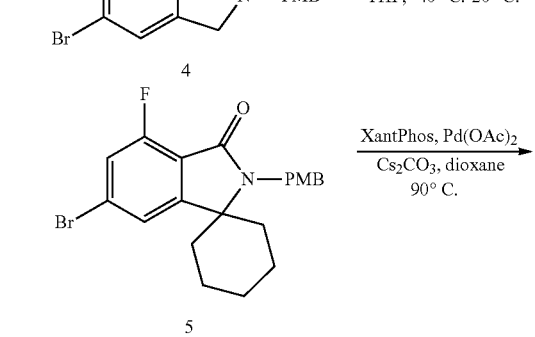

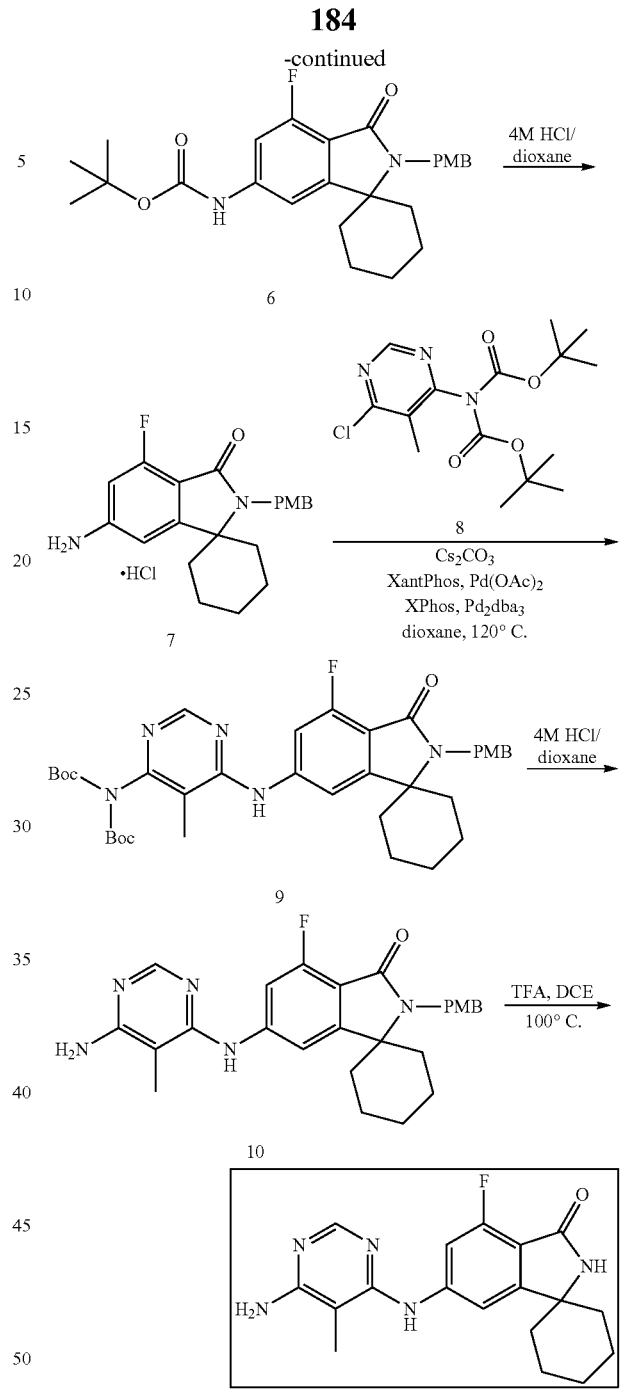

Synthesis of methyl 4-bromo-2-fluoro-6-methylbenzoate (2)

To a solution of 4-bromo-2-fluoro-6-methylbenzoic acid (1, 10.0 g, 43.2 mmol) in dimethylformamide (100 mL) was added potassium carbonate (11.9 g, 86.5 mmol) and iodomethane (12.0 g, 86.5 mmol). The reaction was stirred at room temperature for 16 h. The reaction was quenched with ice water and extracted with ethyl acetate (3×200 mL). The combined organic layer was washed with saturated aqueous ammonium chloride solution followed by brine, dried over sodium sulfate, filtered and concentrated. The crude was purified by silica gel column chromatography eluting with 10-20% ethyl acetate in hexane. Appropriate column fractions were concentrated under reduced pressure to afford methyl 4-bromo-2-fluoro-6-methylbenzoate (2) as a thick brown liquid. Yield: 7.5 g, 70%; $^1$H NMR (400 MHz, DMSO-d$_6$) δ 7.55-7.52 (d, J=9.6 Hz, 1H), 7.45 (s, 1H), 3.86 (s, 3H), 2.32 (s, 3H).

Synthesis of methyl 4-bromo-2-(bromomethyl)-6-fluorobenzoate (3)

To a solution of methyl 4-bromo-2-fluoro-6-methylbenzoate (2, 8.0 g, 32.3 mmol) in carbon tetrachloride (100 mL) was added N-bromosuccinimide (7.49 g, 42.1 mmol) and benzoyl peroxide (784 mg, 3.23 mmol). The reaction was heated at 90° C. for 16 h. After completion, the reaction was cooled to room temperature, diluted with dichloromethane, washed with water and brine, dried over sodium sulfate, filtered and concentrated to afford 4-bromo-2-(bromomethyl)-6-fluorobenzoate (3) as a light brown liquid. Yield: 12 g, crude.

Synthesis of 5-bromo-7-fluoro-2-(4-methoxybenzyl) isoindolin-1-one (4)

To a solution of 4-bromo-2-(bromomethyl)-6-fluorobenzoate (3, 12.0 g, 36.8 mmol) in tetrahydrofuran (150 mL) were added 4-methoxybenzylamine (7.5 g, 55.2 mmol) and diisopropylethylamine (19 mL, 110 mmol). The mixture was stirred at room temperature for 16 h. After completion, the reaction was quenched with ice water and extracted with ethyl acetate (3×150 mL). The combined organic layer was washed with water followed by brine, dried over sodium sulfate, filtered and concentrated. The crude was purified by silica gel column chromatography eluting with 20-30% ethyl acetate in hexane. Appropriate column fractions were concentrated under reduced pressure to afford 5-bromo-7-fluoro-2-(4-methoxybenzyl)isoindolin-1-one (4) as an off-white solid. Yield: 5.5 g, 43%; MS (ESI): m/z 347.93 [M−1]$^−$.

Synthesis of 6'-bromo-4'-fluoro-2'-(4-methoxybenzyl)spiro[cyclohexane-1,1'-isoindolin]-3'-one (5)

To a solution of 5-bromo-7-fluoro-2-(4-methoxybenzyl) isoindolin-1-one (4, 4.3 g, 12.2 mmol) in tetrahydrofuran (100 mL) at −40° C. was added sodium bis(trimethylsilyl) amide (1 M solution in tetrahydrofuran) (36.8 mL, 36.8 mmol). The suspension was stirred at the same temperature for 30 minutes and then a solution of 1,5-diiodopentane (4.83 g, 14.7 mmol) in tetrahydrofuran (10 mL) over a period of 20 min. The reaction was stirred for another 1 h at −40 to −20° C. After completion, the reaction was quenched with saturated aqueous ammonium chloride solution and extracted with ethyl acetate (3×75 mL). The combined organic layer was washed with water followed by brine, dried over sodium sulfate, filtered and concentrated. The crude was purified by silica gel column chromatography eluting with 15-25% ethyl acetate in hexane. Appropriate column fractions were concentrated under reduced pressure to afford 6'-bromo-4'-fluoro-2'-(4-methoxybenzyl)spiro[cyclohexane-1,1'-isoindolin]-3'-one (5) as an off-white solid. Yield: 0.85 g, 16%; MS (ESI) m/z 418.10 [M+1]$^+$.

Synthesis of tert-butyl (4'-fluoro-2'-(4-methoxybenzyl)-3'-oxospiro[cyclohexane-1,1'-isoindolin]-6'-yl) carbamate (6)

The synthesis of intermediate 6 was carried out as described above using the general protocol of Procedure A. Light brown solid; Yield: 800 mg, crude; MS (ESI) m/z 455.13 [M+1]$^+$.

Synthesis of 6'-amino-4'-fluoro-2'-(4-methoxybenzyl)spiro[cyclohexane-1,1'-isoindolin]-3'-one hydrochloride (7)

The synthesis of intermediate 7 was carried out as described above using the general protocol of Procedure C. Yellow solid; Yield: 350 mg, 41%; MS (ESI) m/z 355.40 [M−1]$^+$.

Synthesis of tert-butyl-N-tertbutoxy carbonyl-(6-((4'-fluoro-2'-(4-methoxybenzyl)-3'-oxospiro[cyclohexane-1,1'-isoindolin]-6'-yl)amino)-5-methylpyrimidin-4-yl)carbamate (9)

The synthesis of intermediate 9 was carried out as described above using the general protocol of Procedure A. Brown solid; Yield: 200 mg, crude; MS (ESI) m/z 362.36 [M+1]$^+$.

Synthesis of 6'-((6-amino-5-methylpyrimidin-4-yl) amino)-4'-fluoro-2'-(4-methoxybenzyl)spiro[cyclohexane-1,1'-isoindolin]-3'-one hydrochloride (10)

The synthesis of intermediate 10 was carried out as described above using the general protocol of Procedure C. Yellow solid; Yield: 275 mg, crude; MS (ESI) m/z 462.24 [M+1]$^+$.

Synthesis of 6'-((6-amino-5-methylpyrimidin-4-yl) amino)-4'-fluorospiro[cyclohexane-1,1'-isoindolin]-3'-one (Cpd. No. 89)

The synthesis of compound 89 was carried out as described above using the general protocol of Procedure G. White solid; Yield: 30 mg, 11%; MS (ESI) m/z 342.22 [M+1]$^+$; $^1$H NMR (400 MHz, DMSO-d$_6$) δ 8.86 (s, 1H), 8.52 (s, 1H), 8.05 (s, 1H), 7.62 (d, J=12.8 Hz, 1H), 7.51 (s, 1H), 6.49 (brs, 2H), 1.99 (s, 3H), 1.82-1.69 (m, 7H), 1.45-1.41 (m, 2H), 1.35-1.33 (m, 1H).

Example 90

Synthesis of 6'-((6-amino-5-methylpyrimidin-4-yl) amino)-4'-ethylspiro [cyclohexane-1,1'-isoindolin]-3'-one (Cpd. No. 90)

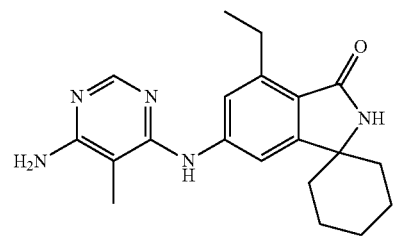

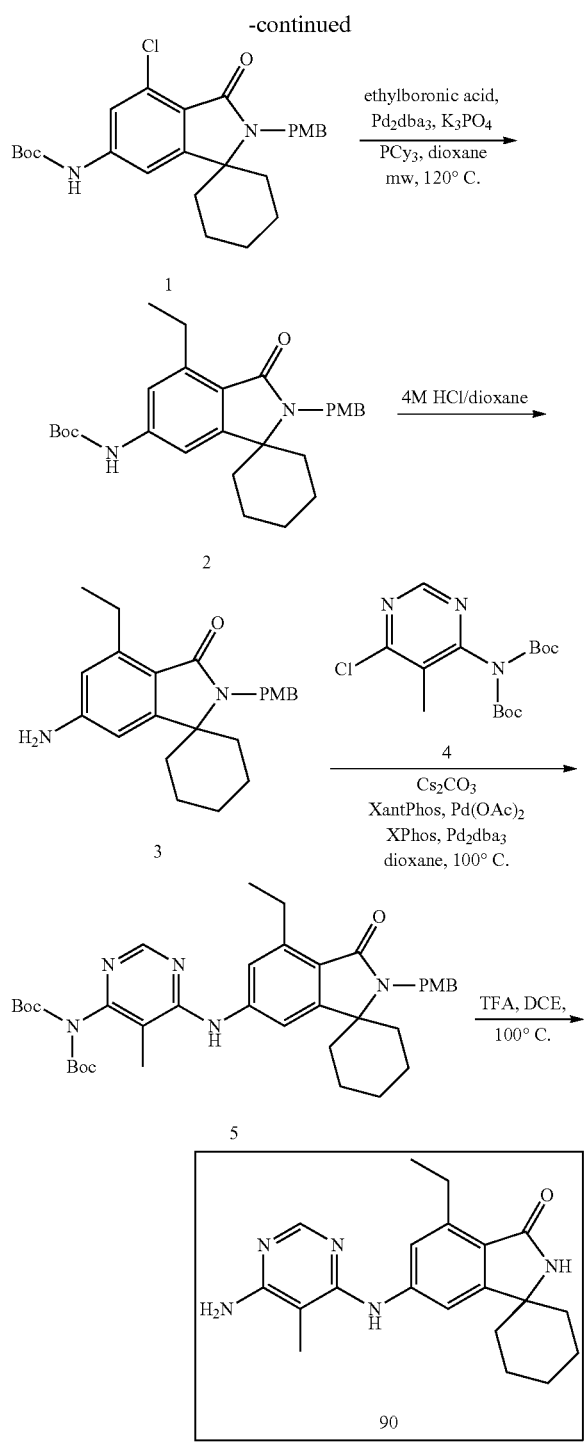

Synthesis of tert-butyl (4'-ethyl-2'-(4-methoxybenzyl)-3'-oxospiro[cyclohexane-1,1'-isoindolin]-6'-yl)carbamate (2)

A mixture of ethylboronic acid (0.24 g, 3.19 mmol), tert-butyl (4'-chloro-2'-(4-methoxybenzyl)-3'-oxospiro[cyclohexane-1,1'-isoindolin]-6'-yl)carbamate (1, 0.30 g, 0.63 mmol) and potassium phosphate (0.40 g, 1.89 mmol) in 1,4-dioxane (10 mL) was purged with argon for 5 min. Tricyclohexylphosphine (18 mg, 0.063 mmol), Tris(dibenzylideneacetone)dipalladium(0) (58 mg, 0.063 mmol) were added and purging was continued for another 5 min. The reaction was sealed and stirred under microwave irradiation at 120° C. for 2 h. After completion, the reaction was diluted with 5% methanol in dichloromethane (150 mL) and passed through alumina bed. The filtrate was concentrated and triturated with dichloromethane and methanol to afford tert-butyl (4'-ethyl-2'-(4-methoxybenzyl)-3'-oxospiro[cyclohexane-1,1'-isoindolin]-6'-yl)carbamate (2) as a brown solid. Yield: 0.30 g, crude; MS (ESI) m/z 465.2 [M+1]$^+$.

Synthesis of 6'-amino-4'-ethyl-2'-(4-methoxybenzyl)spiro[cyclohexane-1,1'-isoindolin]-3'-one (3)

The synthesis of intermediate 3 was carried out as described above using the general protocol of Procedure C. Yellow liquid; Yield: 0.10 g, 42%; MS (ESI) m/z 365.14 [M+1]$^+$.

Synthesis of 6'-((6-(ditert-butoxycarbonyl)amino-5-methylpyrimidin-4-yl)amino)-2'-(4-methoxybenzyl)-4'-methylspiro[cyclohexane-1,1'-isoindolin]-3'-one (5)

The synthesis of intermediate 5 was carried out as described above using the general protocol of Procedure A. Brown solid; Yield: 0.13 g, crude; MS (ESI) m/z 672.4 [M+1]$^+$.

Synthesis of 6'-((6-amino-5-methylpyrimidin-4-yl)amino)-4'-ethylspiro[cyclohexane-1,1'-isoindolin]-3'-one (Cpd. No. 90)

The synthesis of compound 90 was carried out as described above using the general protocol of Procedure G. Yellow solid; Yield: 10 mg, 33%; MS (ESI) m/z 352.15 [M+1]$^+$; $^1$H NMR (400 MHz, DMSO-d$_6$) δ 8.71 (s, 1H), 8.16 (s, 1H), 7.98 (s, 1H), 7.59 (s, 1H), 7.40 (s, 1H), 6.25 (s, 2H), 2.97 (t, J=7.6 Hz, 2H), 1.96 (s, 3H), 1.74-1.68 (m, 3H) 1.38-1.23 (m, 7H), 1.17 (t, J=7.5 Hz, 3H).

Example 91

Synthesis of 6'-((6-amino-5-methylpyrimidin-4-yl)amino)-3'-oxospiro[cyclohexane-1,1'-isoindoline]-4'-carbonitrile (Cpd. No. 91)

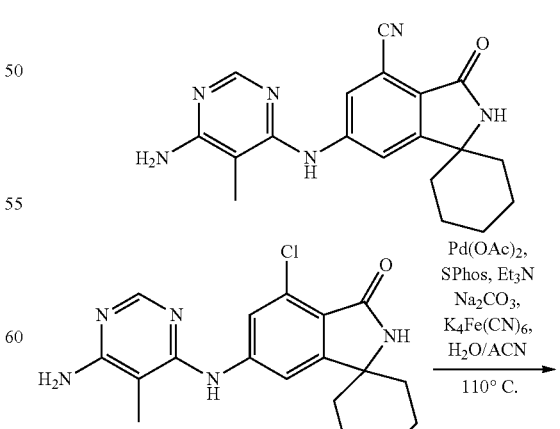

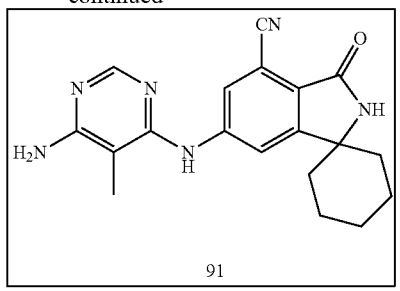

91

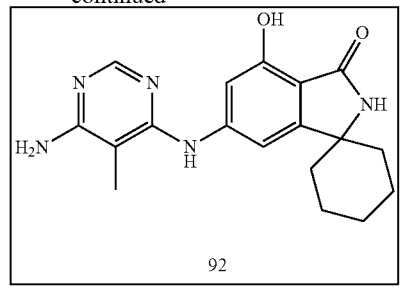

92

Synthesis of 6'-((6-amino-5-methylpyrimidin-4-yl)amino)-3'-oxospiro[cyclohexane-1,1'-isoindoline]-4'-carbonitrile (Cpd. No. 91)

A vial was charged with 6'-((6-amino-5-methylpyrimidin-4-yl)amino)-4'-chlorospiro[cyclohexane-1,1'-isoindolin]-3'-one (1, 0.08 g, 0.22 mmol), palladium acetate (100 mg, 0.44 mmol), SPhos (0.21 g. 0.44 mmol), triethylamine (0.5 ml), sodium carbonate (0.023 g, 0.22 mmol) and Potassium ferrocyanide (0.46 g, 1.1 mmol) in acetonitrile and water. The vial was sealed and the reaction was stirred at 110° C. for 16 h. After completion, the reaction was diluted with 5% methanol in dichloromethane (50 mL) and washed with water. The organic phase was concentrated and purified by prep HPLC to afford 6'-((6-amino-5-methylpyrimidin-4-yl)amino)-3'-oxospiro[cyclohexane-1,1'-isoindoline]-4'-carbonitrile (Cpd. No. 91) as a white solid. Yield: 0.010 g, 13%; MS (ESI) m/z 349.17 [M+1]$^+$; $^1$H NMR (400 MHz, DMSO-d$_6$) δ 9.26 (s, 1H), 8.58 (s, 1H), 8.19 (s, 1H), 8.04 (s, 2H), 6.42 (s, 2H), 1.99 (s, 3H), 1.78-1.69 (m, 8H), 1.44-1.41 (m, 2H).

Example 92

Synthesis of 6'-((6-amino-5-methylpyrimidin-4-yl)amino)-4'-hydroxyspiro[cyclohexane-1,1'-isoindolin]-3'-one (Cpd. No. 92)

Synthesis of 6'-((6-amino-5-methylpyrimidin-4-yl)amino)-4'-hydroxyspiro[cyclohexane-1,1'-isoindolin]-3'-one (Cpd. No. 92)

To a solution of 6'-((6-Amino-5-methylpyrimidin-4-yl)amino)-4'-methoxyspiro[cyclohexane-1,1'-isoindolin]-3'-one (1, 150 mg, 0.42 mmol) in dichloromethane (10 mL) −78° C. was added borontribromide (318 mg, 1.27 mmol) slowly. The reaction was allowed to stir at room temperature for 16 h. The reaction was quenched with methanol and basified with aqueous ammonia. The mixture was extracted with 10% isopropanol in dichloromethane (5×20 mL). The combined organic layer was separated, dried over sodium sulfate, filtered and concentrated. The crude was purified by prep HPCL to afford 6'-((6-amino-5-methylpyrimidin-4-yl)amino)-4'-hydroxyspiro[cyclohexane-1,1'-isoindolin]-3'-one (Cpd. No. 92) as an off-white solid. Yield: 40 mg, 28%; MS (ESI): m/z 340.20 [M+1]$^+$; $^1$H NMR (400 MHz, DMSO-d$_6$) δ 9.11 (s, 1H), 8.68 (s, 1H), 8.14 (s, 1H), 7.99 (s, 1H), 7.18 (s, 1H), 7.10 (s, 1H), 6.28 (s, 2H), 1.96 (s, 3H), 2.05 (s, 3H) 1.68-1.60 (m, 7H), 1.44-1.41 (m, 2H), 1.37-1.30 (m, 1H).

Example 93

Synthesis of 6'-((6-amino-5-methylpyrimidin-4-yl)amino)-7'-hydroxy-4'-methylspiro[cyclohexane-1,1'-isoindolin]-3'-one (Cpd. No. 93)

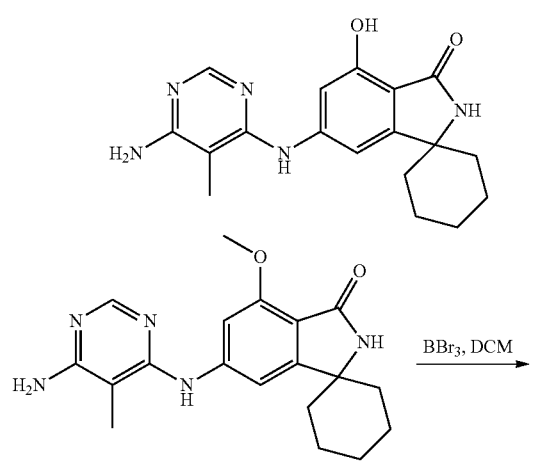

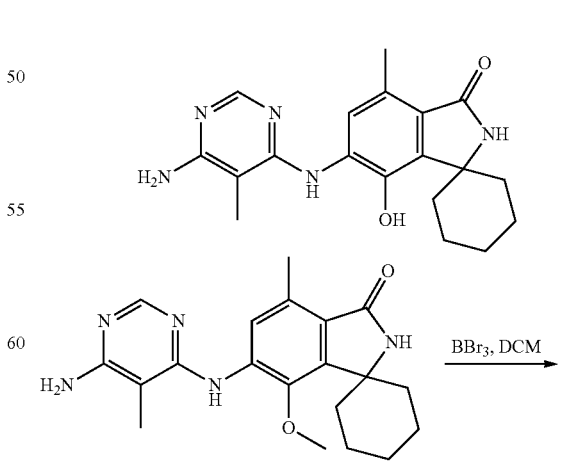

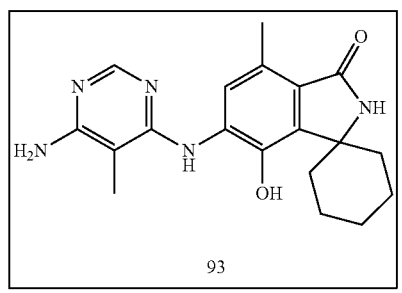

Synthesis of 6'-((6-amino-5-methylpyrimidin-4-yl) amino)-7'-hydroxy-4'-methylspiro[cyclohexane-1,1'-isoindolin]-3'-one (Cpd. No. 93)

To a solution of 6'-((6-amino-5-methylpyrimidin-4-yl)amino)-7'-methoxy-4'-methylspiro[cyclohexane-1,1'-isoindolin]-3'-one (1, 0.37 g, 1 mmol) in dichloromethane (10 mL) is added boron tribromide (0.28 mL, 3 mmol) at 0° C. The reaction is stirred at room temperature for 18 h. After completion the reaction is cooled to 0° C. and quenched with methanol. The mixture is neutralize using aqueous ammonia to pH 7. The solvents is removed and the residue is washed with diethyl ether and pentane to get 6'-((6-amino-5-methylpyrimidin-4-yl)amino)-7'-hydroxy-4'-methylspiro[cyclohexane-1,1'-isoindolin]-3'-one (Cpd. No. 93).

Example 94

Synthesis of 6'-((6-amino-5-methylpyrimidin-4-yl) amino)-7'-methoxy-4'-methylspiro[cyclohexane-1,1'-isoindolin]-3'-one (Cpd. No. 94)

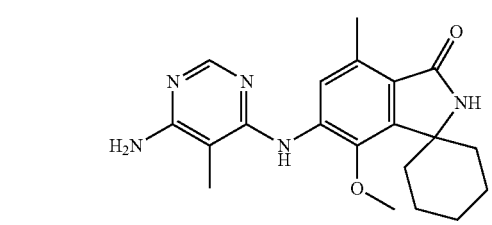

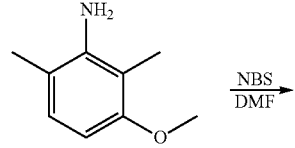

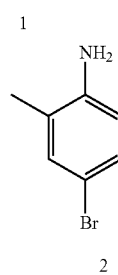

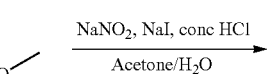

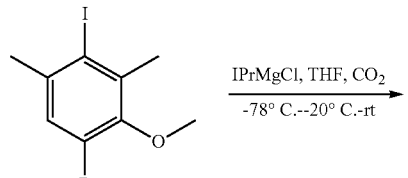

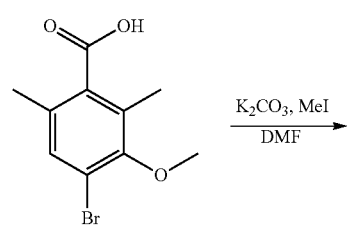

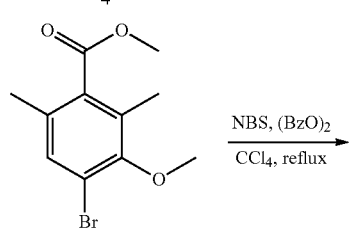

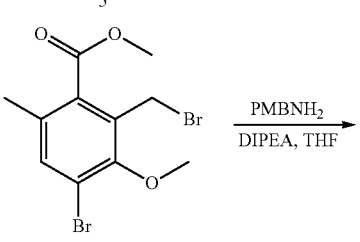

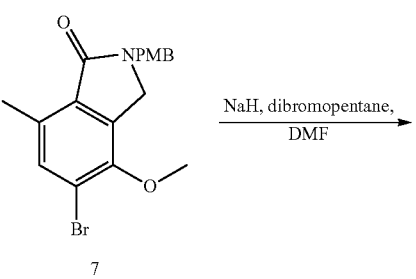

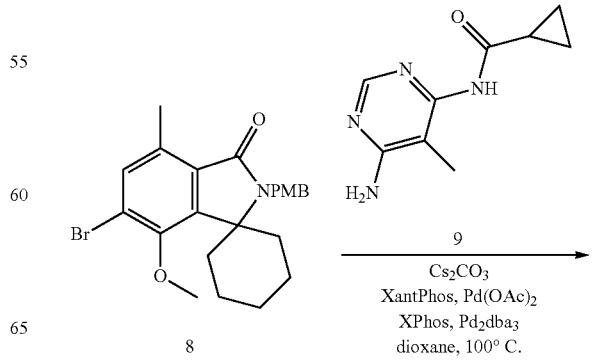

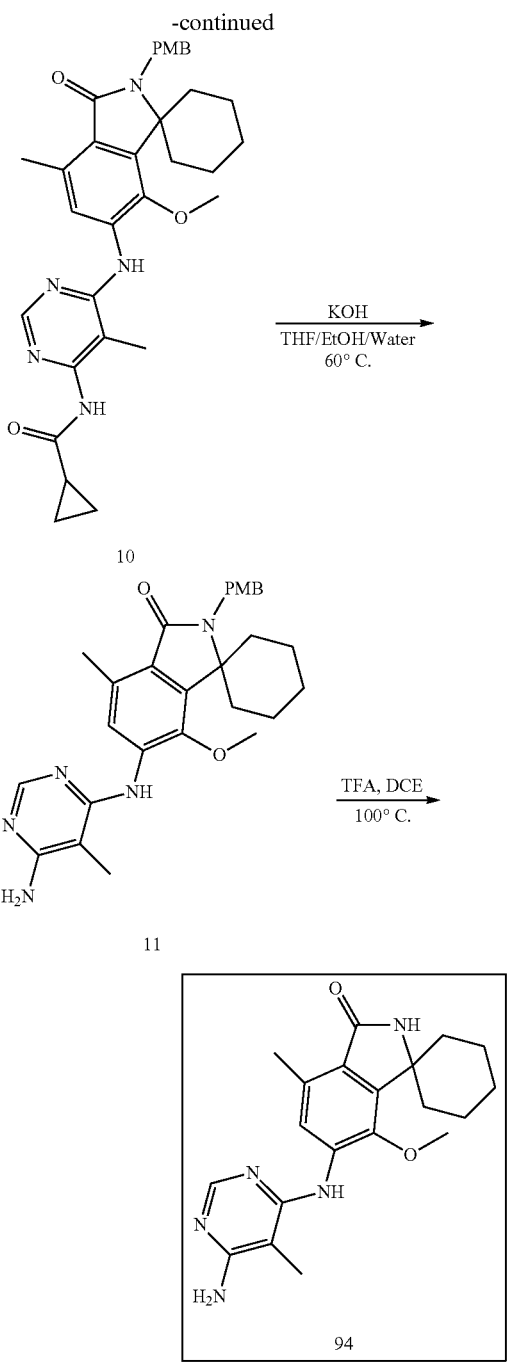

Synthesis of 4-bromo-3-methoxy-2,6-dimethylaniline (2)

To a solution of 3-methoxy-2,6-dimethylaniline (1, 31.2 g, 206.6 mmol) in dimethylformamide (250 mL) at 0° C. was added N-bromosuccinimide (44.16 g, 247.9 mmol) lot wise. The reaction was stirred at room temperature for 4 h. After completion, the reaction was quenched with chilled ammonium chloride solution (200 mL) and extracted with ethyl acetate (2×250 mL). The combined organic layers were washed with water (300 mL) and brine (200 mL). The organic layer was dried over sodium sulfate, filtered and concentrated to afford 4-bromo-3-methoxy-2,6-dimethylaniline (2) as a dark brown liquid. Yield: 28.3 g, 60%; MS (ESI) m/z 230.29 [M+1]$^+$.

Synthesis of 1-bromo-4-iodo-2-methoxy-3,5-dimethylbenzene (3)

To a solution of 4-bromo-3-methoxy-2,6-dimethylaniline (2, 28.3 g, 122.9 mmol) in hydrochloric acid (25 mL) and acetone (246 mL) at −5° C. to 0° C. was added slowly a solution of sodium nitrite (10.18 g, 147.5 mmol) in water (410 mL). The reaction was stirred for 30 min before a solution of sodium iodide (36.8 g, 245.18 mmol) in water (41 mL) was added. The reaction was stirred at room temperature for 16 h. After completion, the reaction was quenched with saturated aqueous sodium thiosulfate solution and extracted with ethyl acetate (2×250 mL). The combined organic layer was washed with water (300 mL) and brine (200 mL). The organic was dried over sodium sulfate, filtered and concentrated to afford 1-bromo-4-iodo-2-methoxy-3,5-dimethylbenzene (3) as a brown liquid. Yield: 41 g, 98%.

Synthesis of 4-bromo-3-methoxy-2,6-dimethylbenzoic acid (4)

To a solution of 1-bromo-4-iodo-2-methoxy-3,5-dimethylbenzene (3, 30.8 g, 90.58 mmol) in tetrahydrofuran (350 mL) at −78° C. was slowly added isopropyl magnesium chloride (181.2 mL, 362.3 mmol, 2 M in tetrahydrofuran). The reaction was stirred at −20° C. for 30 min and then excess dry ice was added slowly over a period of 1 h. The reaction was stirred for 1 h at room temperature. After completion, the reaction was quenched with 2 M hydrochloric acid (100 mL) and extracted with ethyl acetate (2×250 mL). The combined organic layer was washed with water (2×500 mL) and brine (200 mL). The organic layer was dried over sodium sulfate, filtered and concentrated. The crude was triturated with pentane to afford 4-bromo-3-methoxy-2,6-dimethylbenzoic acid (4) as a white solid. Yield: 18 g, 77%; MS (ESI) m/z 256.92 [M−1]$^-$.

Synthesis of methyl 4-bromo-3-methoxy-2,6-dimethylbenzoate (5)

To a solution of 4-bromo-3-methoxy-2,6-dimethylbenzoic acid (4, 18.0 g, 69.5 mmol) in dimethylformamide (160 mL) was added potassium carbonate (19.2 g, 138.99 mmol) followed by iodomethane (5.2 mL, 83.39 mmol). The reaction was stirred at room temperature for 1 h. After completion, the reaction was quenched with chilled water (100 mL) and extracted with ethyl acetate (3×100 mL). The combined organic layer was washed with water (2×200 mL) and brine (200 mL), dried over sodium sulfate, filtered and concentrated to afford methyl 4-bromo-3-methoxy-2,6-dimethylbenzoate (5) as a light yellow liquid. Yield: 18.8 g, 99%; MS (ESI) m/z 274.44 [M+1]$^+$.

Synthesis of methyl 4-bromo-2-(bromomethyl)-3-methoxy-6-methylbenzoate (6)

To a solution of methyl 4-bromo-3-methoxy-2,6-dimethylbenzoate (5, 18.8 g, 69.11 mmol) in carbon tetrachloride (200 mL) was added N-bromosuccinimide (13.53 g, 76.02 mmol) followed by benzoyl peroxide (1.68 g, 6.91 mmol). The reaction was refluxed for 16 h. After completion, the reaction was quenched with chilled water (100 mL) and extracted with dichloromethane (2×150 mL). The combined organic layer was washed with water and brine, dried over magnesium sulfate, filtered and concentrated to afford methyl 4-bromo-2-(bromomethyl)-3-methoxy-6-methylbenzoate (6) as a light brown liquid. Yield: 24 g, crude.

Synthesis of 5-bromo-4-methoxy-2-(4-methoxybenzyl)-7-methylisoindolin-1-one (7)

To a solution of 4-bromo-2-(bromomethyl)-3-methoxy-6-methylbenzoate (24.0 g, 68.17 mmol) in tetrahydrofuran (200 mL) were added p-methoxybenzyl amine (10.7 mL, 81.81 mmol) and diisopropylethylamine (35.6 mL, 204.53 mmol). The reaction was stirred at room temperature for 16 h. After completion, the reaction was quenched with water (100 mL) and extracted with ethyl acetate (2×200 mL). The combined organic layer was washed with water (2×200 mL) and brine (200 mL), dried over sodium sulfate, filtered, concentrated and purified by column chromatography eluting with 20-30% ethyl acetate in hexane. The desired fractions were collected and concentrated under reduced pressure to afford 5-bromo-4-methoxy-2-(4-methoxybenzyl)-7-methylisoindolin-1-one (7) as a white solid. Yield: 15.2 g, 59%; MS (ESI) m/z 377.8 [M+1]$^+$.

Synthesis of 6'-bromo-7'-methoxy-2'-(4-methoxybenzyl)-4'-methylspiro[cyclohexane-1,1'-isoindolin]-3'-one (8)

To a solution of 5-bromo-4-methoxy-2-(4-methoxybenzyl)-7-methylisoindolin-1-one (6.3 g, 16.75 mmol) in dimethylformamide (70 mL) at 0° C. was added sodium hydride (1.67 g, 41.86 mmol). The reaction was stirred for 20 min and a solution of 1,5-dibromopentane (2.5 mL, 18.41 mmol) in dimethylformamide (10 mL) was added slowly. The reaction was stirred at room temperature for 16 h. After completion, the reaction was quenched with saturated aqueous ammonium chloride solution (100 mL) and extracted with ethyl acetate (2×100 mL). The combined organic layer was washed with water (2×150 mL) and brine (100 mL), dried over sodium sulfate, filtered and concentrated. The crude was purified by flash chromatography using 8-10% ethyl acetate in hexane as eluent to afford 6'-bromo-7'-methoxy-2'-(4-methoxybenzyl)-4'-methylspiro[cyclohexane-1,1'-isoindolin]-3'-one (8) as a light yellow sticky solid. Yield: 1.1 g, 15%; MS (ESI) m/z 444.01 [M+1]$^+$.

Synthesis of N-(6-((7'-methoxy-2'-(4-methoxybenzyl)-4'-methyl-3'-oxospiro[cyclohexane-1,1'-isoindolin]-6'-yl)amino)-5-methylpyrimidin-4-yl)cyclopropanecarboxamide (10)

The synthesis of intermediate 10 was carried out as described above using the general protocol of Procedure A. Light brown solid; Yield: 0.12 g, 21%; MS (ESI) m/z 556.27 [M+1]$^+$.

Synthesis of 6'-((6-amino-5-methylpyrimidin-4-yl)amino)-7'-methoxy-2'-(4-methoxybenzyl)-4'-methylspiro[cyclohexane-1,1'-isoindolin]-3'-one (11)

The synthesis of intermediate 11 was carried out as described above using the general protocol of Procedure D. Off-white solid; Yield: 60 mg, 53%; MS (ESI) m/z 488.25 [M+1]$^+$.

Synthesis of 6'-((6-amino-5-methylpyrimidin-4-yl)amino)-7'-methoxy-4'-methylspiro[cyclohexane-1,1'-isoindolin]-3'-one (Cpd. No. 94)

The synthesis of compound 94 was carried out as described above using the general protocol of Procedure G. White solid; Yield: 18 mg, 40%; MS (ESI) m/z 368.25 [M+1]$^+$; $^1$H NMR (400 MHz, DMSO-d$_6$) δ 8.92 (s, 1H), 7.89 (s, 1H), 7.55 (s, 1H), 7.43 (s, 1H), 6.22 (s, 2H), 3.68 (s, 3H), 2.48 (s, 3H), 2.22-2.10 (m, 2H), 1.97 (s, 3H), 1.76-1.62 (m, 5H), 1.38-1.25 (m, 3H).

Example 95

Synthesis of 6'-((6-amino-5-methylpyrimidin-4-yl)amino)-7'-fluoro-4'-methylspiro[cyclohexane-1,1'-isoindolin]-3'-one (Cpd. No. 95)

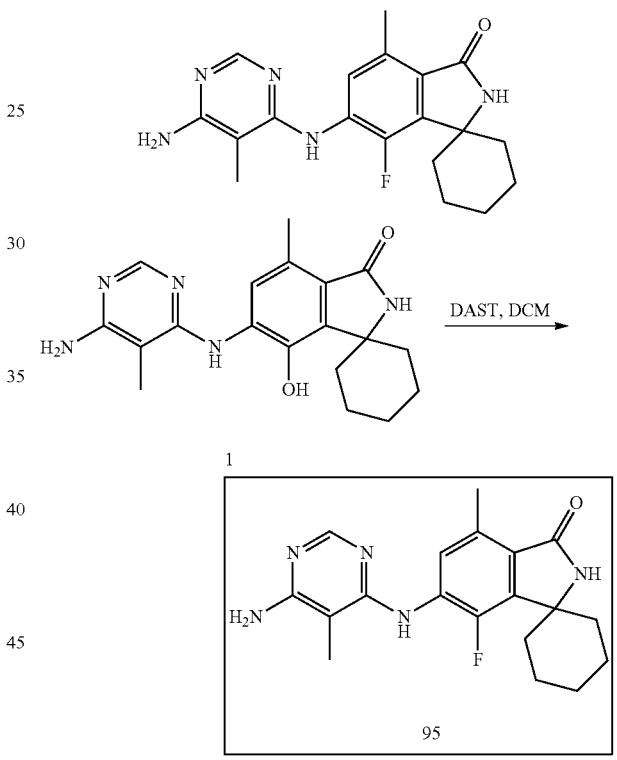

Synthesis of 6'-((6-amino-5-methylpyrimidin-4-yl)amino)-7'-fluoro-4'-methylspiro[cyclohexane-1,1'-isoindolin]-3'-one (Cpd. No. 95)

To a solution of 6'-((6-amino-5-methylpyrimidin-4-yl)amino)-7'-hydroxy-4'-methylspiro[cyclohexane-1,1'-isoindolin]-3'-one (1, 0.35 g, 1 mmol) in dichloromethane (3 mL) at 0° C. is added (diethylamino)sulfur trifluoride (0.26 mL, 2 mmol). The reaction is stirred at room temperature for 6 h. After completion, the reaction is cooled to 0° C. and slowly quench with saturated aqueous sodium bicarbonate solution. The mixture is extracted with 10% methanol in dichloromethane. The organic layer is washed with water and brine, dried over anhydrous sodium sulfate, filtered and concentrated under reduced pressure to afford 6'-((6-amino- 5-methylpyrimidin-4-yl)amino)-7'-fluoro-4'-methylspiro[cyclohexane-1,1'-isoindolin]-3'-one (Cpd. No. 95).

Example 96

Synthesis of 6'-((6-amino-5-methylpyrimidin-4-yl)amino)-7'-chloro-4'-methylspiro[cyclohexane-1,1'-isoindolin]-3'-one (Cpd. No. 96)

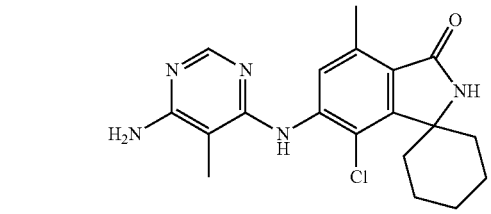

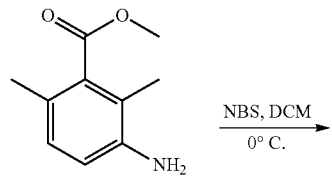

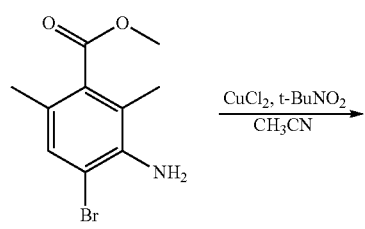

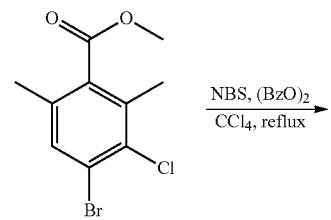

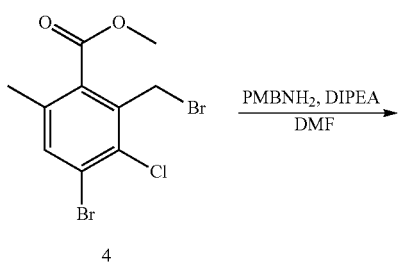

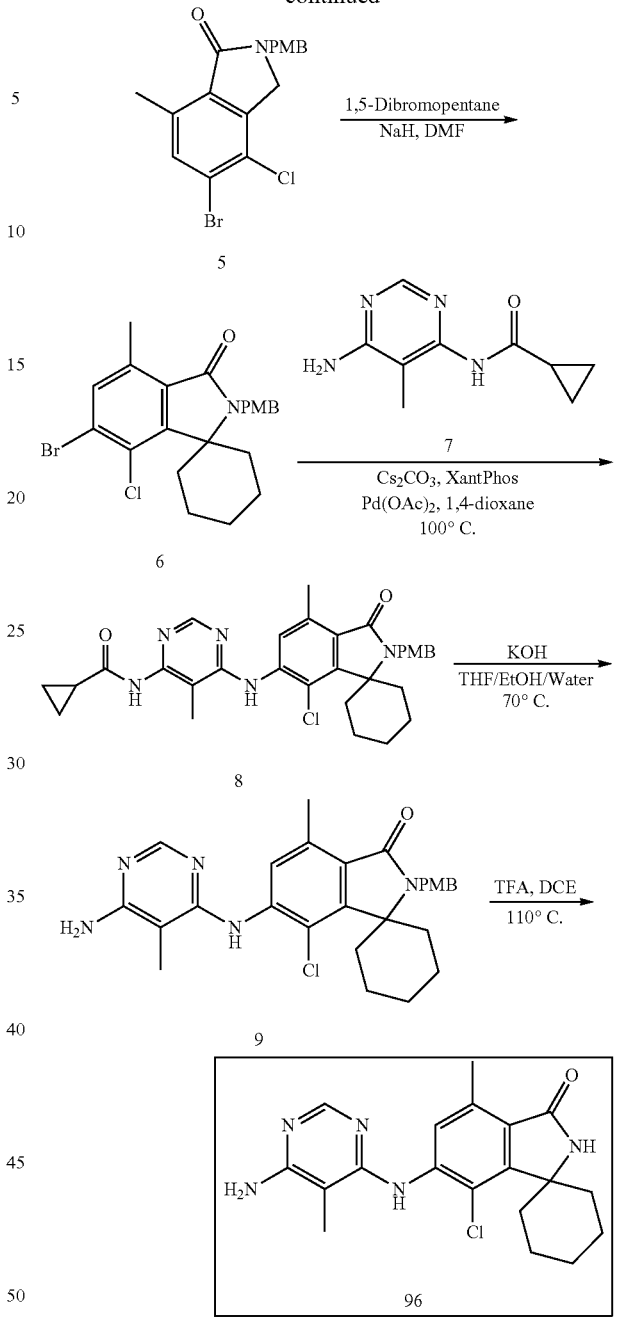

Synthesis of Methyl 3-amino-4-bromo-2,6-dimethylbenzoate (2)

To a solution of methyl 3-amino-2,6-dimethylbenzoate (1, 17.5 g, 97.64 mmol) in dichloromethane (200 mL) at 0° C. was added N-bromosuccinimide (19.11 g, 107.40 mmol). The mixture was stirred for 30 min. After completion, the reaction was quenched with chilled water (250 mL) and extracted with dichloromethane (2×250 mL). The combined organic layer was washed with water (2×300 mL) and brine (200 mL), dried over sodium sulfate, filtered and concentrated to afford methyl 3-amino-4-bromo-2,6-dimethylbenzoate (2) as a dark brown liquid. Yield: 22.10 g, 87%; MS (ESI) m/z 258 [M+1]⁺.

Synthesis of Methyl 4-bromo-3-chloro-2,6-dimethylbenzoate (3)

To a solution of tert-butylnitrite (87.9 g, 852.30 mmol) in acetonitrile (200 mL) at 0° C. was added copper(II) chloride (13.74 g, 102.27 mmol). A solution of methyl 3-amino-4-bromo-2,6-dimethylbenzoate (2, 22.0 g, 85.23 mmol) in acetonitrile (150 mL) was added to the above suspension slowly and the reaction was stirred for 16 h. After completion of reaction, it was quenched with chilled water (250 mL) and extracted with ethyl acetate (2×250 mL). The organic layer was washed with water (2×250 mL) and brine (200 mL), dried over sodium sulfate, filtered and concentrated. The crude was purified via column chromatography eluting with 3-5% ethyl acetate in hexane to afford methyl 4-bromo-3-chloro-2,6-dimethylbenzoate (3) as a light yellow liquid. Yield: 18.0 g, 76%; MS (ESI) m/z 277 [M+1]$^+$.

Synthesis of Methyl 4-bromo-2-(bromomethyl)-3-chloro-6-methylbenzoate (4)

To a solution of methyl 4-bromo-3-chloro-2,6-dimethylbenzoate (3, 18.0 g, 64.85 mmol) in carbon tetrachloride (250 mL) was added N-bromosuccinimide (12.7 g, 71.34 mmol) followed by benzoyl peroxide (3.1 g, 12.97 mmol). The reaction was reflux for 24 h. After completion, the reaction was filtered through a cotton plug. The filtrate was concentrated to dryness to afford methyl 4-bromo-2-(bromomethyl)-3-chloro-6-methylbenzoate (4) as a light brown liquid. Yield: 25.1 g, crude; MS (ESI) m/z 355 [M+1]$^+$.

Synthesis of 5-bromo-4-chloro-2-(4-methoxybenzyl)-7-methylisoindolin-1-one (5)

To a solution of methyl 4-bromo-2-(bromomethyl)-3-chloro-6-methylbenzoate (4, 25.0 g, 70.13 mmol) in dimethylformamide (200 mL) at 0° C. was added p-methoxybenzyl amine (9.6 g, 70.13 mmol) followed by diisopropylethylamine (36.7 mL, 210.41 mmol) slowly. The reaction was stirred at room temperature for 16 h. After completion, the reaction was quenched with chilled water (500 mL) and extracted with ethyl acetate (2×300 mL). The organic layer was washed with water (2×500 mL) and brine (200 mL), dried over sodium sulfate, filtered and concentrated. The crude was purified by column chromatography eluting with 3-5% ethyl acetate in hexane to afford 5-bromo-4-chloro-2-(4-methoxybenzyl)-7-methylisoindolin-1-one (5) as an off-white solid. Yield: 6.0 g, 22%; MS (ESI) m/z 380 [M+1]$^+$.

Synthesis of 6'-Bromo-7'-chloro-2'-(4-methoxybenzyl)-4'-methylspiro[cyclohexane-1,1'-isoindolin]-3'-one (6)

To a solution of 5-bromo-4-chloro-2-(4-methoxybenzyl)-7-methylisoindolin-1-one (5, 2.0 g, 5.23 mmol) in dimethylformamide (35 mL) at 0° C. was added sodium hydride (0.63 g, 15.76 mmol). The reaction was stirred for 10 min and a solution of 1,5-dibromopentane (1.45 g, 6.30 mmol) in dimethylformamide (35 mL) was added slowly. The mixture was stirred at room temperature for 2 h. After completion, the reaction was quenched with chilled water (100 mL) and extracted with ethyl acetate (2×100 mL). The organic layer was washed with water (2×150 mL) and brine (100 mL), dried over sodium sulfate, filtered and concentrated. The crude was purified by flash chromatography using 10-15% ethyl acetate in hexane as eluent to afford 6'-bromo-7'-chloro-2'-(4-methoxybenzyl)-4'-methylspiro[cyclohexane-1,1'-isoindolin]-3'-one (6) as an off-white solid. Yield: 0.80 g, 34%; MS (ESI) m/z 448 [M+1]$^+$.

Synthesis of N-(6-((7'-Chloro-2'-(4-methoxybenzyl)-4'-methyl-3'-oxospiro[cyclohexane-1,1'-isoindolin]-6'-yl)amino)-5-methylpyrimidin-4-yl)cyclopropanecarboxamide (8)

The synthesis of intermediate 8 was carried out as described above using the general protocol of Procedure A. Light brown solid; Yield: 0.25 g, 80%; MS (ESI) m/z 560.0 [M+1]$^+$.

Synthesis of 6'-((6-amino-5-methylpyrimidin-4-yl)amino)-7'-chloro-2'-(4-methoxybenzyl)-4'-methylspiro[cyclohexane-1,1'-isoindolin]-3'-one (9)

The synthesis of intermediate 9 was carried out as described above using the general protocol of Procedure D. Yellow solid; Yield: 0.21 g, crude; MS (ESI) m/z 492 [M+1]$^+$.

Synthesis of 6'-((6-amino-5-methylpyrimidin-4-yl)amino)-7'-chloro-4'-methylspiro[cyclohexane-1,1'-isoindolin]-3'-one (Cpd. No. 96)

The synthesis of compound 96 was carried out as described above using the general protocol of Procedure G. White solid; Yield: 11 mg, 10%; MS (ESI) m/z 372 [M+1]$^+$; $^1$H NMR (400 MHz, DMSO-d$_6$) δ 9.05 (s, 1H), 7.94 (s, 1H), 7.89 (s, 1H), 7.69 (s, 1H), 6.35 (s, 2H), 2.68 (s, 3H), 1.99 (s, 3H), 1.83-1.73 (m, 2H), 1.72-1.62 (m, 5H), 1.39-1.33 (m, 2H).

Example 97

Synthesis of 6'-((6-amino-5-methylpyrimidin-4-yl)amino)-4',7'-dimethylspiro [cyclohexane-1,1'-isoindolin]-3'-one (Cpd. No. 97)

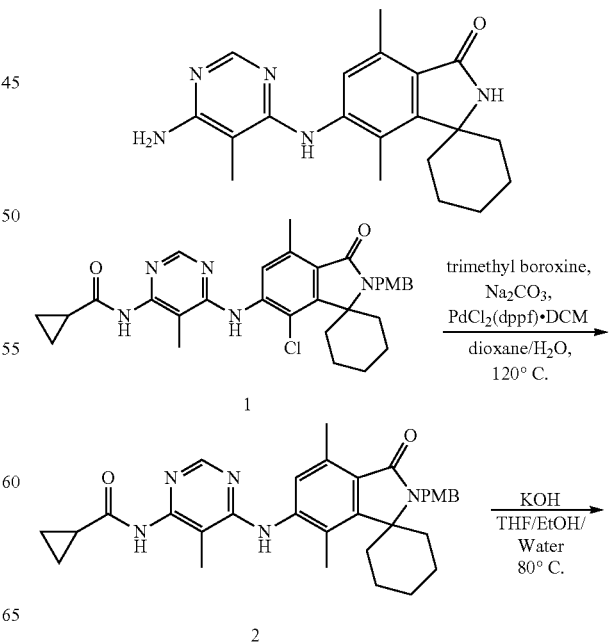

-continued

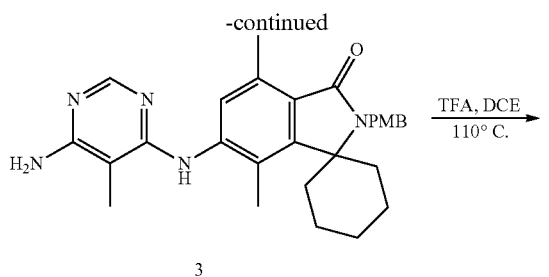

3

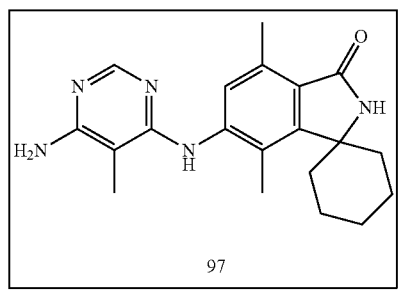

97

Synthesis of N-(6-((2'-(4-methoxybenzyl)-4',7'-dimethyl-3'-oxospiro[cyclohexane-1,1'-isoindolin]-6'-yl)amino)-5-methylpyrimidin-4-yl)cyclopropanecarboxamide (2)

A mixture of N-(6-((7'-chloro-2'-(4-methoxybenzyl)-4'-methyl-3'-oxospiro [cyclohexane-1,1'-isoindolin]-6'-yl)amino)-5-methylpyrimidin-4-yl)cyclopropanecarboxamide (1, 0.56 g, 1 mmol), trimethyl boroxine (0.21 mL, 1.5 mmol) and sodium carbonate (0.32 g, 3 mmol) in 1,4-dioxane (10 mL) and water (2 mL) is purged with argon for 10 min. [1,1'-Bis(diphenylphosphino)ferrocene]dichloropalladium (II), complex with dichloromethane (82 mg, 0.1 mmol) is added and continue purging for another 5 min. The reaction is stirred at 120° C. for 16 h. After completion, the reaction is diluted with ethyl acetate and passed through a celite bed. The filtrate is concentrated and purified with flash chromatography using 20-40% ethyl acetate and hexane as eluent to afford (6-((2'-(4-methoxybenzyl)-4',7'-dimethyl-3'-oxospiro [cyclohexane-1,1'-isoindolin]-6'-yl)amino)-5-methylpyrimidin-4-yl)cyclopropanecarboxamide (2).

Synthesis of 6'-((6-amino-5-methylpyrimidin-4-yl)amino)-2'-(4-methoxybenzyl)-4',7'-dimethylspiro [cyclohexane-1,1'-isoindolin]-3'-one (3)

The synthesis of intermediate 3 is carried out as described above using the general protocol of Procedure D.

Synthesis of 6'-((6-amino-5-methylpyrimidin-4-yl)amino)-4',7'-dimethylspiro [cyclohexane-1,1'-isoindolin]-3'-one (Cpd. No. 97)

The synthesis of compound 97 is carried out as described above using the general protocol of Procedure E.

Example 98

Synthesis of 6'-((6-amino-5-methylpyrimidin-4-yl)amino)-7'-ethyl-4'-methylspiro [cyclohexane-1,1'-isoindolin]-3'-one (Cpd. No. 98)

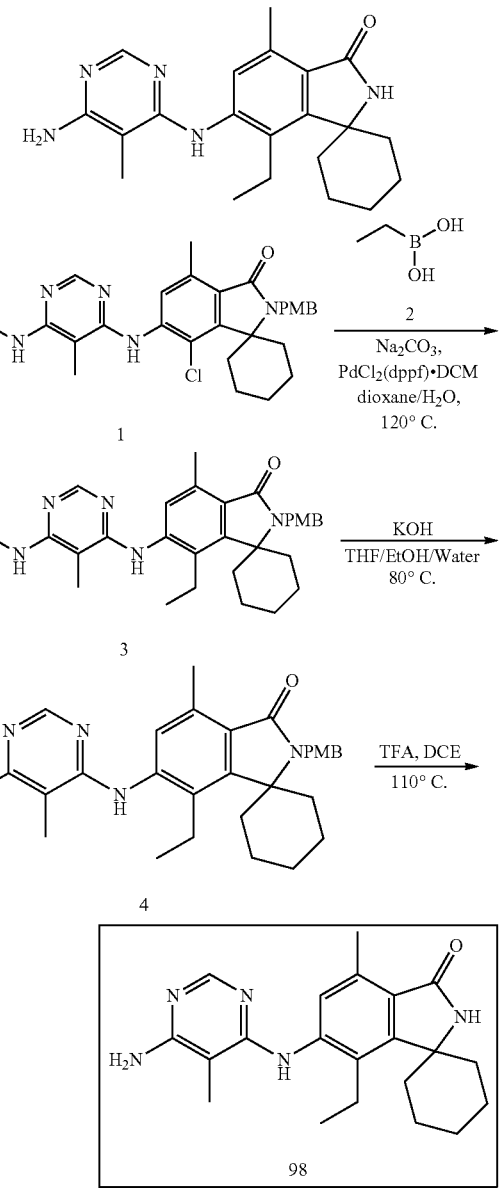

Synthesis of N-(6-((7'-ethyl-2'-(4-methoxybenzyl)-4'-methyl-3'-oxospiro [cyclohexane-1,1'-isoindolin]-6'-yl)amino)-5-methylpyrimidin-4-yl)cyclopropanecarboxamide (3)

A mixture of N-(6-((7'-chloro-2'-(4-methoxybenzyl)-4'-methyl-3'-oxospiro [cyclohexane-1,1'-isoindolin]-6'-yl)amino)-5-methylpyrimidin-4-yl)cyclopropanecarboxamide (1, 0.56 g, 1 mmol), ethylboronic acid (1.5 mmol) and sodium carbonate (0.32 g, 3 mmol) in 1,4-dioxane (10 mL) and water (2 mL) is purged with argon for 10 min. [1,1'-Bis(diphenylphosphino)ferrocene]dichloropalladium(II), complex with dichloromethane (82 mg, 0.1 mmol) is added and continue purging for another 5 min. The reaction is stirred at 120° C. for 16 h. After completion, the reaction is diluted with ethyl acetate and passed through a celite bed. The filtrate is concentrated and purified with flash chromatography using 20-40% ethyl acetate and hexane as eluent to afford N-(6-((7'-ethyl-2'-(4-methoxybenzyl)-4'-methyl-3'-oxospiro [cyclohexane-1,1'-isoindolin]-6'-yl)amino)-5-methylpyrimidin-4-yl)cyclopropanecarboxamide (3).

Synthesis of 6'-((6-amino-5-methylpyrimidin-4-yl)amino)-7'-ethyl-2'-(4-methoxybenzyl)-4'-methylspiro [cyclohexane-1, 1'-isoindolin]-3'-one (4)

The synthesis of intermediate 4 is carried out as described above using the general protocol of Procedure D.

Synthesis of 6'-((6-amino-5-methylpyrimidin-4-yl)amino)-7'-ethyl-4'-methylspiro [cyclohexane-1,1'-isoindolin]-3'-one (Cpd. No. 98)

The synthesis of compound 98 is carried out as described above using the general protocol of Procedure E.

Example 99

Synthesis of 6'-((6-amino-5-methylpyrimidin-4-yl)amino)-4'-methyl-7'-(methylthio) spiro [cyclohexane-1,1'-isoindolin]-3'-one (Cpd. No. 99)

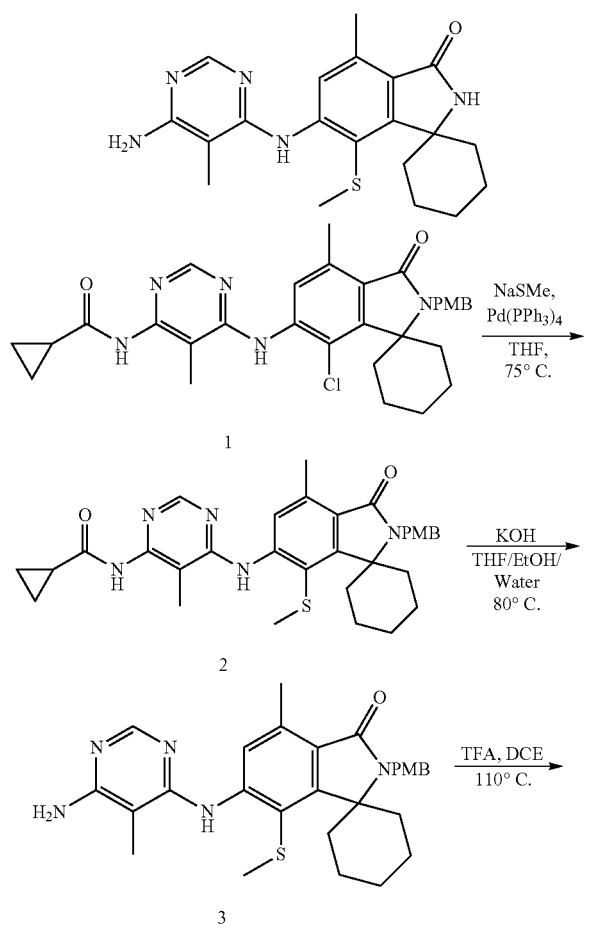

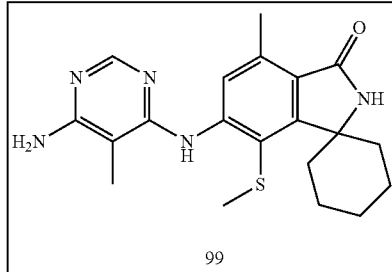

Synthesis of N-(6-((2'-(4-methoxybenzyl)-4'-methyl-7'-(methylthio)-3'-oxospiro [cyclohexane-1,1'-isoindolin]-6'-yl)amino)-5-methylpyrimidin-4-yl)cyclopropanecarboxamide (2)

A mixture of N-(6-((7'-chloro-2'-(4-methoxybenzyl)-4'-methyl-3'-oxospiro [cyclohexane-1,1'-isoindolin]-6'-yl)amino)-5-methylpyrimidin-4-yl)cyclopropanecarboxamide (1, 0.56 g, 1 mmol) and sodium methanethiolate (0.35 g, 5 mmol) in tetrahydrofuran (10 mL) is purged with argon for 10 min. Tetrakis(triphenylphosphine)palladium(0) (116 mg, 0.10 mmol) is added and purging continues for another 5 min. The reaction is stirred at 75° C. for 24 h. After completion, the reaction is diluted with 5% methanol in dichloromethane (150 mL) and passed through an alumina bed. The filtrate is concentrated and purified by flash chromatography using ethyl acetate and hexane as eluent to get N-(6-((2'-(4-methoxybenzyl)-4'-methyl-7'-(methylthio)-3'-oxospiro [cyclohexane-1,1'-isoindolin]-6'-yl)amino)-5-methylpyrimidin-4-yl)cyclopropanecarboxamide (2).

Synthesis of 6'-((6-amino-5-methylpyrimidin-4-yl)amino)-2'-(4-methoxybenzyl)-4'-methyl-7'-(methylthio) spiro [cyclohexane-1,1'-isoindolin]-3'-one (3)

The synthesis of intermediate 3 is carried out as described above using the general protocol of Procedure D.

Synthesis of 6'-((6-amino-5-methylpyrimidin-4-yl)amino)-4'-methyl-7'-(methylthio) spiro[cyclohexane-1,1'-isoindolin]-3'-one (Cpd. No. 99)

The synthesis of compound 99 is carried out as described above using the general protocol of Procedure E.

Example 100

Synthesis of 6'-((6-amino-5-methylpyrimidin-4-yl)amino)-4'-methyl-3'-oxospiro [cyclohexane-1, 1'-isoindoline]-7'-carbonitrile (Cpd. No. 100)

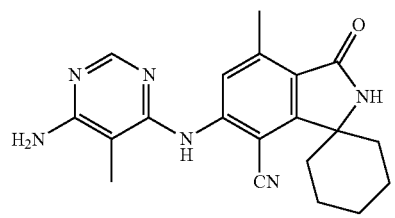

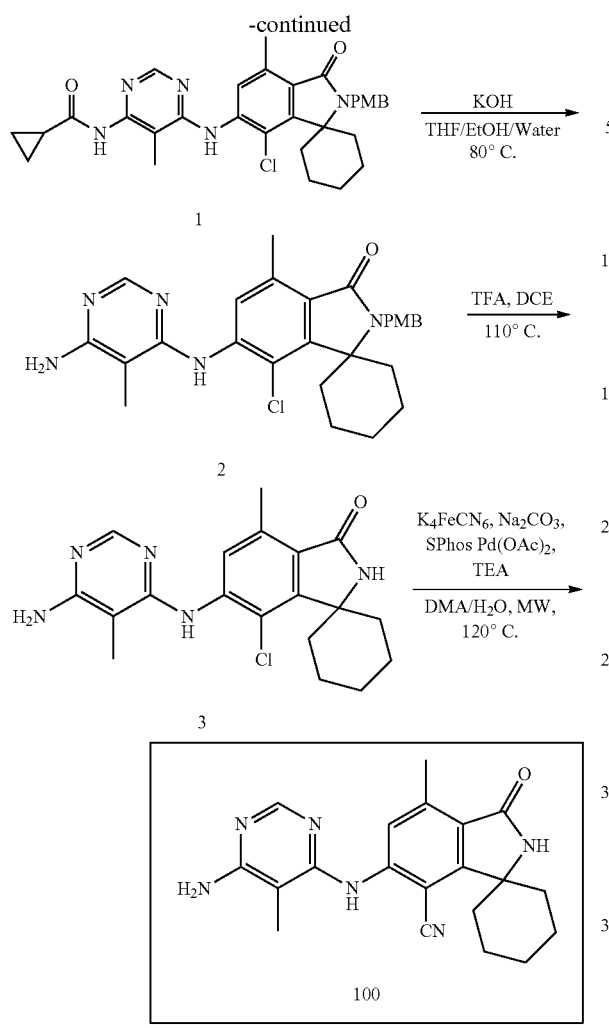

Synthesis 6'-((6-amino-5-methylpyrimidin-4-yl) amino)-7'-chloro-2'-(4-methoxybenzyl)-4'-methylspiro [cyclohexane-1,1'-isoindolin]-3'-one (2)

The synthesis of intermediate 2 is carried out as described above using the general protocol of Procedure D.

Synthesis of 6'-((6-amino-5-methylpyrimidin-4-yl) amino)-7'-chloro-4'-methylspiro [cyclohexane-1,1'-isoindolin]-3'-one (3)

The synthesis of intermediate 3 is carried out as described above using the general protocol of Procedure G.

Synthesis of 6'-((6-amino-5-methylpyrimidin-4-yl) amino)-4'-methyl-3'-oxospiro [cyclohexane-1, 1'-isoindoline]-7'-carbonitrile (Cpd. No. 100)

A mixture of 6'-((6-amino-5-methylpyrimidin-4-yl) amino)-7'-chloro-4'-methylspiro [cyclohexane-1, 1'-isoindolin]-3'-one (3, 0.37 g, 1 mmol), potassium ferrocyanide (1.84 g, 5 mmol), triethylamine (0.42 mL, 3 mmol) and sodium carbonate (0.21 g, 2 mmol) in N,N-dimethylacetamide and water (4:1) is purged with argon for 10 min. SPhos (0.82 g, 2 mmol) and palladium(II) acetate (0.45 g, 2 mmol) are added and purging continues for another 5 min. The reaction is stirred at 120° C. for 1 h under microwave. After completion, the reaction is dilute with 5% methanol in dichloromethane and passed through an alumina bed. The filtrate is concentrated and purified by prep HPLC to get 6'-((6-amino-5-methylpyrimidin-4-yl) amino)-4'-methyl-3'-oxospiro [cyclohexane-1,1'-isoindoline]-7'-carbonitrile (Cpd. No. 100).

Example 101

Synthesis of 7'-acetyl-6'-((6-amino-5-methylpyrimidin-4-yl) amino)-4'-methylspiro [cyclohexane-1, 1'-isoindolin]-3'-one (Cpd. No. 101)

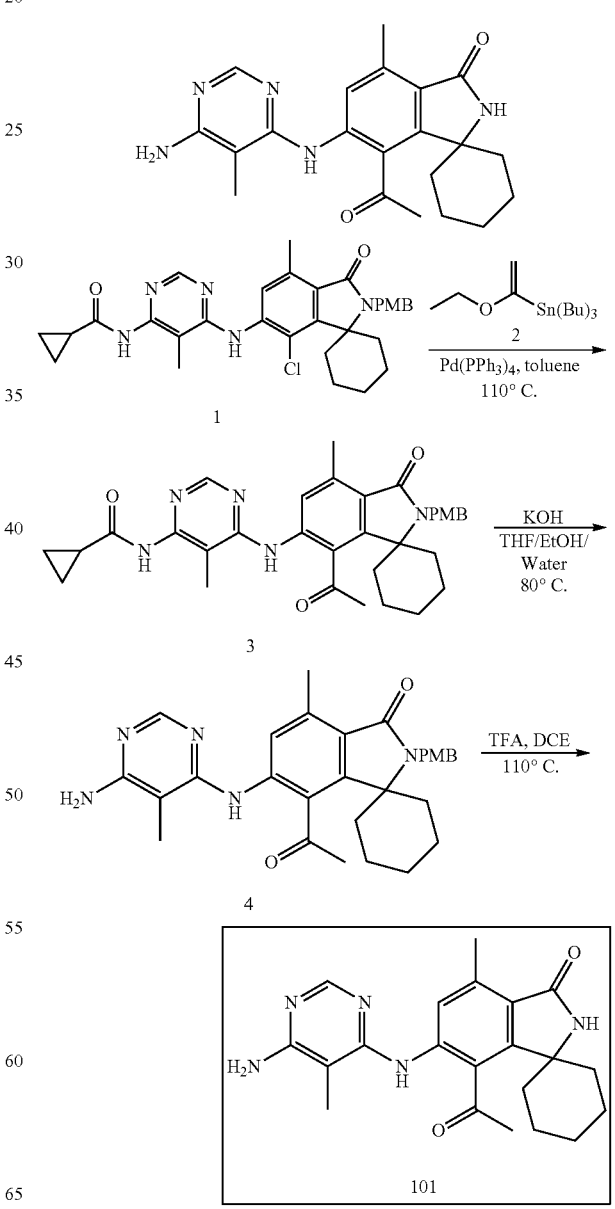

Synthesis of N-(6-((7'-acetyl-2'-(4-methoxybenzyl)-4'-methyl-3'-oxospiro [cyclohexane-1,1'-isoindolin]-6'-yl)amino)-5-methylpyrimidin-4-yl)cyclopropanecarboxamide (3)

A mixture of N-(6-((7'-chloro-2'-(4-methoxybenzyl)-4'-methyl-3'-oxospiro [cyclohexane-1, 1'-isoindolin]-6'-yl) amino)-5-methylpyrimidin-4-yl)cyclopropanecarboxamide (1, 0.56 g, 1 mmol) and tributyl (1-ethoxyvinyl)stannane (2, 0.36 g, 1.2 mmol) in toluene (8 mL) is purged with argon for 10 min. Tetrakis(triphenylphosphine)palladium(0) (0.12 g, 0.1 mmol) is added and purging continues for another 5 min. The reaction is stirred at 110° C. for 16 h. After completion, the reaction is dilute with ethyl acetate and passed through an alumina bed. The filtrate is washed with saturated aqueous solution of potassium fluoride and concentrated. The crude is purified by flash chromatography using 20-40% ethyl acetate and hexane as eluent to get N-(6-((7'-acetyl-2'-(4-methoxybenzyl)-4'-methyl-3'-oxospiro [cyclohexane-1, 1'-isoindolin]-6'-yl) amino)-5-methylpyrimidin-4-yl)cyclopropanecarboxamide (3).

Synthesis of 7'-Acetyl-6'-((6-amino-5-methylpyrimidin-4-yl) amino)-2'-(4-methoxybenzyl)-4'-methyl-spiro [cyclohexane-1,1'-isoindolin]-3'-one (4)

The synthesis of intermediate 4 is carried out as described above using the general protocol of Procedure D.

Synthesis of 7'-acetyl-6'-((6-amino-5-methylpyrimidin-4-yl) amino)-4'-methylspiro [cyclohexane-1,1'-isoindolin]-3'-one (Cpd. No. 101)

The synthesis of compound 101 is carried out as described above using the general protocol of Procedure G.

Example 102

Synthesis of 6'-((6-amino-5-methylpyrimidin-4-yl) amino)-7'-(2-aminoethyl)-4'-methylspiro[cyclohexane-1,1'-isoindolin]-3'-one (Cpd. No. 102)

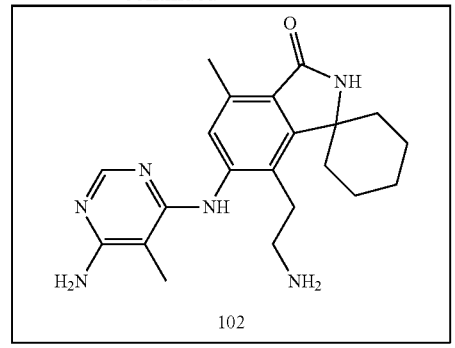

102

Synthesis of 6'-((6-amino-5-methylpyrimidin-4-yl) amino)-7'-(2-aminoethyl)-4' methylspiro[cyclohexane-1,1'-isoindolin]-3'-one (Cpd. No. 102)

To a solution of 2-(6'-(((6-amino-5-methylpyrimidin-4-yl)amino)-4'-methyl-3'-oxospiro[cyclohexane-1,1'-isoindolin]-7'-yl)acetonitrile (1, 0.76 g, 1 mmol) in ethanol (20 mL) at room temperature is added 10% palladium on carbon (76 mg). The reaction is stirred at room temperature under hydrogen for 16 h. After completion, the reaction is filtered through a celite bed. The filtrate is concentrated and purified by flash column chromatography to get 6'-((6-amino-5-methylpyrimidin-4-yl)amino)-7'-(2-aminoethyl)-4'-methylspiro[cyclohexane-1,1'-isoindolin]-3'-one (Cpd. No. 102).

Example 103

Synthesis of 2-(6'-(((6-amino-5-methylpyrimidin-4-yl)amino)-4'-methyl-3'-oxospiro[cyclohexane-1,1'-isoindolin]-7'-yl)acetonitrile (Cpd. No. 103)

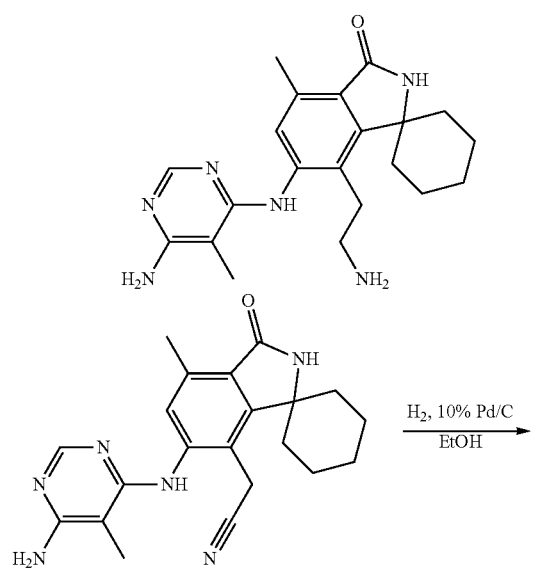

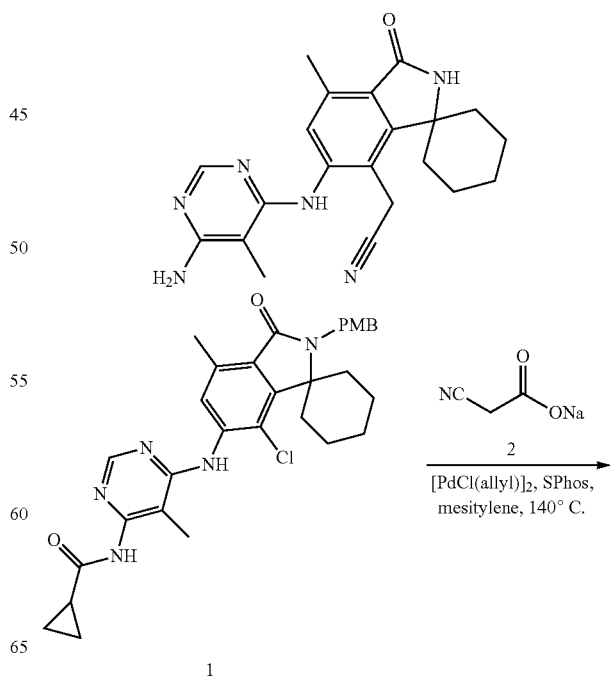

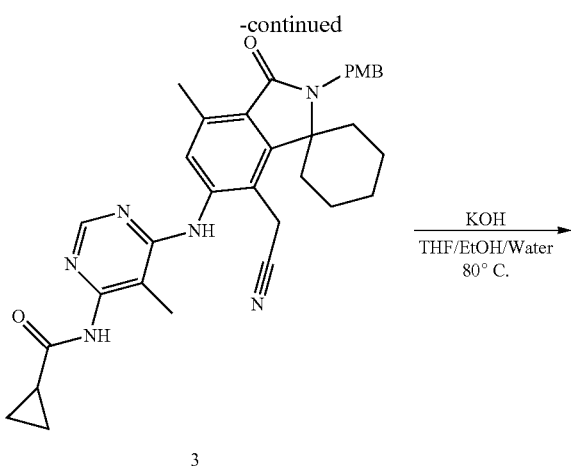

3

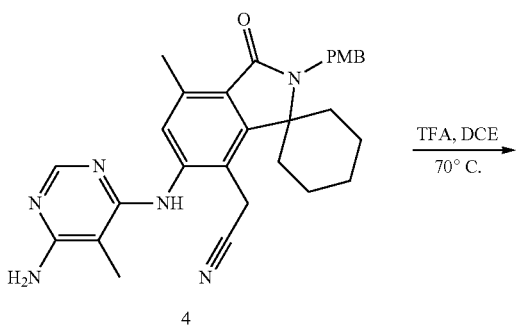

4

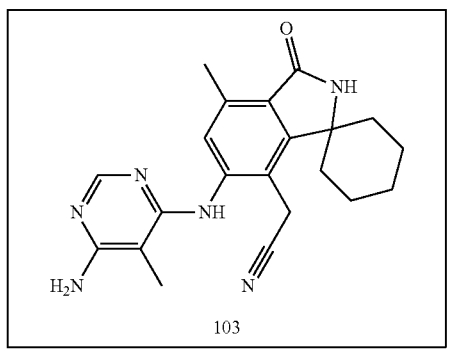

103

Synthesis of N-(6-((7'-(cyanomethyl)-2'-(4-methoxybenzyl)-4'-methyl-3'-oxospiro [cyclohexane-1,1'-isoindolin]-6'-yl)amino)-5-methylpyrimidin-4-yl)cyclopropane carboxamide (3)

To a mixture of N-(6-((7'-chloro-2'-(4-methoxybenzyl)-4'-methyl-3'-oxospiro[cyclohexane-1,1'-isoindolin]-6'-yl)amino)-5-methyl pyrimidin-4-yl)cyclopropanecarboxamide (1, 0.56 g, 1 mmol) in mesitylene (10 mL) at room temperature is added sodium cyanoacetate (2, 80 mg, 0.75 mmol). The mixture is degassed with argon for 5 min. Allylpalladium(II) chloride dimer (36 mg, 0.01 mmol), SPhos (12 mg, 0.03 mmol) are added and the mixture is degassed for another 5 min. The reaction is stirred at 140° C. for 6 h. After completion, the mixture is cooled to room temperature and concentrated. The crude is diluted with water and extracted with 5% methanol in dichloromethane. The organic layer is dried over sodium sulfate, filtered and concentrated. The crude is purified by flash column chromatography to afford N-(6-((7'-(cyanomethyl)-2'-(4-methoxybenzyl)-4'-methyl-3'-oxospiro[cyclohexane-1,1'-isoindolin]-6'-yl)amino)-5-methylpyrimidin-4-yl) cyclopropanecarboxamide (3).

Synthesis of 2-(6'-((6-amino-5-methylpyrimidin-4-yl)amino)-2'-(4-methoxybenzyl)-4'-methyl-3'-oxospiro[cyclohexane-1,1'-isoindolin]-7'-yl)acetonitrile (4)

The synthesis of intermediate 4 is carried out as described above using the general protocol of Procedure D.

Synthesis of 2-(6'-((6-amino-5-methylpyrimidin-4-yl)amino)-4'-methyl-3'-oxospiro [cyclohexane-1,1'-isoindolin]-7'-yl)acetonitrile (Cpd. No. 103)

The synthesis of compound 103 is carried out as described above using the general protocol of Procedure G.

Example 104

Synthesis of 6'-((6-amino-5-methylpyrimidin-4-yl)amino)-4'-methyl-7'-(trifluoromethyl)spiro[cyclohexane-1,1'-isoindolin]-3'-one (Cpd. No. 104)

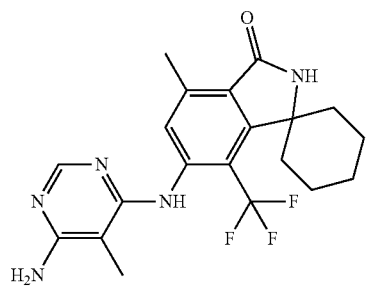

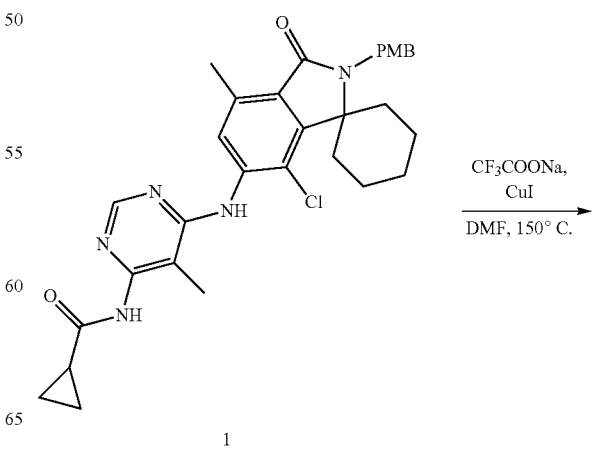

1

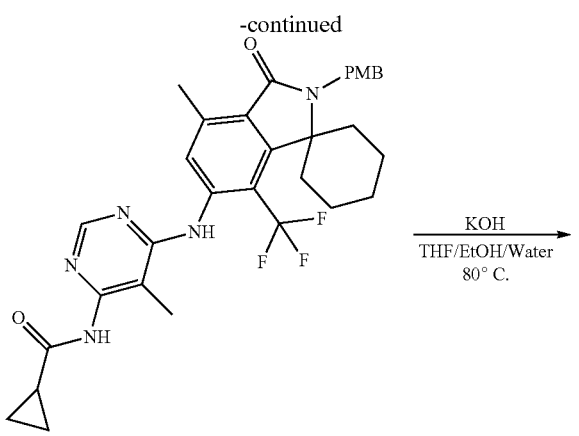

Synthesis of N-(6-((2'-(4-methoxybenzyl)-4'-methyl-3'-oxo-7'-(trifluoromethyl)spiro [cyclohexane-1,1'-isoindolin]-6'-yl)amino)-5-methylpyrimidin-4-yl)cyclopropane carboxamide (2)

To a solution of N-(6-((7'-chloro-2'-(4-methoxybenzyl)-4'-methyl-3'-oxospiro[cyclohexane-1,1'-isoindolin]-6'-yl) amino)-5-methylpyrimidin-4-yl)cyclopropanecarboxamide (1, 0.56 g, 1 mmol) in dimethylformamide (10 mL) are added sodium trifluoroacetate (0.27 g, 2 mmol) and copper (I) iodide (0.38 g, 2 mmol). The reaction is stirred at 140° C. for 16 h. After completion of reaction, the mixture is cooled to room temperature, diluted with water to and extract with 5% methanol in dichloromethane. The organic layer is dried over sodium sulfate, filtered and concentrated. The crude is purified by flash column chromatography to get N-(6-((2'-(4-methoxybenzyl)-4'-methyl-3'-oxo-7'-(trifluoromethyl)spiro[cyclohexane-1,1'-isoindolin]-6'-yl)amino)-5-methylpyrimidin-4-yl)cyclopropanecarboxamide (2).

Synthesis of 6'-((6-amino-5-methylpyrimidin-4-yl)amino)-2'-(4-methoxybenzyl)-4'-methyl-7'-(trifluoromethyl)spiro[cyclohexane-1,1'-isoindolin]-3'-one (3)

The synthesis of intermediate 3 is carried out as described above using the general protocol of Procedure D.

Synthesis of 6'-((6-amino-5-methylpyrimidin-4-yl)amino)-4'-methyl-7'-(trifluoromethyl) spiro[cyclohexane-1,1'-isoindolin]-3'-one (Cpd. No. 104)

The synthesis of compound 104 is carried out as described above using the general protocol of Procedure G.

Example 105

Synthesis of 5-((6-amino-5-methylpyrimidin-4-yl)amino)-7-methyl-1-oxoisoindoline-4-carbonitrile (Cpd. No. 105)

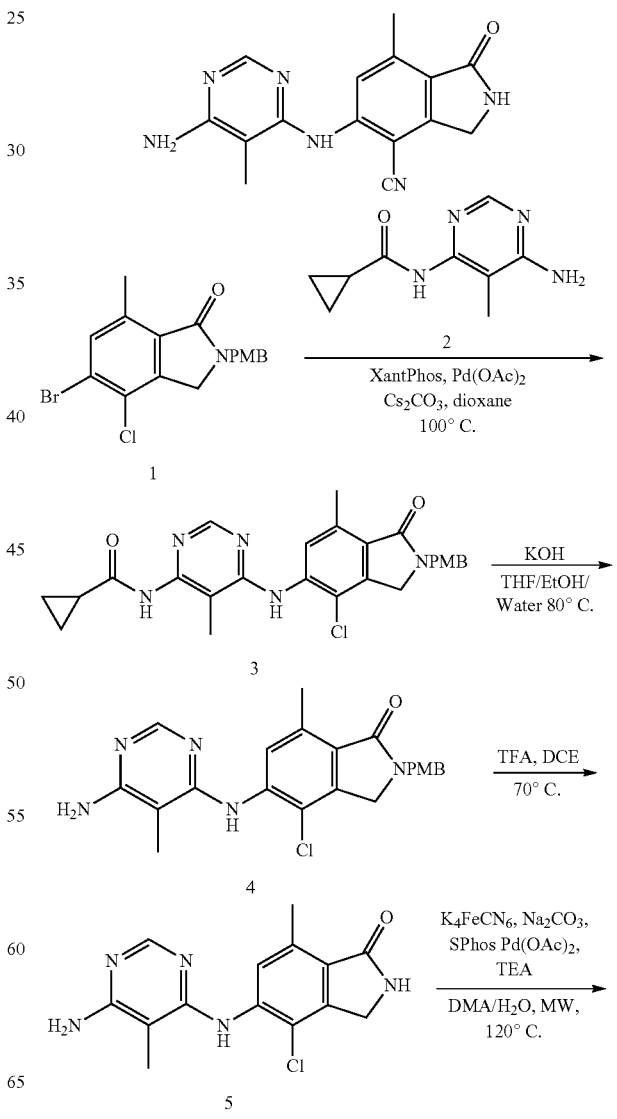

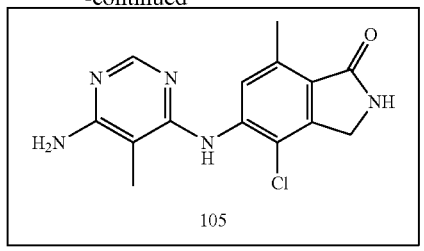

Synthesis of N-(6-((4-chloro-2-(4-methoxybenzyl)-7-methyl-1-oxoisoindolin-5-yl) amino)-5-methylpyrimidin-4-yl) cyclopropanecarboxamide (3)

The synthesis of intermediate 3 is carried out as described above using the general protocol of Procedure A.

Synthesis of 5-((6-amino-5-methylpyrimidin-4-yl) amino)-4-chloro-2-(4-methoxybenzyl)-7-methyl-isoindolin-1-one (4)

The synthesis of intermediate 4 is carried out as described above using the general protocol of Procedure D.

Synthesis of 5-((6-amino-5-methylpyrimidin-4-yl) amino)-4-chloro-7-methylisoindolin-1-one (5)

The synthesis of intermediate 5 is carried out as described above using the general protocol of Procedure G.

Synthesis of 5-((6-amino-5-methylpyrimidin-4-yl) amino)-7-methyl-1-oxoisoindoline-4-carbonitrile (Cpd. No. 105)

A mixture of 5-((6-amino-5-methylpyrimidin-4-yl) amino)-4-chloro-7-methylisoindolin-1-one (5, 0.30 g, 1 mmol), potassium ferrocyanide (1.84 g, 5 mmol), triethylamine (0.42 mL, 3 mmol) and sodium carbonate (0.21 g, 2 mmol) in N,N-dimethylacetamide and water (10 mL, 4:1) is purged with argon for 10 min. SPhos (0.82 g, 2 mmol) and palladium acetate (0.45 g, 2 mmol) are added and purging continues for another 5 min. The reaction is at 120° C. for 1 h under microwave. After completion, the reaction is diluted with 5% methanol in dichloromethane and passed through an alumina bed. The filtrate is concentrated and purified by prep HPLC to get 5-((6-amino-5-methylpyrimidin-4-yl) amino)-7-methyl-1-oxoisoindoline-4-carbonitrile (Cpd. No. 105).

Example 106

Synthesis of 5-((6-amino-5-methylpyrimidin-4-yl) amino)-7-methylisoindolin-1-one (Cpd. No. 106)

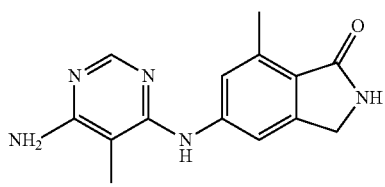

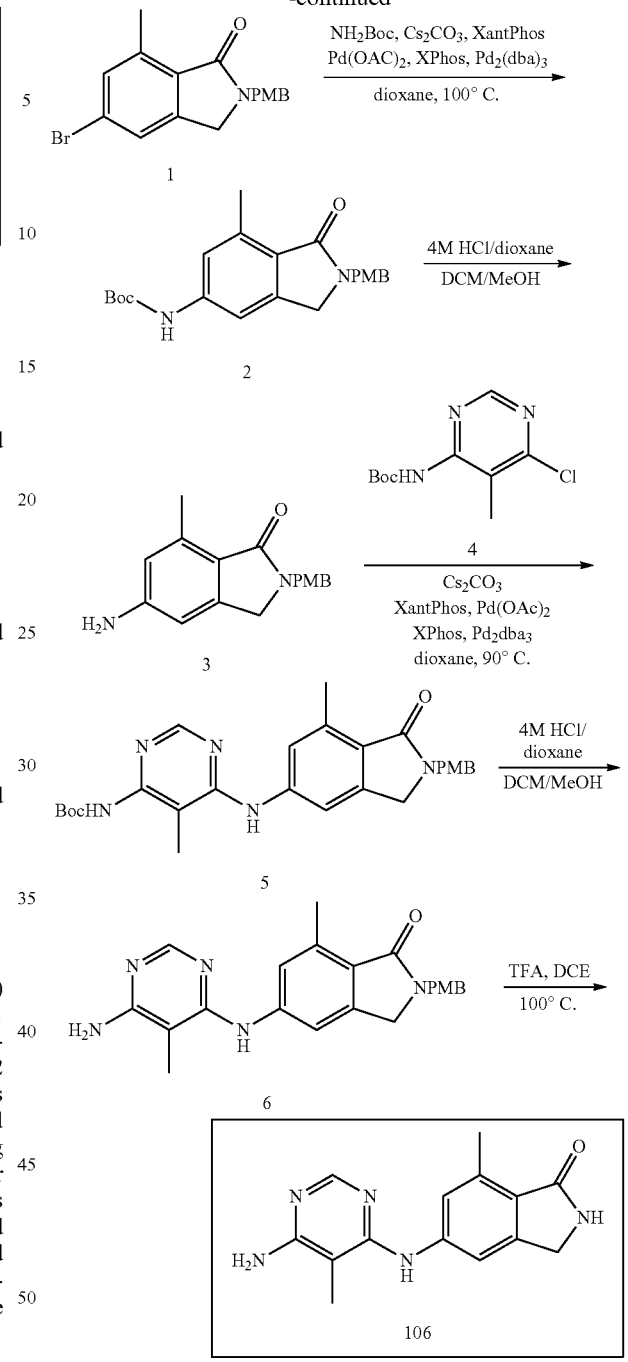

Synthesis of tert-butyl (2-(4-methoxybenzyl)-7-methyl-1-oxoisoindolin-5-yl)carbamate (2)

The synthesis of intermediate 2 is carried out as described above using the general protocol of Procedure A. Yellow solid; Yield: 0.8 g, 83%; MS (ESI) m/z 383 [M+1]$^+$.

Synthesis of 5-amino-2-(4-methoxybenzyl)-7-methylisoindolin-1-one (3)

To a solution of tert-butyl (2-(4-methoxybenzyl)-7-methyl-1-oxoisoindolin-5-yl)carbamate (2, 200 mg, 0.52 mmol) in dichloromethane (20 mL) and methanol (5 mL) at 0° C. was added 4 M hydrogen chloride in dioxane (5 mL). The reaction was stirred at room temperature for 16 h. After completion, solvent was removed under reduced pressure. The crude was then purified by flash column chromatography eluting with 2.5% methanol in dichloromethane to afford 5-amino-2-(4-methoxybenzyl)-7-methylisoindolin-1-one (3) as a yellow solid. Yield: 0.14 g, 95%; MS (ESI) m/z 283.2 [M+1]$^+$.

Synthesis of tert-butyl (6-((2-(4-methoxybenzyl)-7-methyl-1-oxoisoindolin-5-yl)amino)-5-methylpyrimidin-4-yl)carbamate (5)

The synthesis of intermediate 5 was carried out as described above using the general protocol of Procedure A. Yellow solid; Yield: 0.39 g, 62%; MS (ESI) m/z 590.3 [M+1]$^+$.

Synthesis of 5-((6-amino-5-methylpyrimidin-4-yl)amino)-2-(4-methoxybenzyl)-7-methylisoindolin-1-one (6)

To a solution of tert-butyl (6-((2-(4-methoxybenzyl)-7-methyl-1-oxoisoindolin-5-yl)amino)-5-methylpyrimidin-4-yl)carbamate (5, 0.38 g, 0.64 mmol) in dichloromethane (20 mL) and methanol (5 mL) at 0° C. was added 4 M hydrogent chloride in dioxane (10 mL). The reaction was stirred at room temperature for 16 h. After completion, the reaction mixture was cooled to room temperature and concentrated. The crude was washed with ether and dried under vacuum to afford 5-((6-amino-5-methylpyrimidin-4-yl)amino)-2-(4-methoxybenzyl)-7-methylisoindolin-1-one (6) as a yellow solid. Yield: 0.2 g, 80%; MS (ESI) m/z 390.1 [M+1]$^+$.

Synthesis of 5-((6-amino-5-methylpyrimidin-4-yl)amino)-7-methylisoindolin-1-one (Cpd. No. 106)

The synthesis of compound 106 was carried out as described above using the general protocol of Procedure G. Yellow solid; Yield: 30 mg, 16%; MS (ESI) m/z 270.11 [M+1]$^+$; $^1$H NMR: (400 MHz, DMSO-d$_6$) δ 9.11 (s, 1H), 8.32 (s, 1H), 8.25 (s, 1H), 7.50 (s, 1H), 7.25 (s, 1H), 4.27 (s, 2H), 2.49 (s, 3H), 2.04 (s, 2H).

Example 107

Synthesis of 6'-((2-amino-3-methylpyridin-4-yl)amino)-4'-methylspiro[cyclohexane-1,1'-pyrrolo[3,4-c]pyridin]-3'(2'H)-one (Cpd. No. 107)

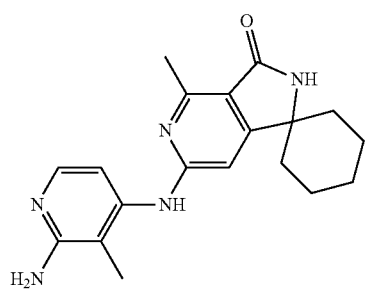

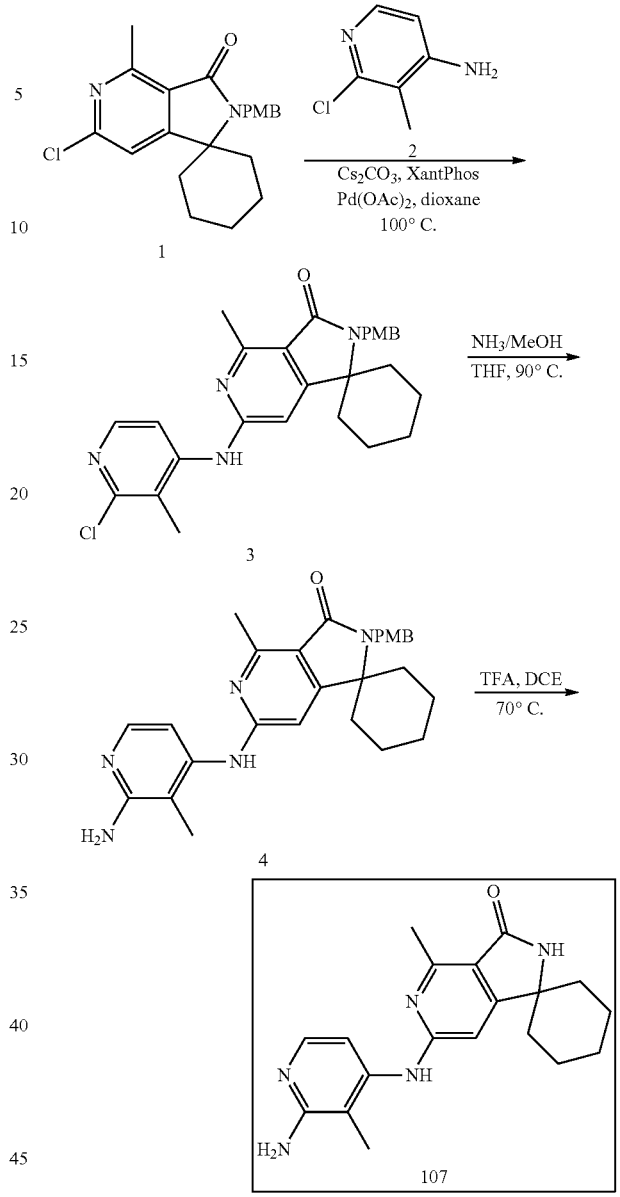

Synthesis of 6'-((2-chloro-3-methylpyridin-4-yl)amino)-2'-(4-methoxybenzyl)-4'-methylspiro[cyclohexane-1,1'-pyrrolo[3,4-c]pyridin]-3'(2'H)-one (3)

The synthesis of intermediate 3 is carried out as described above using the general protocol of Procedure A.

Synthesis of 6'-((2-amino-3-methylpyridin-4-yl)amino)-2'-(4-methoxybenzyl)-4'-methylspiro[cyclohexane-1,1'-pyrrolo[3,4-c]pyridin]-3'(2'H)-one (4)

To a solution of 6'-((2-chloro-3-methylpyridin-4-yl)amino)-2'-(4-methoxybenzyl)-4'-methylspiro[cyclohexane-1,1'-pyrrolo[3,4-c]pyridin]-3'(2'H)-one (3, 0.48 g, 1 mmol) in tetrahydrofuran (5 mL) at 0° C. is added methanolic ammonia (5 mL). The reaction is stirred at 90° C. for 16 h. After completion of reaction, the solvent is evaporated and the residue is triturated with water followed by diethyl ether and dried under reduced pressure to afford 6'-((2-amino-3-methylpyridin-4-yl)amino)-2'-(4-methoxybenzyl)-4'-methylspiro[cyclohexane-1,1'-pyrrolo[3,4-c]pyridin]-3'(2'H)-one (4).

Synthesis of 6'-((2-amino-3-methylpyridin-4-yl)amino)-4'-methylspiro[cyclohexane-1,1'-pyrrolo[3,4-c]pyridin]-3'(2'H)-one (Cpd. No. 107)

The synthesis of compound 107 is carried out as described above using the general protocol of Procedure G.

Example 108

Synthesis of 6'-((6-amino-5-methylpyrimidin-4-yl)amino)-2,2,4'-trimethylspiro[cyclohexane-1,1'-isoindolin]-3'-one (Cpd. No. 108)

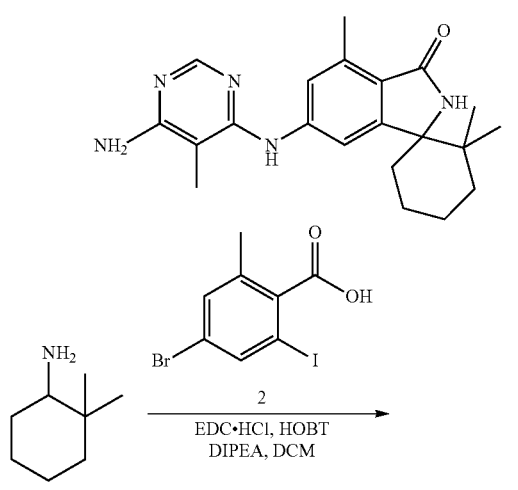

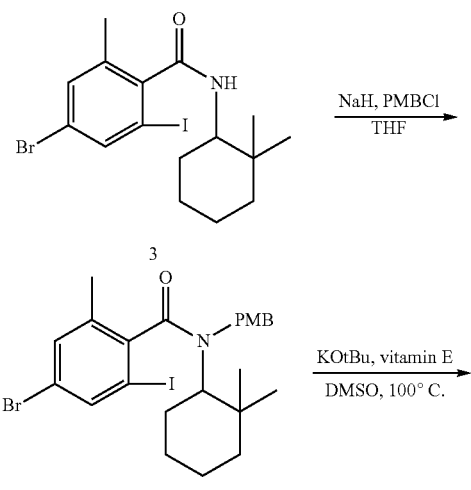

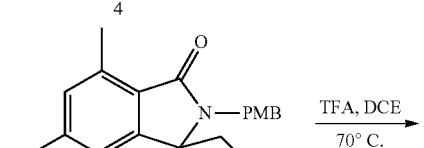

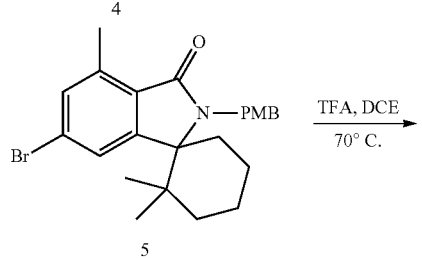

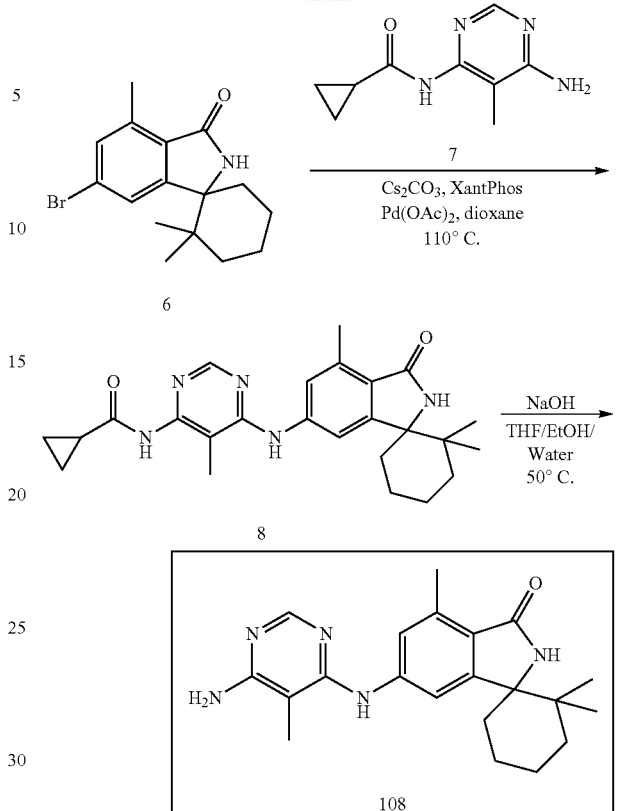

Synthesis of 4-bromo-N-(2,2-dimethylcyclohexyl)-2-iodo-6-methylbenzamide (3)

To a solution of 4-bromo-2-iodo-6-methylbenzoic acid (2, 0.34 g, 1 mmol) in dichloromethane (10 mL) are added 2,2-dimethylcyclohexan-1-amine (1, 0.13 g, 1 mmol), diisopropylethylamine (0.52 mL, 3 mmol), N-(3-dimethylaminopropyl)-N'-ethylcarbodiimide hydrochloride (0.38 g, 2 mmol) and 1-hydroxybenzotriazole (0.27 g, 2 mmol). The reaction is stirred at room temperature for 16 h. After completion of the reaction, the reaction is diluted with water and extract with 5% methanol in dichloromethane. The organic layer dried over anhydrous sodium sulphate, filtered and concentrated. The crude is purified by flash column chromatography to get 4-bromo-N-(2,2-dimethylcyclohexyl)-2-iodo-6-methylbenzamide (3).

Synthesis of 4-bromo-N-(2,2-dimethylcyclohexyl)-2-iodo-N-(4-methoxybenzyl)-6-methylbenzamide (4)

To a solution of 4-bromo-N-(2,2-dimethylcyclohexyl)-2-iodo-6-methylbenzamide (3, 0.45 g, 1 mmol) in tetrahydrofuran (10 mL) at 0° C. is added sodium hydride (48 mg, 2 mmol). The reaction mixture is stirred at room temperature for 10 min before 4-methoxybenzyl chloride (0.16 mL, 1.2 mmol) is added. The reaction is stirred at room temperature for 4 h. After completion of reaction, the reaction is quenched with water and extracted with ethyl acetate. The organic layer is dried over anhydrous sodium sulfate, filtered and concentrated. The crude is purified by flash column chromatography to get 4-bromo-N-(2,2-dimethylcyclohexyl)-2-iodo-N-(4-methoxybenzyl)-6-methylbenzamide (4).

Synthesis of 6'-bromo-2'-(4-methoxybenzyl)-2,2,4'-trimethylspiro[cyclohexane-1,1'-isoindolin]-3'-one (5)

To a solution of 4-bromo-N-(2,2-dimethylcyclohexyl)-2-iodo-N-(4-methoxybenzyl)-6-methylbenzamide (4, 0.57 g, 1 mmol) and vitamin E (22 mg, 0.05 mmol) in dimethyl sulfoxide (10 mL) is added potassium tert-butoxide (0.34 g, 3 mmol). The reaction is stirred at 100° C. for 16 h. After completion of the reaction, the reaction mixture is diluted with water and extracted with 5% methanol in dichloromethane. The organic layer is dried over anhydrous sodium sulphate, filtered and concentrated. The crude is purified by flash column chromatography to get 6'-bromo-2'-(4-methoxybenzyl)-2,2,4'-trimethylspiro[cyclohexane-1,1'-isoindolin]-3'-one (5).

Synthesis of 6'-bromo-2,2,4'-trimethylspiro[cyclohexane-1,1'-isoindolin]-3'-one (6)

The synthesis of intermediate 6 is carried out as described above using the general protocol of Procedure G.

Synthesis of N-(5-methyl-6-((2,2,4'-trimethyl-3'-oxospiro[cyclohexane-1,1'-isoindolin]-6'-yl)amino)pyrimidin-4-yl)cyclopropanecarboxamide (8)

The synthesis of intermediate 8 is carried out as described above using the general protocol of Procedure A.

Synthesis of 6'-((6-amino-5-methylpyrimidin-4-yl)amino)-2,2,4'-trimethylspiro[cyclohexane-1,1'-isoindolin]-3'-one (Cpd. No. 109)

The synthesis of compound 109 is carried out as described above using the general protocol of Procedure D.

Example 109

Synthesis of 6'-((6-amino-5-methylpyrimidin-4-yl)amino)-2,2-difluoro-4'-methylspiro[cyclohexane-1,1'-isoindolin]-3'-one (Cpd. No. 109)

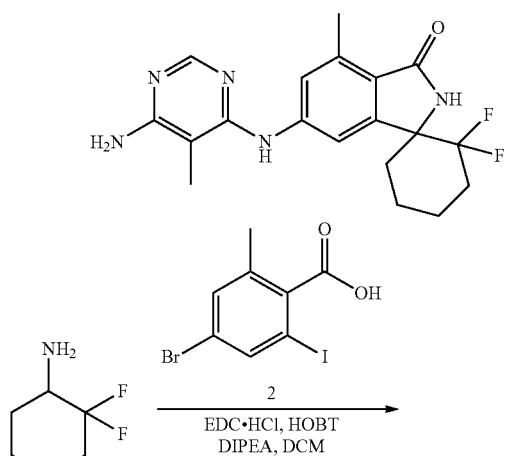

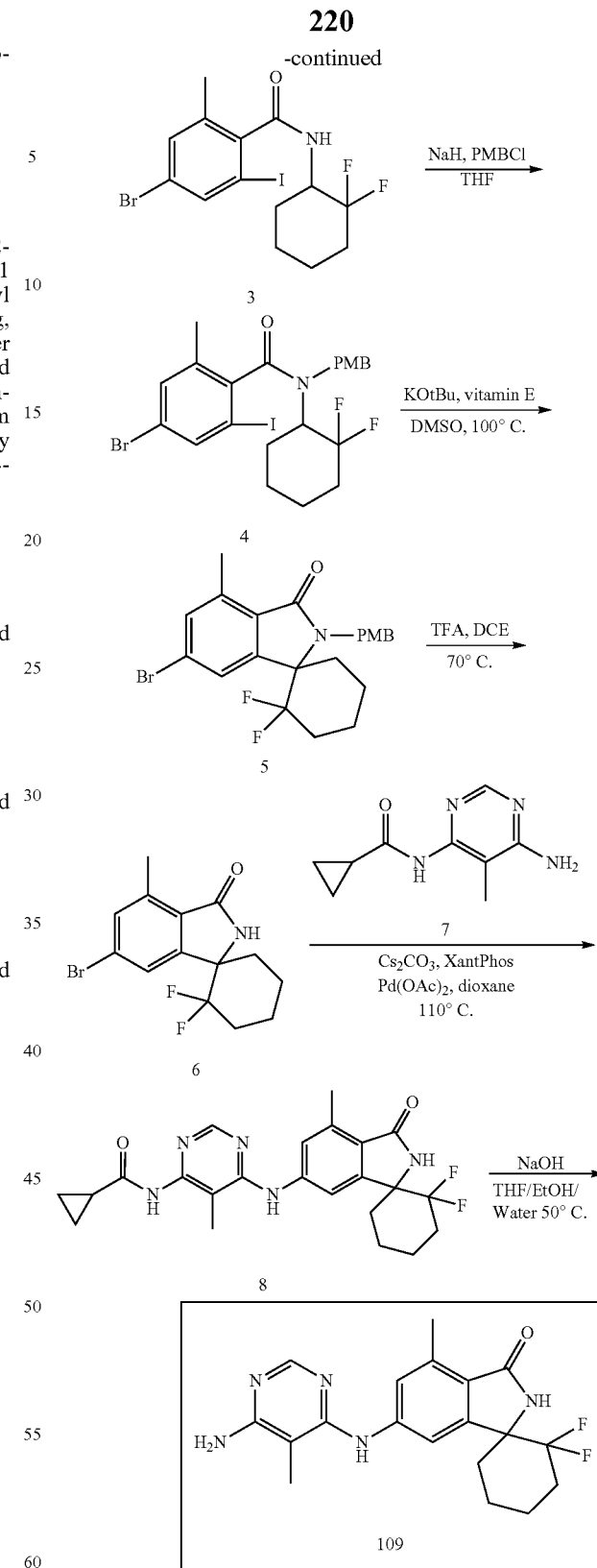

Synthesis of 4-bromo-N-(2,2-difluorocyclohexyl)-2-iodo-6-methylbenzamide (3)

To a solution of 4-bromo-2-iodo-6-methylbenzoic acid (2, 0.34 g, 1 mmol) in dichloromethane (10 mL) are added 2,2-difluorocyclohexan-1-amine (1, 0.14 g, 1 mmol), diisopropylethylamine (0.52 mL, 3 mmol), N-(3-dimethylaminopropyl)-N'-ethylcarbodiimide hydrochloride (0.38 g, 2 mmol) and 1-hydroxybenzotriazole (0.27 g, 2 mmol). The reaction is stirred at room temperature for 16 h. After completion of the reaction, the reaction is diluted with water and extract with 5% methanol in dichloromethane. The organic layer dried over anhydrous sodium sulphate, filtered and concentrated. The crude is purified by flash column chromatography to get 4-bromo-N-(2,2-difluorocyclohexyl)-2-iodo-6-methylbenzamide (3).

Synthesis of 4-bromo-N-(2,2-difluorocyclohexyl)-2-iodo-N-(4-methoxybenzyl)-6-methylbenzamide (4)

To a solution of 4-bromo-N-(2,2-difluorocyclohexyl)-2-iodo-6-methylbenzamide (3, 0.46 g, 1 mmol) in tetrahydrofuran (10 mL) at 0° C. is added sodium hydride (48 mg, 2 mmol). The reaction mixture is stirred at room temperature for 10 min before 4-methoxybenzyl chloride (0.16 mL, 1.2 mmol) is added. The reaction is stirred at room temperature for 4 h. After completion of reaction, the reaction is quenched with water and extracted with ethyl acetate. The organic layer is dried over anhydrous sodium sulfate, filtered and concentrated. The crude is purified by flash column chromatography to get 4-bromo-N-(2,2-difluorocyclohexyl)-2-iodo-N-(4-methoxybenzyl)-6-methylbenzamide (4).

Synthesis of 6'-bromo-2,2-difluoro-2'-(4-methoxybenzyl)-4'-methylspiro[cyclohexane-1,1'-isoindolin]-3'-one (5)

To a solution of 4-bromo-N-(2,2-difluorocyclohexyl)-2-iodo-N-(4-methoxybenzyl)-6-methylbenzamide (4, 0.58 g, 1 mmol) and vitamin E (22 mg, 0.05 mmol) in dimethyl sulfoxide (10 mL) is added potassium tert-butoxide (0.34 g, 3 mmol). The reaction is stirred at 100° C. for 16 h. After completion of the reaction, the reaction mixture is diluted with water and extracted with 5% methanol in dichloromethane. The organic layer is dried over anhydrous sodium sulphate, filtered and concentrated. The crude is purified by flash column chromatography to get 6'-bromo-2,2-difluoro-2'-(4-methoxybenzyl)-4'-methylspiro[cyclohexane-1,1'-isoindolin]-3'-one (5).

Synthesis of 6'-bromo-2,2-difluoro-4'-methylspiro[cyclohexane-1,1'-isoindolin]-3'-one (6)

The synthesis of intermediate 6 is carried out as described above using the general protocol of Procedure G.

Synthesis of N-(6-((2,2-difluoro-4'-methyl-3'-oxospiro[cyclohexane-1,1'-isoindolin]-6'-yl)amino)-5-methylpyrimidin-4-yl)cyclopropanecarboxamide (8)

The synthesis of intermediate 8 is carried out as described above using the general protocol of Procedure A.

Synthesis of 6'-((6-amino-5-methylpyrimidin-4-yl)amino)-2,2-difluoro-4'-methylspiro[cyclohexane-1,1'-isoindolin]-3'-one (Cpd. No. 109)

The synthesis of compound 109 is carried out as described above using the general protocol of Procedure D.

Example 110

Synthesis of 6'-((6-amino-5-methylpyrimidin-4-yl)amino)-4'-methylspiro[cyclohexane-1,1'-inden]-3'(2'H)-one (Cpd. No. 110)

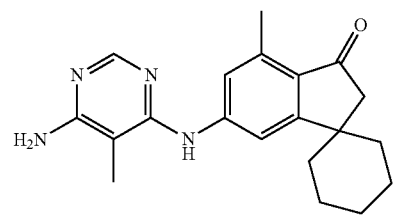

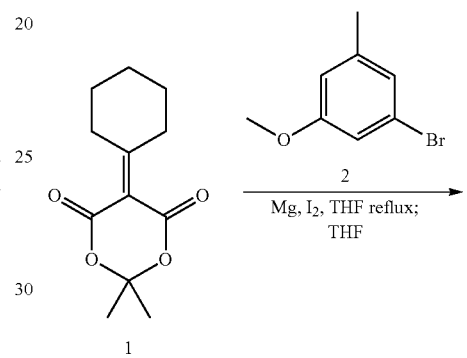

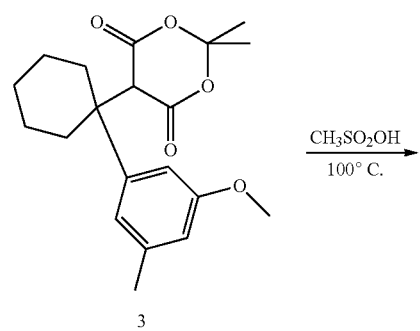

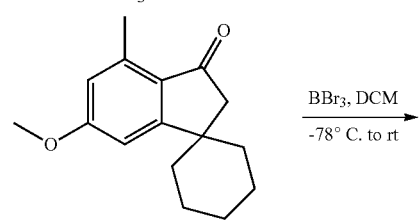

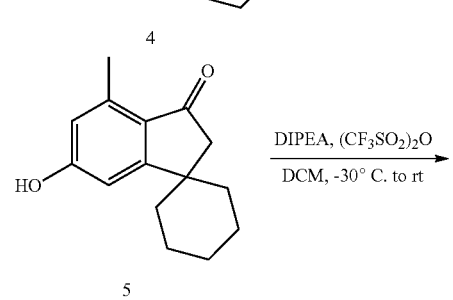

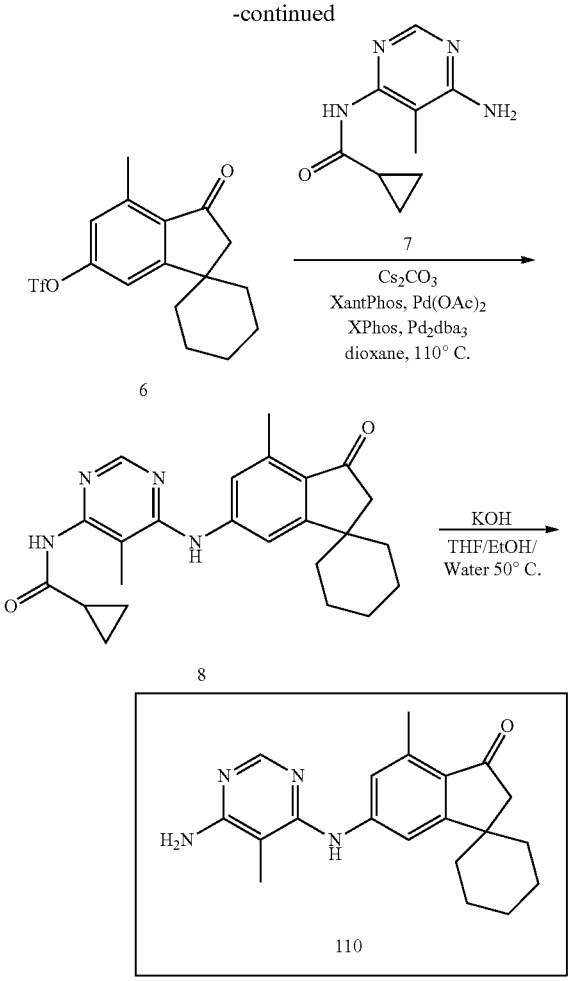

Synthesis of 5-(1-(3-methoxy-5-methylphenyl)cyclohexyl)-2,2-dimethyl-1,3-dioxane-4,6-dione (3)

A solution of 1-bromo-3-methoxy-5-methylbenzene (2, 8.0 g, 39.80 mmol) in tetrahydrofuran (20 mL) was added dropwise to a flask containing Mg turnings (1.36 g, 55.72 mmol) in tetrahydrofuran (30 mL). Catalytic iodine was added to the mixture and refluxed the reaction for 2 h.

To a solution of 5-cyclohexylidene-2,2-dimethyl-1,3-dioxane-4,6-dione (1, 8.0 g, 35.71 mmol) in tetrahydrofuran (50 mL) at 0° C., freshly prepared (3-methoxy-5-methylphenyl)magnesium bromide was added slowly. The reaction was allowed to stir at room temperature for 12 h. On completion, the reaction mixture was quenched with 1 M hydrochloric acid and extracted with ethyl acetate (100 mL). The organic layer was washed with water and brine, dried over anhydrous sodium sulfate, filtered and concentrated to afford 5-(1-(3-methoxy-5-methylphenyl)cyclohexyl)-2,2-dimethyl-1,3-dioxane-4,6-dione as a colorless liquid. Yield: 8.0 g, crude; MS (ESI) m/z 347.12 [M+1]$^+$.

Synthesis of 6'-methoxy-4'-methylspiro[cyclohexane-1,1'-inden]-3'(2'H)-one (4)

A solution of 5-(1-(3-methoxy-5-methylphenyl)cyclohexyl)-2,2-dimethyl-1,3-dioxane-4,6-dione (8.0 g, 23.18 mmol) in methane sulfonic acid (50 mL) in a 250 mL flask was heated at 100° C. for 8 h. After completion, the reaction was quenched with saturated aqueous sodium bicarbonate solution to pH 8 and extracted with ethyl acetate (2×100 mL). The combined organics was then dried over sodium sulfate and concentrated to dryness under vacuum. The crude was then purified by flash column chromatography eluting with 5% ethyl acetate in hexane. The desired fractions were concentrated to dryness under vacuum to afford the 6'-methoxy-4'-methylspiro[cyclohexane-1,1'-inden]-3'(2'H)-one (4) as a colorless liquid. Yield: 2.4 g, 42%; MS (ESI) m/z 245.15 [M+1]$^+$.

Synthesis of 6'-hydroxy-4'-methylspiro[cyclohexane-1,1'-inden]-3'(2'H)-one (5)

To a solution of 6'-methoxy-4'-methylspiro[cyclohexane-1,1'-inden]-3'(2'H)-one (4, 2.4 g, 9.8 mmol) in dichloromethane (30 mL) at −78° C. was added slowly boron tribromide (4.91 g, 19.67 mmol). The reaction was allowed to stir at room temperature for 16 h. After completion, the reaction mixture was quenched with saturated aqueous sodium bicarbonate solution to adjust to pH 8. The mixture was extracted with dichloromethane (2×30 mL). The combined organics was dried over sodium sulfate, filtered and concentrated. The crude was then purified by flash column chromatography eluting with 10% ethyl acetate in hexane. The desired fractions were concentrated to dryness under vacuum to afford the 6'-hydroxy-4'-methylspiro[cyclohexane-1,1'-inden]-3'(2'H)-one (5) as a colorless liquid. Yield: 1.50 g, 66%; MS (ESI) m/z 231.07 [M+1]$^+$.

Synthesis of 4'-methyl-3'-oxo-2',3'-dihydrospiro[cyclohexane-1,1'-inden]-6'-yl trifluoromethanesulfonate (6)

To a solution of 6'-hydroxy-4'-methylspiro[cyclohexane-1,1'-inden]-3'(2'H)-one (5, 1.50 g, 6.55 mmol) in dichloromethane (15 mL) at −30° C., diisopropylethylamine (1.44 g, 11.13 mmol) was added followed by the slow addition of triflic anhydride (2.03 g, 7.20 mmol). The reaction was allowed to stir at room temperature for 1 h. After completion, the reaction mixture was basified by saturated aqueous sodium bicarbonate solution to pH 8. The mixture was extracted with dichloromethane (2×10 mL). The combined organics was dried over sodium sulfate, filtered and concentrated to dryness under vacuum. The crude was then purified by flash column chromatography eluting with 5% ethyl acetate in hexane. The desired fractions were concentrated to dryness under vacuum to afford the 4'-methyl-3'-oxo-2',3'-dihydrospiro[cyclohexane-1,1'-inden]-6'-yl trifluoromethanesulfonate (6) as a colorless liquid. Yield: 1.10 g, 47%; $^1$H NMR (400 MHz, CDCl$_3$) δ 7.19 (s, 1H), 7.00 (s, 1H), 2.66 (s, 3H), 2.61 (s, 2H), 1.82 (m, 2H), 1.68 (m, 2H), 1.56 (m, 3H), 1.42 (m, 3H).

Synthesis of N-(5-methyl-6-((4'-methyl-3'-oxo-2',3'-dihydrospiro[cyclohexane-1,1'-inden]-6'-yl)amino)pyrimidin-4-yl)cyclopropanecarboxamide (8)

The synthesis of intermediate 8 was carried out as described above using the general protocol of Procedure A. Off-white solid; Yield: 1.10 g, crude; MS (ESI) m/z 405.14 [M+1]$^+$.

Synthesis of 6'-((6-amino-5-methylpyrimidin-4-yl)amino)-4'-methylspiro[cyclohexane-1,1'-inden]-3'(2'H)-one (Cpd. No. 110)

The synthesis of compound 110 was carried out as described above using the general protocol of Procedure D.

White solid; Yield: 0.090 g, 10%; MS (ESI) m/z 337.25 [M+1]+; 1H NMR (400 MHz, DMSO-d6) δ 9.10 (s, 1H), 8.28 (s, 1H), 7.51 (s, 1H), 7.47 (s, 2H), 7.31 (s, 1H), 2.46 (s, 3H), 2.44 (s, 2H), 2.03 (s, 3H), 1.63 (m, 5H), 1.38 (m, 4H), 1.20 (m, 1H).

Example 111

Synthesis of 2'-((6-amino-5-methylpyrimidin-4-yl)amino)-4'-methylspiro[cyclohexane-1,7'-cyclopenta[b]pyridin]-5'(6'H)-one (Cpd. No. 111)

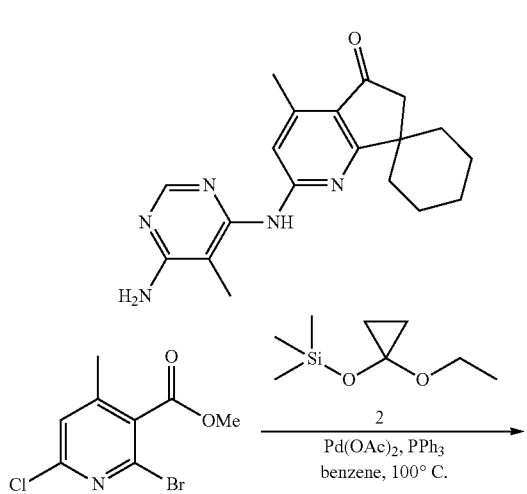

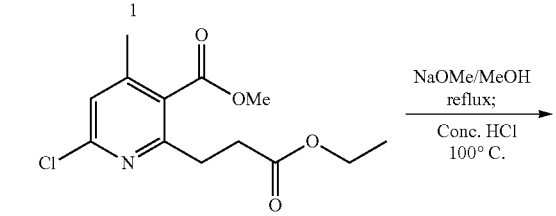

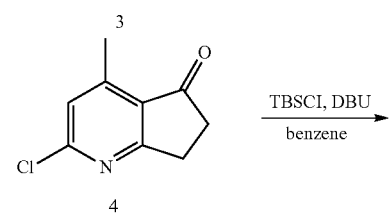

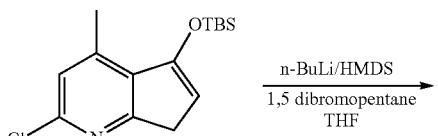

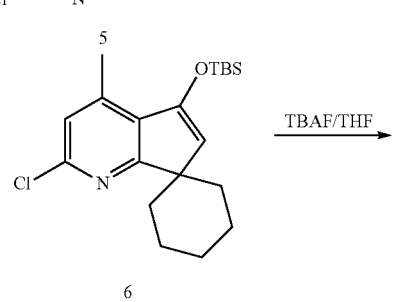

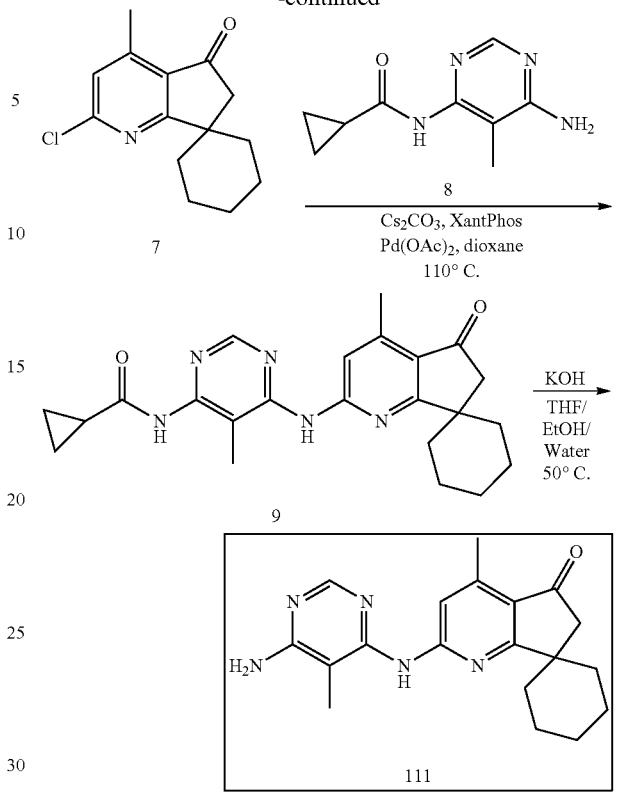

Synthesis of methyl 6-chloro-2-(3-ethoxy-3-oxopropyl)-4-methylnicotinate (3)

A mixture of methyl 2-bromo-6-chloro-4-methylnicotinate (1, 0.26 g, 1 mmol), (1-ethoxycyclopropoxy)trimethylsilane (2, 0.26 g, 1.5 mmol), triphenylphosphine (52 mg, 0.2 mmol), palladium (II) acetate (22 mg, 0.10 mmol) in benzene (10 mL) is purged with argon for 5 min. The reaction is stirred at 100° C. for 5 h. The mixture is cooled to room temperature and filtered through a thin layer of celite. The mixture is diluted with ethyl acetate and washed with saturated aqueous sodium bicarbonate. The organic layer is dried over sodium sulfate, filtered and concentrated. The residue is purified by column chromatography to get methyl 6-chloro-2-(3-ethoxy-3-oxopropyl)-4-methylnicotinate (3).

Synthesis of 2-chloro-4-methyl-6,7-dihydro-5H-cyclopenta[b]pyridin-5-one (4)

To a solution of methyl 6-chloro-2-(3-methoxy-3-oxopropyl)-4-methylnicotinate (3, 0.27 g, 1 mmol) in methanol (10 mL) at 0° C. is added sodium methoxide (0.11 g, 2 mmol). The reaction is stirred at reflux for 3 h. After cooling to room temperature, the solvent is remove and the residue is dissolved in concentrated hydrochloric acid (20 mL) in an ice bath. The resulting mixture is stirred at 100° C. for 2 h. After removing the solvent under reduced pressure, the residue is partitioned between dichloromethane and saturated aqueous sodium bicarbonate solution. The organic layer is dried over sodium sulfate, filtered and concentrated. The crude is purified by column chromatography to get 2-chloro-4-methyl-6,7-dihydro-5H-cyclopenta[b]pyridin-5-one (4).

Synthesis of 5-((tert-butyldimethylsilyl)oxy)-2-chloro-4-methyl-7H-cyclopenta[b]pyridine (5)

To a stirred solution of 2-chloro-4-methyl-6,7-dihydro-5H-cyclopenta[b]pyridin-5-one (4, 0.18 g, 1 mmol) in benzene (15 mL) are added tert-butylchlorodimethylsilane (0.23 g, 1.5 mmol) and 1,8-diazabicyclo[5.4.0]undec-7-ene (0.30 mL, 2 mmol). The reaction is stirred at room temperature for 14 h. After completion, the reaction mixture is diluted with water (25 mL) and extracted with dichloromethane (2×50 mL). The solvent is removed under reduced pressure and purified by column chromatography to get 5-((tert-butyldimethylsilyl)oxy)-2-chloro-4-methyl-7H-cyclopenta[b]pyridine (5).

Synthesis of 5'-((tert-butyldimethylsilyl)oxy)-2'-chloro-4'-methylspiro[cyclohexane-1,7'-cyclopenta[b]pyridine] (6)

To a solution of hexamethyldisilazane (0.32 g, 2 mmol) in tetrahydrofuran (10 mL) at 0° C. is added n-butyllithium (2.5 M in hexanes) (1.2 mL, 3 mmol). The reaction is stirred at 0° C. for 1 h before adding 5-((tert-butyldimethylsilyl)oxy)-2-chloro-4-methyl-7H-cyclopenta[b]pyridine (0.30 g, 1 mmol) in tetrahydrofuran (5 mL). The reaction is stirred at 0° C. for 1 h. A solution of 1,5-dibromopentane (0.14 mL, 1 mmol) in tetrahydrofuran (5 mL) is added. After overnight stirring at room temperature the reaction is quenched with water and extracted with ethyl acetate. The organic layer is dried over sodium sulfate, filtered and concentrated. The crude is purified by flash column chromatography to get 5'-((tert-butyldimethylsilyl)oxy)-2'-chloro-4'-methylspiro[cyclohexane-1,7'-cyclopenta[b]pyridine] (6).

Synthesis of 2'-chloro-4'-methylspiro[cyclohexane-1,7'-cyclopenta[b]pyridin]-5'(6'H)-one (7)

To a solution of 5'-((tert-butyldimethylsilyl)oxy)-2'-chloro-4'-methylspiro[cyclohexane-1,7'-cyclopenta[b]pyridine] (0.36 g, 1 mmol) in tetrahydrofuran (15 mL) is added tetrabutylammonium fluoride (1 M in THF) (2 mL, 2 mmol). The reaction is stirred at room temperature for 14 h. After completion the reaction mixture is diluted with water and extracted with dichloromethane (2×15 mL). The organic layer is dried over sodium sulfate, filtered and concentrated. The crude is purified by flash column chromatography to get 2'-chloro-4'-methylspiro[cyclohexane-1,7'-cyclopenta[b]pyridin]-5'(6'H)-one (7).

Synthesis of N-(5-methyl-6-((4'-methyl-5'-oxo-5',6'-dihydrospiro[cyclohexane-1,7'-cyclopenta[b]pyridin]-2'-yl)amino)pyrimidin-4-yl)cyclopropanecarboxamide (9)

The synthesis of intermediate 9 is carried out as described above using the general protocol of Procedure A.

Synthesis of 2'-((6-amino-5-methylpyrimidin-4-yl)amino)-4'-methylspiro[cyclohexane-1,7'-cyclopenta[b]pyridin]-5'(6'H)-one (Cpd. No. 111)

The synthesis of compound 111 is carried out as described above using the general protocol of Procedure D.

Example 112

Synthesis of N⁴-(3',4'-dimethyl-2',3'-dihydrospiro[cyclohexane-1,1'-inden]-6'-yl)-5-methylpyrimidine-4,6-diamine (Cpd. No. 112)

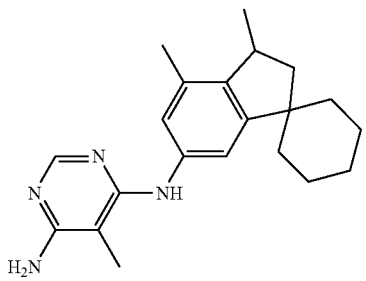

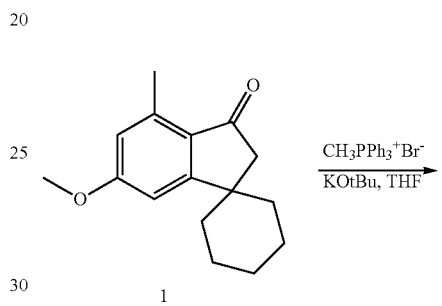

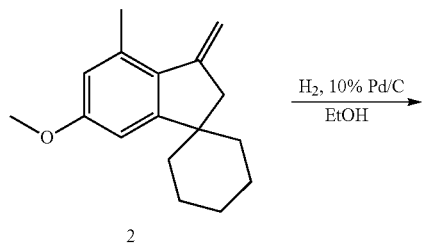

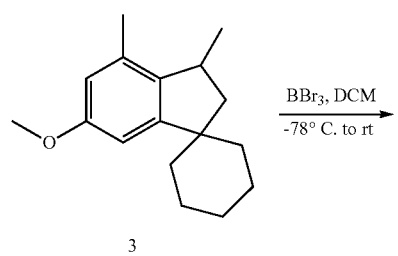

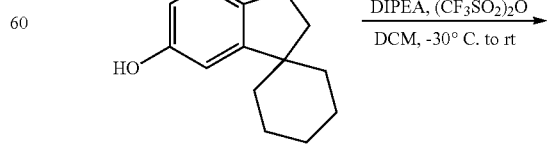

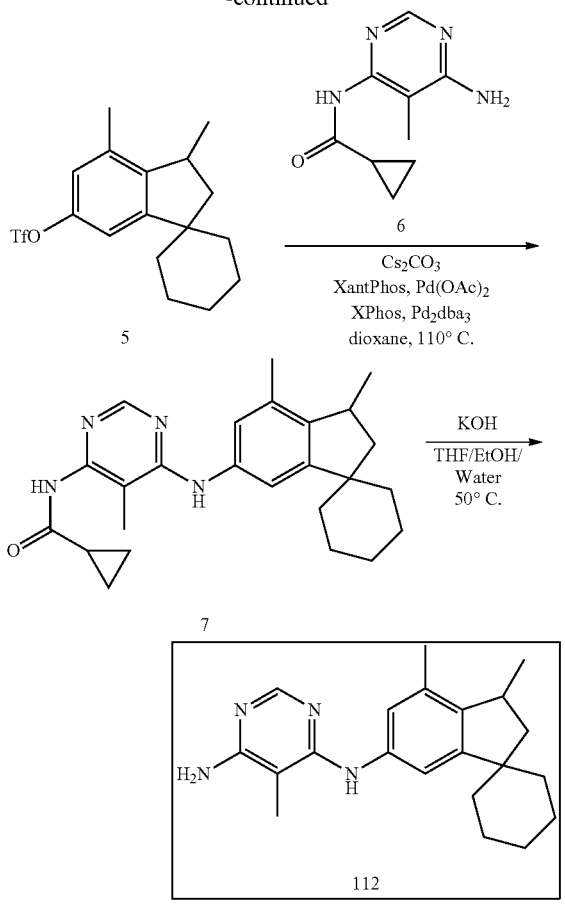

Synthesis of 6'-methoxy-4'-methyl-3'-methylene-2',3'-dihydrospiro[cyclohexane-1,1'-indene](2)

To a suspension of potassium tert-butoxide (1.75 g, 15.60 mmol) in tetrahydrofuran (20 mL) is added methyltriphenylphosphonium bromide (5.46 g, 15.28 mmol). The reaction is stirred at room temperature for 1 h and then cooled to 0° C. A solution of 6'-methoxy-4'-methylspiro[cyclohexane-1,1'-inden]-3'(2'H)-one (1, 3.15 g, 12.89 mmol) in tetrahydrofuran (10 mL) is added. The mixture is stirred at room temperature for 16 h, poured into water and extracted with ethyl acetate. The organic phase is dried over magnesium sulfate, filtered and concentrated. Purification via column chromatography affords 6'-methoxy-4'-methyl-3'-methylene-2',3'-dihydrospiro[cyclohexane-1,1'-indene] (2).

Synthesis of 6'-methoxy-3',4'-dimethyl-2',3'-dihydrospiro[cyclohexane-1,1'-indene] (3)

To a solution of 6'-methoxy-4'-methyl-3'-methylene-2',3'-dihydrospiro[cyclohexane-1,1'-indene] (2, 1.00 g, 4.13 mmol) in ethanol (20 mL) is added 10% palladium on carbon (100 mg). The reaction is purged with hydrogen and stirred at room temperature overnight. The mixture is filtered through a pad of celite, concentrated and purified via column chromatography to afford 6'-methoxy-3',4'-dimethyl-2',3'-dihydrospiro[cyclohexane-1,1'-indene] (3).

Synthesis of 3',4'-dimethyl-2',3'-dihydrospiro[cyclohexane-1,1'-inden]-6'-ol (4)

To a solution of 6'-methoxy-3',4'-dimethyl-2',3'-dihydrospiro[cyclohexane-1,1'-indene] (3, 1.00 g, 4.09 mmol) in dichloromethane (20 mL) at −78° C. is added slowly boron tribromide (0.79 mL, 8.18 mmol). The reaction is allowed to stir at room temperature for 16 h. After completion, the reaction mixture is quenched with saturated aqueous sodium bicarbonate solution to adjust to pH 8. The mixture is extracted with dichloromethane (2×30 mL). The combined organics is dried over sodium sulfate, filtered and concentrated. The crude is then purified via column chromatography to afford 3',4'-dimethyl-2',3'-dihydrospiro[cyclohexane-1,1'-inden]-6'-ol (4).

Synthesis of 3',4'-dimethyl-2',3'-dihydrospiro[cyclohexane-1,1'-inden]-6'-yl trifluoromethanesulfonate (5)

To a solution of 3',4'-dimethyl-2',3'-dihydrospiro[cyclohexane-1,1'-inden]-6'-ol (4, 1.00 g, 4.34 mmol) in dichloromethane (15 mL) at −30° C., diisopropylethylamine (1.28 mL, 7.38 mmol) is added followed by the slow addition of triflic anhydride (0.80 mL, 4.77 mmol). The reaction is allowed to stir at room temperature for 1 h. After completion, the reaction mixture is basified by saturated aqueous sodium bicarbonate solution to pH 8. The mixture is extracted with dichloromethane (2×10 mL). The combined organics is dried over sodium sulfate, filtered and concentrated to dryness under vacuum. The crude is then purified via column chromatography to afford 3',4'-dimethyl-2',3'-dihydrospiro[cyclohexane-1,1'-inden]-6'-yl trifluoromethanesulfonate (5).

Synthesis of N-(6-((3',4'-dimethyl-2',3'-dihydrospiro[cyclohexane-1,1'-inden]-6'-yl)amino)-5-methylpyrimidin-4-yl)cyclopropanecarboxamide (7)

The synthesis of intermediate 7 is carried out as described above using the general protocol of Procedure A.

Synthesis of $N^4$-(3',4'-dimethyl-2',3'-dihydrospiro[cyclohexane-1,1'-inden]-6'-yl)-5-methylpyrimidine-4,6-diamine (Cpd. No. 112)

The synthesis of compound 112 is carried out as described above using the general protocol of Procedure D.

Example 113

Synthesis of 5-methyl-$N^4$-(3',3',4'-trimethyl-2',3'-dihydrospiro[cyclohexane-1,1'-inden]-6'-yl)pyrimidine-4,6-diamine (Cpd. No. 113)

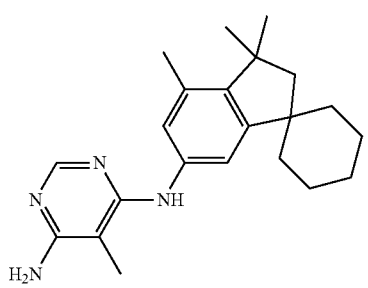

231

-continued

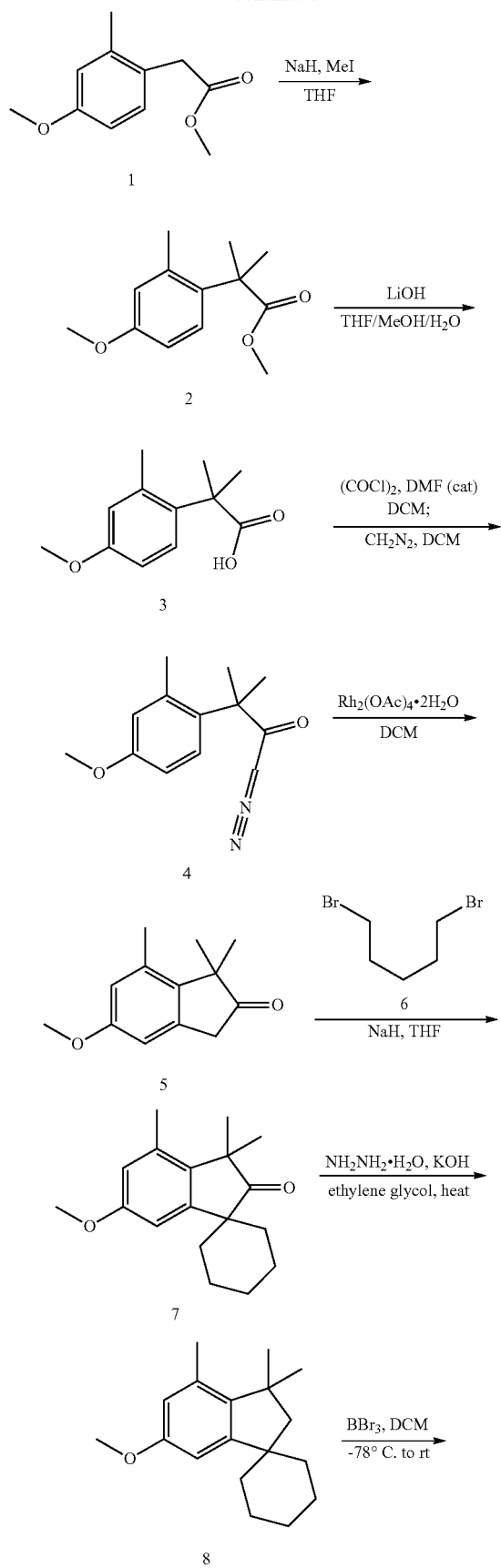

232

-continued

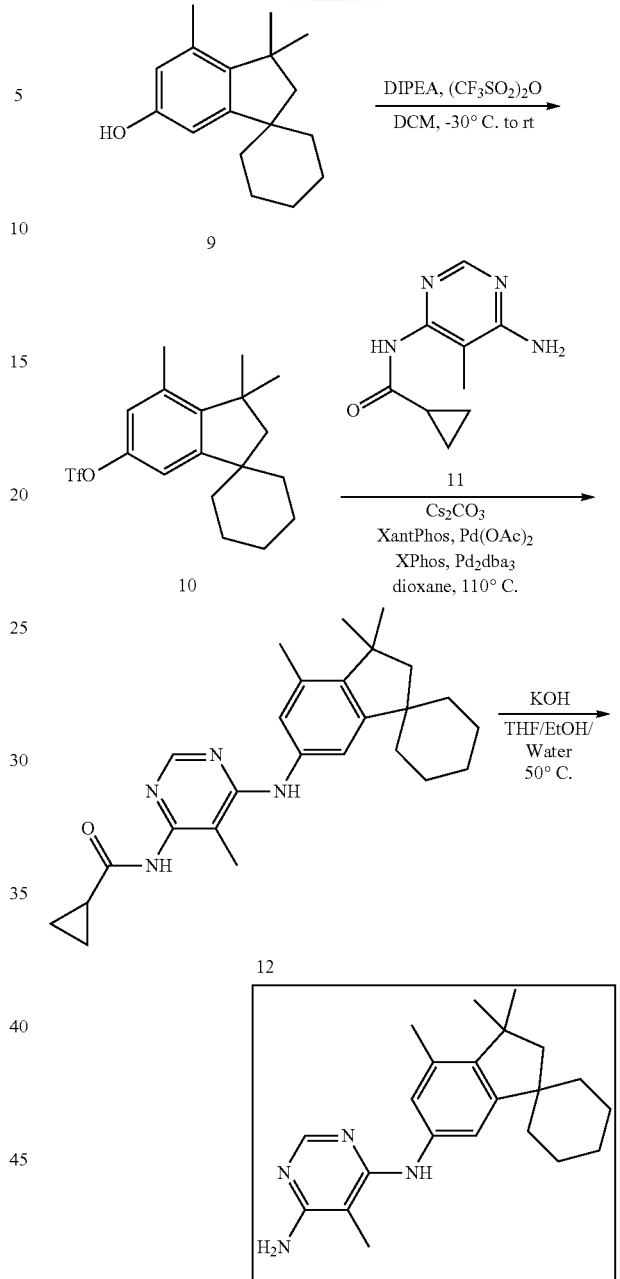

Synthesis of methyl
2-(4-methoxy-2-methylphenyl)-2-methylpropanoate
(2)

To a solution of methyl 2-(4-methoxy-2-methylphenyl) acetate (1, 1.00 g, 5.15 mmol) in tetrahydrofuran (20 mL) at 0° C., sodium hydride (0.31 g, 12.88 mmol) is added portion wise and the reaction mixture is allowed to stir at room temperature for 30 min. Iodomethane (0.96 mL, 15.45 mmol) is added and the reaction mixture is allowed to stir at 70° C. for 16 h. The reaction mixture is quenched with water and is extracted in ethyl acetate. The organic layer is separated, dried over sodium sulphate, filtered and concentrated under reduced pressure. The residue is purified by silica gel column chromatography to afford methyl 2-(4-methoxy-2-methylphenyl)-2-methylpropanoate (2).

Synthesis of 2-(4-methoxy-2-methylphenyl)-2-methylpropanoic acid (3)

To a solution of methyl 2-(4-methoxy-2-methylphenyl)-2-methylpropanoate (2, 1.00 g, 4.50 mmol) in tetrahydrofuran (10 mL) and ethanol (10 mL) is added 1 M lithium hydroxide aqueous solution (10 mL). The reaction is stirred at room temperature overnight. The mixture is diluted with water and extracted with ethyl acetate. The organic layer is washed with brine, dried over sodium sulfate, filtered and concentrated. The crude obtained is further purified via column chromatography to obtain 2-(4-methoxy-2-methylphenyl)-2-methylpropanoic acid (3).

Synthesis of 1-diazo-3-(4-methoxy-2-methylphenyl)-3-methylbutan-2-one (4)

To a solution of 2-(4-methoxy-2-methylphenyl)-2-methylpropanoic acid (3, 1.00 g, 4.80 mmol) in dichloromethane (10 mL) at 0° C. is added oxalyl chloride (1 M in dichloromethane, 5.28 mL, 5.28 mmol) followed by two drops of N,N-dimethylformamide. The reaction is stirred at room temperature for 1 h. The mixture is concentrated and dried under vacuum. The residue is dissolved in dichloromethane (10 mL). To this solution at 0° C. is purged with diazomethane. The reaction is fitted with a calcium chloride drying tube and allowed to stand at room temperature for 16 h. The mixture is purged with nitrogen and concentrated. The residue is purified via column chromatography to afford 1-diazo-3-(4-methoxy-2-methylphenyl)-3-methylbutan-2-one (4).

Synthesis of 5-methoxy-1,1,7-trimethyl-1,3-dihydro-2H-inden-2-one (5)

To a solution of 1-diazo-3-(4-methoxy-2-methylphenyl)-3-methylbutan-2-one (4, 1.00 g, 4.30 mmol) in dichloromethane (10 mL) is added rhodium (II) acetate dimer dihydrate (105 mg, 0.22 mmol). The reaction is stirred at room temperature overnight. The mixture is filtered through a pad of celite, concentrated and purified via column chromatography to afford 5-methoxy-1,1,7-trimethyl-1,3-dihydro-2H-inden-2-one (5).

Synthesis of 6'-methoxy-3',3',4'-trimethylspiro[cyclohexane-1,1'-inden]-2'(3'H)-one (7)

To a solution of 5-methoxy-1,1,7-trimethyl-1,3-dihydro-2H-inden-2-one (5, 1.00 g, 4.90 mmol) in tetrahydrofuran (20 mL) at 0° C., sodium hydride (0.29 g, 12.25 mmol) is added portion wise and the reaction mixture is allowed to stir at room temperature for 30 min. 1,5-Dibromopentane (6, 1.13 g, 4.9 mmol) is added and the reaction mixture is allowed to stir at 70° C. for 16 h. The reaction mixture is quenched with water and is extracted in ethyl acetate. The organic layer is separated, dried over sodium sulphate, filtered and concentrated under reduced pressure. The residue is purified by silica gel column chromatography to afford 6'-methoxy-3',3',4'-trimethylspiro[cyclohexane-1,1'-inden]-2'(3'H)-one (7).

Synthesis of 6'-methoxy-3',3',4'-trimethyl-2',3'-dihydrospiro[cyclohexane-1,1'-indene] (8)

To a solution of 6'-methoxy-3',3',4'-trimethylspiro[cyclohexane-1,1'-inden]-2'(3'H)-one (7, 1.00 g, 3.67 mmol) in ethylene glycol (40 mL) is added hydrazine hydrate solution (78-82%, 0.25 g, 4.04 mmol) followed by potassium hydroxide (0.62 g, 11.01 mmol). The reaction is fitted with a Dean-Stark trap and stirred at 120° C. for 3 h to distill off water and excess hydrazine. The reaction is then stirred at reflux overnight. The mixture is cooled to room temperature, diluted with water and extracted with ethyl acetate. The combined organics is dried over magnesium sulfate, filtered and concentrated. The crude is purified via column chromatography to afford 6'-methoxy-3',3',4'-trimethyl-2',3'-dihydrospiro[cyclohexane-1,1'-indene] (8).

Synthesis of 3',3',4'-trimethyl-2',3'-dihydrospiro[cyclohexane-1,1'-inden]-6'-ol (9)

To a solution of 6'-methoxy-3',3',4'-trimethyl-2',3'-dihydrospiro[cyclohexane-1,1'-indene] (8, 1.00 g, 3.87 mmol) in dichloromethane (20 mL) at −78° C. is added slowly boron tribromide (0.74 mL, 7.74 mmol). The reaction is allowed to stir at room temperature for 16 h. After completion, the reaction mixture is quenched with saturated aqueous sodium bicarbonate solution to adjust to pH 8. The mixture is extracted with dichloromethane (2×30 mL). The combined organics is dried over sodium sulfate, filtered and concentrated. The crude is then purified via column chromatography to afford 3',3',4'-trimethyl-2',3'-dihydrospiro[cyclohexane-1,1'-inden]-6'-ol (9).

Synthesis of 3',3',4'-trimethyl-2',3'-dihydrospiro[cyclohexane-1,1'-inden]-6'-yl trifluoromethanesulfonate (10)

To a solution of 3',3',4'-trimethyl-2',3'-dihydrospiro[cyclohexane-1,1'-inden]-6'-ol (9, 1.00 g, 4.09 mmol) in dichloromethane (15 mL) at −30° C., diisopropylethylamine (1.21 mL, 6.95 mmol) is added followed by the slow addition of triflic anhydride (0.76 mL, 4.50 mmol). The reaction is allowed to stir at room temperature for 1 h. After completion, the reaction mixture is basified by saturated aqueous sodium bicarbonate solution to pH 8. The mixture is extracted with dichloromethane (2×20 mL). The combined organics is dried over sodium sulfate, filtered and concentrated to dryness under vacuum. The crude is then purified via column chromatography to afford 3',3',4'-trimethyl-2',3'-dihydrospiro[cyclohexane-1,1'-inden]-6'-yl trifluoromethanesulfonate (10).

Synthesis of N-(5-methyl-6-((3',3',4'-trimethyl-2',3'-dihydrospiro[cyclohexane-1,1'-inden]-6'-yl)amino)pyrimidin-4-yl)cyclopropanecarboxamide (12)

The synthesis of intermediate 12 is carried out as described above using the general protocol of Procedure A.

Synthesis of 5-methyl-$N^4$-(3',3',4'-trimethyl-2',3'-dihydrospiro[cyclohexane-1,1'-inden]-6'-yl)pyrimidine-4,6-diamine (Cpd. No. 113)

The synthesis of compound 113 is carried out as described above using the general protocol of Procedure D.

Example 114
Synthesis of N⁴-(3',4'-dimethylspiro[cyclohexane-1,1'-isoindolin]-6'-yl)-5-methylpyrimidine-4,6-diamine (Cpd. No. 114)
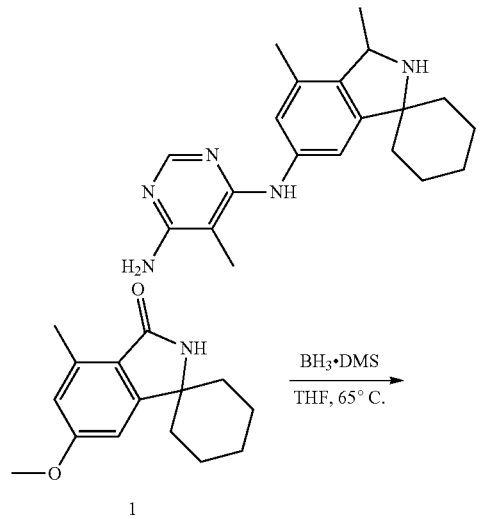
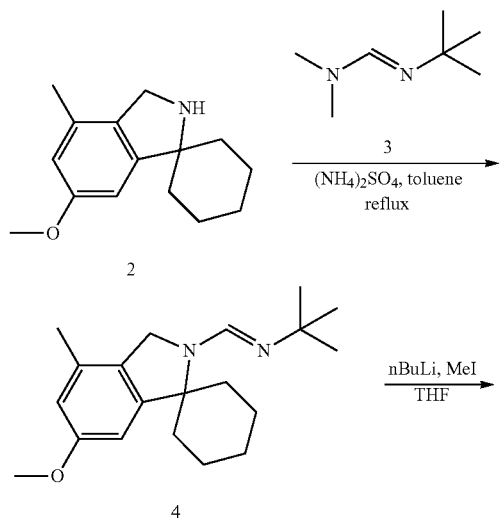
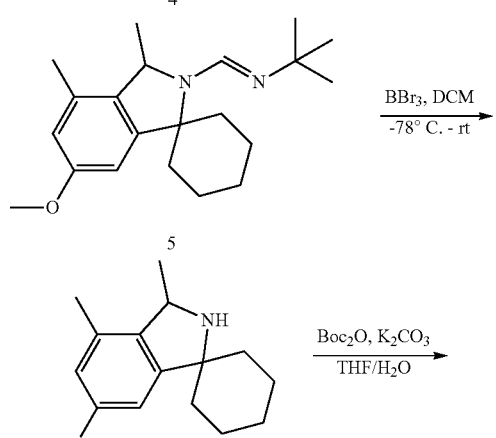
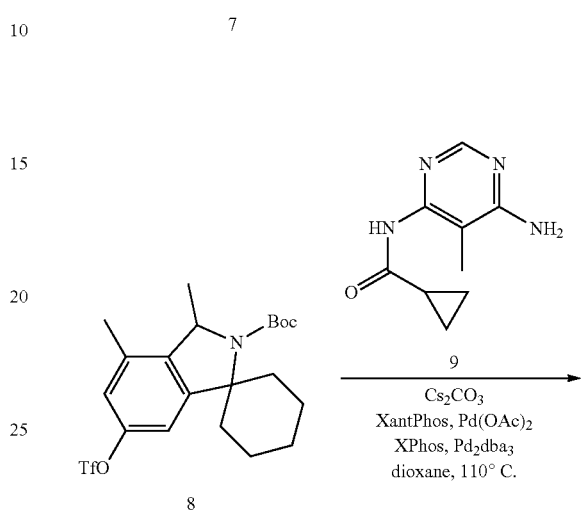

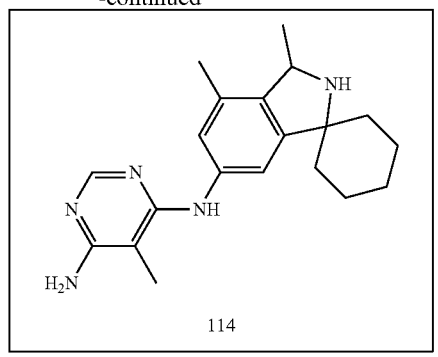

Synthesis of 6'-methoxy-4'-methylspiro[cyclohexane-1,1'-isoindoline] (2)

To a solution of 6'-methoxy-4'-methylspiro[cyclohexane-1,1'-isoindolin]-3'-one (1, 1.00 g, 4.08 mmol) in tetrahydrofuran (20 mL) is added dropwise borane dimethyl sulfide complex (12.24 mL, 24.48 mmol, 2 M in tetrahydrofuran). The reaction is stirred at 65° C. for 7 h, then stirred at room temperature overnight. 0.5 M hydrochloric acid (8 mL) is added dropwise and the mixture is refluxed for 2 h. The mixture is cooled to room temperature, basified with 1 M aqueous sodium hydroxide solution to pH=8 and extracted with ethyl acetate. The combined organics is dried over magnesium sulfate, filtered and concentrated. The crude is purified via column chromatography to afford methyl 6'-methoxy-4'-methylspiro[cyclohexane-1,1'-isoindoline] (2).

Synthesis of N-tert-butyl-1-(6'-methoxy-4'-methylspiro[cyclohexane-1,1'-isoindolin]-2'-yl)methanimine (4)

To a solution of methyl 6'-methoxy-4'-methylspiro[cyclohexane-1,1'-isoindoline] (2, 1.00 g, 4.32 mmol) in toluene (20 mL) is added ammonium sulfate (1.14 g, 8.64 mmol) followed by N'-tert-butyl-N,N-dimethylformimidamide (3, 0.83 g, 6.48 mmol). The reaction is refluxed overnight. The mixture is cooled to room temperature, filtered and concentrated. The crude is purified via column chromatography to afford N-tert-butyl-1-(6'-methoxy-4'-methylspiro[cyclohexane-1,1'-isoindolin]-2'-yl)methanimine (4).

Synthesis of N-tert-butyl-1-(6'-methoxy-3',4'-dimethylspiro[cyclohexane-1,1'-isoindolin]-2'-yl)methanimine (5)

To a solution of N-tert-butyl-1-(6'-methoxy-4'-methylspiro[cyclohexane-1,1'-isoindolin]-2'-yl)methanimine (4, 1.00 g, 3.18 mmol) in tetrahydrofuran (20 mL) at −78° C. is added n-butyl lithium (1.6 M in hexanes, 2.19 mL, 3.50 mmol) dropwise and the reaction is stirred for 30 min. Iodomethane (0.30 mL, 4.77 mmol) is added and the reaction is warmed to room temperature and stirred for 1 h. The reaction mixture is quenched with water and extracted with ethyl acetate. The combined organics is dried over magnesium sulphate, filtered and concentrated. The residue is purified via column chromatography to N-tert-butyl-1-(6'-methoxy-3',4'-dimethylspiro[cyclohexane-1,1'-isoindolin]-2'-yl)methanimine (5).

Synthesis of 3',4'-dimethylspiro[cyclohexane-1,1'-isoindolin]-6'-ol (6)

To a solution of N-tert-butyl-1-(6'-methoxy-3',4'-dimethylspiro[cyclohexane-1,1'-isoindolin]-2'-yl)methanimine (5, 1.00 g, 3.04 mmol) in dichloromethane (20 mL) at −78° C. is added slowly boron tribromide (0.59 mL, 6.08 mmol). The reaction is stirred at room temperature for 16 h. After completion, the reaction mixture is quenched with saturated aqueous sodium bicarbonate solution to adjust to pH 8. The mixture is extracted with dichloromethane (2×30 mL). The combined organics is dried over sodium sulfate, filtered and concentrated. The crude is then purified via column chromatography to afford 3',4'-dimethylspiro[cyclohexane-1,1'-isoindolin]-6'-ol (6).

Synthesis of tert-butyl 6'-hydroxy-3',4'-dimethylspiro[cyclohexane-1,1'-isoindoline]-2'-carboxylate (7)

To a solution of 3',4'-dimethylspiro[cyclohexane-1,1'-isoindolin]-6'-ol (6, 1.00 g, 4.32 mmol) and di-tert-butyl dicarbonate (1.19 mL, 5.18 mmol) in tetrahydrofuran (20 mL) is added a solution of potassium carbonate (1.49 g, 10.80 mmol) in water (20 mL). The reaction is stirred at room temperature overnight. The mixture is diluted with brine and extracted with ethyl acetate. The combined organics is dried over magnesium sulfate, filtered and concentrated. The crude is then purified via column chromatography to afford tert-butyl 6'-hydroxy-3',4'-dimethylspiro[cyclohexane-1,1'-isoindoline]-2'-carboxylate (7).

Synthesis of tert-butyl 3',4'-dimethyl-6'-(((trifluoromethyl)sulfonyl)oxy)spiro[cyclohexane-1,1'-isoindoline]-2'-carboxylate (8)

To a solution of tert-butyl 6'-hydroxy-3',4'-dimethylspiro[cyclohexane-1,1'-isoindoline]-2'-carboxylate (7, 1.00 g, 3.02 mmol) in dichloromethane (15 mL) at −30° C., diisopropylethylamine (0.89 mL, 5.13 mmol) is added followed by the slow addition of triflic anhydride (0.56 mL, 3.32 mmol). The reaction is allowed to stir at room temperature for 1 h. After completion, the reaction mixture is basified by saturated aqueous sodium bicarbonate solution to pH 8. The mixture is extracted with dichloromethane (2×20 mL). The combined organics is dried over sodium sulfate, filtered and concentrated to dryness under vacuum. The crude is then purified via column chromatography to afford tert-butyl 3',4'-dimethyl-6'-(((trifluoromethyl)sulfonyl)oxy)spiro[cyclohexane-1,1'-isoindoline]-2'-carboxylate (8).

Synthesis of tert-butyl 6'-((6-(cyclopropanecarboxamido)-5-methylpyrimidin-4-yl)amino)-3',4'-dimethylspiro[cyclohexane-1,1'-isoindoline]-2'-carboxylate (10)

The synthesis of intermediate 10 is carried out as described above using the general protocol of Procedure A.

Synthesis of N-(6-((3',4'-dimethylspiro[cyclohexane-1,1'-isoindolin]-6'-yl)amino)-5-methylpyrimidin-4-yl)cyclopropanecarboxamide (11)

The synthesis of intermediate 11 is carried out as described above using the general protocol of Procedure C.

Synthesis of N⁴-(3',4'-dimethylspiro[cyclohexane-1,1'-isoindolin]-6'-yl)-5-methylpyrimidine-4,6-diamine (Cpd. No. 114)
The synthesis of compound 114 is carried out as described above using the general protocol of Procedure D.
Example 115
Synthesis of 5-methyl-N⁴-(3',3',4'-trimethylspiro[cyclohexane-1,1'-isoindolin]-6'-yl)pyrimidine-4,6-diamine (Cpd. No. 115)
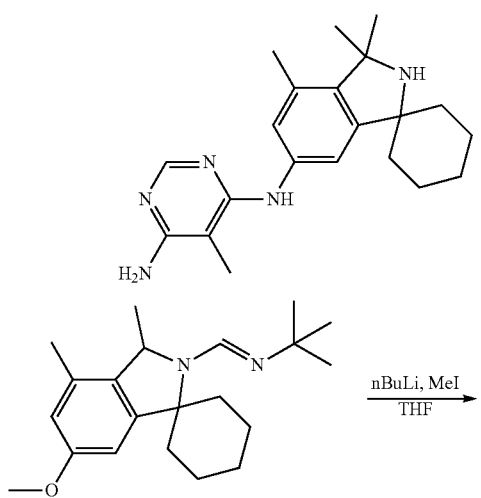
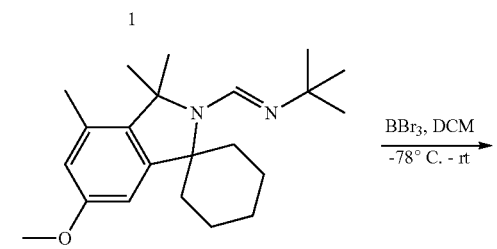
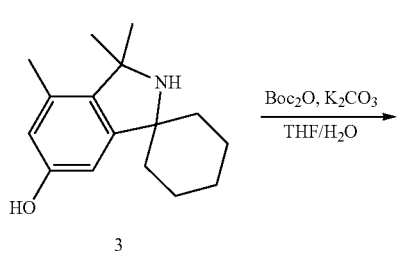
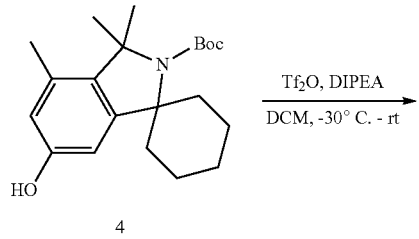
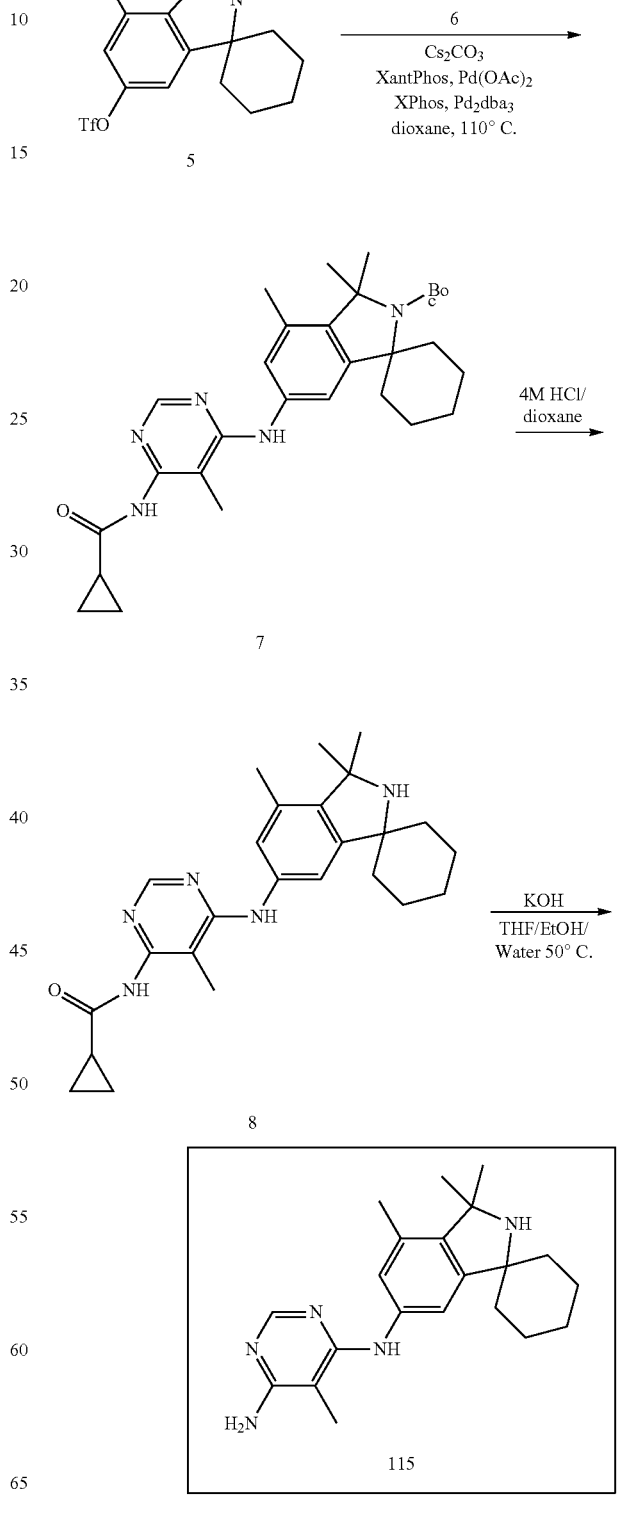

Synthesis of N-tert-butyl-1-(6'-methoxy-3',3',4'-trimethylspiro[cyclohexane-1,1'-isoindolin]-2'-yl)methanimine (2)

To a solution of N-tert-butyl-1-(6'-methoxy-3',4'-dimethylspiro[cyclohexane-1,1'-isoindolin]-2'-yl)methanimine (1, 1.00 g, 3.04 mmol) in tetrahydrofuran (20 mL) at −78° C. is added n-butyl lithium (1.6 M in hexanes, 2.09 mL, 3.34 mmol) dropwise and the reaction is stirred for 30 min. Iodomethane (0.28 mL, 4.56 mmol) is added and the reaction is warmed to room temperature and stirred for 1 h. The reaction mixture is quenched with water and extracted with ethyl acetate. The combined organics is dried over magnesium sulphate, filtered and concentrated. The residue is purified via column chromatography to N-tert-butyl-1-(6'-methoxy-3',4'-dimethylspiro[cyclohexane-1,1'-isoindolin]-2'-yl)methanimine (2).

Synthesis of 3',3',4'-trimethylspiro[cyclohexane-1,1'-isoindolin]-6'-ol (3)

To a solution of N-tert-butyl-1-(6'-methoxy-3',4'-dimethylspiro[cyclohexane-1,1'-isoindolin]-2'-yl)methanimine (2, 1.00 g, 2.92 mmol) in dichloromethane (20 mL) at −78° C. is added slowly boron tribromide (0.56 mL, 5.84 mmol). The reaction is stirred at room temperature for 16 h. After completion, the reaction mixture is quenched with saturated aqueous sodium bicarbonate solution to adjust to pH 8. The mixture is extracted with dichloromethane (2×30 mL). The combined organics is dried over sodium sulfate, filtered and concentrated. The crude is then purified via column chromatography to afford 3',3',4'-trimethylspiro[cyclohexane-1,1'-isoindolin]-6'-ol (3).

Synthesis of tert-butyl 6'-hydroxy-3',3',4'-trimethylspiro[cyclohexane-1,1'-isoindoline]-2'-carboxylate (4)

To a solution of 3',3',4'-trimethylspiro[cyclohexane-1,1'-isoindolin]-6'-ol (3, 1.00 g, 4.08 mmol) and di-tert-butyl dicarbonate (1.12 mL, 4.90 mmol) in tetrahydrofuran (20 mL) is added a solution of potassium carbonate (1.41 g, 10.20 mmol) in water (20 mL). The reaction is stirred at room temperature overnight. The mixture is diluted with brine and extracted with ethyl acetate. The combined organics is dried over magnesium sulfate, filtered and concentrated. The crude is then purified via column chromatography to afford tert-butyl 6'-hydroxy-3',3',4'-trimethylspiro[cyclohexane-1,1'-isoindoline]-2'-carboxylate (4).

Synthesis of tert-butyl 3,3',4'-trimethyl-6'-(((trifluoromethyl)sulfonyl)oxy)spiro[cyclohexane-1,1'-isoindoline]-2'-carboxylate (5)

To a solution of tert-butyl 6'-hydroxy-3',3',4'-trimethylspiro[cyclohexane-1,1'-isoindoline]-2'-carboxylate (4, 1.00 g, 2.89 mmol) in dichloromethane (15 mL) at −30° C., diisopropylethylamine (0.86 mL, 4.91 mmol) is added followed by the slow addition of triflic anhydride (0.54 mL, 3.18 mmol). The reaction is allowed to stir at room temperature for 1 h. After completion, the reaction mixture is basified by saturated aqueous sodium bicarbonate solution to pH 8. The mixture is extracted with dichloromethane (2×20 mL). The combined organics is dried over sodium sulfate, filtered and concentrated to dryness under vacuum. The crude is then purified via column chromatography to afford tert-butyl 3',3',4'-trimethyl-6'-(((trifluoromethyl) sulfonyl)oxy)spiro[cyclohexane-1,1'-isoindoline]-2'-carboxylate (5).

Synthesis of tert-butyl 6'-((6-(cyclopropanecarboxamido)-5-methylpyrimidin-4-yl)amino)-3',3',4'-trimethylspiro[cyclohexane-1,1'-isoindoline]-2'-carboxylate (7)

The synthesis of intermediate 7 is carried out as described above using the general protocol of Procedure A.

Synthesis of N-(5-methyl-6-((3',3',4'-trimethylspiro[cyclohexane-1,1'-isoindolin]-6'-yl)amino)pyrimidin-4-yl)cyclopropanecarboxamide (8)

The synthesis of intermediate 8 is carried out as described above using the general protocol of Procedure C.

Synthesis of 5-methyl-N$^4$-(3',3',4'-trimethylspiro[cyclohexane-1,1'-isoindolin]-6'-yl)pyrimidine-4,6-diamine (Cpd. No. 115)

The synthesis of compound 115 is carried out as described above using the general protocol of Procedure D.

Example 116

Synthesis of 5-methyl-N$^4$-(4'-methyl-2'H-dispiro[cyclohexane-1,1'-indene-3',1"-cyclopropan]-6'-yl)pyrimidine-4,6-diamine (Cpd. No. 116)

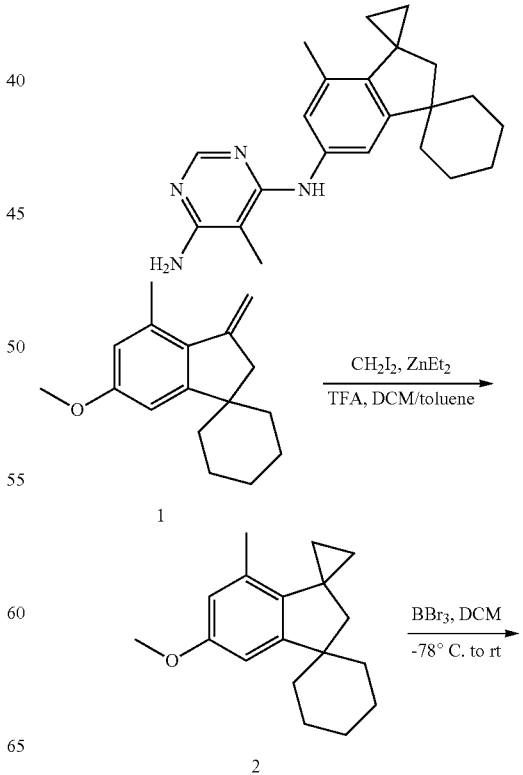

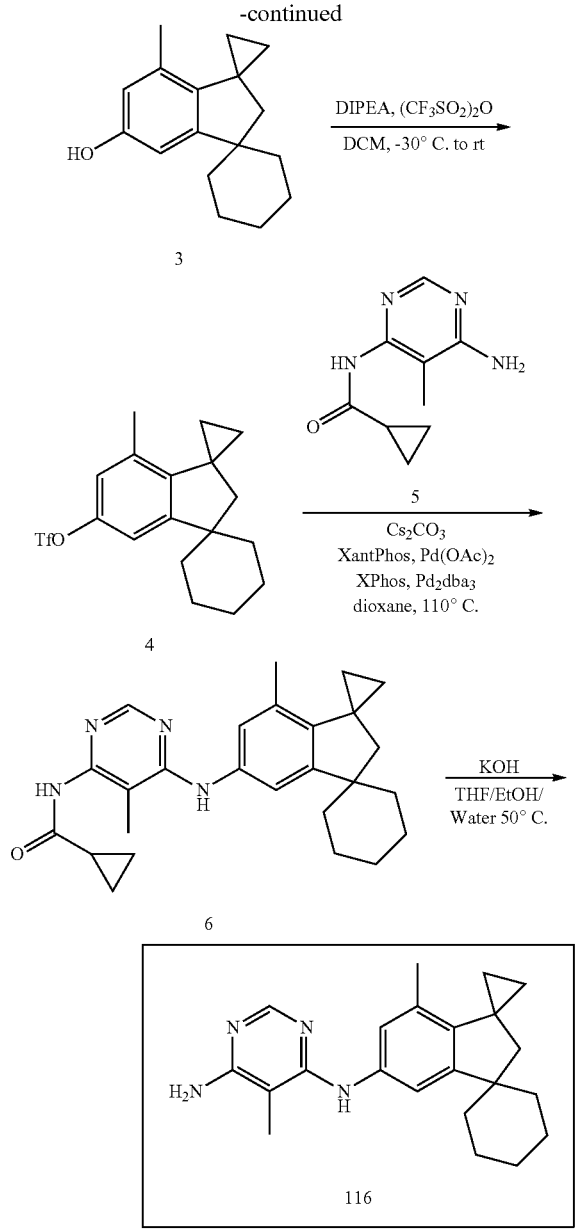

Synthesis of 6'-methoxy-4'-methyl-2'H-dispiro[cyclohexane-1,1'-indene-3',1''-cyclopropane](2)

A 1.1 M toluene solution of diethyl zinc (15.02 mL, 16.52 mmol) is added to a reaction vessel containing dichloromethane (20 mL) and cooled to 0° C. Trifluoroacetic acid (1.26 mL, 16.52 mmol) is added to the resulting solution and the reaction is stirred at 0° C. for 15 min. To the cooled solution is added diiodomethane (1.33 mL, 16.52 mmol), and the reaction is stirred for an additional 15 min at 0° C. Then, a solution of 6'-methoxy-4'-methyl-3'-methylene-2',3'-dihydrospiro[cyclohexane-1,1'-indene] (1, 1.00 g, 4.13 mmol) in dichloromethane (10 mL) is added. The reaction is maintained 0° C. for another 15 min, then allowed to gradually warm to room temperature. Upon completion, the reaction is quenched with a saturated aqueous ammonium chloride solution (40 mL) and diluted with dichloromethane (40 mL). The combined organics is washed with brine (40 mL), dried over magnesium sulfate, filtered and concentrated. The crude is purified via flash chromatography to afford 6'-methoxy-4'-methyl-2'H-dispiro[cyclohexane-1,1'-indene-3',1''-cyclopropane] (2).

Synthesis of 4'-methyl-2'H-dispiro[cyclohexane-1,1'-indene-3',1''-cyclopropan]-6'-ol (3)

To a solution of 6'-methoxy-4'-methyl-2'H-dispiro[cyclohexane-1,1'-indene-3',1''-cyclopropane] (2, 0.75 g, 2.92 mmol) in dichloromethane (20 mL) at −78° C. is added slowly boron tribromide (0.56 mL, 5.84 mmol). The reaction is stirred at room temperature for 16 h. After completion, the reaction mixture is quenched with saturated aqueous sodium bicarbonate solution to adjust to pH 8. The mixture is extracted with dichloromethane (2×30 mL). The combined organics is dried over sodium sulfate, filtered and concentrated. The crude is then purified via column chromatography to afford 4'-methyl-2'H-dispiro[cyclohexane-1,1'-indene-3',1''-cyclopropan]-6'-ol (3).

Synthesis of 4'-methyl-2'H-dispiro[cyclohexane-1,1'-indene-3',1''-cyclopropan]-6'-yl trifluoromethanesulfonate (4)

To a solution of 4'-methyl-2'H-dispiro[cyclohexane-1,1'-indene-3',1''-cyclopropan]-6'-ol (3, 0.70 g, 2.89 mmol) in dichloromethane (15 mL) at −30° C., diisopropylethylamine (0.86 mL, 4.91 mmol) is added followed by the slow addition of triflic anhydride (0.54 mL, 3.18 mmol). The reaction is allowed to stir at room temperature for 1 h. After completion, the reaction mixture is basified by saturated aqueous sodium bicarbonate solution to pH 8. The mixture is extracted with dichloromethane (2×20 mL). The combined organics is dried over sodium sulfate, filtered and concentrated to dryness under vacuum. The crude is then purified via column chromatography to afford 4'-methyl-2'H-dispiro[cyclohexane-1,1'-indene-3',1''-cyclopropan]-6'-yl trifluoromethanesulfonate (4).

Synthesis of N-(5-methyl-6-((4'-methyl-2'H-dispiro[cyclohexane-1,1'-indene-3',1''-cyclopropan]-6'-yl)amino)pyrimidin-4-yl)cyclopropanecarboxamide (6)

The synthesis of intermediate 6 is carried out as described above using the general protocol of Procedure A.

Synthesis of 5-methyl-N$^4$-(4'-methyl-2'H-dispiro[cyclohexane-1,1'-indene-3',1''-cyclopropan]-6'-yl)pyrimidine-4,6-diamine (Cpd. No. 116)

The synthesis of compound 116 is carried out as described above using the general protocol of Procedure D.

Example 117: MNK Biochemical Enzymatic Assay

Compounds are screened for MNK inhibition using the ADP-Glo kinase assay kit (Promega, catalogue No. V9101). All kinase reactions are performed in Reaction Buffer E (15 mM HEPES pH7.4, 20 mM NaCl, 1 mM EGTA, 10 mM MgCl$_2$, 0.1 mg/ml BGG, and 0.02% Tween-20). Final MNK1 reactions contained 10 nM recombinant MNK1 (Life Technologies, PR9138A), 100 μM MNK substrate peptide Ac-TATKSGSTTKNR-NH2 (amino acid sequence shown SEQ ID NO: 1) (American Peptide Company), 300 μM ATP, and varying concentrations of the inhibitory compound of interest. Final MNK2 reactions contained 3 nM recombinant MNK2 (Life Technologies, PV5607), 50 µM MNK substrate peptide Ac-TATKSGSTTKNR-NH2 (amino acid sequence shown SEQ ID NO: 1) (American Peptide Company), 10 µM ATP, and varying concentrations of the inhibitory compound of interest. Final DMSO concentration in each reaction is 1%.

Kinase reactions are carried out in 96-well half-area white flat-bottom polystyrene plates in a final volume of 25 µl. MNK1/2 enzymes are pre-incubated with compound and peptide substrate for 5 minutes prior to the addition of ATP. After the addition of ATP, kinase reactions are incubated at room temperature for 40 minutes. Reactions are subsequently stopped by the addition of 25 µl of ADP-Glo Reagent and incubating for an additional 40 minutes. The final luminescent signal used for kinase activity readout is produced by the addition of 45 µl of Kinase Detection Reagent (ADP-Glo kit, Promega) and incubating for 40 minutes. The luminescent signal is detected using a Victor 2 multilabel counter (Perkin Elmer) and the concentration of compound necessary to achieve inhibition of enzyme activity by 50% ($IC_{50}$) is calculated using signals from an 8-point compound dilution series.

The results of these assays are set forth in Table 1 below. To this end, $IC_{50}$ values of less than 0.01 µM are labelled as "+++", from 0.01 to 0.1 µM are labelled as "++", and greater than 0.1 to 10.0 µM are labelled as "+" (NA means "not available").

TABLE 1

| MNK Biochemical Enzymatic Assay (IC50) | | |
| --- | --- | --- |
| Cpd. No. | $IC_{50}$ Mnk1 | Mnk2 |
| 1 | ++ | NA |
| 2 | ++ | NA |
| 3 | + | NA |
| 4 | + | NA |
| 5 | + | NA |
| 6 | ++ | NA |
| 7 | − | NA |
| 8 | ++ | ++ |
| 9 | − | NA |
| 10 | ++ | ++ |
| 11 | +++ | ++ |
| 12 | +++ | +++ |
| 13 | ++ | ++ |
| 14 | NA | − |
| 15 | + | ++ |
| 16 | NA | + |
| 17 | +++ | +++ |
| 18 | NA | + |
| 19 | +++ | ++ |
| 20 | NA | + |
| 21 | NA | + |
| 22 | + | ++ |
| 23 | + | ++ |
| 24 | +++ | + |
| 25 | NA | + |
| 26 | NA | + |
| 27 | NA | + |
| 28 | NA | + |
| 29 | NA | + |
| 30 | NA | + |
| 31 | NA | − |
| 32 | NA | + |
| 33 | ++ | ++ |
| 34 | NA | − |
| 35 | +++ | +++ |
| 36 | +++ | +++ |
| 37 | +++ | +++ |
| 38 | ++ | + |
| 39 | ++ | + |
| 40 | + | + |
| 41 | NA | + |
| 42 | +++ | +++ |
| 43 | +++ | +++ |
| 44 | NA | +++ |
| 45 | NA | − |
| 46 | NA | +++ |
| 47 | NA | +++ |
| 48 | NA | +++ |
| 49 | NA | ++ |
| 50 | NA | +++ |
| 51 | NA | +++ |
| 52 | NA | +++ |
| 53 | NA | +++ |
| 54 | NA | +++ |
| 55 | NA | ++ |
| 56 | NA | ++ |
| 57 | NA | +++ |
| 58 | NA | +++ |
| 59 | NA | +++ |
| 60 | NA | NA |
| 61 | NA | NA |
| 62 | NA | NA |
| 63 | NA | NA |
| 64 | NA | NA |
| 65 | NA | NA |
| 66 | NA | NA |
| 67 | NA | NA |
| 68 | NA | NA |
| 69 | NA | NA |
| 70 | NA | NA |
| 71 | NA | NA |
| 72 | NA | NA |
| 73 | NA | NA |
| 74 | NA | NA |
| 75 | NA | NA |
| 76 | NA | NA |
| 77 | NA | NA |
| 78 | NA | NA |
| 79 | NA | NA |
| 80 | NA | NA |
| 81 | NA | NA |
| 82 | NA | NA |
| 83 | NA | NA |
| 84 | NA | NA |
| 85 | NA | NA |
| 86 | NA | NA |
| 87 | NA | NA |
| 88 | NA | NA |
| 89 | NA | NA |
| 90 | NA | NA |
| 91 | NA | NA |
| 92 | NA | NA |
| 93 | NA | NA |
| 94 | NA | NA |
| 95 | NA | NA |
| 96 | NA | NA |
| 97 | NA | NA |
| 98 | NA | NA |
| 99 | NA | NA |
| 100 | NA | NA |
| 101 | NA | NA |
| 102 | NA | NA |
| 103 | NA | NA |
| 104 | NA | NA |
| 105 | NA | NA |
| 106 | NA | NA |
| 107 | NA | NA |
| 108 | NA | NA |
| 109 | NA | NA |
| 110 | NA | NA |
| 111 | NA | NA |

Example 118: peIF4E Signaling Cellular Assay

Phosphorylated eIF4E is assayed using the CisBio peIF4E HTRF® assay kit (CisBio, catalogue No. 64EF4PEG). Cells are plated in 96-well tissue-culture treated plate in appropriate growth medium (90 μL). Compounds (10×) are diluted using 3-fold serial dilutions in cell culture medium and added to cells. Plates are incubated for 2 hrs at 37° C. The cell supernatant is carefully removed either by aspirating supernatant or by flicking the plate. Immediately 50 μL of supplemented lysis buffer (1×) is added and incubated for at least 30 minutes at room temperature under shaking. After homogenization by pipeting up and down, 16 μL of cell lysate is transferred from the 96-well cell-culture plate to a 384-well small volume white plate. 4 μL of premixed antibody solutions (vol/vol) is prepared in the detection buffer and added. The plate is covered with a plate sealer and incubated overnight at room temperature. The fluorescence emissions at two different wavelengths are read (665 nm and 620 nm) on a Wallac Victor2. Emission ratios are converted into percent inhibitions and imported into GraphPad Prism software. The concentration of compound necessary to achieve inhibition of enzyme activity by 50% ($IC_{50}$) is calculated using concentrations ranging from 20 μM to 0.1 nM (12-point curve). $IC_{50}$ values are determined using a nonlinear regression model available in GraphPad Prism 5.

The results of these assays are set forth in Table 2 below. To this end, $IC_{50}$ values of less than 0.05 μM are labelled as "+++", from 0.05 to 1.0 μM are labelled as "++", greater than 1.0 to 100 μM are labelled as "+", and NA means "not available".

TABLE 2 peIF4E Signaling Cellular Assay (IC50)

| Cpd. No. | $IC_{50}$ |
| --- | --- |
| 1 | NA |
| 2 | NA |
| 3 | NA |
| 4 | NA |
| 5 | NA |
| 6 | NA |
| 7 | NA |
| 8 | + |
| 9 | NA |
| 10 | + |
| 11 | + |
| 12 | ++ |
| 13 | + |
| 14 | NA |
| 15 | + |
| 16 | NA |
| 17 | ++ |
| 18 | NA |
| 19 | ++ |
| 20 | NA |
| 21 | NA |
| 22 | + |
| 23 | + |
| 24 | ++ |
| 25 | NA |
| 26 | NA |
| 27 | NA |
| 28 | NA |
| 29 | + |
| 30 | NA |
| 31 | NA |
| 32 | NA |
| 33 | + |
| 34 | NA |
| 35 | ++ |
| 36 | ++ |
| 37 | NA |
| 38 | + |
| 39 | + |
| 40 | NA |
| 41 | NA |
| 42 | + |
| 43 | +++ |
| 44 | ++ |
| 45 | NA |
| 46 | +++ |
| 47 | ++ |
| 48 | +++ |
| 49 | + |
| 50 | +++ |
| 51 | +++ |
| 52 | + |
| 53 | ++ |
| 54 | +++ |
| 55 | +++ |
| 56 | ++ |
| 57 | +++ |
| 58 | +++ |
| 59 | +++ |
| 60 | ++ |
| 61 | + |
| 62 | + |
| 63 | ++ |
| 64 | ++ |
| 65 | ++ |
| 66 | ++ |
| 67 | + |
| 68 | ++ |
| 69 | ++ |
| 70 | +++ |
| 71 | +++ |
| 72 | +++ |
| 73 | +++ |
| 74 | ++ |
| 75 | +++ |
| 76 | ++ |
| 77 | +++ |
| 78 | + |
| 79 | ++ |
| 80 | ++ |
| 81 | ++ |
| 82 | NA |
| 83 | +++ |
| 84 | ++ |
| 85 | ++ |
| 86 | ++ |
| 87 | ++ |
| 88 | ++ |
| 89 | ++ |
| 90 | ++ |
| 91 | + |
| 92 | + |
| 93 | ++ |
| 94 | ++ |
| 95 | NA |
| 96 | + |
| 97 | NA |
| 98 | NA |
| 99 | NA |
| 100 | NA |
| 101 | NA |
| 102 | NA |
| 103 | NA |
| 104 | NA |
| 105 | NA |
| 106 | + |
| 107 | NA |
| 108 | NA |
| 109 | NA |
| 110 | ++ |
| 111 | NA |

Example 119: Pharmacokinetic Studies

Groups of Balb/c mice or Sprague-Dawley rats (n≥3 per dose group) are administered single doses of test compound. Compounds are formulated either as solutions in 10% N-methylpyrrolidone, 90% polyethyleneglycol 400 or as suspensions in 0.5% methylcellulose in water for oral gavage administration at a nominal dose level of 10 mg/kg. Compounds are formulated in 10% dimethylisosorbide, 15% ethanol, 35% propylene glycol, and 40% saline (or 40% D5W) for intravenous administration at a nominal dose level of 1 mg/kg. For intravenously dosed animals, blood samples are collected at 0.083, 0.25, 0.5, 1, 2, 4, 8, and 24 h post dose. For orally dosed animals, blood samples are collected at 0.25, 0.5, 1, 2, 4, 8, and 24 h post dose. Blood samples are collected from mice either serially via submandibular vein (approximately 0.1 mL each) or terminally via cardiac puncture (approximately 0.5 mL each). Blood samples are collected serially from rats via jugular vein catheter (approximately 0.2 mL each). Each blood sample is collected into a tube that is chilled and contains potassium EDTA as the anticoagulant. Plasma is separated and stored at approximately −80 C until analysis. Following protein precipitation with acetonitrile containing an internal standard, plasma samples are analyzed using a liquid chromatography/high-resolution mass spectrometry (LC-HRMS) method to determine plasma concentrations. Plasma concentration versus time data are subjected to noncompartmental pharmacokinetic analysis using Phoenix™ Winnonlin® (Certara LP) to determine pharmacokinetic parameters, including Area Under the Curve (AUC), Clearance (Cl), Volume of Distribution at Steady-State (Vss), and terminal half-life (T1/2). Data from orally and intravenously dose are highlighted in Tables 3 and 4, respectively.

TABLE 3

Mean Pharmacokinetics Parameters in Male Sprague Dawley Rats Following a Single Oral Gavage Administration at 10 mg/kg (N = 3/group)

| Cpd. No. | Formulation | $T_{1/2}$ (h) | $T_{max}$ (h) | $C_{max}$ (μg/mL) | $AUC_{0\text{-}inf}$ (h * μg/mL) | F (%) |
|---|---|---|---|---|---|---|
| 55 | 1 | 2.59 | 4 | 0.425 | 2.65 | 25.0 |
| 57 | 2 | 3.27 | 0.833 | 0.584 | 2.49 | 14.5 |
| 58 | 1 | 9.15 | 0.417 | 0.417 | 1.37 | 27.9 |
| 71[a] | 1 | 2.90 | 0.500 | 1.14 | 5.66 | 63.9 |
| 72 | 1 | 2.75 | 0.667 | 1.38 | 2.74 | 24.2 |

[a] N = 2 (plasma levels from 1 of 3 animals appeared anomolously low and was excluded from PK calculations)
Formulation: 1 = 10% NMP/90% PEG400; 2 = 10% DMA/90% PEG300

TABLE 4

Mean Pharmacokinetic Parameters in Male Sprague Dawley Rats Following a Single Intravenous Bolus Administration at 1 mg/kg (N = 3/group)

| Cpd. No. | Formulation | CL (mL/min/kg) | T½ (h) | Vss (L/kg) | $AUC_{0\text{-}inf}$ (h * μg/mL) |
|---|---|---|---|---|---|
| 55 | 1 | 16.6 | 7.34 | 6.56 | 1.06 |
| 57 | 2 | 11.1 | 7.78 | 3.46 | 1.72 |
| 58 | 1 | 35.3 | 9.44 | 13.2 | 0.491 |
| 71 | 1 | 19.1 | 4.15 | 3.90 | 0.886 |
| 72 | 1 | 14.8 | 8.48 | 4.59 | 1.13 |

Formulation: 1 = 10% NMP/15% EtOH/35% PEG400/40% D5W; 2 = 10% DMA/15% EtOH/35% PEG400/40% D5W The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:
1. A compound according to Formula (I):

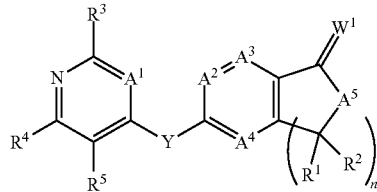

or a stereoisomer, a tautomer or a pharmaceutically acceptable salt thereof wherein:
A$^1$ is —N—; A$^2$ is —N— or —CR$^{6a}$;
A$^3$ is —N— or —CR$^7$;
A$^4$ is —N— or —CR$^{6b}$;
A$^5$ is —NR$^8$ or —CR$^{5a}$R$^{5b}$;
W$^1$ is O, S, NH, NO(R$^9$) or CR$^{9a}$R$^{9b}$;
Y is —O—, —S—, —C(O)—, —NR$^{10}$, —S=O, —S(O)$_2$—, —CH$_2$— or —CH(OH);
n is 1, 2 or 3;
R$^1$ and R$^2$ independently are —H, —NHR$^{10}$, NHR$^{10}$-alkylene, (C$_1$-C$_8$)alkyl, (C$_2$-C$_8$)alkenyl, (C$_2$-C$_8$)alkynyl, cycloalkyl, heterocyclyl, heteroaryl, aryl, arylalkylene, cycloalkylalkylene, heterocyclylalkylene, or heteroarylalkylene, such that at least one of R$^1$ or R$^2$ is not —H; or
R$^1$ and R$^2$ together with the carbon atom to which they are attached form a cycloalkyl or heterocyclyl ring;
R$^3$, R$^4$, R$^5$ and R$^{6b}$ independently are —H, —OH, —CN, —SR$^{10}$, halogen, —S(O)$_2$(C$_1$-C$_8$) alkyl, —C(O)NHR$^{10}$, —C(O)NR$^{10}$R$^{10}$, —NHR$^{10}$, —NR$^{10}$R$^{10}$, NHR$^{10}$-alkylene, NR$^{10}$R$^{10}$-alkylene, (C$_1$-C$_8$)alkyl, (C$_2$-C$_8$)alkenyl, (C$_2$-C$_8$)alkynyl, (C$_1$-C$_8$)haloalkyl, —O(C$_1$-C$_8$)alkyl, —O(C$_1$-C$_8$)haloalkyl, —O(C$_1$-C$_8$)alkyleneNHR$^{10}$, —O(C$_1$-C$_8$)alkyleneNR$^{10}$R$^{10}$, cycloalkyl, heterocyclyl, heteroaryl, aryl, arylalkylene, cycloalkylalkylene, heterocyclylalkylene, heteroarylalkylene, alkylaminyl, alkylcarbonylaminyl, cycloalkylcarbonylaminyl, cycloalkylaminyl, or heterocyclylaminyl; or
R$^4$ and R$^5$ together with the respective carbon atoms to which they are attached form a fused aryl, cycloalkyl, heterocyclyl or heteroaryl ring;
R$^{6a}$ is —H, —OH, halogen, —CN, acetyl, —(C$_1$-C$_8$) alkyl, —S(C$_1$-C$_8$)alkyl, —(C$_2$-C$_8$)alkenyl, —(C$_2$-C$_8$) alkynyl, —O(C$_1$-C$_8$)alkyl, —(C$_1$-C$_8$)haloalkyl, —NHR$^{10}$, —NR$^{10}$R$^{10}$, NHR$^{10}$-alkylene, NR$^{10}$R$^{10}$-alkylene or —O(C$_1$-C$_8$)haloalkyl;
R$^7$ is —H, —OH, —SH, —CN, —S(O)$_2$R$^{10}$, halogen, —S(C$_1$-C$_8$)alkyl, —NHR$^{10}$, —NR$^{10}$R$^{10}$, (C$_1$-C$_8$)alkyl, (C$_2$-C$_8$)alkenyl, (C$_2$-C$_8$)alkynyl, (C$_1$-C$_8$)haloalkyl, —O(C$_1$-C$_8$)haloalkyl, —O(C$_1$-C$_8$)alkyl, —O(C$_1$-C$_8$) alkyleneNHR$^{10}$, —O(C$_1$-C$_8$)alkyleneNR$^{10}$R$^{10}$, —(C$_1$-C$_8$)alkyleneNHR$^{10}$, —(C$_1$-C$_8$)alkyleneNR$^{10}$R$^{10}$, —S(C$_1$-C$_8$)alkyl, cycloalkyl, heterocyclyl, heteroaryl or aryl;
R$^8$ is —H, —OH, acetyl, —(C$_1$-C$_8$)alkyl, —C(O)alkyl, —C(O)cycloalkyl, —C(O)O—(C$_1$-C$_8$)alkyl, cycloalkyl, aryl, heteroaryl or heterocyclyl;
R$^{8a}$ and R$^{8b}$ independently are —H, —OH, acetyl, —(C$_1$-C$_8$)alkyl, —O(C$_1$-C$_8$)alkyl, C(O)alkyl, —C(O)cycloalkyl, —C(O)O—(C$_1$-C$_8$)alkyl, cycloalkyl, aryl, heteroaryl or heterocyclyl;

R$^9$, R$^{9a}$ and R$^{9b}$ are independently —H, (C$_1$-C$_8$)alkyl, (C$_2$-C$_8$)alkenyl, (C$_2$-C$_8$)alkynyl, cycloalkyl, heterocyclyl, heteroaryl, aryl, arylalkylene, cycloalkylalkylene, heterocyclylalkylene, or heteroarylalkylene; or
R$^{9a}$ and R$^{9b}$ together with the carbon atom to which they are attached form a cycloalkyl or heterocyclyl ring;
R$^{10}$ is —H, —OH, —C(O)O(C$_1$-C$_8$)alkyl, —C(O)(C$_1$-C$_8$)alkyl, —C(O)—NH$_2$, —C(O)—NH(C$_1$-C$_8$)alkyl, NH$_2$—C(O)-alkylene, —S(C$_1$-C$_8$)alkyl, acetyl, —(C$_1$-C$_8$)alkyl, (C$_2$-C$_8$)alkenyl, (C$_2$-C$_8$)alkynyl, —O(C$_1$-C$_8$) alkyl, (C$_1$-C$_8$) haloalkyl, alkylcarbonylaminyl, alkylaminyl, —C(O)alkyl, C(O)cycloalkyl, —C(O)O—(C$_1$-C$_8$)alkyl, aryl, heteroaryl, heterocyclyl or cycloalkyl;
wherein any alkyl, cycloalkyl, heterocyclyl, heteroaryl, aryl, arylalkylene, cycloalkylalkylene, heterocyclylalkylene, heteroarylalkylene, alkylaminyl, alkylcarbonylaminyl, cycloalkylcarbonylaminyl, cycloalkylaminyl, or heterocyclylaminyl is optionally substituted with 1, 2, or 3 groups selected from —OH, —CN, —SH, —S(O)NH$_2$, —S(O)NH$_2$, halogen, —NH$_2$, —NH(C$_1$-C$_4$)alkyl, —N[(C$_1$-C$_4$)alkyl]$_2$, —C(O)NH$_2$, —COOH, —COOMe, acetyl, —(C$_1$-C$_8$)alkyl, —O(C$_1$-C$_8$)alkyl (C$_2$-C$_8$)alkenyl, (C$_2$-C$_8$)alkynyl, haloalkyl, thioalkyl, cyanomethylene, alkylaminyl, NH$_2$—C(O)-alkylene, NH$_2$—C(O)-alkylene, —NH (Me)-C(O)-alkylene, —CH$_2$—C(O)-lower alkyl, —C(O)-lower alkyl, alkylcarbonylaminyl, cycloalkyl, cycloalkylalkylene, cycloalkylalkenylene, cycloalkylcarbonylaminyl, cycloalkylaminyl, —CH$_2$—C(O)-cycloalkyl, —C(O)-cycloalkyl, —CH$_2$—C(O)-aryl, —CH$_2$-aryl, —C(O)-aryl, —CH$_2$—C(O)-heterocyclyl, —C(O)-heterocycloalkyl, heterocyclylaminyl or heterocyclyl.

2. The compound according to claim 1 wherein W$^1$ is O, A$^5$ is —NR$^8$ and R$^8$ is —H.
3. The compound according to claim 1 wherein Y is —NR$^{10}$ and subscript "n" is 1.
4. The compound according to claim 3 wherein R$^{10}$ is —H or —(C$_1$-C$_8$)alkyl.
5. The compound according to claim 1 wherein at least one of R$^1$ or R$^2$ is methyl, ethyl, i-propyl, —NH$_2$, aminomethylene, CH$_3$—OC(O)NH-methylene or thiophene.
6. The compound according to claim 1 wherein R$^1$ and R$^2$ together with the carbon atom to which they are attached form a cycloalkyl ring selected from the group consisting of cyclobutyl, cyclopentyl, cyclohexyl, 2,2-dimethylcyclobutyl, 4-aminocyclohexyl, 4-methylcyclohexyl, 4-ethylcyclohexyl, 2,2-difluoroethyl-4-cyclohexyl, 4,4-difluorocyclohexy, 4-cyanocyclohexyl, 4-trifluoromethylcyclohexyl, 4-hydroxycyclohexyl, 3-hydroxycyclopently, 3-aminocyclopentyl and 3-methylcyclopentyl.
7. The compound according to claim 1 wherein A$^2$ is —CH, A$^4$ is —CR$^{6b}$ and —CR$^{6b}$ is —C(OH), —C(CN), —C(F), —C(Cl), —C(OMe), —C(Me), —C(Et), —C(CF$_3$), —C(aminoalkylene), —C(SMe) or —C[C(O)Me].
8. The compound according to claim 1 wherein A$^2$ is —CH, A$^3$ is —CR$^7$ and —CR$^7$— is —C(OH), —C(CN), —C(F), —C(Cl), —C(OMe), —C(Me), —C(Et), —C(CHF$_2$) or —C(CF$_3$).
9. The compound according to claim 1 wherein R$^3$, R$^4$ and R$^5$ independently are —H.
10. The compound according to claim 1 wherein R$^3$ is —H and R$^4$ and R$^5$ independently are chlorine, fluorine, methyl, ethyl, difluoromethyl, trifluoromethyl, methoxy, —CN, —NHR$^{10}$ or —O(C$_1$-C$_8$)alkylNHR$^{10}$.

11. The compound according to claim 9 wherein $R^{10}$ is —H, —C(O)alkyl or —C(O)cycloalkyl.

12. The compound according to claim 1 wherein $R^3$ is —H and $R^4$ and $R^5$ together with the respective carbon atoms to which they are attached form a fused cycloalkyl, heterocyclyl, or heteroaryl ring.

13. The compound according to claim 11 wherein the heterocyclyl ring is morpholine, pyrrolidine or pyrrolidin-2-one.

14. The compound according to claim 11 wherein the heteroaryl ring is imidazole, thiazole, thiophene, pyrazole, N-methylpyrazole or pyridine.

15. The compound according to claim 1 selected from

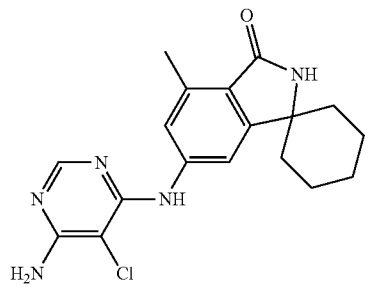

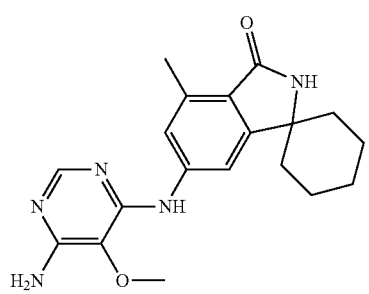

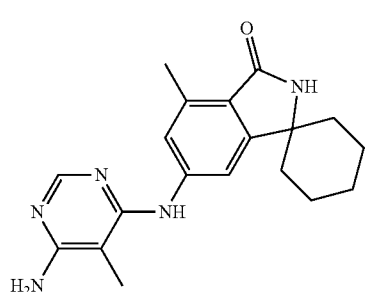

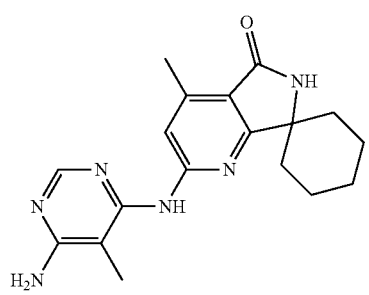

-continued

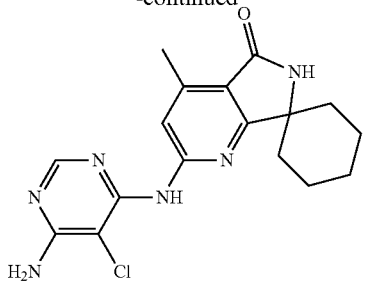

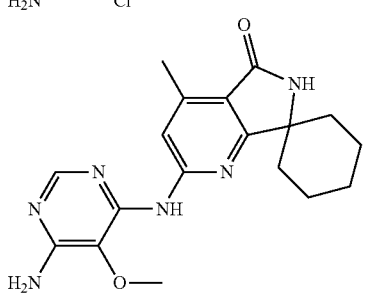

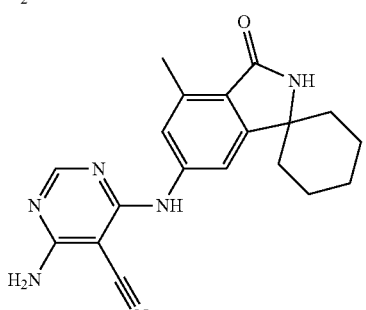

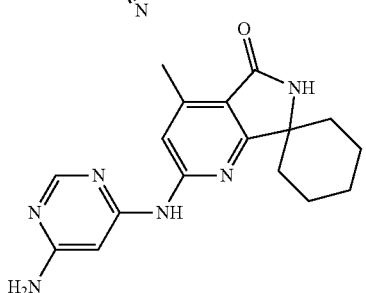

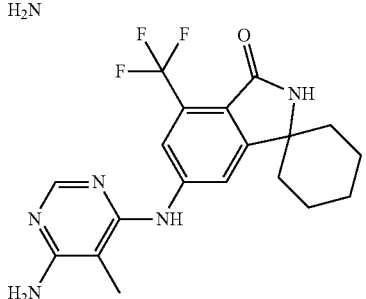

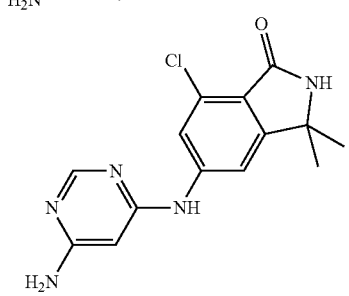

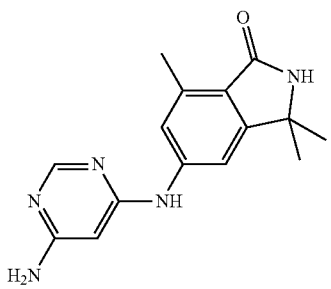
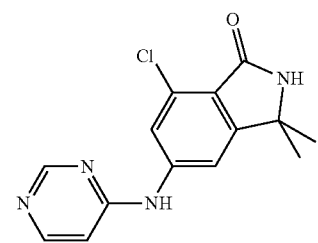
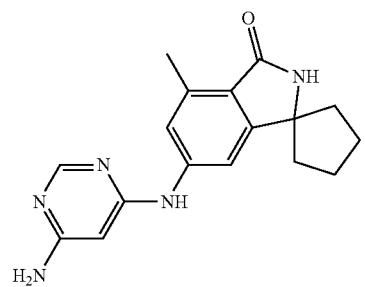
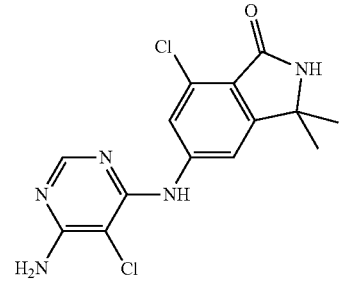
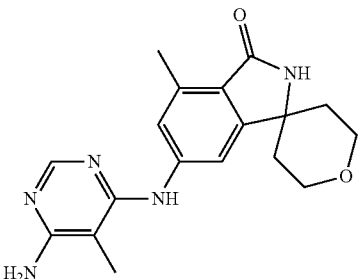
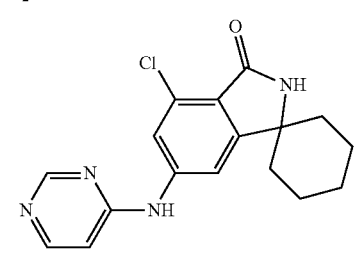
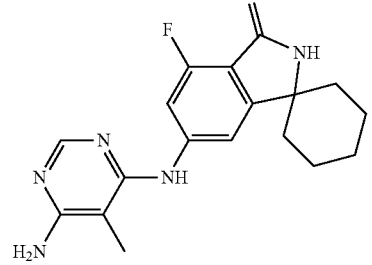
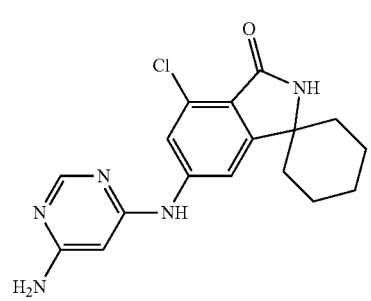
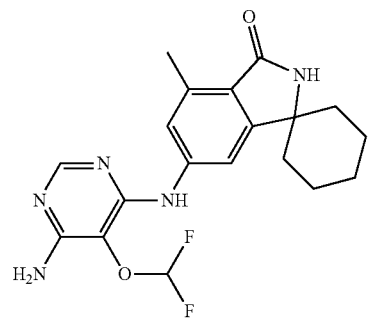
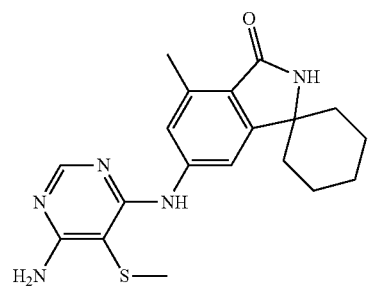
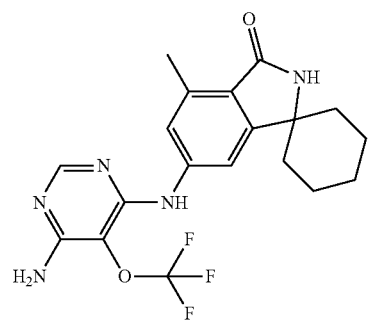

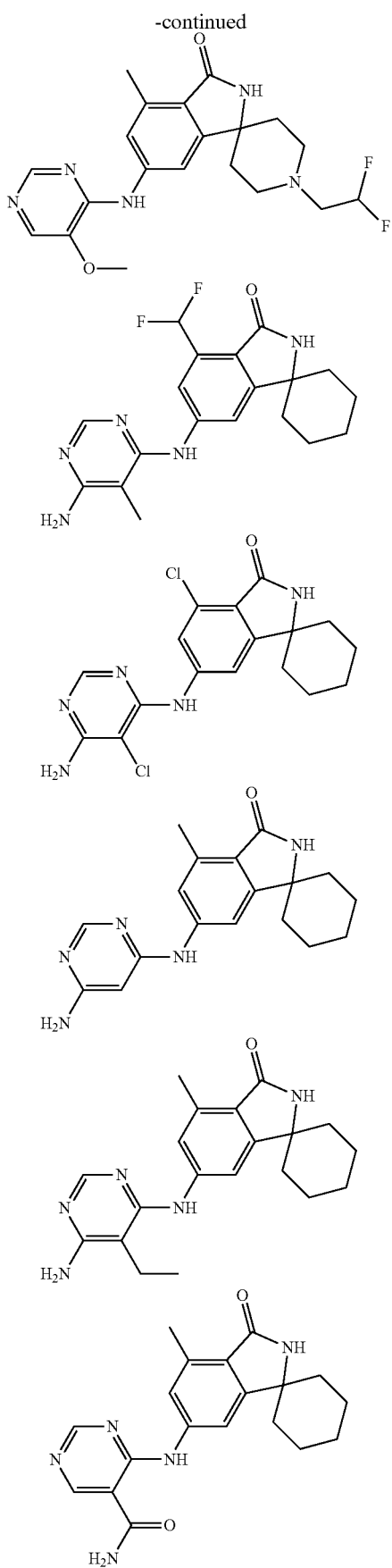

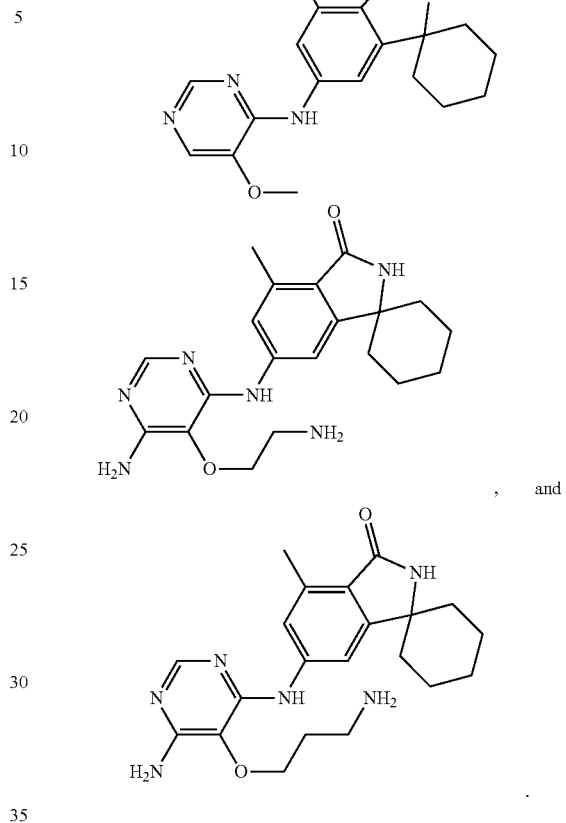

or a stereoisomer, a tautomer, or a pharmaceutically acceptable salt thereof.

16. A pharmaceutical composition comprising (i) a therapeutically effective amount of at least one compound according to claim 1 or a stereoisomer, a tautomer or a pharmaceutically acceptable salt thereof; (ii) in combination with a pharmaceutically acceptable carrier, diluent or excipient.

17. A method for attenuating or inhibiting the activity of Mnk in at least one cell overexpressing Mnk, comprising contacting the at least one cell with a compound according to claim 1 or a stereoisomer, tautomer or pharmaceutically acceptable salt thereof.

18. The method of claim 17 wherein the at least one cell is a colorectal cancer cell, a gastric cancer cell, a bladder cancer cell, an esophageal cancer cell, a head and neck cancer cell, a malignant glioma cell, a glioblastoma cell, a hepatocellular cancer cell, a thyroid cancer cell, a lung cancer cell, a leukemia cell, a B-cell lymphoma cell, a T-cell lymphoma cell, a hairy cell lymphoma cell, a non-small cell cancer cell, a small-cell lung cancer cell, a Hodgkin's lymphoma cell, a non-Hodgkin's lymphoma cell, a Burkitt's lymphoma cell, a pancreatic cancer cell, a pancreatic carcinoma cell, a melanoma cell, a multiple myeloma cell, a myelodysplastic syndrome, a brain cancer cell, a CNS cancer cell, a renal cell carcinoma cell, a prostate cancer cell, a castration-resistant prostate cancer cell, a cervical cancer cell, an urothelial cancer cell, an ovarian cancer cell, a breast cancer cell, or a triple-negative breast cancer cell.

19. The method of claim 17, wherein the at least one cell is a cancer cell.

* * * * *

SEQUENCE LISTING

<160> NUMBER OF SEQ ID NOS: 1

<210> SEQ ID NO 1
<211> LENGTH: 12
<212> TYPE: PRT
<213> ORGANISM: Artificial Sequence
<220> FEATURE:
<223> OTHER INFORMATION: Amino acid sequence in MNK substrate peptide

<400> SEQUENCE: 1

Thr Ala Thr Lys Ser Gly Ser Thr Thr Lys Asn Arg
1               5                   10